US011136309B2

(12) United States Patent
Sparks et al.

(10) Patent No.: US 11,136,309 B2
(45) Date of Patent: Oct. 5, 2021

(54) METALLOENZYME INHIBITOR COMPOUNDS

(71) Applicant: PhaseBio Pharmaceuticals, Inc., Malvern, PA (US)

(72) Inventors: Steven Sparks, Apex, NC (US); Christopher M. Yates, Raleigh, NC (US); Sammy R. Shaver, Chapel Hill, NC (US)

(73) Assignee: PHASEBIO PHARMACEUTICALS, INC., Malvern, PA (US)

( * ) Notice: Subject to any disclaimer, the term of this patent is extended or adjusted under 35 U.S.C. 154(b) by 0 days.

(21) Appl. No.: 16/746,098

(22) Filed: Jan. 17, 2020

(65) Prior Publication Data

US 2020/0392112 A1    Dec. 17, 2020

Related U.S. Application Data

(62) Division of application No. 15/858,015, filed on Dec. 29, 2017, now Pat. No. 10,538,511.

(60) Provisional application No. 62/440,199, filed on Dec. 29, 2016.

(51) Int. Cl.
*C07D 403/04* (2006.01)
*C07D 471/04* (2006.01)

(52) U.S. Cl.
CPC ......... *C07D 403/04* (2013.01); *C07D 471/04* (2013.01)

(58) Field of Classification Search
CPC .............................. C07D 403/04; C07D 471/04
USPC ....................................................... 514/269
See application file for complete search history.

(56) References Cited

U.S. PATENT DOCUMENTS

| | | |
|---|---|---|
| 4,738,851 A | 4/1988 | Schoenwald et al. |
| 4,882,150 A | 11/1989 | Kaufman |
| 4,921,475 A | 5/1990 | Sibalis |
| 5,008,110 A | 4/1991 | Benecke et al. |
| 5,077,033 A | 12/1991 | Viegas et al. |
| 5,087,240 A | 2/1992 | Sibalis |
| 5,088,977 A | 2/1992 | Sibalis |
| 5,106,863 A | 4/1992 | Hajos et al. |
| 5,163,899 A | 11/1992 | Sibalis |
| 5,164,189 A | 11/1992 | Farhadieh et al. |
| 5,254,346 A | 10/1993 | Tucker et al. |
| 5,290,561 A | 3/1994 | Farhadieh et al. |
| 5,336,168 A | 8/1994 | Sibalis |
| 5,352,456 A | 10/1994 | Fallon et al. |
| 5,403,841 A | 4/1995 | Lang et al. |
| 5,407,713 A | 4/1995 | Wilfong et al. |
| 5,521,222 A | 5/1996 | Ali et al. |
| 5,698,219 A | 12/1997 | Valdivia et al. |
| 5,776,445 A | 7/1998 | Cohen et al. |
| 5,800,807 A | 9/1998 | Hu et al. |
| 6,056,950 A | 5/2000 | Saettone et al. |
| 6,197,934 B1 | 3/2001 | DeVore et al. |
| 6,261,547 B1 | 7/2001 | Bawa et al. |
| 7,169,801 B2 | 1/2007 | Bressi et al. |
| 7,855,202 B2 | 12/2010 | Vidal Juan et al. |
| 8,188,131 B2 | 5/2012 | Edge et al. |
| 8,188,282 B2 | 5/2012 | Alonso et al. |
| 8,735,586 B2 | 5/2014 | Alonso et al. |
| 10,538,511 B2 | 1/2020 | Sparks et al. |
| 2008/0027044 A1 | 1/2008 | Lewis et al. |
| 2008/0255085 A1 | 10/2008 | Arvidsson et al. |
| 2008/0312175 A1 | 12/2008 | Yao et al. |
| 2009/0105266 A1 | 4/2009 | Glatthar et al. |
| 2011/0236307 A1 | 9/2011 | Jones |
| 2016/0074367 A1 | 3/2016 | Rogers et al. |

FOREIGN PATENT DOCUMENTS

| | | |
|---|---|---|
| CN | 103626783 A | 3/2014 |
| EP | 2624832 B1 | 9/2017 |
| WO | WO 2003/035065 A1 | 5/2003 |
| WO | WO 2005/111018 A1 | 11/2005 |
| WO | WO 2006/080821 A1 | 8/2006 |
| WO | WO 2008/009348 A1 | 1/2008 |
| WO | WO 2009/000413 A1 | 12/2008 |
| WO | WO 2009/045385 A1 | 4/2009 |
| WO | WO 2009/100438 A2 | 8/2009 |
| WO | WO 2009/156462 A2 | 12/2009 |
| WO | WO 2010/130796 A1 | 11/2010 |
| WO | WO 2011/061168 A1 | 5/2011 |
| WO | WO 2012/012478 A1 | 1/2012 |
| WO | WO 2013/034047 A1 | 3/2013 |
| WO | WO 2015/188369 A1 | 12/2015 |
| WO | WO 2018/118781 A1 | 6/2018 |

OTHER PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
International Search Report and Written Opinion dated Jun. 29, 2018 for Application No. PCT/US2017/068190, 16 pages.
International Search Report and Written Opinion dated Jul. 6, 2018 for Application No. PCT/US2017/068180, 16 pages.
[No Author Listed], Compound Summary for CID 45792664. PubChem, NIH, U.S. National Library of Medicine, National Center for Biotechnology Information. Jun. 21, 2010. https://pubchem.ncbi.nlm.nih.gov/compound/45792664 [last accessed Apr. 24, 2018], 11 pages.
[No Author Listed], Compound Summary for CID 71940203. PubChem, NIH, U.S. National Library of Medicine, National Center for Biotechnology Information. Nov. 29, 2013. https://pubchem.ncbi.nlm.nih.gov/compound/71940203 [last accessed Apr. 24, 2018], 10 pages.

(Continued)

*Primary Examiner* — Kristin A Vajda
(74) *Attorney, Agent, or Firm* — Cooley LLP

(57) ABSTRACT

Provided are compounds having metalloenzyme modulating activity, and methods of treating diseases, disorders or symptoms thereof mediated by such metalloenzymes.

4 Claims, No Drawings

(56) References Cited

OTHER PUBLICATIONS

[No Author Listed], Search Results. Aurora Fine Chemicals. Date unknown. http://online.aurorafinechemicals.com/navigate.asp?pgNo=1 [last accessed Apr. 24, 2018], 25 pages.
[No Author Listed], Auto-Immune Diseases. MedlinePlus. Jul. 21, 2014. http://www.nlm.nih.gov/medlineplus/autoimmunedisease.html [last accessed Oct. 29, 2018], 5 pages.
[No Author Listed], Infections: MedlinePlus. Jul. 6, 2016. https://medlineplus.gov/infections.html [last accessed Oct. 29, 2018], 10 pages.
[No Author Listed], Definition of Cancer. MedicineNet.com. Sep. 18, 2004. http://www.medterms.com [last accessed Oct. 29, 2018], 1 page.
[No Author Listed], Myeloproliferative disorders. University of Maryland Medical Center. Feb. 2, 2016. http://umm.edu/health/medical/altmed/condition/myeloproliferative-disorders [last accessed Oct. 29, 2018], 8 pages.
[No Author Listed], Neurological Disorders. Sep. 26, 2016. UCSF Medical Center https://www.ucsfhealth.org/conditions/neurological_disorders/ [last accessed Oct. 29, 2018], 1 page.
[No Author Listed], Search Results. ChemSpace. Date unknown. https://chem-space.com/search/5ac4e53b-7bf084-266f2302-fbfd7af?currency=usd&per_page=48&uom=g [last accessed Apr. 24, 2018], 3 pages.
Brown, Contribution of aldosterone to cardiovascular and renal inflammation and fibrosis, Nat Rev Nephrol, Aug. 2013; 9(8):459-69. doi: 10.1038/nmeph.2013.110. Epub Jun. 18, 2013. Review.
D'Ydewalle et al., HDAC6 inhibitors reverse axonal loss in a mouse model of mutant HSPBI-induced Charcot-Marie-Tooth disease. Nat Med. Jul. 24, 2011; 17(8):968-74. doi: 10.1038/nm.2396.
Deliyanti et al. Neovascularization is attenuated with aldosterone synthase inhibition in rats with retinopathy. Hypertension, 2012;59:607-13. doi: 10.1161/HYPERTENSIONAHA.111.188136. Epub Jan. 23, 2012.
Escher, et al. High aldosterone-to-renin variants of CYP11B2 and pregnancy outcome. Nephrol Dial Transplant. Jun. 2009;24(6):1870-5. doi: 10.1093/ndt/gfn763. Epub Jan. 16, 2009.
Extended European Search Report, dated May 28, 2020 for European Application No. 17886279.3, 10 pages.
Extended European Search Report, dated Jul. 24, 2020 for European Application No. 17887556.3, 10 pages.
Goker, et al., Synthesis and Potent Antifungal Activity Against Candida Species of Some Novel IH-Benzimidazoles. J. Heterocyclic Chem. Sep. 2, 2009; 46:936-48. doi: 10.1002/jhet.I79.
Haggerty et al., Domain-selective small-molecule inhibitor of histone deacetylase 6 (HDAC6)-mediated tubulin deacetylation. Proc Natl Acad Sci USA Apr. 15, 2003;100(8):4389-94. Epub Apr. 3, 2003.
Houlden et al., Mutations in the HSP27 (HSPBI) gene cause dominant, recessive, and sporadic distal HMN/CMT type 2. Neurology. Nov. 18, 2008;71(21):1660-8. doi: 10.1212/01.wnl.0000319696.14225.67. Epub Oct. 1, 2008.
Hoyt et al., Discovery of Benzimidazole CYP11B2 Inhibitors with in Vivo Activity in Rhesus Monkeys. ACS Med Chem Lett. Apr. 7, 2015;6(5):573-8. doi: 10.1021/acsmedchemlett.5b00054. eCollection May 14, 2015.
Kijima et al., Small heat shock protein 27 mutation in a Japanese patient with distal hereditary motor neuropathy. J Hum Genet. 2005;50(9):473-6. Epub Sep. 10, 2005.
Li et al. CYP11B2 expression in HSCs and its effect on hepatic fibrogenesis. World J Gastroenterol, 2000; 6(6):885-7.
Li et al. Novel mutations in the CYP11B2 gene causing aldosterone synthase deficiency. Mol Med Rep, Apr. 2016;13 (4): 3127-32. doi: 10.3892/mmr.2016.4906. Epub Feb. 18, 2016.
Meredith et al., "Discovery and in Vivo Evaluation of Potent Dual CY11B2 (Aldosterone Synthase) and CYP11B1 Inhibitors," ACS Medicinal Chemistry Letters, 2013, 4, 1203-1207.
Milokhov et al., "Reaction of 2-Hetaryl-2-(tetrahydro-2-furanyliden)acetonitriles with 1,3-N,N Binucleophiles," Synlett, 2012, 23:2063-2068.
Namsolleck et al. Aldosterone synthase inhibitors in cardiovascular and renal diseases. Nephrology Dialysis Transplantation, Feb. 2014; 29(1):i62-i68. Aldosterone synthase inhibitors in cardiovascular and renal diseases. doi: https://doi.org/10.1093/ndt/gft402.
Pacurari et al., "The Renin-Angiotensin-aldosterone system in vascular inflammation and remodeling," Int J Inflam. 2014;2014:689360. doi: 10.1155/2014/689360. Epub Apr. 6, 2014. Review.
Papillon et al., "Discovery of N-[5-(6-Chloro-3-cyano-1-methyl-1H-indol-2-yl)-pyridin-3-ylmethyl]-ethanesulfonamide, a Cortisol-Sparing CYP11B2 Inhibitor that Lowers Aldosterone in Human Subjects," J. Med. Chem., 2015, 58, 9382-9394.
Pindur et al., "Cyclization reactions of 2,2'-bis-N-methylindolyl to potential protein kinase C inhibitors", Heterocycles, 1994, vol. 38, No. 10, pp. 2267-2276.
Sajith et al., Design, synthesis and structure-activity relationship (SAR) studies of imidazo[4,5-b]pyridine derived purine isosteres and their potential as cytotoxic agents, European Journal of Medicinal Chemistry, 2015, 89, 21-31.
Sajith et al., "Microwave enhanced Suzuki coupling: a diversity-oriented approach to the synthesis of highly functionalised 3-substituted-2-aryl/heteroaryl imidazo[4,5-b]pyridines," Tetrahedron Letters, (2012), 53: 1036-1041.
Savitha et al., "Palladium-Catalyzed Suzuki Cross-Coupling of 2-HaloDeazapurines with Potassium Organotrifluoroborate Salts in the Regioselective Synthesis of Imidazo[4,5-b]pyridine Analogues," Aust. J. Chem. 2016, 69, 618-630.
Supuran, Carbonic anhydrases: novel therapeutic applications for inhibitors and activators. Nat Rev Drug Discov. Feb. 2008;7(2):168-81. doi: 10.1038/nrd2467. Review.
WebMD, "Inherited Metabolic Disorders.: Types, Causes, Symptoms and Treatments," 2014, 5 pages, retrieved from http://www.webmd.com/a-to-z-guides/inherited-metabolic-disorder-types-and-treatments?page-2>.
Xue et al., "Cu(i) recognition via cation-π and methionine interactions in CusF," Nature Chemical Biology, (2008) vol. 4, No. 2, 107-109.

* cited by examiner

METALLOENZYME INHIBITOR COMPOUNDS

CROSS-REFERENCE TO RELATED APPLICATIONS

The present application is a Divisional application of U.S. application Ser. No. 15/858,015, filed Dec. 29, 2017 (now issued U.S. Pat. No. 10,538,511), which claims priority under 35 U.S.C. § 119(e) to U.S. Provisional Patent Application Ser. No. 62/440,199, filed Dec. 29, 2016. The entirety of which is incorporated herein by reference.

BACKGROUND

Aldosterone is a steroid hormone secreted from the adrenal gland which binds and activates the mineralocorticoid receptor (MR). In the primary cells of the distal tubules and collecting ducts of the kidney, MR activation leads to sodium and water retention with excretion of potassium resulting in plasma volume expansion leading to increased blood pressure (BP). Excess aldosterone measured in circulation is termed primary aldosteronism (PA) and occurs when aldosterone production is dysregulated by the renin-angiotensin-aldosterone system (RAAS). PA was initially identified in patients with adrenal adenomas with recent evidence suggesting an increase in prevalence associated with obesity. PA is a common cause of secondary hypertension with the prevalence of PA ranging from 14-21% in patients with resistant hypertension (RHTN), a condition defined as BP remaining above goal despite the concurrent use of 3 antihypertensive agents of different classes including a diuretic agent. Recent studies have shown an association between excess aldosterone, RHTN, and obstructive sleep apnea (OSA) which is worsened by aldosterone-mediated fluid retention.

Local overproduction of aldosterone has been noted in several severe disease states even when no significant plasma elevation is observed. In patients with chronic congestive heart failure (CHF), aldosterone levels in failing heart tissue is higher than in peripheral plasma. In animal models of kidney disease, local production of aldosterone in the renal cortex is postulated to contribute to disease progression. In both these states, local elevated aldosterone levels contribute to harmful effects via both MR-dependent and MR-independent mechanisms including the generation of reactive oxygen species and endothelial dysfunction leading to inflammation and stimulation of cell growth and proliferation with upregulated collagen deposition leading to fibrosis.

Antagonists of MR, including spironolactone and eplerenone, have been extensively used to block the effects of aldosterone binding to MR. Significant reductions in morbidity and mortality in patients with heart failure or myocardial infarction have been demonstrated with these agents in combination with angiotensin-converting enzyme (ACE) inhibitors and diuretics (RALES & EPHESUS trials). Side effects including hyperkalemia are seen with both agents with the nonselective spironolactone also eliciting gynaecomastia via nonselective modulation of the progesterone and androgen receptors. Additionally, elevations of renin and aldosterone result from MR antagonism and thus the MR-independent (non-genomic) effects of aldosterone are exacerbated.

In contrast to MR antagonists, inhibition of CYP1B2 (aldosterone synthase), the key enzyme in aldosterone biosynthesis, should afford the beneficial effects of MR antagonism without the deleterious buildup of aldosterone leading to activation of MR-independent inflammatory and fibrotic states. CYP1B2 is a mitochondrial cytochrome P450 enzyme which converts 11-deoxycorticosterone to aldosterone. Selective inhibition of CYP1B2 represents a promising treatment for aldosterone related diseases.

The highly homologous metalloenzyme CYP11B1 (11-β-steroid-hydroxylase) catalyzes the formation of the primary glucocorticoid cortisol from 11-deoxycortisol. Given the high degree of homology between CYP11B2 and CYP11B1 (93%), the development of selective CYP11B2 inhibitors has been a significant challenge. The inhibitor Osilodrostat (LCI-699) was developed as a CYP11B2 inhibitor for the treatment of hypertension but was abandoned due to its potent inhibition of CYP11B1. Selective compounds which block the production of aldosterone via CYP11B2 without inhibition of cortisol production via CYP11B1 are described herein.

Living organisms have developed tightly regulated processes that specifically import metals, transport them to intracellular storage sites and ultimately transport them to sites of use. One of the most important functions of metals such as zinc and iron in biological systems is to enable the activity of metalloenzymes. Metalloenzymes are enzymes that incorporate metal ions into the enzyme active site and utilize the metal as a part of the catalytic process. More than one-third of all characterized enzymes are metalloenzymes.

The function of metalloenzymes is highly dependent on the presence of the metal ion in the active site of the enzyme. It is well recognized that agents which bind to and inactivate the active site metal ion dramatically decrease the activity of the enzyme. Nature employs this same strategy to decrease the activity of certain metalloenzymes during periods in which the enzymatic activity is undesirable. For example, the protein TIMP (tissue inhibitor of metalloproteases) binds to the zinc ion in the active site of various matrix metalloprotease enzymes and thereby arrests the enzymatic activity. The pharmaceutical industry has used the same strategy in the design of therapeutic agents. For example, the azole antifungal agents fluconazole and voriconazole contain a 1-(1,2,4-triazole) group that binds to the heme iron present in the active site of the target enzyme lanosterol demethylase and thereby inactivates the enzyme. Another example includes the zinc-binding hydroxamic acid group that has been incorporated into most published inhibitors of matrix metalloproteinases and histone deacetylases. Another example is the zinc-binding carboxylic acid group that has been incorporated into most published angiotensin-converting enzyme inhibitors.

In the design of clinically safe and effective metalloenzyme inhibitors, use of the most appropriate metal-binding group for the particular target and clinical indication is critical. If a weakly binding metal-binding group is utilized, potency may be suboptimal. On the other hand, if a very tightly binding metal-binding group is utilized, selectivity for the target enzyme versus related metalloenzymes may be suboptimal. The lack of optimal selectivity can be a cause for clinical toxicity due to unintended inhibition of these off-target metalloenzymes. One example of such clinical toxicity is the unintended inhibition of human drug metabolizing enzymes such as CYP2C9, CYP2C19 and CYP3A4 by the currently-available azole antifungal agents such as fluconazole and voriconazole. It is believed that this off-target inhibition is caused primarily by the indiscriminate binding of the currently utilized 1-(1,2,4-triazole) to iron in the active site of CYP2C9, CYP2C19 and CYP3A4. Another example of this is the joint pain that has been observed in many clinical trials of matrix metalloproteinase inhibitors. This toxicity is considered to be related to inhibition of off-target metalloenzymes due to indiscriminate binding of the hydroxamic acid group to zinc in the off-target active sites.

Therefore, the search for metal-binding groups that can achieve a better balance of potency and selectivity remains an important goal and would be significant in the realization of therapeutic agents and methods to address currently unmet needs in treating and preventing diseases, disorders and symptoms thereof.

BRIEF SUMMARY OF THE INVENTION

The invention is directed towards compounds (e.g., any of those delineated herein), methods of modulating activity of metalloenzymes, and methods of treating diseases, disorders or symptoms thereof. The methods can comprise the compounds herein.

It is understood that the embodiments of the invention discussed below with respect to the preferred variable selections can be taken alone or in combination with one or more embodiments, or preferred variable selections, of the invention, as if each combination were explicitly listed herein.

In one aspect, provided are compounds of Formula I:

or pharmaceutically acceptable salts, co-crystals, tautomers, stereoisomers, solvates, hydrates, polymorphs, isotopically enriched derivatives, or prodrugs thereof, wherein:

A is N or $CR^5$;
W is N or $CR^6$;
X is N or $CR^6$;
Y is N or $CR^6$;
Z is N or $CR^6$;
provided that no more than two of W, X, Y, and Z are N;
$R^1$ is hydrogen, halogen, cyano, acyl, alkyl, alkenyl, alkynyl, haloalkyl, alkoxy, haloalkoxy, cycloalkyl, cycloalkoxy, aryl, arylalkyl, heteroaryl, heteroarylalkyl, heterocycloalkyl, heterocycloalkylalkyl, $NR^aR^b$, $NHSO_2R^c$, $(CH_2)_nNR^aR^b$, $(CH_2)_nNHSO_2R^d$, $(CH_2)_nNHCO_2R^d$, $CO_2R^e$, $COR^f$, $(CH_2)_nOR^f$, or $CR^eR^{f'}OH$;
$R^2$ is hydrogen, halogen, cyano, acyl, alkyl, alkenyl, alkynyl, haloalkyl, alkoxy, haloalkoxy, cycloalkyl, cycloalkoxy, aryl, arylalkyl, heteroaryl, heteroarylalkyl, heterocycloalkyl, heterocycloalkylalkyl, $NR^aR^b$, $NHSO_2R^c$, $CH_2NR^aR^b$, $CH_2NHSO_2R^d$, $CO_2R^e$, $COR^f$, $CH_2OR^f$, or $CR^eR^{f'}OH$;
$R^3$ is hydrogen, halogen, cyano, acyl, alkyl, alkenyl, alkynyl, haloalkyl, alkoxy, haloalkoxy, cycloalkyl, cycloalkoxy, aryl, arylalkyl, heteroaryl, heteroarylalkyl, heterocycloalkyl, heterocycloalkylalkyl, $NR^aR^b$, $NHSO_2R^c$, $(CH_2)_nNR^aR^b$, $(CH_2)_nNHSO_2R^d$, $CO_2R^e$, $COR^f$, $(CH_2)_nOR^f$, or $CR^eR^{f'}OH$;
each n is independently 1, 2, 3, 4, 5, 6, 7, 8, 9, or 10;
$R^4$ is alkyl, cycloalkyl, haloalkyl, or heteroalkyl;
$R^5$ is hydrogen, alkyl, haloalkyl, heteroalkyl, or cycloalkyl;

each occurrence of $R^6$ is, independently, hydrogen, halogen, cyano, haloalkyl, alkyl, cycloalkyl, alkoxy, haloalkoxy, alkylsulfonyl, or carboxyl; and each occurrence of $R^a$, $R^b$, $R^c$, $R^d$, $R^e$, and $R^f$ are, independently, hydrogen, acyl, alkyl, alkenyl, alkynyl, heteroalkyl, haloalkyl, cycloalkyl, heterocycloalkyl, aryl, heteroaryl, alkoxyalkyl, $C(O)OC_{1-6}$ alkyl, $C(O)C_{1-6}$ alkyl, a nitrogen protecting group when attached to a nitrogen atom, or an oxygen protecting group when attached to an oxygen atom; or $R^a$ and $R^b$ together with the atoms to which they are attached form a heterocycloalkyl ring; or $R^e$ and $R^f$ together with the atoms to which they are attached form a cycloalkyl ring.

In certain embodiments, $R^1$ is hydrogen, halogen, cyano, alkyl, haloalkyl, alkoxy, $NR^aR^b$, or $CH_2NR^aR^b$.

In certain embodiments, $R^1$ is hydrogen, halogen, cyano, alkyl, $NR^aR^b$, or haloalkyl; and $R^a$ and $R^b$ are, independently, hydrogen, alkyl, or heteroalkyl.

In certain embodiments, $R^1$ is alkyl or haloalkyl.
In certain embodiments, $R^1$ is $C_{1-6}$ alkyl or $C_{1-6}$ haloalkyl.
In certain embodiments, $R^1$ is haloalkyl.
In certain embodiments, $R^1$ is $C_{1-6}$ haloalkyl.
In certain embodiments, $R^1$ is fluoroalkyl. In certain embodiments, $R^1$ is $C_{1-6}$ fluoroalkyl.
In certain embodiments, $R^1$ is $C_{1-3}$ fluoroalkyl. In certain embodiments, $R^1$ is difluoromethyl or trifluoromethyl. In certain embodiments, $R^1$ is difluoromethyl. In certain embodiments, $R^1$ is trifluoromethyl.

In certain embodiments, $R^2$ is hydrogen or alkyl.
In certain embodiments, $R^2$ is hydrogen or $C_{1-6}$ alkyl.
In certain embodiments, $R^2$ is hydrogen or $C_{1-3}$ alkyl.
In certain embodiments, $R^2$ is hydrogen.
In certain embodiments, $R^3$ is hydrogen or alkyl.
In certain embodiments, $R^3$ is hydrogen or $C_{1-6}$ alkyl.
In certain embodiments, $R^3$ is hydrogen or $C_{1-3}$ alkyl.
In certain embodiments, $R^3$ is hydrogen.
In certain embodiments, $R^2$ is hydrogen and $R^3$ is hydrogen.

In certain embodiments, $R^4$ is alkyl or cycloalkyl.
In certain embodiments, $R^4$ is $C_{1-4}$ alkyl or $C_{3-5}$ cycloalkyl.
In certain embodiments, $R^4$ is $C_{1-4}$ alkyl. In certain embodiments, $R^4$ is $C_{3-5}$ cycloalkyl. In certain embodiments, $R^4$ is cyclopentyl. In certain embodiments, $R^4$ is cyclobutyl. In certain embodiments, $R^4$ is cyclopropyl.

In certain embodiments, each $R^6$ is, independently, hydrogen, halogen, cyano, alkoxy, haloalkoxy or alkylsulfonyl.
In certain embodiments, each $R^6$ is, independently, hydrogen, halogen, or cyano.
In certain embodiments, each $R^6$ is, independently, hydrogen, chloro, fluoro, or cyano.
In certain embodiments, each $R^6$ is, independently, hydrogen, fluoro, or cyano.
In certain embodiments, each $R^6$ is, independently, hydrogen, or halogen.
In certain embodiments, each $R^6$ is, independently, hydrogen, chloro, or fluoro.
In certain embodiments, each $R^6$ is, independently, hydrogen or fluoro.
In certain embodiments, each $R^6$ is, independently, hydrogen or cyano.
In certain embodiments, each $R^6$ is halogen. In certain embodiments, each $R^6$ is chloro or fluoro. In certain embodiments, each $R^6$ is fluoro. In certain embodiments, each $R^6$ is cyano.
In certain embodiments, A is $CR^5$ and $R^5$ is hydrogen, $C_{1-4}$ alkyl, or $C_{3-5}$ cycloalkyl.

In certain embodiments, A is N.

In certain embodiments, no more than one of W, X, Y, and Z is N.

In certain embodiments, W, X, Y, and Z are each $CR^6$.

In certain embodiments, Z is N.

In certain embodiments, X is N.

In certain embodiments, the compound of Formula I is a compound of Formula I-a:

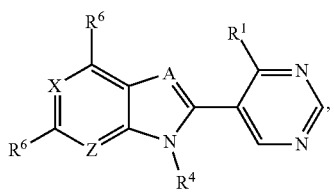

I-a or a pharmaceutically acceptable salt, co-crystal, tautomer, stereoisomer, solvate, hydrate, polymorph, isotopically enriched derivative, or prodrug thereof, wherein $R^1$, $R^4$, $R^6$, A, X, and Z are as defined herein.

In certain embodiments, the compound of Formula I is a compound of Formula I-b:

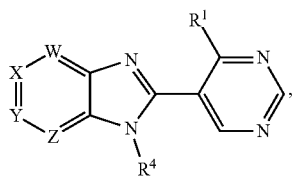

I-b or a pharmaceutically acceptable salt, co-crystal, tautomer, stereoisomer, solvate, hydrate, polymorph, isotopically enriched derivative, or prodrug thereof, wherein $R^1$, $R^4$, W, X, Y, and Z are as defined herein.

In certain embodiments, the compound of Formula I is a compound of Formula I-c:

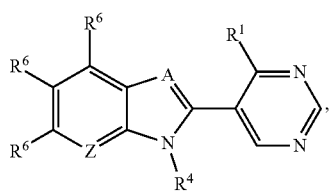

I-c or a pharmaceutically acceptable salt, co-crystal, tautomer, stereoisomer, solvate, hydrate, polymorph, isotopically enriched derivative, or prodrug thereof, wherein $R^1$, $R^4$, $R^6$, and Z are as defined herein.

In certain embodiments, the compound of Formula I is a compound of Formula I-d:

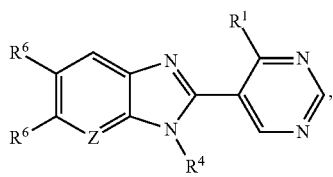

I-d or a pharmaceutically acceptable salt, co-crystal, tautomer, stereoisomer, solvate, hydrate, polymorph, isotopically enriched derivative, or prodrug thereof, wherein $R^1$, $R^4$, $R^6$, and Z are as defined herein.

In certain embodiments, the compound of Formula I is a compound of Formula I-e:

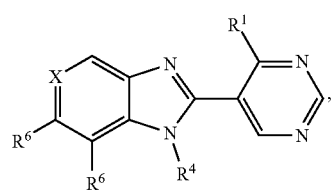

I-e or a pharmaceutically acceptable salt, co-crystal, tautomer, stereoisomer, solvate, hydrate, polymorph, isotopically enriched derivative, or prodrug thereof, wherein $R^1$, $R^4$, $R^6$, and X are as defined herein.

In certain embodiments, the compound of Formula I is a compound of Formula I-f:

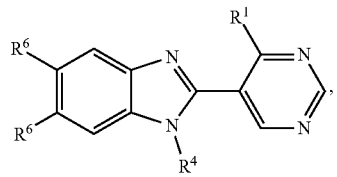

I-f or a pharmaceutically acceptable salt, co-crystal, tautomer, stereoisomer, solvate, hydrate, polymorph, isotopically enriched derivative, or prodrug thereof, wherein $R^1$, $R^4$, and $R^6$ are as defined herein.

In certain embodiments, the aforementioned compounds of formula I-f are those wherein: $R^4$ is alkyl or cycloalkyl; and $R^6$ is hydrogen or halo, wherein at least one $R^6$ is halo.

In certain embodiments, the aforementioned compounds of formula I-f are those wherein: $R^4$ is alkyl or cycloalkyl; and $R^6$ is halo.

In certain embodiments, the aforementioned compounds of formula I-f are those wherein: $R^4$ is alkyl or cycloalkyl; $R^6$ is hydrogen or halo, wherein at least one $R^6$ is halo; and $R^1$ is hydrogen, halogen, cyano, acyl, alkyl, haloalkyl, alkoxy, haloalkoxy, $NR^aR^b$, $NHSO_2R^c$, $CH_2NR^aR^b$, $CH_2NHSO_2R^d$, $CO_2R^e$, $COR^f$, $CH_2OR^f$, or $CR^eR^fOH$.

In certain embodiments, the aforementioned compounds of formula I-f are those wherein: $R^1$ is alkyl or haloalkyl; $R^4$ is alkyl or cycloalkyl; and $R^6$ is hydrogen or halo, wherein at least one $R^6$ is halo.

In certain embodiments, the aforementioned compounds of formula I-f are those wherein: $R^1$ is alkyl or haloalkyl; $R^4$ is alkyl or cycloalkyl; and $R^6$ is halo.

In certain embodiments, the compound of Formula I is a compound of Formula I-g:

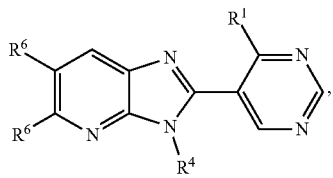

I-g or a pharmaceutically acceptable salt, co-crystal, tautomer, stereoisomer, solvate, hydrate, polymorph, isotopically enriched derivative, or prodrug thereof, wherein $R^1$, $R^4$, and $R^6$ are as defined herein.

In certain embodiments, the aforementioned compounds of formula I-g are those wherein: $R^4$ is alkyl or cycloalkyl; $R^6$ is hydrogen or halo, wherein at least one $R^6$ is halo.

In certain embodiments, the aforementioned compounds of formula I-g are those wherein: $R^4$ is alkyl or cycloalkyl; and $R^6$ is halo.

In certain embodiments, the aforementioned compounds of formula I-g are those wherein: $R^1$ is alkyl or haloalkyl; $R^4$ is alkyl or cycloalkyl; and $R^6$ is halo.

In certain embodiments, the compound of Formula I is a compound selected from the group consisting of:

1-cyclopropyl-6-fluoro-2-(pyrimidin-5-yl)-1H-benzo[d]imidazole (1);
1-cyclopropyl-6,7-difluoro-2-(pyrimidin-5-yl)-1H-benzo[d]imidazole (2);
1-cyclopropyl-2-(pyrimidin-5-yl)-1H-benzo[d]imidazole-6-carbonitrile (3);
1-cyclopropyl-6-fluoro-2-(4-methylpyrimidin-5-yl)-1H-benzo[d]imidazole (4);
1-cyclopropyl-2-(4-ethylpyrimidin-5-yl)-6-fluoro-1H-benzo[d]imidazole (5);
1-cyclopropyl-6-fluoro-2-(4-methoxypyrimidin-5-yl)-1H-benzo[d]imidazole (6);
1-cyclopropyl-5,6-difluoro-2-(pyrimidin-5-yl)-1H-benzo[d]imidazole (7);
1-cyclopropyl-2-(4-ethylpyrimidin-5-yl)-1H-benzo[d]imidazole-6-carbonitrile (8);
2-(4-Chloropyrimidin-5-yl)-1-cyclopropyl-6-fluoro-1H-benzo[d]imidazole (9);
5-(1-Cyclopropyl-6-fluoro-1H-benzo[d]imidazol-2-yl)pyrimidine-4-carbonitrile (10);
6-chloro-1-cyclopropyl-2-(4-ethylpyrimidin-5-yl)-1H-benzo[d]imidazole (11);
5-(1-Cyclopropyl-6-fluoro-1H-benzo[d]imidazol-2-yl)-N-methylpyrimidin-4-amine (12);
1-cyclopropyl-6-fluoro-2-(4-isopropylpyrimidin-5-yl)-1H-benzo[d]imidazole (13);
1-cyclopropyl-6-fluoro-2-(4-propylpyrimidin-5-yl)-1H-benzo[d]imidazole (14);
1-cyclopropyl-2-(4-(difluoromethyl)pyrimidin-5-yl)-6-fluoro-1H-benzo[d]imidazole (15);
1-ethyl-2-(4-ethylpyrimidin-5-yl)-6-fluoro-1H-benzo[d]imidazole (16);
1-cyclopropyl-2-(4-ethylpyrimidin-5-yl)-6,7-difluoro-1H-benzo[d]imidazole (17);
1-ethyl-2-(4-methylpyrimidin-5-yl)-1H-benzo[d]imidazole-6-carbonitrile (18);
N-((5-(1-cyclopropyl-6-fluoro-1H-benzo[d]imidazol-2-yl)pyrimidin-4-yl)methyl)acetamide (19);
1-cyclopropyl-6-fluoro-2-(2-methylpyrimidin-5-yl)-1H-benzo[d]imidazole (20);
1-cyclopropyl-2-(4-methylpyrimidin-5-yl)-1H-benzo[d]imidazole-6-carbonitrile (21);
1-cyclopropyl-5,6-difluoro-2-(4-isopropylpyrimidin-5-yl)-1H-benzo[d]imidazole (22);
6-chloro-1-cyclopropyl-2-(pyrimidin-5-yl)-1H-benzo[d]imidazole (23);
6-chloro-1-cyclopropyl-2-(4-isopropylpyrimidin-5-yl)-1H-benzo[d]imidazole (24);
1-cyclopropyl-6-methoxy-2-(pyrimidin-5-yl)-1H-benzo[d]imidazole (25);
1-cyclopropyl-6-(methylsulfonyl)-2-(pyrimidin-5-yl)-1H-benzo[d]imidazole (26);
1-cyclopropyl-2-(4-(difluoromethyl)pyrimidin-5-yl)-5,6-difluoro-1H-benzo[d]imidazole (27);
1-cyclopropyl-2-(4-isopropylpyrimidin-5-yl)-1H-benzo[d]imidazole-6-carbonitrile (28);
1-cyclopropyl-2-(4,6-dimethylpyrimidin-5-yl)-6-fluoro-1H-benzo[d]imidazole (29);
1-cyclopropyl-5,6-difluoro-2-(4-(trifluoromethyl)pyrimidin-5-yl)-1H-benzo[d]imidazole (30);
5-(1-cyclopropyl-5,6-difluoro-1H-benzo[d]imidazol-2-yl)-N-methylpyrimidin-4-amine (31);
5-(1-cyclopropyl-5,6-difluoro-1H-benzo[d]imidazol-2-yl)-N,N-dimethylpyrimidin-4-amine (32);
5-(1-cyclopropyl-5,6-difluoro-1H-benzo[d]imidazol-2-yl)-N-(2-methoxyethyl)pyrimidin-4-amine (33);
N-(tert-butyl)-5-(1-cyclopropyl-5,6-difluoro-1H-benz[d]imidazol-2-yl)pyrimidin-4-amine (34);
1-cyclopropyl-2-(2,4-dichloropyrimidin-5-yl)-6-fluoro-1H-benzo[d]imidazole (35);
5-(1-cyclopropyl-5,6-difluoro-1H-benzo[d]imidazol-2-yl)-N-(2,2,2-trifluoroethyl)pyrimidin-4-amine (36);
5-(1-cyclopropyl-5,6-difluoro-1H-benzo[d]imidazol-2-yl)-N-(3,3,3-trifluoropropyl)pyrimidin-4-amine (37);
6-chloro-1-cyclopropyl-5-fluoro-2-(pyrimidin-5-yl)-1H-benzo[d]imidazole (38);
1-cyclopropyl-2-(4-(methylamino)pyrimidin-5-yl)-1H-benzo[d]imidazole-6-carbonitrile (39);
1-cyclopropyl-2-(4-propylpyrimidin-5-yl)-1H-benzo[d]imidazole-6-carbonitrile (40);
1-ethyl-2-(4-isopropylpyrimidin-5-yl)-1H-benzo[d]imidazole-6-carbonitrile (41);
1-cyclopropyl-2-(pyrimidin-5-yl)-6-(trifluoromethoxy)-1H-benzo[d]imidazole (42);
2-(pyrimidin-5-yl)-1-(2,2,2-trifluoroethyl)-1H-benzo[d]imidazole-6-carbonitrile (43);
1-cyclopropyl-5,6-difluoro-2-(4-methylpyrimidin-5-yl)-1H-benzo[d]imidazole (44);
1-cyclopropyl-2-(4-ethylpyrimidin-5-yl)-5,6-difluoro-1H-benzo[d]imidazole (45);
5-(1-cyclopropyl-5,6-difluoro-1H-benzo[d]imidazol-2-yl)pyrimidine-4-carbonitrile (46);
6-chloro-1-ethyl-2-(pyrimidin-5-yl)-1H-indole (47);
5-chloro-3-cyclopropyl-2-(4-methylpyrimidin-5-yl)-3H-imidazo[4,5-b]pyridine (48);
2-(4-methylpyrimidin-5-yl)-1-(2,2,2-trifluoroethyl)-1H-benzo[d]imidazole-6-carbonitrile (49);
6-chloro-1-cyclopropyl-2-(4-(difluoromethyl)pyrimidin-5-yl)-1H-benzo[d]imidazole (50);
2-(4-(difluoromethyl)pyrimidin-5-yl)-1-ethyl-1H-benzo[d]imidazole-6-carbonitrile (51);
3-cyclopropyl-2-(4-methylpyrimidin-5-yl)-3H-imidazo[4,5-b]pyridine-5-carbonitrile (52);
2-(4-(trifluoromethyl)pyrimidin-5-yl)-1-ethyl-1H-benzo[d]imidazole-6-carbonitrile (53);

1-cyclopropyl-2-(4-(difluoromethyl)pyrimidin-5-yl)-1H-benzo[d]imidazole-6-carbonitrile (54);
6-chloro-1-cyclopropyl-2-(4-methylpyrimidin-5-yl)-1H-imidazo[4,5-c]pyridine (55);
1-cyclopropyl-2-(4-methylpyrimidin-5-yl)-1H-imidazo[4,5-c]pyridine-6-carbonitrile (56);
1-cyclopropyl-2-(pyrimidin-5-yl)-4,5,67-tetrahydro-1H-benzo[d]imidazole (57);
3-cyclopropyl-5-methoxy-2-(4-methylpyrimidin-5-yl)-3H-imidazo[4,5-b]pyridine (58);
N-(2-(5-(1-cyclopropyl-5,6-difluoro-1H-benzo[d]imidazol-2-yl)pyrimidin-4-yl)ethyl)acetamide (59);
1-cyclopropyl-2-(4-(trifluoromethyl)pyrimidin-5-yl)-1H-benzo[d]imidazole-6-carbonitrile (60);
5-chloro-3-cyclopropyl-2-(4-(trifluoromethyl)pyrimidin-5-yl)-3H-imidazo[4,5-b]pyridine (61);
5-chloro-3-cyclopropyl-2-(4-(difluoromethyl)pyrimidin-5-yl)-3H-imidazo[4,5-b]pyridine (62);
3-cyclopropyl-2-(4-(difluoromethyl)pyrimidin-5-yl)-3H-imidazo[4,5-b]pyridine-5-carbonitrile (63);
1-cyclopropyl-2-(4-(1,1-difluoroethyl)pyrimidin-5-yl)-1H-benzo[d]imidazole-6-carbonitrile (64);
3-cyclopropyl-2-(4-(trifluoromethyl)pyrimidin-5-yl)-3H-imidazo[4,5-b]pyridine-5-carbonitrile (65);
6-chloro-3-cyclopropyl-2-(4-(trifluoromethyl)pyrimidin-5-yl)-3H-imidazo[4,5-b]pyridine (66);
1-ethyl-5,6-difluoro-2-(4-(trifluoromethyl)pyrimidin-5-yl)-1H-benzo[d]imidazole (67);
5-chloro-3-ethyl-2-(4-(trifluoromethyl)pyrimidin-5-yl)-3H-imidazo[4,5-b]pyridine (68);
3-ethyl-2-(4-(trifluoromethyl)pyrimidin-5-yl)-3H-imidazo[4,5-b]pyridine-5-carbonitrile (69);
1-cyclopropyl-2-(4-(trifluoromethyl)pyrimidin-5-yl)-1H-benzo[d]imidazole-6-carboxylic acid (70);
1-cyclopropyl-2-(4-(1,1-difluoroethyl)pyrimidin-5-yl)-5,6-difluoro-1H-benzo[d]imidazole (71);
1-cyclopropyl-2-(4-cyclopropylpyrimidin-5-yl)-5,6-difluoro-1H-benzo[d]imidazole (72);
1-cyclopropyl-2-(4-(2-hydroxypropan-2-yl)pyrimidin-5-yl)-1H-benzo[d]imidazole-6-carbonitrile (73); pharmaceutically acceptable salts, co-crystals, tautomers, stereoisomers, solvates, hydrates, polymorphs, isotopically enriched derivatives, and prodrugs thereof.

In one aspect, the compound of Formula I is that wherein the compound inhibits (or is identified to inhibit) aldosterone synthase (CYP11B2).

The compounds herein include those wherein the compound is identified as attaining affinity, at least in part, for a metalloenzyme by formation of one or more of the following types of chemical interactions or bonds to a metal: sigma bonds, covalent bonds, coordinate-covalent bonds, ionic bonds, pi bonds, delta bonds, or backbonding interactions. The compounds can also attain affinity through weaker interactions with the metal such as van der Waals interactions, pi cation interactions, pi-anion interactions, dipole-dipole interactions, ion-dipole interactions. In one aspect, the compound is identified as having a bonding interaction with the metal via the pyrimidine moiety.

Methods for assessing metal-ligand binding interactions are known in the art as exemplified in references including, for example, "Principles of Bioinorganic Chemistry" by Lippard and Berg, University Science Books, (1994); "Mechanisms of Inorganic Reactions" by Basolo and Pearson John Wiley & Sons Inc; 2nd edition (September 1967); "Biological Inorganic Chemistry" by Ivano Bertini, Harry Gray, Ed Stiefel, Joan Valentine, University Science Books (2007); Xue et al. "Nature Chemical Biology", vol. 4, no. 2, 107-109 (2008).

In another aspect, provided are pharmaceutical compositions comprising the compound of Formula I and a pharmaceutically acceptable carrier.

In another aspect, provided are methods of modulating metalloenzyme activity in a subject, comprising contacting the subject with a compound of Formula I, in an amount and under conditions sufficient to modulate metalloenzyme activity.

In another aspect, provided are methods of treating a subject suffering from or susceptible to a disorder or disease, wherein the subject has been identified as in need of treatment for the disorder or disease, comprising administering to said subject in need thereof, an effective amount of a compound or pharmaceutical composition of Formula I, such that said subject is treated for said disorder.

In another aspect the subject is an animal other than a human.

In another aspect, provided are methods of treating a subject suffering from or susceptible to a metalloenzyme-related disorder or disease, comprising administering to the subject an effective amount of a compound or pharmaceutical composition of Formula I.

In another aspect, provided are methods of treating a subject suffering from or susceptible to a metalloenzyme-related disorder or disease, wherein the subject has been identified as in need of treatment for a metalloenzyme-related disorder or disease, comprising administering to said subject in need thereof, an effective amount of a compound or pharmaceutical composition of Formula I, such that said subject is treated for said disorder.

In another aspect, provided are methods of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical composition of Formula I, such that metalloenzyme activity in said subject is modulated (e.g., down regulated, inhibited).

The methods herein include those wherein the disease or disorder is mediated by any of aromatase (CYP19), a member of the cyclooxygenase family, lanosterol demethylase (CYP51), a member of the nitric oxide synthase family, thromboxane synthase (CYP5a), thyroid peroxidase, 17-alpha hydroxylase/17,20-lyase (CYP17), cytochrome P450 2A6 (CYP2A6), heme oxygenase, indoleamine 2,3-dioxygenase, retinoic acid hydroxylase (CYP26), vitamin D hydroxylase (CYP24), sterol 27-hydroxylase (CYP27), cytochrome P450 3A5 (CYP3A5), cholesterol 24-hydroxylase (CYP46), cytochrome P450 4F2 (CYP4F2), myeloperoxidase, or 11-beta-hydroxylase (CYP11B1).

The methods herein include those wherein the disease or disorder is cancer, cardiovascular disease, inflammatory disease, infectious disease, metabolic disease, ophthalmologic disease, central nervous system (CNS) disease, urologic disease, or gastrointestinal disease.

The methods herein include those wherein the disease or disorder is hypertension, resistant hypertension, morbidities associated with primary or secondary hyperaldosteronism and adrenal hyperplasia, pulmonary arterial hypertension, heart failure, diastolic dysfunction, left ventricular diastolic dysfunction, diastolic heart failure, systolic dysfunction, systolic heart failure, hypokalemia, renal failure, chronic renal failure, restenosis, nephropathy, post-myocardial infarction, coronary heart disease, fibrosis, diseases characterized by increased collagen formation, fibrosis and matrix remodeling following hypertension, fibrosis and matrix remodeling following endothelial cell dysfunction, cardiovascular diseases such as atherosclerosis, atrial fibrillation, renal dysfunction, liver diseases, non-alcoholic steatohepatitis, vascular diseases, retinopathy, neuropathy, insulinopathy, endothelial dysfunction, myocardial fibrosis, vascular fibrosis, myocardial necrotic lesions, vascular damage, myocardial infarction, left ventricular hypertrophy, vascular wall hypertrophy, endothelial thickening, fibrinoid necrosis of the arteries, kidney diseases, diabetic nephropathy, glomerulosclerosis, glomerulonephritis, nephritic syndrome, polycystic kidney disease, diabetes mellitus, metabolic syndrome, insulin resistance, sleep apnea, obstructive sleep apnea, muscular dystrophy, liver cirrhosis, non-alcoholic fatty liver disease, renal disorders, diabetic renal disorders, or stroke.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

DETAILED DESCRIPTION

Definitions

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present disclosure "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression. Note that "enzyme inhibition" (e.g., metalloenzyme inhibition) is distinguished and described below.

The term "modulate" refers to increases or decreases in the activity of an enzyme in response to exposure to a compound of the present disclosure.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 µg/kg to about 200 mg/kg, preferably about 0.01 mg/kg to about 200 mg/kg, more preferably about 0.015 mg/kg to about 30 mg/kg of body weight. In other embodiments, the therapeutically effect amount may range from about 1.0 pM to about 10 µM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 µg/kg to about 200 mg/kg of body weight, one time per day for between about 1 to 10 weeks, preferably between 2 to 8 weeks, more preferably between about 3 to 7 weeks, and even more preferably for about 4, 5, or 6 weeks. In another example, a subject may be treated daily for several years in the setting of a chronic condition or illness. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branched or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the present disclosure are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments±20%, in some embodiments±10%, in some embodiments±5%, in some embodiments±1%, in some embodiments±0.5%, and in some embodiments ±0.1% from the specified amount, as such variations are appropriate to perform the disclosed methods or employ the disclosed compositions.

Use of the word "inhibitor" herein is meant to mean a molecule that exhibits activity for inhibiting a metalloenzyme. By "inhibit" herein is meant to decrease the activity of metalloenzyme, as compared to the activity of metalloenzyme in the absence of the inhibitor. In some embodiments, the term "inhibit" means a decrease in metalloenzyme activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in metalloenzyme activity of about 5% to about 25%, about 25% to about 50%, about 50% to about 75%, or about 75% to 100%. In some embodiments, inhibit means a decrease in metalloenzyme activity of about 95% to 100%, e.g., a decrease in activity of 95%, 96%, 97%, 98%, 99%, or 100%. Such decreases can be measured using a variety of techniques that would be recognizable by one of skill in the art. Particular assays for measuring individual activity are described below.

Furthermore, the compounds of the present disclosure include olefins having either geometry: "Z" refers to what is referred to as a "cis" (same side) configuration whereas "E" refers to what is referred to as a "trans" (opposite side) configuration. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "haloalkyl" refers to an alkyl group that is substituted by one or more halo substituents. Examples of haloalkyl groups include fluoromethyl, difluoromethyl, trifluoromethyl, bromomethyl, chloromethyl, and 2,2,2-trifluoroethyl.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "arylalkenyl" refers to an unsaturated hydrocarbon chain that may be a straight chain or branched chain, containing 2 to 12 carbon atoms and at least one carbon-carbon double bond wherein one or more of the $sp^2$ hybridized carbons of the alkenyl unit attaches to an aryl moiety. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The term "arylalkynyl" refers to an unsaturated hydrocarbon chain that may be a straight chain or branched chain, containing 2 to 12 carbon atoms and at least one carbon-carbon triple bond wherein one or more of the sp hybridized carbons of the alkynyl unit attaches to an aryl moiety. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl substituent.

As used herein, the term "halogen", "hal" or "halo" means —F, —Cl, —Br or —I.

The term "alkylthio" refers to an —S-alkyl substituent.

The term "alkoxyalkyl" refers to an -alkyl-O-alkyl substituent.

The term "haloalkoxy" refers to an —O-alkyl that is substituted by one or more halo substituents. Examples of haloalkoxy groups include trifluoromethoxy, and 2,2,2-trifluoroethoxy.

The term "haloalkoxyalkyl" refers to an -alkyl-O-alkyl' where the alkyl' is substituted by one or more halo substituents.

The term "haloalkylaminocarbonyl" refers to a —C(O)-amino-alkyl where the alkyl is substituted by one or more halo substituents.

The term "haloalkylthio" refers to an —S-alkyl that is substituted by one or more halo substituents. Examples of haloalkylthio groups include trifluoromethylthio, and 2,2,2-trifluoroethylthio.

The term "haloalkylcarbonyl" refers to an —C(O)-alkyl that is substituted by one or more halo substituents. An example of a haloalkylcarbonyl group includes trifluoroacetyl.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "cycloalkoxy" refers to an —O-cycloalkyl substituent.

The term "cycloalkoxyalkyl" refers to an -alkyl-O-cycloalkyl substituent.

The term "cycloalkylalkoxy" refers to an —O-alkyl-cycloalkyl substituent.

The term "cycloalkylaminocarbonyl" refers to an —C(O)—NH-cycloalkyl substituent.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "aryloxy" refers to an —O-aryl substituent.

The term "arylalkoxy" refers to an —O-alkyl-aryl substituent.

The term "arylalkylthio" refers to an —S-alkyl-aryl substituent.

The term "arylthioalkyl" refers to an -alkyl-S-aryl substituent.

The term "arylalkylaminocarbonyl" refers to a —C(O)-amino-alkyl-aryl substituent.

The term "arylalkylsulfonyl" refers to an —S(O)$_2$-alkyl-aryl substituent.

The term "arylalkylsulfinyl" refers to an —S(O)-alkyl-aryl substituent.

The term "aryloxyalkyl" refers to an -alkyl-O-aryl substituent.

The term "alkylaryl" refers to an -aryl-alkyl substituent.

The term "arylalkyl" refers to an -alkyl-aryl substituent.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heteroarylalkyl" refers to an -alkyl-heteroaryl substituent.

The term "heteroaryloxy" refers to an —O-heteroaryl substituent.

The term "heteroarylalkoxy" refers to an —O-alkyl-heteroaryl substituent.

The term "heteroaryloxyalkyl" refers to an -alkyl-O-heteroaryl substituent.

The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "heterocycloalkylalkyl" refers to an -alkyl-heterocycloalkyl substituent.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carboxamido, carbamido, carbamyl, thioureido, thiocyanato, sulfoamido, sulfonylalkyl, sulfonylaryl, mercaptoalkoxy, N-hydroxyamidinyl, or N'-aryl, N"-hydroxyamidinyl.

Compounds of the present disclosure can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2nd Edition*, Carlson R, Ed, 2005; Elsevier Science Ltd.; Jähnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

As can be appreciated by the skilled artisan, methods of synthesizing the compounds of the formulae herein will be evident to those of ordinary skill in the art, including in the schemes and examples herein. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired compounds of the present disclosure.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present disclosure. The compounds herein may also be represented in multiple tautomeric forms, in such instances, the present disclosure expressly includes all tautomeric forms of the compounds described herein, even though only a single tautomeric form may be represented. All such isomeric forms of such compounds herein are expressly included in the present disclosure. All crystal forms and polymorphs of the compounds described herein are expressly included in the present disclosure. Also embodied are extracts and fractions comprising compounds of the present disclosure. The term isomers is intended to include diastereoisomers, enantiomers, regioisomers, structural isomers, rotational isomers, tautomers, and the like. For compounds which contain one or more stereogenic centers, e.g., chiral compounds, the methods of the present disclosure may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the present disclosure is administered to cells or a subject.

Methods of Treatment

In one aspect, provided are methods of treating a subject suffering from or susceptible to a disorder or disease, comprising administering to the subject an effective amount of a compound or pharmaceutical composition of Formula I.

In other aspects, provided are methods of treating a subject suffering from or susceptible to a disorder or disease, wherein the subject has been identified as in need of treatment for a metalloenzyme-mediated disorder or disease, comprising administering to said subject in need thereof, an effective amount of a compound or pharmaceutical composition of Formula I, such that said subject is treated for said disorder.

In one aspect, provided are methods of modulating the metalloenzyme activity of a cell in a subject, comprising contacting the subject with a compound of Formula I, in an amount and under conditions sufficient to modulate metalloenzyme activity.

In one embodiment, the modulation is inhibition.

In another aspect, provided are methods of treating a subject suffering from or susceptible to a metalloenzyme-mediated disorder or disease, comprising administering to the subject an effective amount of a compound or pharmaceutical composition of Formula I.

In other aspects, provided are methods of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical composition of Formula I, such that said subject is treated for said disorder.

In certain embodiments, provided are methods of treating a disease, disorder or symptom thereof, wherein the disorder is cancer, cardiovascular disease, endocrinologic disease, inflammatory disease, infectious disease, gynecologic disease, metabolic disease, ophthalmologic disease, central nervous system (CNS) disease, urologic disease, or gastrointestinal disease. In certain embodiments the disease is hypertension, resistant hypertension, morbidities associated with primary or secondary hyperaldosteronism and adrenal hyperplasia, pulmonary arterial hypertension, heart failure, diastolic dysfunction, left ventricular diastolic dysfunction, diastolic heart failure, systolic dysfunction, systolic heart failure, hypokalemia, renal failure, chronic renal failure, restenosis, nephropathy, post-myocardial infarction, coronary heart disease, fibrosis, diseases characterized by increased collagen formation, fibrosis and matrix remodeling following hypertension, fibrosis and matrix remodeling following endothelial cell dysfunction, cardiovascular diseases such as atherosclerosis, atrial fibrillation, renal dysfunction, liver diseases, non-alcoholic steatohepatitis, vascular diseases, retinopathy, neuropathy, insulinopathy, endothelial dysfunction, myocardial fibrosis, vascular fibrosis, myocardial necrotic lesions, vascular damage, myocardial infarction, left ventricular hypertrophy, vascular wall hypertrophy, endothelial thickening, fibrinoid necrosis of the arteries, kidney diseases, diabetic nephropathy, glomerulosclerosis, glomerulonephritis, nephritic syndrome, polycystic kidney disease, diabetes mellitus, metabolic syndrome, insulin resistance, sleep apnea, obstructive sleep apnea, muscular dystrophy, liver cirrhosis, non-alcoholic fatty liver disease, renal disorders, diabetic renal disorders, or stroke.

In certain embodiments, the subject is a mammal, preferably a primate or human.

In another embodiment, provided are methods as described above, wherein the effective amount of the compound of Formula I is as described above.

In another embodiment, provided are methods as described above, wherein the compound of Formula I is administered intravenously, intramuscularly, subcutaneously, intracerebroventricularly, orally or topically.

In another embodiment, provided are methods as described herein wherein the compound of Formula I demonstrates selectivity for an activity range against a target enzyme (e.g., aldosterone synthase (CYP11B2) $IC_{50}$<1.0 µM).

In other embodiments, provided are methods as described above, wherein the compound of Formula I is administered alone or in combination with one or more other therapeutics. In a further embodiment, the additional therapeutic agent is an anti-cancer agent, antifungal agent, cardiovascular agent, anti-inflammatory agent, chemotherapeutic agent, an anti-angiogenesis agent, cytotoxic agent, an anti-proliferation agent, metabolic disease agent, ophthalmologic disease agent, central nervous system (CNS) disease agent, urologic disease agent, or gastrointestinal disease agent.

In a certain embodiments, the additional therapeutic agent is an agent for the treatment of hypertension, agent for the treatment of primary aldosteronism, agent for the treatment of kidney disease, agent for the treatment of congestive heart failure, agent for the treatment of atherosclerotic conditions, agent for the treatment of diabetes, agent for the treatment of obesity, or agent for the treatment of metabolic disease.

Exemplary additional therapeutic agents include, but are not limited to, renin inhibitors, angiotensin converting enzyme (ACE) inhibitors, dual inhibitors of angiotensin converting enzyme (ACE) and neutral endopeptidase (NEP), angiotensin II receptor blockers (ARB), mineralocorticoid receptor antagonists (MRA), neutral endopeptidase inhibitors (NEP), neprilysin inhibitors, calcium channel blockers, alpha-adrenergic blockers, beta-adrenergic blockers, diuretics (including loop diuretics), potassium channel activators, endothelin receptor antagonists, endothelin 1 receptor agonists, soluble guanylate cyclase stimulators, vasodilators, HMG-CoA reductase inhibitors, niacin and niacin receptor agonists, Niemann-Pick C1-like 1 (NPC1L1) inhibitors, insulin or insulin analogs, biguanides (e.g., metformin), sulfonylureas, peroxisome proliferator-activated receptor (PPAR) agonists and partial agonists including PPARγ agonists and other PPAR ligands, dipeptidyl peptidase-4 (DPP4) inhibitors, glucagon-like peptide 1 (GLP-1), GLP-1 receptor agonists, and sodium-glucose co-transporter 2 (SGLT2) inhibitors.

Another object of the present disclosure is the use of a compound as described herein (e.g., a compound of Formula I) in the manufacture of a medicament for use in the treatment of a metalloenzyme-mediated disorder or disease. Another object of the present disclosure is the use of a compound as described herein (e.g., a compound of Formula I) for use in the treatment of a metalloenzyme-mediated disorder or disease. Another object of the present disclosure is the use of a compound as described herein (e.g., a compound of Formula I) in the manufacture of an agricultural composition for use in the treatment or prevention of a metalloenzyme-mediated disorder or disease in agricultural or agrarian settings.

Pharmaceutical Compositions

In one aspect, provided are pharmaceutical compositions comprising the compound of Formula I and a pharmaceutically acceptable carrier.

In another embodiment, provided are pharmaceutical compositions further comprising an additional therapeutic agent. In a further embodiment, the additional therapeutic agent is an anti-cancer agent, antifungal agent, cardiovascular agent, anti-inflammatory agent, chemotherapeutic agent, an anti-angiogenesis agent, cytotoxic agent, an anti-proliferation agent, metabolic disease agent, ophthalmologic disease agent, central nervous system (CNS) disease agent, urologic disease agent, or gastrointestinal disease agent.

In certain embodiments, the additional therapeutic agent is an agent for the treatment of hypertension, agent for the treatment of primary aldosteronism, agent for the treatment of kidney disease, agent for the treatment of congestive heart failure, agent for the treatment of atherosclerotic conditions, agent for the treatment of diabetes, agent for the treatment of obesity, or agent for the treatment of metabolic disease.

Exemplary additional therapeutic agents include, but are not limited to, renin inhibitors, angiotensin converting enzyme (ACE) inhibitors, dual inhibitors of angiotensin converting enzyme (ACE) and neutral endopeptidase (NEP), angiotensin II receptor blockers (ARB), mineralocorticoid receptor antagonists (MRA), neutral endopeptidase inhibitors (NEP), neprilysin inhibitors, calcium channel blockers, alpha-adrenergic blockers, beta-adrenergic blockers, diuretics (including loop diuretics), potassium channel activators, endothelin receptor antagonists, endothelin 1 receptor agonists, soluble guanylate cyclase stimulators, vasodilators, HMG-CoA reductase inhibitors, niacin and niacin receptor agonists, Niemann-Pick C1-like 1 (NPC1L1) inhibitors, insulin or insulin analogs, biguanides (e.g., metformin), sulfonylureas, peroxisome proliferator-activated receptor (PPAR) agonists and partial agonists including PPARγ agonists and other PPAR ligands, dipeptidyl peptidase-4 (DPP4) inhibitors, glucagon-like peptide 1 (GLP-1), GLP-1 receptor agonists, and sodium-glucose co-transporter 2 (SGLT2) inhibitors.

In one aspect, provided are kits comprising an effective amount of a compound of Formula I, in unit dosage form, together with instructions for administering the compound to a subject suffering from or susceptible to a metalloenzyme-mediated disease or disorder, including cancer, cardiovascular disease, endocrinologic disease, inflammatory disease, infectious disease, gynecologic disease, metabolic disease, ophthalmologic disease, central nervous system (CNS) disease, urologic disease, or gastrointestinal disease. In other embodiments, the disease, disorder or symptom thereof is hypertension, resistant hypertension, morbidities associated with primary or secondary hyperaldosteronism and adrenal hyperplasia, pulmonary arterial hypertension, heart failure, diastolic dysfunction, left ventricular diastolic dysfunction, diastolic heart failure, systolic dysfunction, systolic heart failure, hypokalemia, renal failure, chronic renal failure, restenosis, nephropathy, post-myocardial infarction, coronary heart disease, fibrosis, diseases characterized by increased collagen formation, fibrosis and matrix remodeling following hypertension, fibrosis and matrix remodeling following endothelial cell dysfunction, cardiovascular diseases such as atherosclerosis, atrial fibrillation, renal dysfunction, liver diseases, non-alcoholic steatohepatitis, vascular diseases, retinopathy, neuropathy, insulinopathy, endothelial dysfunction, myocardial fibrosis, vascular fibrosis, myocardial necrotic lesions, vascular damage, myocardial infarction, left ventricular hypertrophy, vascular wall hypertrophy, endothelial thickening, fibrinoid necrosis of the arteries, kidney diseases, diabetic nephropathy, glomerulosclerosis, glomerulonephritis, nephritic syndrome, polycystic kidney disease, diabetes mellitus, metabolic syndrome, insulin resistance, sleep apnea, obstructive sleep apnea, muscular dystrophy, liver cirrhosis, non-alcoholic fatty liver disease, renal disorders, diabetic renal disorders, or stroke.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present disclosure contain both basic and acidic functionalities that allow the compounds to be converted into either base or acid addition salts. Other pharmaceutically acceptable carriers known to those of skill in the art are suitable for the present disclosure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

In addition to salt forms, the present disclosure provides compounds which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

The present disclosure also provides a pharmaceutical composition, comprising an effective amount a compound described herein and a pharmaceutically acceptable carrier. In an embodiment, a compound of Formula I is administered to a subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of the disclosure may be varied so as to obtain an amount of the active ingredient which is effective to achieve the desired therapeutic response for a particular patient, composition, and mode of administration, without being toxic (or unacceptably toxic) to the patient.

In use, at least one compound according to the present disclosure is administered in a pharmaceutically effective amount to a subject in need thereof in a pharmaceutical carrier by intravenous, intramuscular, subcutaneous, or intracerebroventricular injection or by oral administration or topical application. In accordance with the present disclosure, a compound of the disclosure may be administered alone or in conjunction with a second, different therapeutic. By "in conjunction with" is meant together, substantially simultaneously or sequentially. In one embodiment, a compound of the disclosure is administered acutely. The compound of the disclosure may therefore be administered for a short course of treatment, such as for about 1 day to about 1 week. In another embodiment, the compound of the disclosure may be administered over a longer period of time to ameliorate chronic disorders, such as, for example, for about one week to several months depending upon the condition to be treated.

By "pharmaceutically effective amount" as used herein is meant an amount of a compound of the disclosure, high enough to significantly positively modify the condition to be treated but low enough to avoid serious side effects (at a reasonable benefit/risk ratio), within the scope of sound medical judgment. A pharmaceutically effective amount of a compound of the disclosure will vary with the particular goal to be achieved, the age and physical condition of the patient being treated, the severity of the underlying disease, the duration of treatment, the nature of concurrent therapy and the specific compound employed. For example, a therapeutically effective amount of a compound of the disclosure administered to a child or a neonate will be reduced proportionately in accordance with sound medical judgment. The effective amount of a compound of the disclosure will thus be the minimum amount which will provide the desired effect.

A decided practical advantage of the present disclosure is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the disclosure may be required to be coated in a material to protect the compound from the action of enzymes, acids and other natural conditions which may inactivate the compound. In order to administer a compound of the disclosure by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, mannitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present. Solubilizing agents, including for example, cremaphore and beta-cyclodextrins can also used in the pharmaceutical compositions herein.

Pharmaceutical compositions comprising the active compounds of the present disclosure (or prodrugs thereof) can be manufactured by means of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

Pharmaceutical compositions of the present disclosure subject matter can take a form suitable for virtually any mode of administration, including, for example, topical, ocular, oral, buccal, systemic, nasal, injection, transdermal, rectal, vaginal, and the like, or a form suitable for administration by inhalation or insufflation.

For topical administration, the active compound(s) or prodrug(s) can be formulated as solutions, gels, ointments, creams, suspensions, and the like.

Systemic formulations include those designed for administration by injection, e.g., subcutaneous, intravenous, intramuscular, intrathecal or intraperitoneal injection, as well as those designed for transdermal, transmucosal, oral, or pulmonary administration.

Useful injectable preparations include sterile suspensions, solutions or emulsions of the active compound(s) in aqueous or oily vehicles. The compositions also can contain formulating agents, such as suspending, stabilizing and/or dispersing agent. The formulations for injection can be presented in unit dosage form (e.g., in ampules or in multidose containers) and can contain added preservatives.

Alternatively, the injectable formulation can be provided in powder form for reconstitution with a suitable vehicle, including but not limited to sterile pyrogen free water, buffer, dextrose solution, and the like, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, lozenges, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p-hydroxybenzoates or sorbic acid). The preparations also can contain buffer salts, preservatives, flavoring, coloring and sweetening agents as appropriate.

Preparations for oral administration can be suitably formulated to give controlled release of the active compound or prodrug, as is well known.

For buccal administration, the compositions can take the form of tablets or lozenges formulated in a conventional manner.

For rectal and vaginal routes of administration, the active compound(s) can be formulated as solutions (for retention enemas), suppositories, or ointments containing conventional suppository bases, such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH5 to pH7, with a pH of about pH 5.5 being typical.

For ocular administration, the active compound(s) or prodrug(s) can be formulated as a solution, emulsion, suspension, and the like, suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851, each of which is incorporated herein by reference in its entirety.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed.

The pharmaceutical compositions can, if desired, be presented in a pack or dispenser device which can contain one or more unit dosage forms containing the active compound(s). The pack can, for example, comprise metal or plastic foil, such as a blister pack. The pack or dispenser device can be accompanied by instructions for administration.

The active compound(s) or prodrug(s) of the present disclosure, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound can be administered to a patient at risk of developing one of the previously described diseases. A patient at risk of developing a disease can be a patient having characteristics placing the patient in a designated group of at risk patients, as defined by an appropriate medical professional or group. A patient at risk may also be a patient that is commonly or routinely in a setting where development of the underlying disease that may be treated by administration of a metalloenzyme inhibitor according to the present disclosure could occur. In other words, the at risk patient is one who is commonly or routinely exposed to the disease or illness causing conditions or may be acutely exposed for a limited time. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular compound as measured in as in vitro assay, such as the in vitro fungal MIC or MFC and other in vitro assays described in the Examples section. Calculating dosages to achieve such circulating blood or serum concentrations taking into account the bioavailability of the particular compound is well within the capabilities of skilled artisans. For guidance, see Fingl & Woodbury, "General Principles," In: *Goodman and Gilman's The Pharmaceutical Basis of Therapeutics*, Chapter 1, pp. 1-46, latest edition, Pagamonon Press, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

General Experimental Procedures

Definitions of variables in the structures in schemes herein are commensurate with those of corresponding positions in the formulae delineated herein. The example compounds listed in Table 2 were characterized by the HPLC and LCMS methods described in Table 1.

TABLE 1

HPLC and LCMS methods

| | HPLC | LCMS |
|---|---|---|
| a | Column: ZORBAX-SCB-C18 (150 × 4.6 mm, 3.5 μ); ACN: 0.05% Aq TFA; 1.0 mL/min | Column: X-Select CSH C-18 (50 × 3.0 mm, 2.5 μm); 2.5 mM NH$_4$OOCH in water: 5% ACN; ACN: 5% 2.5 mM NH$_4$OOCH in water: 0.80 mL/min |
| b | Column: X-Select-CSH-C18 (150 × 4.6 mm, 3.5 μm); 0.05% TFA + 5% ACN: ACN + 5% 0.05% TFA; 1.0 mL/min | Column: Kinotex EVO C-18 (50 × 3.0 mm, 2.6 μm); 2.5 mM NH$_4$OOCH in water: 5% ACN; ACN: 5% 2.5 mM NH$_4$OOCH in water: 0.80 mL/min |
| c | Column: X-Select-CSH-C18 (150 × 4.6 mm, 3.5 μm); 5 mM NH$_4$OAc: ACN; 1.0 mL/min. | Column: Ascentis Express C-18 (50 × 3.0 mm, 2.7 μm); 0.025% Aq TFA + 5% ACN: ACN: 5% 0.025% Aq TFA: 1.2 mL/min |
| d | Column: X-Select-CSH-C18 (150 × 4.6 mm, 3.5 μm); 5 mM NH$_4$CO$_3$: ACN; 1.0 mL/min. | Column: X-Select CSH C-18 (50 × 3.0 mm, 2.5 μm); 2.5 mM Aq NH$_4$OAc: ACN; 0.80 mL/min |
| e | Column: Atlantis-T3 (150 × 4.6 mm, 3.0 μm); 5 mM NH$_4$OAc: ACN; 1.0 mL/min. | Column: Kinotex EVO C-18 (50 × 3.0 mm, 2.6 μm); 2.5 mM Aq NH$_4$OAc: ACN; 0.80 mL/m |

Common Abbreviations

ACN acetonitrile
br broad
d doublet
dd doublet of doublets
dba dibenzylideneacetone
DIPEA diisopropylethylamine
dppf 1,1'-ferrocenediyl-bis(diphenylphosphine)
h hour(s)
HRMS high resolution mass spectrometry
HPLC high performance liquid chromatography
LCMS liquid chromatography and mass spectrometry
MS mass spectrometry
MW microwave
m multiplet
min minutes
mL milliliter(s)
m/z mass to charge ratio
NMR nuclear magnetic resonance
ppm parts per million
rt or RT room temperature
s singlet
t triplet
TLC thin layer chromatography

Preparation of Int-1

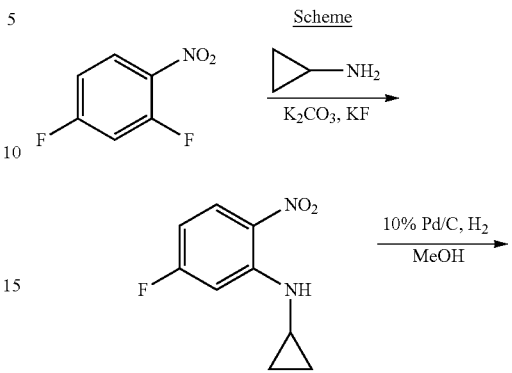

Scheme

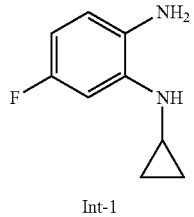

Int-1

N-Cyclopropyl-5-fluoro-2-nitroaniline

To a stirred solution of 2,4-difluoro-1-nitrobenzene (25 g, 157.23 mmol) in potassium fluoride (9.12 g, 157.23 mmol) under an inert atmosphere was added potassium carbonate (21.7 g, 157.23 mmol) followed by cyclopropanamine (10.75 g, 188.68 mmol) drop wise at room temperature. The reaction mixture was stirred at room temperature for 2 h. After consumption of starting material (by TLC), the reaction mixture was diluted with water (200 mL) and extracted with ethyl acetate (EtOAc) (2×200 mL). The combined organic extracts were dried over anhydrous Na$_2$SO$_4$ and concentrated under reduced pressure. The crude material was purified by silica gel column chromatography (eluent: 5% EtOAc/hexane) to afford N-cyclopropyl-5-fluoro-2-nitroaniline (26 g, 132.65 mmol, 84%) as yellow solid.

$^1$H NMR (500 MHz, CDCl$_3$): δ 8.20 (dd, J=9.3, 6.1 Hz, 1H), 6.95 (dd, J=11.4, 2.7 Hz, 1H), 6.45-6.39 (m, 1H), 2.59-2.53 (m, 1H), 0.97-0.92 (m, 2H), 0.71-0.65 (m, 2H).

N$^1$-Cyclopropyl-5-fluorobenzene-1,2-diamine (Int-1)

To a stirred solution of N-cyclopropyl-5-fluoro-2-nitroaniline (24 g, 122.45 mmol) in methanol (MeOH) (300 mL) under an inert atmosphere was added 10% Pd/C (50% wet, 2.4 g) at room temperature. The reaction mixture was stirred at room temperature under a hydrogen atmosphere (balloon pressure) for 8 h. After consumption of starting material (by TLC), the reaction mixture was filtered through a pad of celite and washed with methanol (100 mL). The filtrate was concentrated under reduced pressure to afford N$^1$-cyclopropyl-5-fluorobenzene-1,2-diamine Int-1 (18 g, 108.43 mmol, 88%) as brown syrup.

$^1$H NMR (400 MHz, DMSO-d$_6$): δ 6.52 (dd, J=11.6, 2.8 Hz, 1H), 6.45 (dd, J=8.4, 6.0 Hz, 1H), 6.18 (td, J=8.5, 2.9 Hz, 1H), 5.28 (s, 1H), 4.30 (br s, 2H), 2.36-2.28 (m, 1H), 0.74-0.68 (m, 2H), 0.42-0.37 (m, 2H).

LC-MS: m/z 166.8 [M+H]$^+$ at 1.64 RT (72.46% purity).

Preparation of Int-2 & Int-3

Scheme

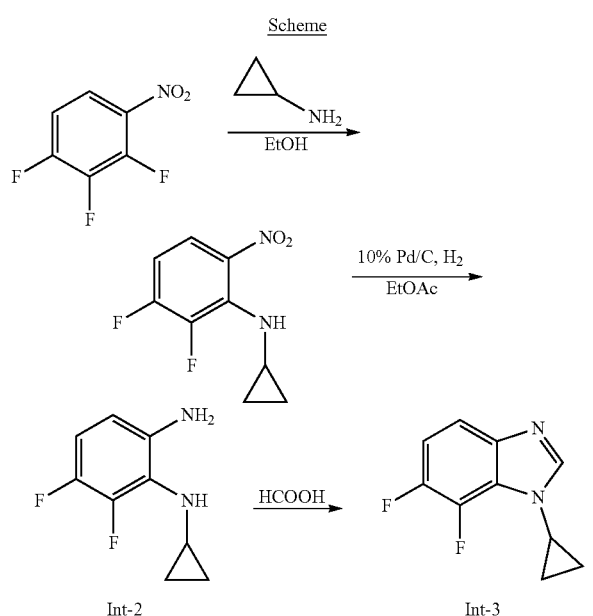

N-Cyclopropyl-2,3-difluoro-6-nitroaniline

To a stirred solution of 1,2,3-trifluoro-4-nitrobenzene (10 g, 56.5 mmol) in ethanol (EtOH) (200 mL) under an inert atmosphere was added cyclopropanamine (3.22 g, 56.5 mmol) drop wise at room temperature. The reaction mixture was stirred at room temperature for 16 h. After consumption of starting material (by TLC), the volatiles were removed under reduced pressure. The crude material was purified by silica gel column chromatography (eluent: 10% EtOAc/hexane) to afford N-cyclopropyl-2,3-difluoro-6-nitroaniline (8 g, 37.38 mmol, 66%) as pale yellow viscous syrup.

$^1$H NMR (500 MHz, DMSO-d$_6$): δ 7.96-7.91 (m, 1H), 7.75 (br s, 1H), 6.87-6.80 (m, 1H), 3.03-2.97 (m, 1H), 0.78-0.72 (m, 2H), 0.68-0.63 (m, 2H).

N$^1$-Cyclopropyl-5,6-difluorobenzene-1,2-diamine (Int-2)

To a stirred solution of N-cyclopropyl-2,3-difluoro-6-nitroaniline (8 g, 37.38 mmol) in EtOAc (200 mL) under an inert atmosphere was added 10% Pd/C (50% wet, 2 g) at room temperature. The reaction mixture was stirred at room temperature under a hydrogen atmosphere (balloon pressure) for 6 h. After consumption of starting material (by TLC), the reaction mixture was filtered through a pad of celite and the celite bed was washed with methanol (60 mL). The filtrate was concentrated under reduced pressure. The crude material was purified by silica gel column chromatography (eluent: 10% EtOAc/hexane) to afford N$^1$-cyclopropyl-5,6-difluorobenzene-1,2-diamine Int-2 (4.3 g, 23.37 mmol, 62%) as brown viscous syrup.

$^1$H NMR (400 MHz, DMSO-d$_6$): δ 6.55-6.46 (m, 1H), 6.32-6.26 (m, 1H), 4.69 (s, 2H), 4.54 (br s, 1H), 2.73-2.65 (m, 1H), 0.58-0.52 (m, 2H), 0.48-0.42 (m, 2H).

LC-MS: m/z 185.0 [M+H]$^+$ at 2.97 RT (61.14% purity).

1-Cyclopropyl-6,7-difluoro-1H-benzo[d]imidazole (Int-3)

To N$^1$-cyclopropyl-5,6-difluorobenzene-1,2-diamine Int-2 (1 g, 5.43 mmol) under an inert atmosphere was added formic acid (10 mL) at room temperature. The reaction mixture was heated to 100° C. and stirred for 6 h. After consumption of starting material (by TLC), the volatiles were removed under reduced pressure. The residue was basified with saturated sodium bicarbonate solution (30 mL) and extracted with CH$_2$Cl$_2$ (2×40 mL). The combined organic extracts were dried over anhydrous Na$_2$SO$_4$ and concentrated under reduced pressure. The crude material was purified by silica gel column chromatography (eluent: 50% EtOAc/hexane) to afford 1-cyclopropyl-6,7-difluoro-1H-benzo[d]imidazole Int-3 (700 mg, 3.61 mmol, 67%) as brown solid.

$^1$H NMR (500 MHz, DMSO-d$_6$): δ 8.30 (s, 1H), 7.49 (dd, J=8.8, 3.3 Hz, 1H), 7.32-7.24 (m, 1H), 3.77-3.70 (m, 1H), 1.21-1.15 (m, 2H), 1.15-1.10 (m, 2H).

LC-MS: m/z 195.0 [M+H]$^+$ at 2.83 RT (82.37% purity).

Preparation of Int-4 & Int-5

Scheme

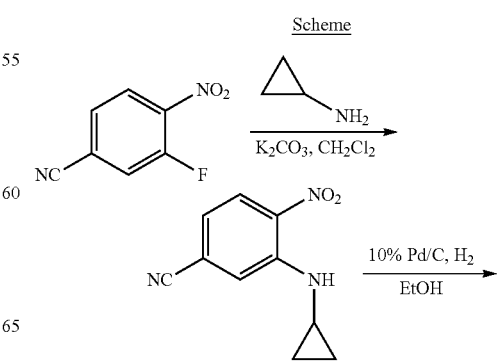

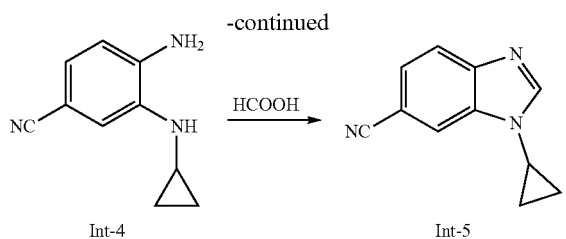

3-(Cyclopropylamino)-4-nitrobenzonitrile

To a stirred solution of 3-fluoro-4-nitrobenzonitrile (1 g, 6.02 mmol) in CH$_2$Cl$_2$ (5 mL) under an inert atmosphere was added potassium carbonate (1.66 g, 12.05 mmol) and cyclopropanamine (3.33 mL, 48.19 mmol) drop wise at room temperature. The reaction mixture was stirred at room temperature for 4 h. After consumption of starting material (by TLC), the reaction mixture was diluted with water (30 mL) and extracted with EtOAc (2×40 mL). The combined organic extracts were dried over anhydrous Na$_2$SO$_4$ and concentrated under reduced pressure to afford 3-(cyclopropylamino)-4-nitrobenzonitrile (900 mg, 4.43 mmol, 74%) as yellow solid.

$^1$H NMR (400 MHz, CDCl$_3$): δ 8.24 (d, J=8.7 Hz, 1H), 8.07 (br s, 1H), 7.64 (d, J=1.7 Hz, 1H), 6.93 (dd, J=8.7, 1.7 Hz, 1H), 2.62-2.57 (m, 1H), 1.03-0.97 (m, 2H), 0.72-0.67 (m, 2H).

LC-MS: m/z 201.9 [M−H]$^+$ at 3.25 RT (99.61% purity).

4-Amino-3-(cyclopropylamino)benzonitrile (Int-4)

To a stirred of solution of 3-(cyclopropylamino)-4-nitrobenzonitrile (900 mg, 4.43 mmol) in ethanol (10 mL) under an inert atmosphere was added 10% Pd/C (50% wet, 500 mg) at room temperature. The reaction mixture was stirred at room temperature under a hydrogen atmosphere (balloon pressure) for 5 h. After consumption of starting material (by TLC), the reaction mixture was filtered through a pad of celite and washed with EtOAc (30 mL). The filtrate was concentrated under reduced pressure. The crude material was purified by silica gel column chromatography (eluent: 20% EtOAc/hexane) to afford 4-amino-3-(cyclopropylamino)benzonitrile Int-4 (500 mg, 2.89 mmol, 65%) as an off white solid.

$^1$H NMR (400 MHz, DMSO-d$_6$): δ 6.93 (d, J=1.9 Hz, 1H), 6.87 (dd, J=8.0, 1.9 Hz, 1H), 6.55 (d, J=8.0 Hz, 1H), 5.49 (s, 2H), 5.43 (s, 1H), 2.40-2.34 (m, 1H), 0.77-0.71 (m, 2H), 0.42-0.37 (m, 2H).

1-Cyclopropyl-1H-benzo[d]imidazole-6-carbonitrile (Int-5)

A solution of 4-amino-3-(cyclopropylamino)benzonitrile Int-4 (500 mg, 2.89 mmol) in formic acid (5 mL) under an inert atmosphere was heated to reflux temperature and stirred for 5 h. After consumption of starting material (by TLC), the volatiles were removed under reduced pressure. The residue was diluted with water (10 mL), neutralized with saturated sodium bicarbonate solution (20 mL) and extracted with EtOAc (2×30 mL). The combined organic extracts were dried over anhydrous Na$_2$SO$_4$ and concentrated under reduced pressure. The crude material was purified by silica gel column chromatography (eluent: 50% EtOAc/hexane) to afford 1-cyclopropyl-1H-benzo[d]imidazole-6-carbonitrile Int-5 (250 mg, 1.37 mmol, 56%) as an off white solid.

$^1$H NMR (500 MHz, DMSO-d$_6$): δ 8.50 (s, 1H), 8.21 (d, J=0.9 Hz, 1H), 7.82 (d, J=8.1 Hz, 1H), 7.62 (dd, J=8.4, 1.4 Hz, 1H), 3.59-3.54 (m, 1H), 1.15-1.05 (m, 4H).

LC-MS: m/z 184.0 [M+H]$^+$ at 2.46 RT (87.33% purity).

Preparation of Int-6

Scheme

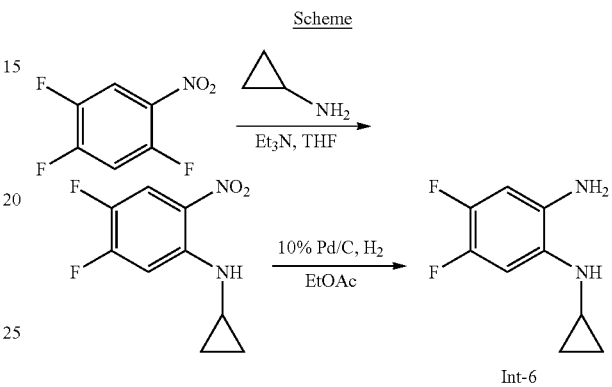

N-Cyclopropyl-4,5-difluoro-2-nitroaniline

To 1,2,4-trifluoro-5-nitrobenzene (20 g, 112.99 mmol) in tetrahydrofuran (THF) (100 mL) under an inert atmosphere was added triethylamine (47.2 mL, 338.98 mmol) and cyclopropanamine (7 g, 124.29 mmol) drop wise at 0° C. The reaction mixture was stirred at 60° C. for 2 h. After consumption of starting material (by TLC), the reaction mixture was diluted with water (100 mL) and extracted with EtOAc (2×100 mL). The combined organic extracts were dried over anhydrous Na$_2$SO$_4$ and concentrated under reduced pressure. The crude material was purified by silica gel column chromatography (eluent: 5% EtOAc/hexane) to afford N-cyclopropyl-4, 5-difluoro-2-nitroaniline (11.8 g, 55.14 mmol, 48%) as yellow solid.

$^1$H NMR (500 MHz, DMSO-d$_6$): δ 8.20-8.12 (m, 1H), 8.10 (s, 1H), 7.35-7.30 (m, 1H), 2.63-2.60 (m, 1H), 0.90-0.83 (m, 2H), 0.65-0.60 (m, 2H).

N$^1$-Cyclopropyl-4,5-difluorobenzene-1,2-diamine (Int-6)

To a stirred solution of N-cyclopropyl-4,5-difluoro-2-nitroaniline (5 g, 23.36 mmol) in ethyl acetate (100 mL) under an inert atmosphere was added 10% Pd/C (50% wet, 2.5 g) at room temperature. The reaction mixture was stirred at room temperature under a hydrogen atmosphere (balloon pressure) for 5 h. After consumption of starting material (by TLC), the reaction mixture was filtered through a pad of celite and washed with methanol (15 mL) and EtOAc (10 mL). The filtrate was concentrated under reduced pressure to obtain N$^1$-cyclopropyl-4,5-difluorobenzene-1,2-diamine Int-6 (4 g, crude) as brown viscous syrup which was used directly without further purification.

$^1$H NMR (400 MHz, DMSO-d$_6$): δ 6.63-6.60 (m, 1H), 6.48-6.43 (m, 1H), 5.17 (br s, 1H), 4.60 (brs, 2H), 2.32-2.28 (m, 1H), 0.70-0.66 (m, 2H), 0.39-0.35 (m, 2H)

Preparation of Int-7

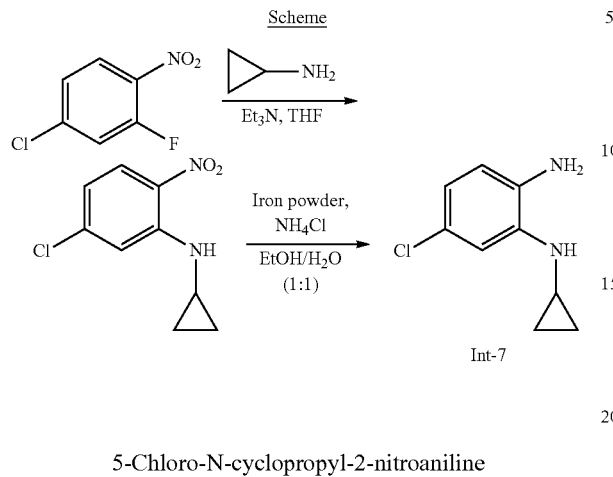

5-Chloro-N-cyclopropyl-2-nitroaniline

To a stirred solution of 4-chloro-2-fluoro-1-nitrobenzene (1 g, 5.7 mmol) in THF (20 mL) under an inert atmosphere was added triethylamine (2.38 mL, 17.09 mmol) and cyclopropanamine (0.43 mL, 6.27 mmol) at room temperature. The reaction mixture was heated to 80° C. and stirred for 16 h. After consumption of starting material (by TLC), the reaction mixture was diluted with ice cold water (40 mL) and extracted with EtOAc (2×40 mL). The combined organic extracts were dried over anhydrous $Na_2SO_4$ and concentrated under reduced pressure. The crude material was purified by silica gel column chromatography (eluent: 2% EtOAc/hexane) to afford 5-chloro-N-cyclopropyl-2-nitroaniline (1 g, 4.72 mmol, 83%) as yellow solid.

$^1$H NMR (400 MHz, DMSO-$d_6$): δ 8.08 (d, J=9.2 Hz, 2H), 7.37 (d, J=2.3 Hz, 1H), 6.79 (dd, J=9.2, 2.3 Hz, 1H), 2.69-2.63 (m, 1H), 0.92-0.86 (m, 2H), 0.68-0.61 (m, 2H).

LC-MS: m/z 213.2 [M+H]$^+$ at 4.68 RT (97.21% purity).

5-Chloro-N$^1$-cyclopropylbenzene-1,2-diamine (Int-7)

To a stirred of solution of 5-chloro-N-cyclopropyl-2-nitroaniline (250 mg, 1.27 mmol) in a mixture of ethanol/water (1:1, 10 mL) under an inert atmosphere was added iron powder (356 mg, 6.38 mmol) and $NH_4Cl$ (341 mg, 6.38 mmol) at room temperature. The reaction mixture was heated to 80° C. and stirred for 5 h. After consumption of starting material (by TLC), the reaction mixture was filtered through a pad of celite and the celite bed was washed with ethanol (30 mL). The filtrate was concentrated under reduced pressure to afford compound 5-chloro-N$^1$-cyclopropylbenzene-1,2-diamine Int-7 (200 mg) as brown syrup. This material was used directly without further purification.

$^1$H NMR (500 MHz, DMSO-$d_6$): δ 6.69 (d, J=2.3 Hz, 1H), 6.50-6.40 (m, 2H), 5.28 (br s, 1H), 4.64 (br s, 2H), 2.37-2.30 (m, 1H), 0.75-0.69 (m, 2H), 0.42-0.37 (m, 2H).

LC-MS: m/z 182.9 [M+H]$^+$ at 2.85 RT (86.58% purity).

Preparation of Int-8 & Int-9

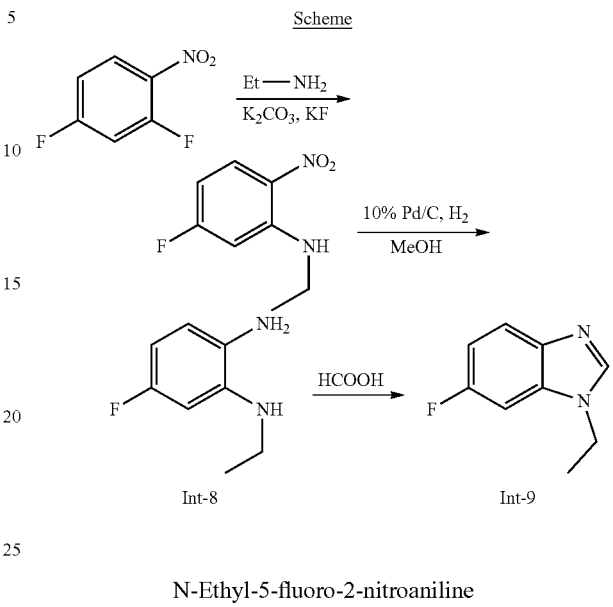

N-Ethyl-5-fluoro-2-nitroaniline

To 2,4-difluoro-1-nitrobenzene (1 g, 6.29 mmol) in potassium fluoride (365 mg, 6.29 mmol) under an inert atmosphere was added potassium carbonate (868 mg, 6.29 mmol) followed by ethylamine (Aq. 70%, 0.5 mL, 7.55 mmol) at room temperature. The reaction mixture was stirred at room temperature for 3 h. After consumption of starting material (by TLC), the reaction mixture was diluted with water (40 mL) and extracted with EtOAc (2×40 mL). The combined organic extracts were dried over anhydrous $Na_2SO_4$ and concentrated under reduced pressure. The crude material was purified by silica gel column chromatography (eluent: 5% EtOAc/hexane) to afford N-ethyl-5-fluoro-2-nitroaniline (1 g, 5.43 mmol, 86%) as yellow solid.

$^1$H NMR (400 MHz, CDCl$_3$): δ 8.21 (dd, J=9.5, 6.1 Hz, 1H), 8.09 (br s, 1H), 6.47 (dd, J=11.5, 2.6 Hz, 1H), 6.39-6.32 (m, 1H), 3.35-3.26 (m, 2H), 1.38 (t, J=7.2 Hz, 3H).

LC-MS: m/z 184.8 [M+H]$^+$ at 2.61 RT (99.56% purity).

N$^1$-Ethyl-5-fluorobenzene-1,2-diamine (Int-8)

To a stirred solution of N-ethyl-5-fluoro-2-nitroaniline (1 g, 5.43 mmol) in methanol (5 mL) under an inert atmosphere was added 10% Pd/C (50% wet, 150 mg) at room temperature. The reaction mixture was stirred at room temperature under a hydrogen atmosphere (balloon pressure) for 2 h. After consumption of starting material (by TLC), the reaction mixture was filtered through a pad of celite and the celite bed was washed with methanol (2×30 mL). The filtrate was concentrated under reduced pressure to obtain N$^1$-ethyl-5-fluorobenzene-1,2-diamine Int-8 (650 mg, crude) as brown syrup which was used directly without further purification.

LC-MS: m/z 154.8 [M+H]$^+$ at 1.42 RT (87.21% purity).

1-Ethyl-6-fluoro-1H-benzo[d]imidazole (Int-9)

A solution of N$^1$-ethyl-5-fluorobenzene-1,2-diamine Int-8 (400 mg, 2.6 mmol) in formic acid (2 mL) under an inert atmosphere was heated to 100° C. and stirred for 16 h. After consumption of starting material (by TLC), the reaction mixture was basified with saturated sodium carbonate solution (30 mL) and extracted with EtOAc (2×30 mL). The combined organic extracts were dried over anhydrous Na$_2$SO$_4$ and concentrated under reduced pressure. The crude material was purified by silica gel column chromatography (eluent: 50% EtOAc/hexane) to afford 1-ethyl-6-fluoro-1H-benzo[d]imidazole Int-9 (350 mg, 2.13 mmol, 76%) as brown solid.

$^1$H NMR (500 MHz, CD$_3$OD): δ 8.19 (s, 1H), 7.64 (dd, J=8.8, 4.8 Hz, 1H), 7.35 (dd, J=9.0, 2.3 Hz, 1H), 7.06 (td, J=9.3, 2.3 Hz, 1H), 4.30 (q, J=7.2 Hz, 2H), 1.51 (t, J=7.4 Hz, 3H).

LC-MS: m/z 164.9 [M+H]$^+$ at 2.55 RT (85.97% purity).

Preparation of Int-10

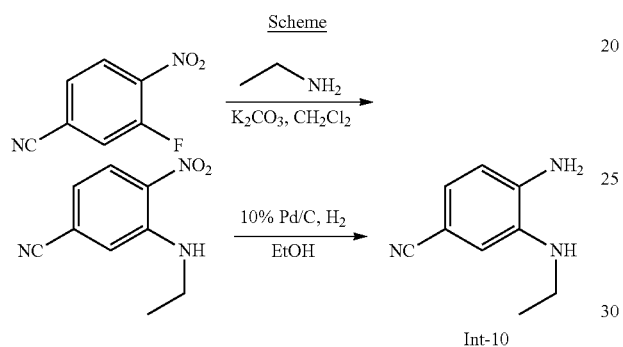

3-(Ethylamino)-4-nitrobenzonitrile

To a stirred solution of 3-fluoro-4-nitrobenzonitrile (2 g, 12.05 mmol) in CH$_2$Cl$_2$ (250 mL) under an inert atmosphere was added potassium carbonate (3.32 g, 24.09 mmol) and ethylamine (Aq. 70%, 2.17 g, 48.19 mmol) at room temperature. The reaction mixture was stirred at room temperature for 6 h. After consumption of starting material (by TLC), the reaction mixture was quenched with water (60 mL) and extracted with EtOAc (2×60 mL). The combined organic extracts were dried over anhydrous Na$_2$SO$_4$ and concentrated under reduced pressure to afford 3-(ethylamino)-4-nitrobenzonitrile (1.9 g) as yellow solid which was used directly without further purification.

$^1$H NMR (500 MHz, DMSO-d$_6$): δ 8.22-8.10 (m, 2H), 7.58 (br s, 1H), 7.00 (br d, J=8.7 Hz, 1H), 3.48-3.38 (m, 2H), 1.21 (br t, J=6.9 Hz, 3H).

LC-MS: m/z 192.1 [M+H]$^+$ at 4.10 RT (98.96% purity).

4-Amino-3-(ethylamino) benzonitrile (Int-10)

To a stirred of solution of 3-(ethylamino)-4-nitrobenzonitrile (1.9 g, crude) in ethanol (20 mL) under an inert atmosphere was added 10% Pd/C (50% wet, 190 mg) at room temperature. The reaction mixture was stirred at room temperature under a hydrogen atmosphere (balloon pressure) for 5 h. After consumption of starting material (by TLC), the reaction mixture was filtered through a pad of celite and washed with methanol (50 mL) and EtOAc (30 mL). The filtrate was concentrated under reduced pressure to afford 4-amino-3-(ethylamino)benzonitrile Int-10 (1.5 g) as an off white solid which was used directly without further purification.

LC-MS: m/z 161.9 [M+H]$^+$ at 2.11 RT (60.88% purity).

Preparation of Int-11

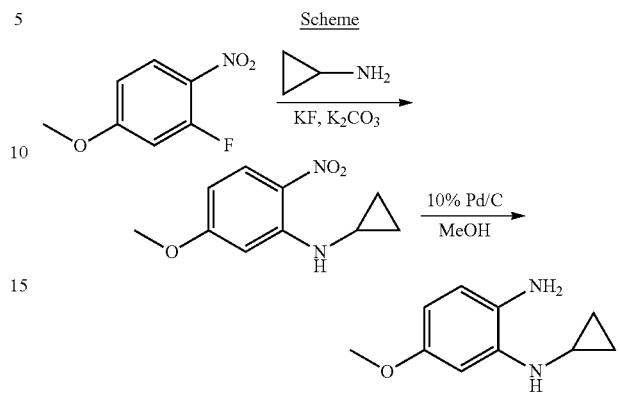

N-Cyclopropyl-5-methoxy-2-nitroaniline

To a mixture of 2-fluoro-4-methoxy-1-nitrobenzene (1 g, 5.84 mmol) and potassium fluoride (340 mg, 5.84 mmol) under an inert atmosphere was added potassium carbonate (800 mg, 5.84 mmol) and cyclopropylamine (0.48 mL) at room temperature. The reaction mixture was stirred at room temperature for 3 h. After consumption of starting material (by TLC), the reaction mixture was diluted with water (20 mL) and extracted with EtOAc (2×20 mL). The combined organic extracts were washed with water (20 mL), dried over anhydrous Na$_2$SO$_4$ and concentrated under reduced pressure. The crude material was purified by silica gel column chromatography (eluent: 5-7% EtOAc/hexane) to afford N-cyclopropyl-5-methoxy-2-nitroaniline (1.15 g, 5.52 mmol, 95%) as yellow solid.

$^1$H NMR (400 MHz, CDCl$_3$): δ 8.29 (s, 1H), 8.13 (d, J=9.5 Hz, 1H), 6.64 (d, J=2.6 Hz, 1H), 6.32-6.21 (m, 1H), 3.89 (s, 3H), 2.58-2.53 (m, 1H), 0.97-0.85 (m, 2H), 0.71-0.64 (m, 2H)

N$^1$-Cyclopropyl-5-methoxybenzene-1,2-diamine (Int-11)

To a stirred solution of N-cyclopropyl-5-methoxy-2-nitroaniline (1.1 g, 5.28 mmol) in MeOH:EtOAc (1:1, 20 mL) under an inert atmosphere was added 10% Pd/C (120 mg) at room temperature. The reaction mixture was stirred at room temperature under a hydrogen atmosphere (balloon pressure) for 6 h. After consumption of starting material (by TLC), the reaction mixture was filtered through a pad of celite and washed with methanol (30 mL). The filtrate was concentrated under reduced pressure to obtain N1-cyclopropyl-5-methoxybenzene-1,2-diamine Int-11 (900 mg, 5.05 mmol, 96%) as brown syrup.

$^1$H NMR (400 MHz, DMSO-d$_6$): δ 6.43 (d, J=8.3 Hz, 1H), 6.39 (d, J=2.8 Hz, 1H), 6.02 (dd, J=8.3, 2.8 Hz, 1H), 5.05 (s, 1H), 4.02 (brs, 2H), 3.61 (s, 3H), 2.51-2.49 (m, 1H), 0.71-0.65 (m, 2H), 0.42-0.35 (m, 2H)

Preparation of Int-12

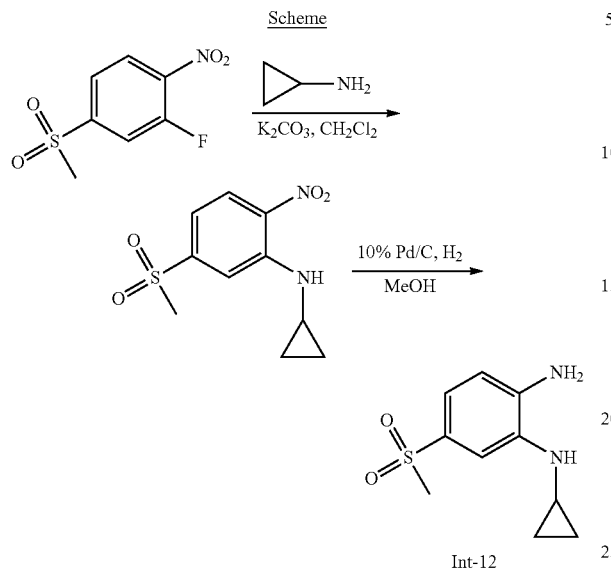

Int-12

N-Cyclopropyl-5-(methylsulfonyl)-2-nitroaniline

To a mixture of 2-fluoro-4-(methylsulfonyl)-1-nitrobenzene (500 mg, 2.28 mmol) in CH$_2$Cl$_2$ (10 mL) under an inert atmosphere was added potassium carbonate (630 mg, 4.56 mmol) and cyclopropylamine (260 mg, 4.56 mmol) at room temperature. The reaction mixture was stirred at room temperature for 16 h. After consumption of starting material (by TLC), the reaction mixture was diluted with water (20 mL) and extracted with CH$_2$Cl$_2$ (2×20 mL). The combined organic extracts were washed with water (20 mL), dried over anhydrous Na$_2$SO$_4$ and concentrated under reduced pressure to obtain N-cyclopropyl-5-(methylsulfonyl)-2-nitroaniline (500 mg, 1.95 mmol, 86%) as yellow solid.

$^1$H NMR (500 MHz, CDCl$_3$): δ 8.33 (d, J=9.3 Hz, 1H), 8.16 (brs, 1H), 7.92 (s, 1H), 7.17 (dd, J=8.7, 1.7 Hz, 1H), 3.10 (s, 3H), 2.69-2.58 (m, 1H), 1.07-0.96 (m, 2H), 0.74-0.61 (m, 2H)

N$^1$-Cyclopropyl-5-(methylsulfonyl)benzene-1,2-diamine (Int-12)

To a stirred solution of N-cyclopropyl-5-(methylsulfonyl)-2-nitroaniline (500 mg, 1.95 mmol) in MeOH (10 mL) under an inert atmosphere was added 10% Pd/C (200 mg) at room temperature. The reaction mixture was stirred at room temperature under a hydrogen atmosphere (balloon pressure) for 6 h. After consumption of starting material (by TLC), the reaction mixture was filtered through a pad of celite and washed with EtOAc (30 mL). The filtrate was concentrated under reduced pressure to obtain N1-cyclopropyl-5-(methylsulfonyl) benzene-1,2-diamine Int-12 (300 mg, 5.05 mmol, 68%) as brown syrup.

$^1$H NMR (500 MHz, DMSO-d$_6$): δ 7.15 (s, 1H), 6.99 (dd, J=8.1, 2.3 Hz, 1H), 6.60 (d, J=8.1 Hz, 1H), 5.45-5.42 (m, 3H), 3.01 (s, 3H), 2.40 (brs, 1H), 0.78-0.68 (m, 2H), 0.46-0.34 (m, 2H)

Preparation of Int-13

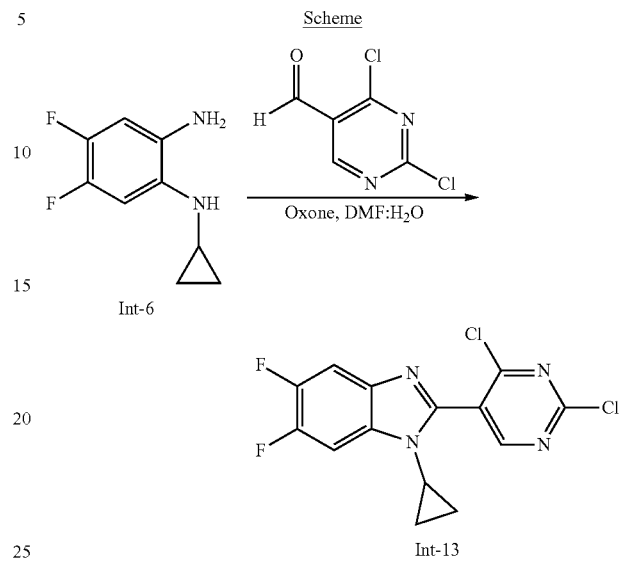

Int-13

1-Cyclopropyl-2-(2,4-dichloropyrimidin-5-yl)-5,6-difluoro-1H-benzo[d]imidazole (Int-13)

To a stirred solution of Int-6 (2.2 g, 11.95 mmol) in N,N-dimethylformamide (DMF) (22 mL) under an inert atmosphere was added 2,4-dichloropyrimidine-5-carbaldehyde (2.53 g, 14.34 mmol), oxone (5.49 g, 23.91 mmol) and water (2.2 mL) at room temperature. The reaction mixture was stirred at room temperature for 2 h. After consumption of starting material (by TLC), the reaction mixture was diluted with water (100 mL) and extracted with CH$_2$Cl$_2$ (2×100 mL). The combined organic extracts were washed with water (50 mL), dried over anhydrous Na$_2$SO$_4$ and concentrated under reduced pressure. The crude material was purified by silica gel column chromatography (eluent: 20% EtOAc/hexane) to afford 1-cyclopropyl-2-(2,4-dichloropyrimidin-5-yl)-5,6-difluoro-1H-benzo[d]imidazole Int-13 (1.5 g, 4.41 mmol, 38%) as an off-white solid.

$^1$H NMR (500 MHz, CDCl$_3$): δ 8.80 (s, 1H), 7.62-7.59 (m, 1H), 7.46-7.42 (m, 1H), 3.53-3.48 (m, 1H), 1.22-1.02 (m, 2H), 0.74-0.66 (m, 2H)

Preparation of Int-14

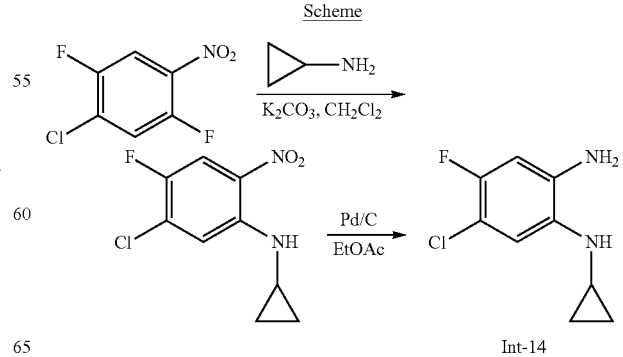

Int-14

5-Chloro-N-cyclopropyl-4-fluoro-2-nitroaniline

To a stirred solution of 1-chloro-2,5-difluoro-4-nitrobenzene (500 mg, 2.59 mmol) in CH$_2$Cl$_2$ (10 mL) under an inert atmosphere was added potassium carbonate (715 mg, 5.18 mmol) and cyclopropanamine (305 mg, 5.18 mmol) at 0° C. The reaction mixture was stirred at room temperature for 24 h. After consumption of starting material (by TLC), the reaction mixture was diluted with water (20 mL) and extracted with CH$_2$Cl$_2$ (2×20 mL). The combined organic extracts were dried over anhydrous Na$_2$SO$_4$ and concentrated under reduced pressure to obtain 5-chloro-N-cyclopropyl-4-fluoro-2-nitroaniline (400 mg, 1.73 mmol, 67%) as yellow solid.

$^1$H NMR (500 MHz, CDCl$_3$): δ 7.97 (d, J=9.3 Hz, 2H), 7.37 (d, J=6.4 Hz, 1H), 2.57-2.54 (m, 1H), 1.00-0.91 (m, 2H), 0.71-0.59 (m, 2H)

5-Chloro-N$^1$-cyclopropyl-4-fluorobenzene-1,2-diamine (Int-14)

To a stirred solution of 5-chloro-N-cyclopropyl-4-fluoro-2-nitroaniline (400 mg, 1.74 mmol) in EtOAc (10 mL) under an inert atmosphere was added 10% Pd/C (50% wet, 100 mg) at room temperature. The reaction mixture was evacuated and stirred at room temperature under a hydrogen atmosphere (balloon pressure) for 5 h. After consumption of starting material (by TLC), the reaction mixture was filtered through a pad of celite and the celite bed was washed with EtOAc (40 mL). The filtrate was concentrated under reduced pressure to obtain 5-chloro-N1-cyclopropyl-4-fluorobenzene-1,2-diamine Int-14 (280 mg, 1.40 mmol, 81%) as an off white solid.

$^1$H NMR (500 MHz, DMSO-d$_6$): δ 6.68 (d, J=7.5 Hz, 1H), 6.47 (d, J=11.6 Hz, 1H), 5.16 (brs, 1H), 4.96 (brs, 2H), 2.34-2.27 (m, 1H), 0.74-0.67 (m, 2H), 0.42-0.28 (m, 2H)

Preparation of Int-15

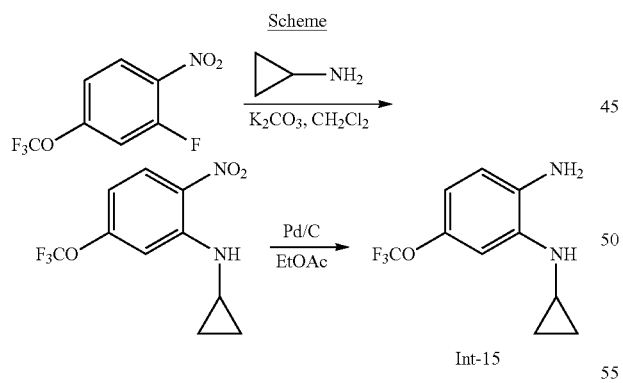

Int-15

N-Cyclopropyl-2-nitro-5-(trifluoromethoxy)aniline

To a stirred solution of 2-fluoro-1-nitro-4-(trifluoromethoxy) benzene (250 mg, 1.11 mmol) in CH$_2$Cl$_2$(10 mL) under an inert atmosphere was added potassium carbonate (307 mg, 2.22 mmol) and cyclopropanamine (131 mg, 2.22 mmol) at 0° C. The reaction mixture was stirred at room temperature for 16 h. After consumption of starting material (by TLC), the reaction mixture was diluted with water (20 mL) and extracted with CH$_2$Cl$_2$(2×20 mL). The combined organic extracts were dried over anhydrous Na$_2$SO$_4$ and concentrated under reduced pressure to obtain N-cyclopropyl-2-nitro-5-(trifluoromethoxy)aniline (200 mg, 0.76 mmol, 69%) as yellow solid.

$^1$H NMR (400 MHz, CDCl$_3$): δ 8.21 (d, J=9.5 Hz, 1H), 8.15 (brs, 1H), 7.10 (s, 1H), 6.55-6.46 (m, 1H), 2.59-2.55 (m, 1H), 1.00-0.92 (m, 2H), 0.72-0.62 (m, 2H)

N$^1$-Cyclopropyl-5-(trifluoromethoxy)benzene-1,2-diamine (Int-15)

To a stirred solution of N-cyclopropyl-2-nitro-5-(trifluoromethoxy) aniline (200 mg, 0.76 mmol) in MeOH (5 mL) under an inert atmosphere was added 10% Pd/C (50% wet, 100 mg) at room temperature. The reaction mixture was evacuated and stirred at room temperature under a hydrogen atmosphere (balloon pressure) for 6 h. After consumption of starting material (by TLC), the reaction mixture was filtered through a pad of celite and the celite bed was washed with EtOAc (40 mL). The filtrate was concentrated under reduced pressure to obtain N1-cyclopropyl-5-(trifluoromethoxy)benzene-1,2-diamine Int-15 (200 mg, crude) as an off white solid.

$^1$H NMR (500 MHz, DMSO-d$_6$): δ 6.63 (s, 1H), 6.50 (d, J=8.7 Hz, 1H), 6.37 (d, J=8.1 Hz, 1H), 5.36 (brs, 1H), 4.76 (brs, 2H), 2.33 (brs, 1H), 0.73-0.70 (m, 2H), 0.43-0.36 (m, 2H)

Preparation of Int-16

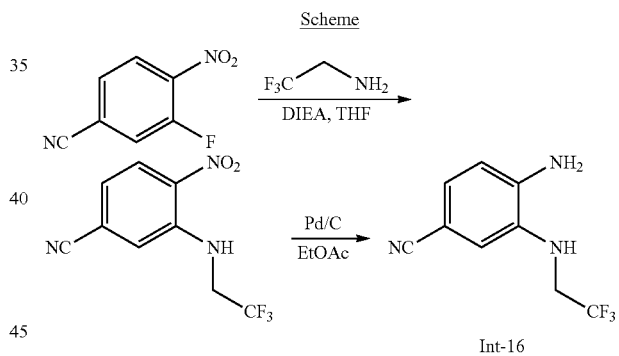

Int-16

4-Nitro-3-((2,2,2-trifluoroethyl)amino)benzonitrile

To a stirred solution of 3-fluoro-4-nitrobenzonitrile (200 mg, 1.2 mmol) in THF (2 mL) under an inert atmosphere was added 2,2,2-trifluoroethan-1-amine (0.11 mL, 1.44 mmol) and diisopropylethylamine (0.45 mL, 2.4 mmol) at room temperature. The reaction mixture was stirred at 100° C. for 16 h. After consumption of starting material (by TLC), the reaction mixture was diluted with water (20 mL) and extracted with EtOAc (2×20 mL). The combined organic extracts were washed with water (20 mL), dried over anhydrous Na$_2$SO$_4$ and concentrated under reduced pressure. The crude material was purified by silica gel column chromatography (eluent: 15-20% EtOAc/hexane) to afford 4-nitro-3-((2,2,2-trifluoroethyl amino)benzonitrile (260 mg, 1.09 mmol, 88%) as yellow solid.

$^1$H NMR (400 MHz, DMSO-d$_6$): δ 8.35-8.27 (m, 1H), 8.22 (d, J=8.7 Hz, 1H), 7.91 (s, 1H), 7.19 (dd, J=8.7, 1.5 Hz, 1H), 4.46-4.33 (m, 2H)

4-Amino-3-((2,2,2-trifluoroethyl)amino)benzonitrile (Int-16)

To a stirred solution of 4-nitro-3-((2,2,2-trifluoroethyl)amino) benzonitrile (250 mg, 1.08 mmol) in EtOAc (5 mL) under an inert atmosphere was added 10% Pd/C (50% wet, 50 mg) at room temperature. The reaction mixture was stirred at room temperature under a hydrogen atmosphere (balloon pressure) for 3-4 h. After consumption of starting material (by TLC), the reaction mixture was filtered through a pad of celite and washed with methanol (30 mL). The filtrate was concentrated under reduced pressure to obtain 4-amino-3-((2,2,2-trifluoroethyl) amino)benzonitrile Int-16 (195 mg, 0.93 mmol, 84%) as an off-white solid.

$^1$H NMR (500 MHz, DMSO-$d_6$): δ 6.94 (s, 1H), 6.90 (dd, J=8.1, 1.7 Hz, 1H), 6.60 (d, J=8.1 Hz, 1H), 5.62 (s, 2H), 5.41 (t, J=6.7 Hz, 1H), 4.05-3.95 (m, 2H)

Preparation of Int-17

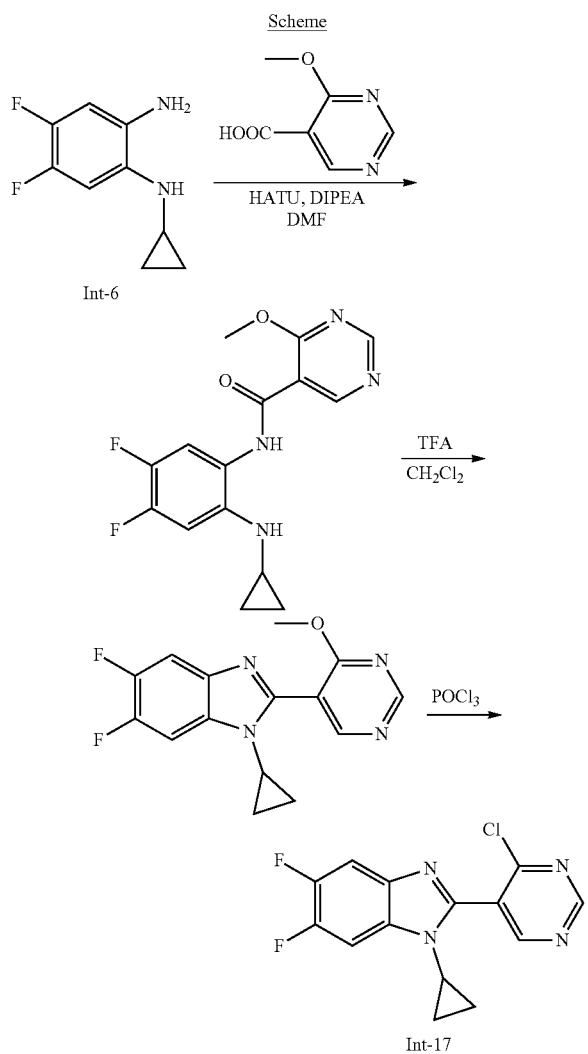

N-(2-(Cyclopropylamino)-4,5-difluorophenyl)-4-methoxypyrimidine-5-carboxamide To a stirred solution of N1-cyclopropyl-4,5-difluorobenzene-1,2-diamine Int-6 (300 mg, 1.63 mmol) in DMF (3 mL) under an inert atmosphere was added 4-methoxypyrimidine-5-carboxylic acid 2 (251 mg, 1.63 mmol), N-[(Dimethylamino)-1H-1,2,3-triazolo-[4,5-b]pyridin-1-ylmethylene]-N-methylmethanaminium hexafluorophosphate N-oxide (HATU) (743 mg, 1.95 mmol) and ethyldiisopropylamine (1.1 mL, 6.52 mmol) at room temperature. The reaction mixture was stirred at room temperature for 16 h. After consumption of starting material (by TLC), the reaction mixture was diluted with water (20 mL) and extracted with EtOAc (2×20 mL). The combined organic extracts were dried over anhydrous $Na_2SO_4$ and concentrated under reduced pressure. The crude material was purified by silica gel column chromatography (eluent: 50% EtOAc/hexane) to afford N-(2-(cyclopropylamino)-4,5-difluorophenyl)-4-methoxypyrimidine-5-carboxamide (300 mg, 0.93 mmol, 57%) as an off-white solid.

$^1$H NMR (400 MHz, $CD_3OD$): δ 9.05 (s, 1H), 8.89 (s, 1H), 7.48-7.43 (m, 1H), 7.03-6.98 (m, 1H), 4.21 (s, 3H), 2.46-2.41 (m 1H), 0.80-0.78 (m, 2H), 0.54-0.40 (m, 2H)

1-Cyclopropyl-5,6-difluoro-2-(4-methoxypyrimidin-5-yl)-1H-benzo[d]imidazole

To a stirred solution of N-(2-(cyclopropylamino)-4,5-difluorophenyl)-4-methoxypyrimidine-5-carboxamide (300 mg, 0.93 mmol) in $CH_2Cl_2$ (5 mL) under an inert atmosphere was added trifluoroacetic acid (TFA) (0.5 mL) at room temperature. The reaction mixture was stirred at room temperature for 16 h. After consumption of starting materials (by TLC), the reaction mixture quenched with saturated sodium bicarbonate solution (20 mL) and extracted with EtOAc (2×20 mL). The combined organic extracts were dried over anhydrous $Na_2SO_4$ and concentrated under reduced pressure. The crude material was purified by silica gel column chromatography (eluent: 80% EtOAc/Hexane) to afford 1-cyclopropyl-5,6-difluoro-2-(4-methoxypyrimidin-5-yl)-1H-benzo[d]imidazole (100 mg, 0.33 mmol, 35%) as an off white solid.

$^1$H NMR (400 MHz, $CD_3OD$): δ 8.95 (s, 1H), 8.74 (s, 1H), 7.68-7.63 (m, 1H), 7.58-7.54 (m, 1H), 4.13 (s, 3H), 3.58-3.52 (m, 1H), 1.08-0.95 (m, 2H), 0.78-0.53 (m, 2H)

2-(4-Chloropyrimidin-5-yl)-1-cyclopropyl-5,6-difluoro-1H-benzo[d]imidazole (Int-17)

To a stirred solution of 1-cyclopropyl-5,6-difluoro-2-(4-methoxypyrimidin-5-yl)-1H-benzo[d]imidazole (100 mg, 0.33 mmol) in phosphoryl chloride (0.6 mL, 6.62) under an inert atmosphere at room temperature was heated at 100° C. for 2 h. After consumption of starting material (by TLC), the reaction mixture was basified with saturated sodium bicarbonate solution (10 mL) and extracted with EtOAc (2×10 mL). The combined organic extracts were dried over anhydrous $Na_2SO_4$ and concentrated under reduced pressure. The crude material was washed with n-pentane (2×5 mL) to afford 2-(4-chloropyrimidin-5-yl)-1-cyclopropyl-5,6-difluoro-1H-benzo[d]imidazole Int-17 (80 mg, 0.26 mmol, 79%) as an off white solid.

$^1$H NMR (500 MHz, $CD_3OD$): δ 9.20 (s, 1H), 9.03 (s, 1H), 7.73-7.70 (m, 1H), 7.63-7.60 (m, 1H), 3.63-3.52 (m, 1H), 1.10-0.99 (m, 2H), 0.79-0.66 (m, 2H)

Preparation of Int-18

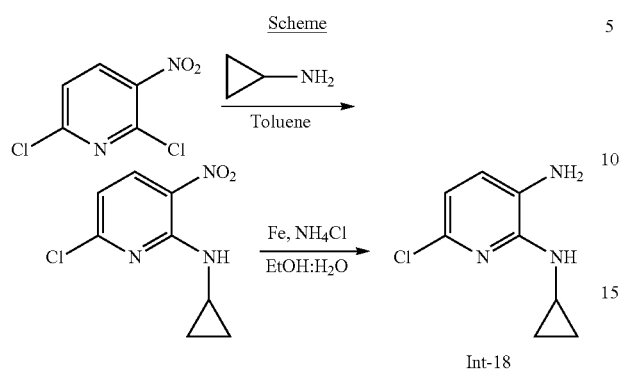

Int-18

6-Chloro-N-cyclopropyl-3-nitropyridin-2-amine

To a stirred solution of 2,6-dichloro-3-nitropyridine (5 g, 26.04 mmol) in toluene (25 mL) under an inert atmosphere was added cyclopropylamine (3.7 mL, 52.08 mmol) at 0° C. The reaction mixture was stirred at 0° C. for 1 h. The reaction mixture was warmed to room temperature and stirred for 2 h. After consumption of starting material (by TLC), the reaction mixture was diluted with water (50 mL) and extracted with EtOAc (2×50 mL). The combined organic extracts were washed with brine (20 mL), dried over anhydrous $Na_2SO_4$ and concentrated under reduced pressure. The crude material was purified by silica gel column chromatography (eluent: 10% EtOAc/Hexane) to afford 6-chloro-N-cyclopropyl-3-nitropyridin-2-amine (4 g, 18.77 mmol, 72%) as a pale yellow solid.

$^1$H NMR (500 MHz, $CDCl_3$): δ 8.34 (d, J=8.7 Hz, 2H), 6.66 (d, J=8.7 Hz, 1H), 3.10-3.05 (m, 1H), 0.97-0.93 (m, 2H), 0.67-0.64 (m, 2H)

6-Chloro-$N^2$-cyclopropylpyridine-2,3-diamine (Int-18)

To a stirred solution of 6-chloro-N-cyclopropyl-3-nitropyridin-2-amine (1 g, 4.69 mmol) in EtOH:water (1:1, 10 mL) under an inert atmosphere was added iron (1.3 g, 23.47 mmol) and ammonium chloride (1.2 g, 23.47 mmol) at room temperature. The reaction mixture was heated to 80° C. for 1 h. After consumption of starting material (by TLC), the reaction mixture was diluted with water (20 mL) and extracted with EtOAc (2×20 mL). The combined organic extracts were washed with brine (20 mL), dried over anhydrous $Na_2SO_4$ and concentrated under reduced pressure to obtain 6-chloro-N2-cyclopropylpyridine-2,3-diamine Int-18 (700 mg, crude) as a pale yellow solid which was used directly without further purification.

LC-MS: m/z 183.9 $[M+H]^+$ at 2.07 RT (58.13% purity).

Preparation of Int-19

Scheme

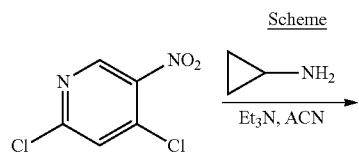

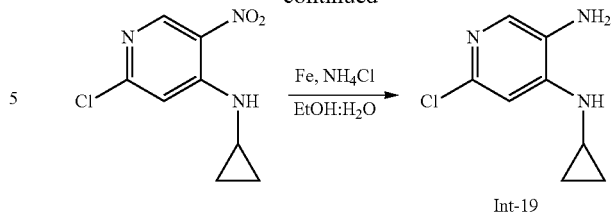

Int-19

2-Chloro-N-cyclopropyl-5-nitropyridin-4-amine

To a stirred solution of 2,4-dichloro-5-nitropyridine (1 g, 5.20 mmol) in acetonitrile (ACN) (1.4 mL) under an inert atmosphere was added triethylamine (1.4 mL, 10.41 mmol) and cyclopropanamine (300 mg, 5.20 mmol) at room temperature. The reaction mixture was stirred at room temperature for 2 h. After consumption of starting material (by TLC), the reaction mixture was quenched with water (100 mL) which produced a solid which was filtered and dried under reduced pressure to afford 2-chloro-N-cyclopropyl-5-nitropyridin-4-amine (1 g, 4.69 mmol, 90%) as an off white solid which was used directly without further purification.

$^1$H NMR (500 MHz, $CDCl_3$): δ 9.03 (s, 1H), 8.19 (brs, 1H), 7.19 (s, 1H), 2.68-2.58 (m, 1H), 1.05-1.03 (m, 2H), 0.78-0.68 (m, 2H)

6-Chloro-$N^4$-cyclopropylpyridine-3,4-diamine (Int-19)

To a stirred of solution of 2-chloro-N-cyclopropyl-5-nitropyridin-4-amine (1.1 g, 5.16 mmol) in a mixture of ethanol/water (1:1, 10 mL) under an inert atmosphere was added iron powder (1.4 g, 25.82 mmol) and ammonium chloride (1.39 g, 25.82 mmol) at room temperature. The reaction mixture was heated to 90° C. and stirred for 4 h. After consumption of starting material (by TLC), the reaction mixture was filtered through a pad of celite and the pad was washed with EtOAc (50 mL). The filtrate was concentrated under reduced pressure to afford 6-chloro-$N^4$-cyclopropylpyridine-3,4-diamine Int-19 (900 mg, 4.91 mmol, 95%) as brown syrup which was used directly without further purification.

$^1$H NMR (400 MHz, DMSO-$d_6$): δ 7.37 (s, 1H), 6.58 (s, 1H), 6.14 (s, 1H), 4.70 (s, 2H), 2.45-2.36 (m, 1H), 0.82-0.70 (m, 2H), 0.49-0.37 (m, 2H)

Preparation of Int-20

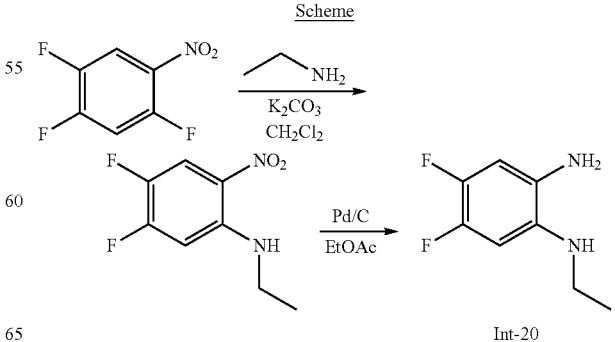

Int-20

N-Ethyl-4,5-difluoro-2-nitroaniline

To a stirred solution of 1, 2, 4-trifluoro-5-nitrobenzene (2 g, 11.29 mmol) in CH$_2$Cl$_2$ (10 mL) was added potassium carbonate (3.1 g, 22.59 mmol) and ethanamine (559 mg, 12.42 mmol) at room temperature. The reaction mixture was stirred at room temperature for 16 h. After consumption of starting material (by TLC), the reaction mixture was diluted with water (100 mL) and extracted with CH$_2$Cl$_2$ (2×100 mL). The combined organic extracts were dried over anhydrous Na$_2$SO$_4$ and concentrated under reduced pressure. The crude material was purified by silica gel column chromatography (eluent: 10% EtOAc/hexane) to afford N-ethyl-4, 5-difluoro-2-nitroaniline (800 mg, 3.96 mmol, 35%) as a yellow solid.

$^1$H NMR (500 MHz, DMSO-d$_6$): δ 8.19 (br s, 1H), 8.13 (dd, J=11.0, 8.7 Hz, 1H), 7.14 (dd, J=13.9, 7.0 Hz, 1H), 3.40-3.33 (m, 2H), 1.20 (t, J=7.2 Hz, 3H)

LC-MS: m/z 203.1 [M+H]$^+$ at 3.53 RT (98.40% purity)

N$^1$-Ethyl-4,5-difluorobenzene-1, 2-diamine (Int-20)

To a stirred solution of N-ethyl-4, 5-difluoro-2-nitroaniline (800 mg, 3.96 mmol) in ethylacetate (5 mL) under inert atmosphere was added 10% Pd/C (50% wet, 500 mg) at room temperature. The reaction mixture was stirred at room temperature under hydrogen atmosphere (balloon pressure) for 16 h. After consumption of starting material (by TLC), the reaction mixture was filtered through a pad of celite and the bed was washed with EtOAc (50 mL). The filtrate was concentrated under reduced pressure to obtain N$^1$-ethyl-4, 5-difluorobenzene-1, 2-diamine Int-20 (500 mg) as a black liquid. The crude material was used without further purification.

$^1$H NMR (500 MHz, DMSO-d$_6$): δ 6.47 (dd, J=12.8, 8.1 Hz, 1H), 6.30 (dd, J=13.3, 8.1 Hz, 1H), 4.64 (br s, 2H), 4.44 (t, J=5.2 Hz, 1H), 3.00-2.94 (m, 2H), 1.17 (t, J=7.2 Hz, 3H)
LC-MS: m/z 173.2 [M+H]$^+$ at 3.16 RT (64.65% purity)

Preparation of Int-21

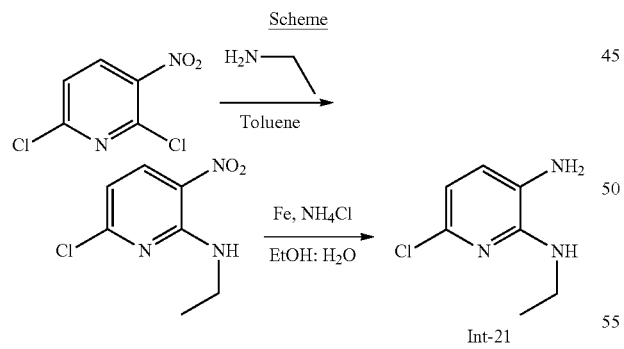

Int-21

6-Chloro-N-ethyl-3-nitropyridin-2-amine

To a stirred solution of 2, 6-dichloro-3-nitropyridine (2 g, 10.40 mmol) in toluene (8.5 mL) under inert atmosphere was added ethyl amine (1.35 mL) at 0° C. The reaction mixture was warmed to room temperature and stirred for 3 h. After consumption of starting material (by TLC), the reaction mixture was diluted with water (50 mL) and extracted with EtOAc (2×50 mL). The combined organic extracts were dried over anhydrous Na$_2$SO$_4$ and concentrated under reduced pressure. The crude material was purified by silica gel column chromatography (eluent: 2% EtOAc/hexane) to afford 6-chloro-N-ethyl-3-nitropyridin-2-amine (800 mg, 3.98 mmol, 38%) as a yellow solid.

$^1$H NMR (500 MHz, DMSO-d$_6$): δ 8.70 (brs, 1H), 8.40 (d, J=7.5 Hz, 1H), 6.75 (d, J=8.1 Hz, 1H), 3.55-3.50 (m, 2H), 1.18 (t, J=7.0 Hz, 3H)

LC-MS: m/z 202 [M+H]$^+$ at 2.63 RT (99.85% purity).

6-Chloro-N$^2$-ethylpyridine-2, 3-diamine (Int-12)

To a stirred solution of 6-chloro-N-ethyl-3-nitropyridin-2-amine (550 mg, 2.73 mmol) in EtOH:water (1:1, 20 mL) under inert atmosphere was added iron powder (763.4 g, 13.68 mmol) and ammonium chloride (738.7 mg, 13.68 mmol) at room temperature. The reaction mixture was heated to 80° C. for 1 h. After consumption of starting material (by TLC), the reaction mixture was diluted with water (30 mL) and extracted with EtOAc (2×30 mL). The combined organic extracts were washed with brine (30 mL), dried over anhydrous Na$_2$SO$_4$ and concentrated under reduced pressure to obtain 6-chloro-N$^2$-ethylpyridine-2, 3-diamine Int-21 (452 mg) as a black solid. The crude material was used in the next step without further purification.

$^1$H NMR (500 MHz, DMSO-d$_6$): δ 6.67 (d, J=7.5 Hz, 1H), 6.33 (d, J=8.1 Hz, 1H), 5.85 (br s, 1H), 4.88 (brs, 2H), 3.37-3.25 (m, 2H), 1.15 (t, J=7.0 Hz, 3H)

LC-MS: m/z 172 [M+H]$^+$ at 1.72 RT (85.88% purity)

Preparation of Int-22

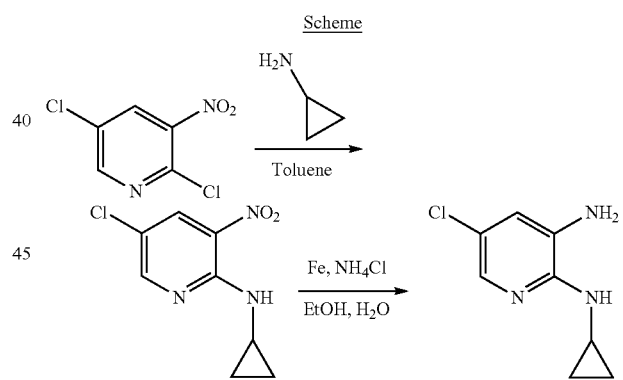

Int-22

5-Chloro-N-cyclopropyl-3-nitropyridin-2-amine

To a stirred solution of 2,5-dichloro-3-nitropyridine (1 g, 5.23 mmol) in toluene (10 mL) under inert atmosphere was added cyclopropylamine (0.73 mL, 10.47 mmol) at 0° C. The reaction mixture was stirred at room temperature for 48 h. After consumption of starting material (by TLC), the reaction mixture was diluted with water (40 mL) and extracted with EtOAc (2×60 mL). The combined organic extracts were dried over anhydrous Na$_2$SO$_4$ and concentrated under reduced pressure to afford 5-chloro-N-cyclopropyl-3-nitropyridin-2-amine (700 mg) as an orange solid. The crude material was used in the next step without further purification.

¹H NMR (400 MHz, CDCl₃): δ 8.45 (d, J=2.5 Hz, 1H), 8.41 (d, J=2.4 Hz, 1H), 8.18 (br s, 1H), 3.05-2.97 (m, 1H), 0.98-0.91 (m, 2H), 0.68-0.62 (m, 2H)
LC-MS: m/z 214 [M+H]⁺ at 3.03 RT (98.66% purity)

5-Chloro-N²-cyclopropylpyridine-2,3-diamine (Int-22)

To a stirred solution of 5-chloro-N-cyclopropyl-3-nitropyridin-2-amine (200 mg, crude) in EtOH:water (1:1, 20 mL) was added iron powder (262 mg, 4.69 mmol) and ammonium chloride (253 mg, 4.69 mmol) at room temperature. The reaction mixture was heated to 80° C. and stirred for 3 h. After consumption of starting material (by TLC), the reaction mixture was filtered through a pad of celite and washed with EtOAc. The filtrate was diluted with water (30 mL) and extracted with EtOAc (2×50 mL). The combined organic extracts were dried over anhydrous Na₂SO₄ and concentrated under reduced pressure to obtain 5-chloro-N²-cyclopropylpyridine-2,3-diamine Int-22 (120 mg) as a black solid. This crude material was used in the next step without further purification.

¹H NMR (500 MHz, DMSO-d₆): δ 7.35 (d, J=1.7 Hz, 1H), 6.67 (d, J=2.3 Hz, 1H), 6.00 (br s, 1H), 5.02 (br s, 2H), 2.72-2.63 (m, 1H), 0.68-0.63 (m, 2H), 0.41-0.37 (m, 2H)
LC-MS: m/z 183.9 [M+H]⁺ at 1.87 RT (88.05% purity)

Example 1

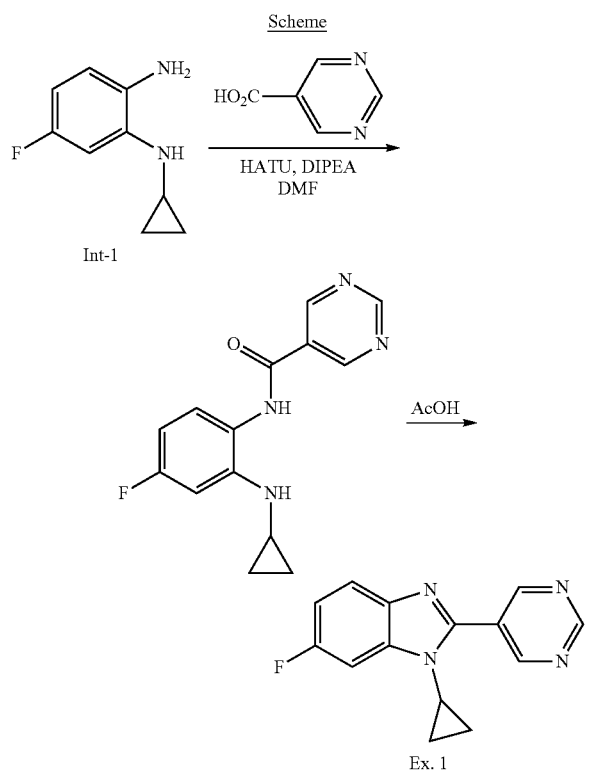

Ex. 1

N-(2-(Cyclopropylamino)-4-fluorophenyl)pyrimidine-5-carboxamide

To a stirred solution of N1-cyclopropyl-5-fluorobenzene-1,2-diamine Int-1 (300 mg, 1.81 mmol) in N,N-dimethylformamide (DMF) (3 mL) under an inert atmosphere was added pyrimidine-5-carboxylic acid (224 mg, 1.81 mmol), HATU (824 mg, 2.17 mmol) and ethyldiisopropylamine (1.26 mL, 7.23 mmol) at room temperature. The reaction mixture was stirred at room temperature for 8 h. After consumption of starting material (by TLC), the reaction mixture was diluted with water (30 mL) and extracted with EtOAc (2×40 mL). The combined organic extracts were dried over anhydrous Na₂SO₄ and concentrated under reduced pressure. The crude material was purified by silica gel column chromatography (eluent: 40% EtOAc/hexane) to afford N-(2-(cyclopropylamino)-4-fluorophenyl)pyrimidine-5-carboxamide (210 mg, 0.77 mmol, 41%) as dark brown solid.

¹H NMR (400 MHz, DMSO-d₆): δ 9.77 (s, 1H), 9.34 (s, 1H), 9.28 (s, 2H), 7.14 (dd, J=8.5, 6.5 Hz, 1H), 6.75 (dd, J=11.8, 2.8 Hz, 1H), 6.42 (td, J=8.5, 2.8 Hz, 1H), 6.10 (s, 1H), 2.36-2.34 (m, 1H), 0.78-0.71 (m, 2H), 0.48-0.41 (m, 2H).
LC-MS: m/z 271.1 [M−H]⁺ at 1.96 RT (83.56% purity).

1-Cyclopropyl-6-fluoro-2-(pyrimidin-5-yl)-1H-benzo[d]imidazole (Ex. 1)

To N-(2-(cyclopropylamino)-4-fluorophenyl)pyrimidine-5-carboxamide (210 mg, 0.77 mmol) was added acetic acid (AcOH) (0.5 mL) under an inert atmosphere and the mixture was stirred at 100° C. for 8 h. After consumption of starting material (by TLC), the reaction mixture was neutralized with saturated sodium bicarbonate solution (30 mL) and extracted with EtOAc (2×30 mL). The combined organic extracts were dried over anhydrous Na₂SO₄ and concentrated under reduced pressure. The crude material was purified by silica gel column chromatography (eluent: 2% MeOH/CH₂Cl₂) to afford 1-cyclopropyl-6-fluoro-2-(pyrimidin-5-yl)-1H-benzo[d]imidazole Ex. 1 (90 mg, 0.35 mmol, 46%) as an off white solid.

¹H NMR (400 MHz, DMSO-d₆): δ 9.40 (s, 2H), 9.34 (s, 1H), 7.76 (dd, J=8.8, 4.9 Hz, 1H), 7.53 (dd, J=9.1, 2.5 Hz, 1H), 7.19-7.12 (m, 1H), 3.91-3.83 (m, 1H), 1.18-1.11 (m, 2H), 0.78-0.71 (m, 2H).
LC-MS: m/z 255.0 [M+H]⁺ at 1.85 RT (99.02% purity).
HPLC: 99.44%.

Example 2

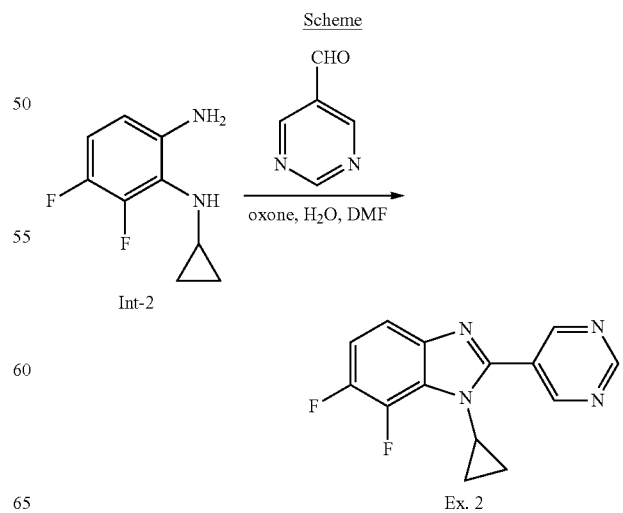

Ex. 2

1-Cyclopropyl-6,7-difluoro-2-(pyrimidin-5-yl)-1H-benzo[d]imidazole (Ex. 2)

To a stirred solution of N1-cyclopropyl-5,6-difluorobenzene-1,2-diamine Int-2 (200 mg, 1.09 mmol) in DMF (2 mL) under an inert atmosphere was added pyrimidine-5-carbaldehyde (129 mg, 1.19 mmol), oxone (198 mg, 1.3 mmol), and water (0.2 mL) at room temperature. The reaction mixture was stirred at room temperature for 3 h. After consumption of starting material (by TLC), the reaction mixture was quenched with water (20 mL) and stirred for 10 min. The precipitated solid was filtered, washed with n-hexane (2×7 mL) and dried under vacuum to afford 1-cyclopropyl-6,7-difluoro-2-(pyrimidin-5-yl)-1H-benzo[d]imidazole Ex. 2 (90 mg, 0.33 mmol, 30%) as a white solid.

$^1$H NMR (400 MHz, DMSO-$d_6$): δ 9.38 (s, 2H), 9.36 (s, 1H), 7.60-7.55 (m, 1H), 7.39-7.30 (m, 1H), 4.11-4.03 (m, 1H), 1.13-1.06 (m, 2H), 0.85-0.79 (m, 2H).

LC-MS: m/z 272.9 [M+H]$^+$ at 2.75 RT (97.90% purity). HPLC: 99.01%.

Example 3

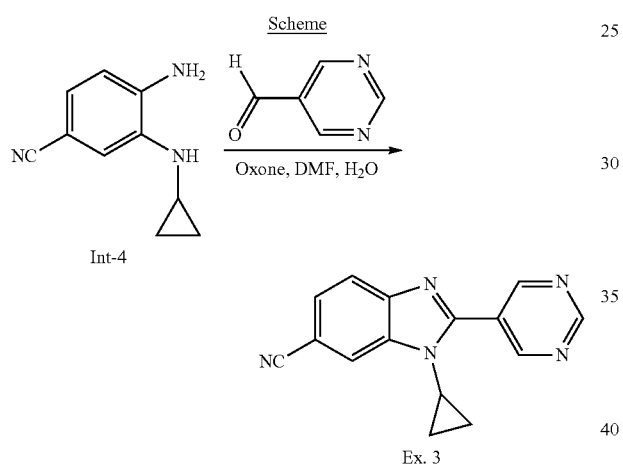

Ex. 3

1-Cyclopropyl-2-(pyrimidin-5-yl)-1H-benzo[d]imidazole-6-carbonitrile (Ex. 3)

To a stirred solution of 4-amino-3-(cyclopropylamino)benzonitrile Int-4 (100 mg, 0.58 mmol) in DMF (3 mL) under an inert atmosphere was added pyrimidine-5-carbaldehyde (62 mg, 0.58 mmol), oxone (108 mg, 0.69 mmol), and water (0.2 mL) at room temperature. The reaction mixture was stirred at room temperature for 4 h. After consumption of starting material (by TLC), the reaction mixture was diluted with saturated potassium carbonate solution (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 100% EtOAc) to afford 1-cyclopropyl-2-(pyrimidin-5-yl)-1H-benzo[d]imidazole-6-carbonitrile Ex. 3 (70 mg, 0.27 mmol, 47%) as an off white solid.

$^1$H NMR (400 MHz, DMSO-$d_6$): δ 9.45 (s, 2H), 9.38 (s, 1H), 8.31-8.29 (m, 1H), 7.92 (dd, J=8.3, 0.4 Hz, 1H), 7.70 (dd, J=8.3, 1.6 Hz, 1H), 3.96-3.90 (m, 1H), 1.21-1.15 (m, 2H), 0.82-0.77 (m, 2H).

LC-MS: m/z 262.0 [M+H]$^+$ at 2.46 RT (99.46% purity). HPLC: 99.61%.

Example 4

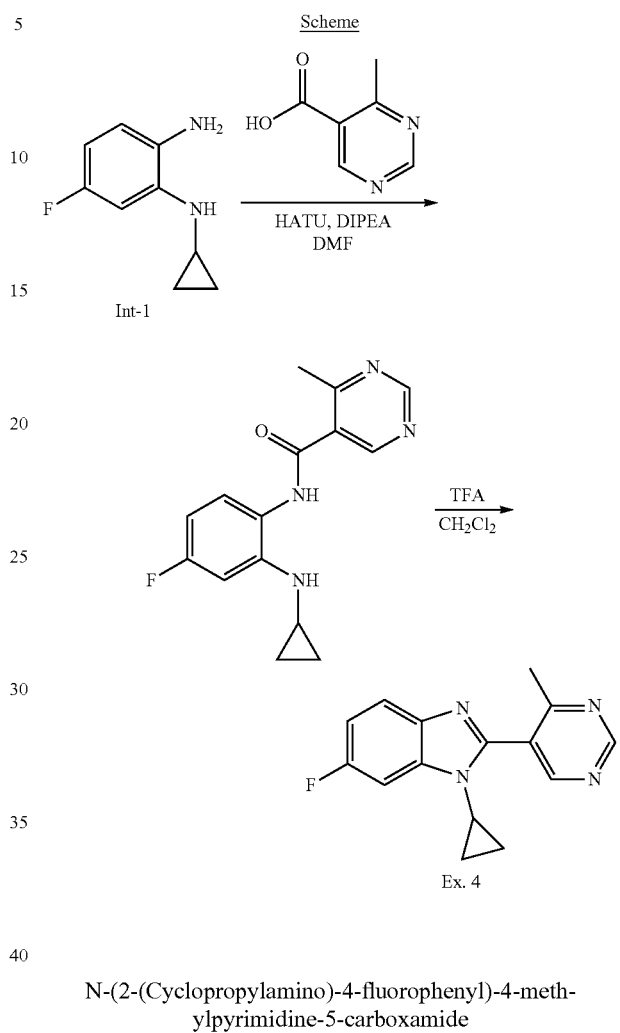

Ex. 4

N-(2-(Cyclopropylamino)-4-fluorophenyl)-4-methylpyrimidine-5-carboxamide

To a stirred solution of N1-cyclopropyl-5-fluorobenzene-1,2-diamine Int-1 (200 mg, 1.2 mmol) in DMF (2 mL) under an inert atmosphere was added 4-methylpyrimidine-5-carboxylic acid (166 mg, 1.2 mmol), HATU (549 mg, 1.44 mmol) and ethyldiisopropylamine (0.84 mL, 4.82 mmol) at room temperature. The reaction mixture was stirred at room temperature for 4 h. After consumption of starting material (by TLC), the reaction mixture was quenched with water (20 mL) and extracted with Et$_2$O (2×20 mL). The combined organic extracts were dried over anhydrous Na$_2$SO$_4$ and concentrated under reduced pressure. The crude material was washed with n-hexane (2×15 mL) to afford N-(2-(cyclopropylamino)-4-fluorophenyl)-4-methylpyrimidine-5-carboxamide (200 mg, 0.7 mmol, 58%) as an off white solid which was used directly without further purification.

LC-MS: m/z 286.9 [M+H]$^+$ at 2.72 RT (96.85% purity).

1-Cyclopropyl-6-fluoro-2-(4-methylpyrimidin-5-yl)-1H-benzo[d]imidazole (Ex. 4)

To a stirred solution of N-(2-(cyclopropylamino)-4-fluorophenyl)-4-methylpyrimidine-5-carboxamide (200 mg, 0.7 mmol) in CH₂Cl₂ (3 mL) under an inert atmosphere was added trifluoroacetic acid (0.5 mL) drop wise at room temperature. The reaction mixture was stirred at room temperature for 16 h. After consumption of starting material (by TLC), the volatiles were removed under reduced pressure. The residue was diluted with water (5 mL), basified with saturated sodium bicarbonate solution (15 mL) and extracted with CH₂Cl₂ (2×20 mL). The combined organic extracts were dried over anhydrous Na₂SO₄ and concentrated under reduced pressure. The crude material was purified by preparative HPLC to afford 1-cyclopropyl-6-fluoro-2-(4-methylpyrimidin-5-yl)-1H-benzo[d]imidazole Ex. 4 (50 mg, 0.19 mmol, 27%) as an off white solid.

$^1$H NMR (500 MHz, DMSO-d$_6$): δ 9.20 (s, 1H), 9.05 (s, 1H), 7.74 (dd, J=9.0, 4.9 Hz, 1H), 7.52 (dd, J=9.1, 2.5 Hz, 1H), 7.19-7.13 (m, 1H), 3.65-3.59 (m, 1H), 2.56 (s, 3H), 0.99-0.94 (m, 2H), 0.65-0.61 (m, 2H).

LC-MS: m/z 269.0 [M+H]⁺ at 2.68 RT (99.10% purity). HPLC: 99.12%.

Example 5

Scheme

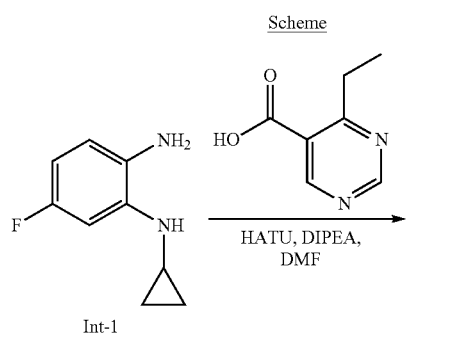

Int-1

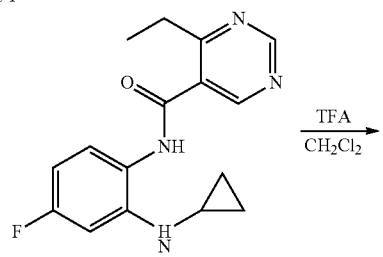

Ex. 5

N-(2-(Cyclopropylamino)-4-fluorophenyl)-4-ethylpyrimidine-5-carboxamide

To a stirred solution of N1-cyclopropyl-5-fluorobenzene-1,2-diamine Int-1 (200 mg, 1.2 mmol) in DMF (3 mL) under an inert atmosphere was added 4-ethylpyrimidine-5-carboxylic acid (183 mg, 1.2 mmol), HATU (549 mg, 1.44 mmol) and ethyldiisopropylamine (0.84 mL, 4.82 mmol) at room temperature. The reaction mixture was stirred at room temperature for 4 h. After consumption of starting material (by TLC), the reaction mixture was quenched with ice cold water (30 mL). The precipitated solid was filtered, washed with water (2×5 mL) and dried under vacuum to obtain N-(2-(cyclopropylamino)-4-fluorophenyl)-4-ethylpyrimidine-5-carboxamide (300 mg, crude) as brown solid which was used directly without further purification.

$^1$H NMR (400 MHz, DMSO-d$_6$): δ 9.63 (s, 1H), 9.17 (s, 1H), 8.99 (s, 1H), 7.27 (dd, J=8.5, 6.4 Hz, 1H), 6.77 (dd, J=11.8, 2.9 Hz, 1H), 6.45 (td, J=8.5, 2.9 Hz, 1H), 5.89 (s, 1H), 2.91 (q, J=7.5 Hz, 2H), 2.40-2.36 (m, 1H), 1.24 (t, J=7.5 Hz, 3H), 0.80-0.73 (m, 2H), 0.47-0.41 (m, 2H).

LC-MS: m/z 301.3 [M+H]⁺ at 3.81 RT (85.79% purity).

1-Cyclopropyl-2-(4-ethylpyrimidin-5-yl)-6-fluoro-1H-benzo[d]imidazole (Ex. 5)

To a stirred solution of N-(2-(cyclopropylamino)-4-fluorophenyl)-4-ethylpyrimidine-5-carboxamide (300 mg, 1.0 mmol) in CH₂Cl₂ (5 mL) under an inert atmosphere was added trifluoroacetic acid (0.5 mL) drop wise at room temperature. The reaction mixture was stirred at room temperature for 16 h. After consumption of starting material (by TLC), the volatiles were removed under reduced pressure. The residue was diluted with EtOAc (40 mL) and washed with saturated sodium bicarbonate solution (20 mL). The organic layer was separated, dried over anhydrous Na₂SO₄ and concentrated under reduced pressure. The crude material was purified by silica gel column chromatography (eluent: 50% EtOAc/hexane) to afford 1-cyclopropyl-2-(4-ethylpyrimidin-5-yl)-6-fluoro-1H-benzo[d]imidazole Ex. 5 (50 mg, 0.18 mmol, 18%) as a brown solid.

$^1$H NMR (400 MHz, DMSO-d$_6$): δ 9.26 (s, 1H), 9.05 (s, 1H), 7.74 (dd, J=8.8, 4.9 Hz, 1H), 7.52 (dd, J=9.0, 2.5 Hz, 1H), 7.19-7.12 (m, 1H), 3.63-3.56 (m, 1H), 2.86 (q, J=7.4 Hz, 2H), 1.18 (t, J=7.5 Hz, 3H), 0.99-0.93 (m, 2H), 0.64-0.59 (m, 2H).

LC-MS: m/z 282.9 [M+H]⁺ at 2.87 RT (99.73% purity). HPLC: 99.78%.

Example 6

Scheme

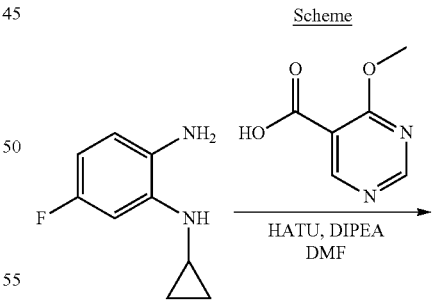

Int-1

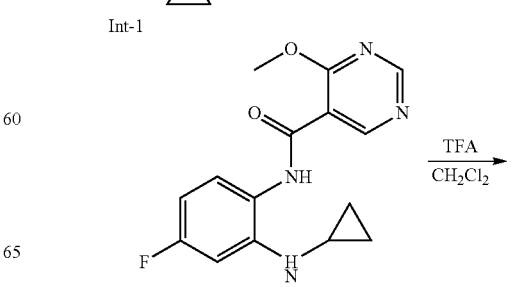

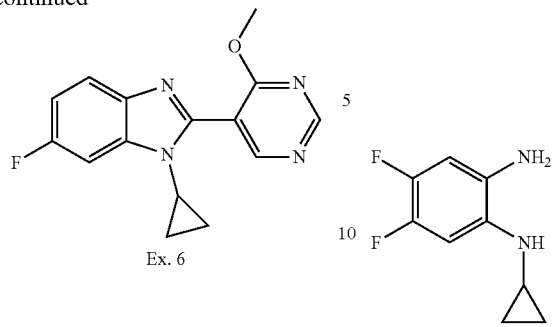

Ex. 6

N-(2-(Cyclopropylamino)-4-fluorophenyl)-4-methoxypyrimidine-5-carboxamide

To a stirred solution of N1-cyclopropyl-5-fluorobenzene-1,2-diamine Int-1 (300 mg, 1.81 mmol) in DMF (4 mL) under an inert atmosphere was added 4-methoxypyrimidine-5-carboxylic acid (278 mg, 1.81 mmol), HATU (824 mg, 2.17 mmol) and ethyldiisopropylamine (1.26 mL, 7.23 mmol) drop wise at room temperature. The reaction mixture was stirred at room temperature for 4 h. After consumption of starting material (by TLC), the reaction mixture was quenched with water (20 mL) and extracted with Et$_2$O (2×20 mL). The combined organic extracts were dried over anhydrous Na$_2$SO$_4$ and concentrated under reduced pressure to obtain N-(2-(cyclopropylamino)-4-fluorophenyl)-4-methoxypyrimidine-5-carboxamide (250 mg, crude) as brown solid which was used directly without further purification.

LC-MS: m/z 302.9 [M+H]$^+$ at 3.01 RT (97.99% purity).

1-Cyclopropyl-6-fluoro-2-(4-methoxypyrimidin-5-yl)-1H-benzo[d]imidazole (Ex. 6)

To a stirred solution of N-(2-(cyclopropylamino)-4-fluorophenyl)-4-methoxypyrimidine-5-carboxamide (200 mg, 0.66 mmol) in CH$_2$Cl$_2$ (5 mL) under an inert atmosphere was added trifluoroacetic acid (0.8 mL) drop wise at room temperature. The reaction mixture was stirred at room temperature for 24 h. After consumption of starting material (by TLC), the volatiles were removed under reduced pressure. The residue was basified with saturated sodium bicarbonate solution (20 mL) and extracted with CH$_2$Cl$_2$ (2×20 mL). The combined organic extracts were dried over anhydrous Na$_2$SO$_4$ and concentrated under reduced pressure. The crude material was purified by preparative HPLC to afford 1-cyclopropyl-6-fluoro-2-(4-methoxypyrimidin-5-yl)-1H-benzo[d]imidazole Ex. 6 (30 mg, 0.1 mmol, 12%) as a white solid.

$^1$H NMR (400 MHz, CD$_3$OD): δ 8.95 (s, 1H), 8.74 (s, 1H), 7.67 (dd, J=8.8, 4.7 Hz, 1H), 7.46 (dd, J=8.8, 2.1 Hz, 1H), 7.13-7.08 (m, 1H), 4.13 (s, 3H), 3.57-3.51 (m, 1H), 1.04-0.98 (m, 2H), 0.73-0.68 (m, 2H).

LC-MS: m/z 284.9 [M+H]$^+$ at 2.84 RT (99.47% purity). HPLC: 97.92%.

Example 7

Scheme

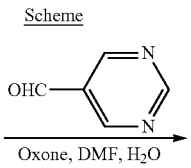

Int-6

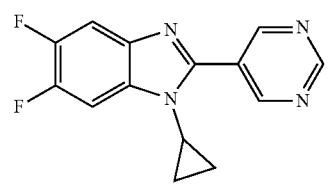

Ex. 7

1-Cyclopropyl-5,6-difluoro-2-(pyrimidin-5-yl)-1H-benzo[d]imidazole (Ex. 7)

To a stirred solution of N1-cyclopropyl-4,5-difluorobenzene-1,2-diamine Int-6 (200 mg, crude) in DMF (2 mL) under an inert atmosphere was added oxone (198 mg, 1.3 mmol), pyrimidine-5-carbaldehyde (129 mg, 1.19 mmol) and water (0.2 mL) at room temperature. The reaction mixture was stirred at room temperature for 24 h. After consumption of starting material (by TLC), the reaction mixture was diluted with ice cold water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 50% EtOAc/hexane) to afford 1-cyclopropyl-5,6-difluoro-2-(pyrimidin-5-yl)-1H-benzo[d]imidazole Ex. 7 (25 mg, 0.09 mmol, 5%) as an off white solid.

$^1$H NMR (400 MHz, CD$_3$OD): δ 9.38 (s, 2H), 9.31 (s, 1H), 7.69 (dd, J=10.2, 7.2 Hz, 1H), 7.59 (dd, J=10.4, 7.3 Hz, 1H), 3.84-3.78 (m, 1H), 1.26-1.20 (m, 2H), 0.84-0.79 (m, 2H).

LC-MS: m/z 273.3 [M+H]$^+$ at 3.63 RT (98.80% purity). HPLC: 98.42%.

Example 8

Scheme

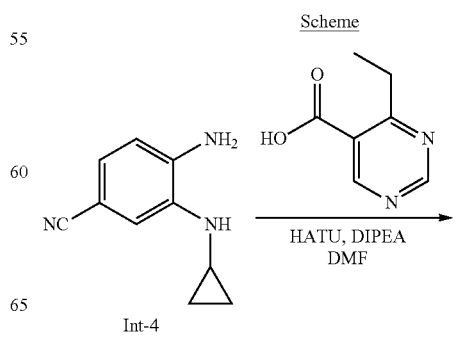

Int-4

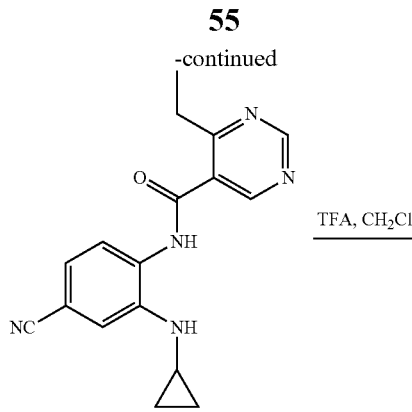

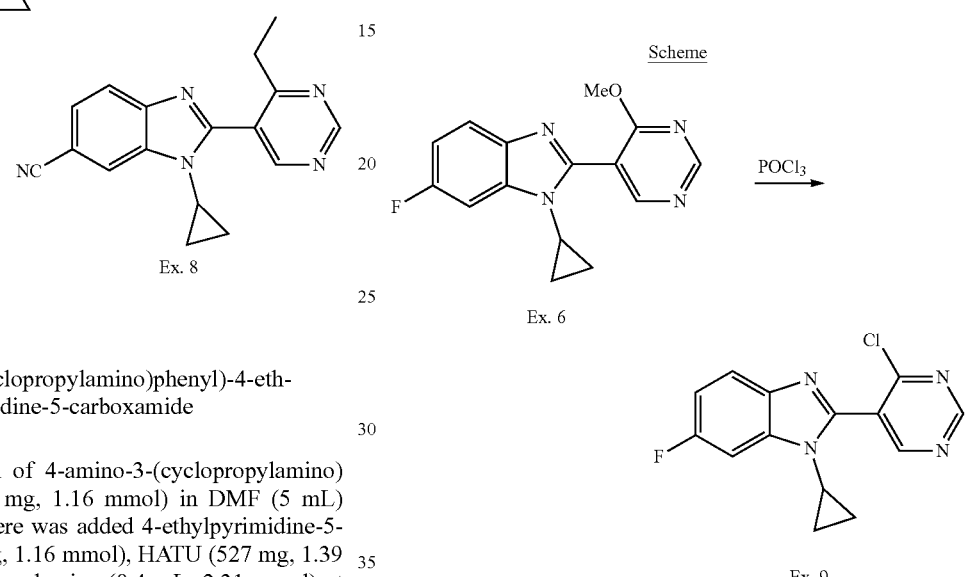

N-(4-Cyano-2-(cyclopropylamino)phenyl)-4-ethylpyrimidine-5-carboxamide

To a stirred solution of 4-amino-3-(cyclopropylamino) benzonitrile Int-4 (200 mg, 1.16 mmol) in DMF (5 mL) under an inert atmosphere was added 4-ethylpyrimidine-5-carboxylic acid (176 mg, 1.16 mmol), HATU (527 mg, 1.39 mmol) and ethyldiisopropylamine (0.4 mL, 2.31 mmol) at room temperature. The reaction mixture was stirred at room temperature for 4 h. After consumption of starting material (by TLC), the reaction mixture was diluted with water (20 mL) and extracted with EtOAc (2×20 mL). The combined organic extracts were dried over anhydrous $Na_2SO_4$ and concentrated under reduced pressure to afford N-(4-cyano-2-(cyclopropylamino phenyl)-4-ethylpyrimidine-5-carboxamide (250 mg, crude) as brown liquid which was used directly without further purification.

LC-MS: m/z 306.1 [M–H]+ at 2.85 RT (49.15% purity).

1-Cyclopropyl-2-(4-ethylpyrimidin-5-yl)-1H-benzo[d]imidazole-6-carbonitrile (Ex. 8)

To a stirred solution of N-(4-cyano-2-(cyclopropylamino) phenyl)-4-ethylpyrimidine-5-carboxamide (250 mg, crude) in $CH_2Cl_2$ (5 mL) under an inert atmosphere was added trifluoroacetic acid (0.2 mL) at room temperature. The reaction mixture was stirred at room temperature for 12 h. After consumption of starting material (by TLC), the volatiles were removed under reduced pressure. The residue was neutralized with saturated sodium bicarbonate solution and extracted with $CH_2Cl_2$ (2×30 mL). The combined organic extracts were dried over anhydrous $Na_2SO_4$ and concentrated under reduced pressure. The crude material was purified by preparative HPLC to afford 1-cyclopropyl-2-(4-ethylpyrimidin-5-yl)-1H-benzo[d]imidazole-6-carbonitrile Ex. 8 (40 mg, 0.14 mmol, 12% for two steps) as an off white solid.

$^1$H NMR (400 MHz, $CD_3OD$): δ 9.27 (s, 1H), 8.98 (s, 1H), 8.23 (d, J=0.9 Hz, 1H), 7.87 (d, J=8.4 Hz, 1H), 7.67 (dd, J=8.3, 1.4 Hz, 1H), 3.65-3.58 (m, 1H), 2.88 (q, J=7.5 Hz, 2H), 1.26 (t, J=7.5 Hz, 3H), 1.13-1.05 (m, 2H), 0.79-0.72 (m, 2H).

LC-MS: m/z 289.9 [M+H]+ at 2.28 RT (98.94% purity).

HPLC: 92.05%.

Example 9

2-(4-Chloropyrimidin-5-yl)-1-cyclopropyl-6-fluoro-1H-benzo[d]imidazole (Ex. 9)

The mixture of 1-cyclopropyl-6-fluoro-2-(4-methoxypyrimidin-5-yl)-1H-benzo[d]imidazole Ex. 6 (200 mg, 0.7 mmol) in phosphoryl chloride (1.31 mL, 14.08 mmol) under an inert atmosphere was heated to 100° C. for 4 h. After consumption of starting material (by TLC), the reaction mixture was concentrated under reduced pressure. The residue was basified with saturated sodium bicarbonate solution to pH ~8 and extracted with EtOAc (2×20 mL). The combined organic extracts were dried over anhydrous $Na_2SO_4$ and concentrated under reduced pressure. The crude material was purified by silica gel column chromatography (eluent: 60% EtOAc/hexane) to afford 2-(4-chloropyrimidin-5-yl)-1-cyclopropyl-6-fluoro-1H-benzo[d]imidazole Ex. 9 (130 mg, 0.45 mmol, 64%) as an off white solid.

$^1$H NMR (400 MHz, $CD_3OD$): δ 9.20 (s, 1H), 9.04 (s, 1H), 7.72 (dd, J=8.9, 4.6 Hz, 1H), 7.51 (dd, J=8.8, 2.3 Hz, 1H), 7.20-7.13 (m, 1H), 3.62-3.57 (m, 1H), 1.08-1.02 (m, 2H), 0.78-0.73 (m, 2H).

LC-MS: m/z 288.9 [M+H]+ at 2.55 RT (96.61% purity).

HPLC: 96.08%.

Example 10

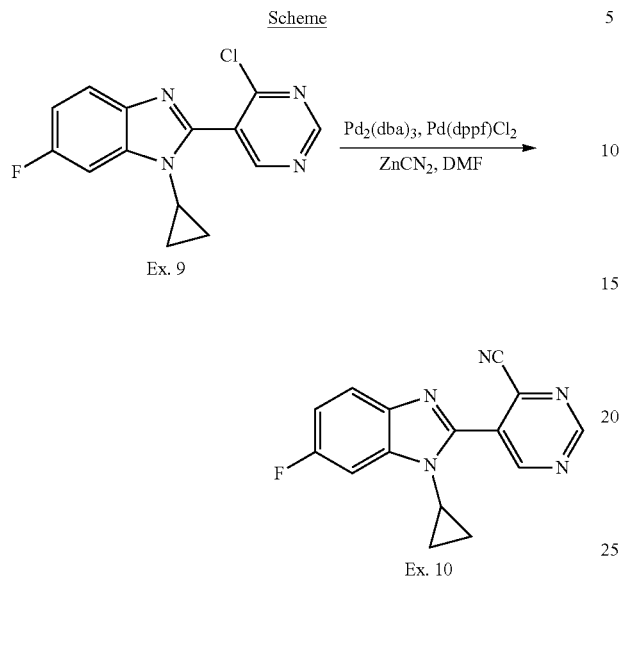

5-(1-Cyclopropyl-6-fluoro-1H-benzo[d]imidazol-2-yl)pyrimidine-4-carbonitrile (Ex. 10)

To a stirred solution of 2-(4-chloropyrimidin-5-yl)-1-cyclopropyl-6-fluoro-1H-benzo[d]imidazole Ex. 9 (80 mg, 0.28 mmol) in DMF (0.8 mL) under an inert atmosphere was added $Zn(CN)_2$ (19 mg, 0.17 mmol) at room temperature. The reaction mixture was degassed under argon for 10 min. To this was added $Pd_2(dba)_3$ (13 mg, 0.01 mmol) and $Pd(dppf)Cl_2$ (10 mg, 0.01 mmol) at room temperature. The reaction mixture was heated to 100° C. and stirred for 2 h. After consumption of starting material (by TLC), the reaction mixture was diluted with EtOAc (25 mL), filtered through a pad of celite and the celite bed was washed with EtOAc (10 mL). The organic layer was washed with water (20 mL), dried over anhydrous $Na_2SO_4$ and concentrated under reduced pressure. The crude material was purified by silica gel column chromatography (eluent: 60% EtOAc/hexane) to afford 5-(1-cyclopropyl-6-fluoro-1H-benzo[d]imidazol-2-yl)pyrimidine-4-carbonitrile Ex. 10 (40 mg, 0.14 mmol, 52%) as an off white solid.

$^1$H NMR (400 MHz, $CD_3OD$): δ 9.51 (s, 1H), 9.50 (s, 1H), 7.78 (dd, J=8.9, 4.8 Hz, 1H), 7.55 (dd, J=8.7, 2.3 Hz, 1H), 7.23-7.16 (m, 1H), 3.79-3.74 (m, 1H), 1.20-1.13 (m, 2H), 0.81-0.75 (m, 2H).

LC-MS: m/z 279.9 [M+H]$^+$ at 2.60 RT (99.22% purity).

HPLC: 97.83%.

Example 11

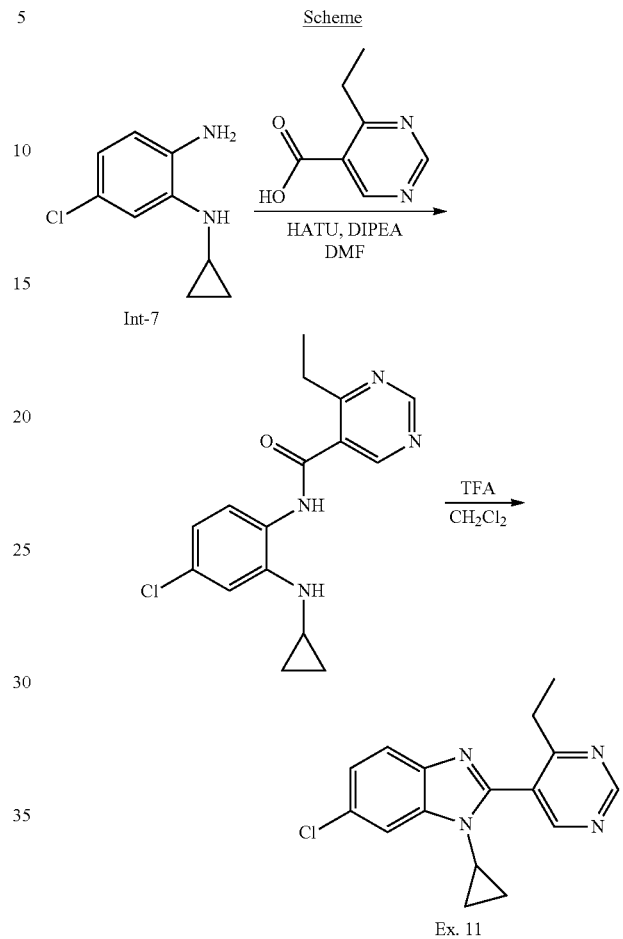

N-(4-Chloro-2-(cyclopropylamino)phenyl)-4-ethylpyrimidine-5-carboxamide

To a stirred solution of 5-chloro-N1-cyclopropylbenzene-1,2-diamine Int-7 (200 mg, 1.1 mmol) in DMF (5 mL) under an inert atmosphere was added 4-ethylpyrimidine-5-carboxylic acid (167 mg, 1.1 mmol), HATU (501 mg, 1.32 mmol) and ethyldiisopropylamine (0.77 mL, 4.39 mmol) at 0° C. The reaction mixture was warmed to room temperature and stirred for 16 h. After consumption of starting material (by TLC), the reaction mixture was diluted with ice cold water (20 mL) and extracted with EtOAc (2×20 mL). The combined organic extracts were dried over anhydrous $Na_2SO_4$ and concentrated under reduced pressure to obtain N-(4-chloro-2-(cyclopropylamino)phenyl)-4-ethylpyrimidine-5-carboxamide (200 mg, crude) as an off white solid.

LC-MS: m/z 316.9 [M+H]$^+$ at 2.81 RT (99.10% purity).

6-Chloro-1-cyclopropyl-2-(4-ethylpyrimidin-5-yl)-1H-benzo[d]imidazole (Ex. 11)

To a stirred solution of N-(4-chloro-2-(cyclopropylamino)phenyl)-4-ethylpyrimidine-5-carboxamide (150 mg, 0.47 mmol) in $CH_2Cl_2$ (5 mL) under an inert atmosphere was added trifluoroacetic acid (0.2 mL) at 0° C. The reaction mixture was warmed to room temperature and stirred for 16 h. After consumption of starting material (by TLC), the reaction mixture was quenched with saturated sodium bicarbonate solution (20 mL) and extracted with EtOAc (2×20 mL). The combined organic extracts were dried over anhydrous $Na_2SO_4$ and concentrated under reduced pressure. The crude material was purified by preparative HPLC to afford 6-chloro-1-cyclopropyl-2-(4-ethylpyrimidin-5-yl)-1H-benzo[d]imidazole Ex. 11 (30 mg, 0.1 mmol, 21%) as an off white solid.

$^1$H NMR (400 MHz, DMSO-$d_6$): δ 9.27 (s, 1H), 9.05 (s, 1H), 7.77-7.72 (m, 2H), 7.33 (dd, J=8.6, 2.1 Hz, 1H), 3.63-3.58 (m, 1H), 2.86 (q, J=7.5 Hz, 2H), 1.18 (t, J=7.5 Hz, 3H), 1.01-0.94 (m, 2H), 0.66-0.59 (m, 2H).

LC-MS: m/z 298.9 [M+H]$^+$ at 2.68 RT (97.65% purity). HPLC: 96.38%.

Example 12

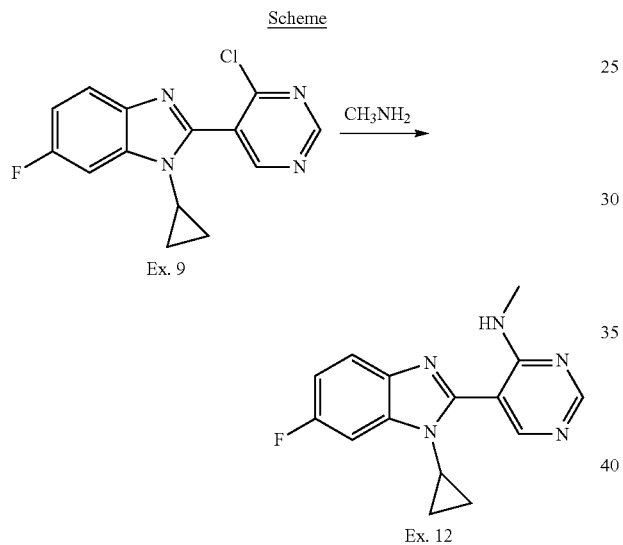

5-(1-Cyclopropyl-6-fluoro-1H-benzo[d]imidazol-2-yl)-N-methylpyrimidin-4-amine (Ex. 12)

Methylamine (33% in absolute EtOH, 0.09 mL, 2.08 mmol)) was added to 2-(4-chloropyrimidin-5-yl)-1-cyclopropyl-6-fluoro-1H-benzo[d]imidazole Ex. 9 (60 mg, 0.21 mmol) at room temperature under an inert atmosphere and stirred for 2 h. After consumption of starting material (by TLC), the reaction mixture was quenched with water (20 mL) and filtered. The obtained solid was washed with diethyl ether (2×5 mL) and n-pentane (2×5 mL) to afford 5-(1-cyclopropyl-6-fluoro-1H-benzo[d]imidazol-2-yl)-N-methylpyrimidin-4-amine Ex. 12 (25 mg, 0.09 mmol, 42%) as an off white solid.

$^1$H NMR (400 MHz, $CD_3OD$): δ 8.64 (s, 1H), 8.56 (s, 1H), 7.68 (dd, J=8.9, 4.8 Hz, 1H), 7.44 (dd, J=8.9, 2.4 Hz, 1H), 7.13-7.06 (m, 1H), 3.66-3.61 (m, 1H), 3.06 (s, 3H), 1.23-1.16 (m, 2H), 0.81-0.76 (m, 2H).

LC-MS: m/z 283.9 [M+H]$^+$ at 2.44 RT (98.09% purity). HPLC: 98.48%.

Example 13

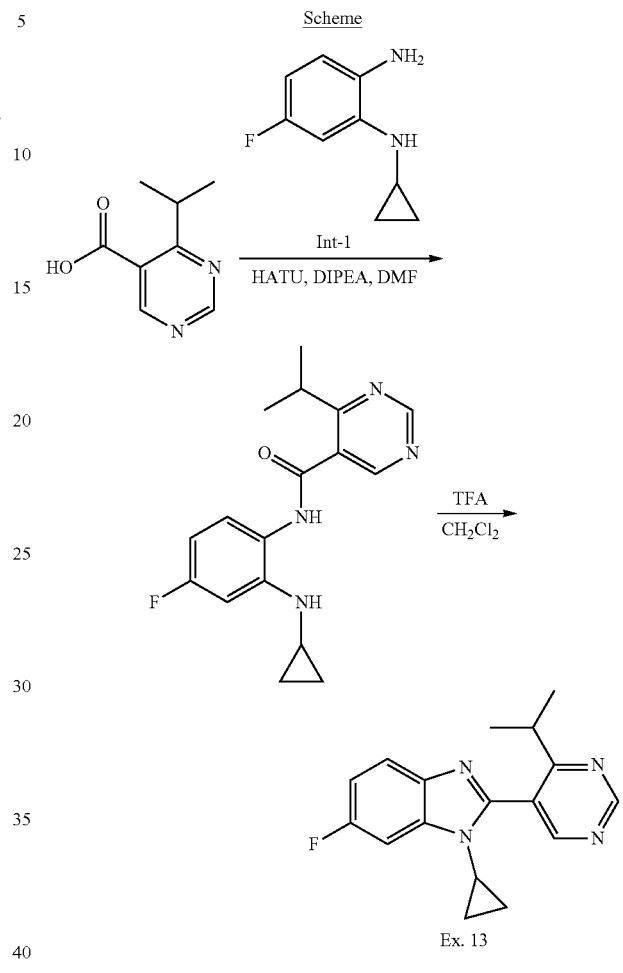

N-(2-(Cyclopropylamino)-4-fluorophenyl)-4-isopropylpyrimidine-5-carboxamide

To a stirred solution of N1-cyclopropyl-5-fluorobenzene-1,2-diamine Int-1 (200 mg, 1.2 mmol) in DMF (2 mL) under an inert atmosphere was added 4-isopropylpyrimidine-5-carboxylic acid (200 mg, 1.2 mmol), HATU (549 mg, 1.44 mmol) and ethyldiisopropylamine (0.84 mL, 4.82 mmol) at room temperature. The reaction mixture was stirred at room temperature for 16 h. After consumption of starting material (by TLC), the reaction mixture was quenched with water (20 mL). The obtained solid was filtered and washed with diethylether (2×15 mL) to afford N-(2-(cyclopropylamino)-4-fluorophenyl)-4-isopropylpyrimidine-5-carboxamide (200 mg, crude) as black solid which was used directly without further purification.

LC-MS: m/z 315.0 [M+H]$^+$ at 2.84 RT (45.59% purity).

1-Cyclopropyl-6-fluoro-2-(4-isopropylpyrimidin-5-yl)-1H-benzo[d]imidazole (Ex. 13)

To a stirred solution of N-(2-(cyclopropylamino)-4-fluorophenyl)-4-isopropylpyrimidine-5-carboxamide (200 mg, crude) in $CH_2Cl_2$ (2 mL) under an inert atmosphere was added trifluoroacetic acid (0.5 mL) at room temperature. The reaction mixture was stirred at room temperature 16 h. After consumption of starting material (by TLC), the volatiles were removed under reduced pressure. The residue was basified with saturated sodium bicarbonate solution (30 mL) and extracted with EtOAc (2×20 mL). The combined organic extracts were dried over anhydrous $Na_2SO_4$ and concentrated under reduced pressure. The crude material was purified by preparative HPLC to afford 1-cyclopropyl-6-fluoro-2-(4-isopropylpyrimidin-5-yl)-1H-benzo[d]imidazole Ex. 13 (20 mg, 0.07 mmol, 6% for two steps) as brown solid.

$^1$H NMR (400 MHz, $CD_3OD$): δ 9.27 (s, 1H), 8.89 (s, 1H), 7.70 (dd, J=8.8, 4.7 Hz, 1H), 7.50 (dd, J=8.8, 2.4 Hz, 1H), 7.18-7.11 (m, 1H), 3.52-3.45 (m, 1H), 3.19-3.09 (m, 1H), 1.27 (d, J=6.8 Hz, 6H), 1.08-1.01 (m, 2H), 0.76-0.69 (m, 2H).

LC-MS: m/z 297.0 [M+H]$^+$ at 2.28 RT (96.25% purity). HPLC: 98.59%.

Example 14

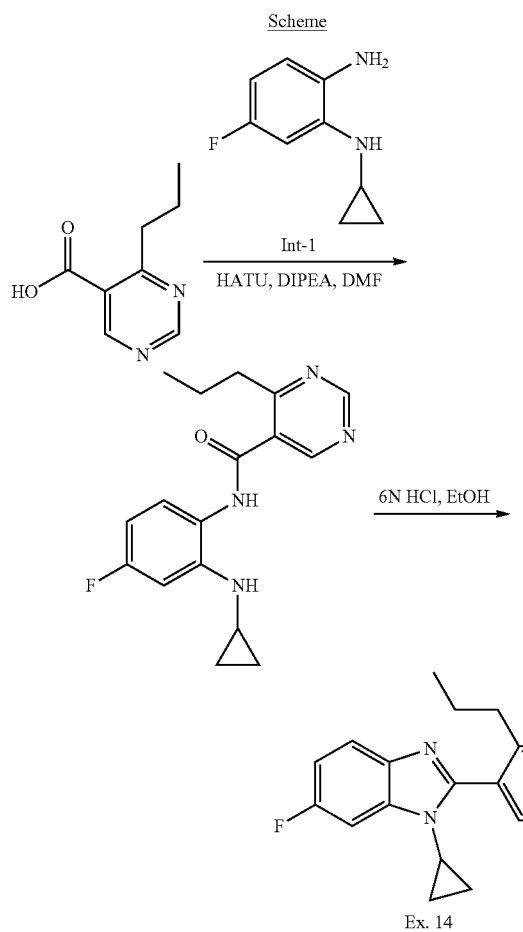

Ex. 14

N-(2-(Cyclopropylamino)-4-fluorophenyl)-4-propylpyrimidine-5-carboxamide

To a stirred solution of 4-propylpyrimidine-5-carboxylic acid (300 mg, 1.81 mmol) in DMF (4 mL) under an inert atmosphere was added and Int-1 (300 mg, 1.81 mmol), HATU (1.03 g, 2.71 mmol) and ethyldiisopropylamine (1.26 mL, 7.23 mmol) at 0° C. The reaction mixture was warmed to room temperature and stirred for 16 h. After consumption of starting material (by TLC), the reaction mixture was quenched with water (30 mL) and stirred for 30 min. The precipitated solid was filtered and dissolved in $CH_2Cl_2$ (60 mL). The organics were dried over anhydrous $Na_2SO_4$ and concentrated under reduced pressure to afford N-(2-(cyclopropylamino)-4-fluorophenyl)-4-propylpyrimidine-5-carboxamide (250 mg, crude) as brown syrup which was used directly without further purification.

$^1$H NMR (400 MHz, DMSO-d$_6$): δ 9.66 (s, 1H), 9.16 (s, 1H), 9.00 (s, 1H), 7.26 (dd, J=8.6, 6.3 Hz, 1H), 6.77 (dd, J=11.8, 2.9 Hz, 1H), 6.46 (td, J=8.5, 2.9 Hz, 1H), 5.85 (s, 1H), 2.90-2.84 (m, 2H), 2.42-2.35 (m, 1H), 1.79-1.67 (m, 2H), 0.91 (t, J=7.4 Hz, 3H), 0.79-0.73 (m, 2H), 0.47-0.40 (m, 2H).

LC-MS: m/z 315.1 [M+H]$^+$ at 2.34 RT (72.79% purity).

1-Cyclopropyl-6-fluoro-2-(4-propylpyrimidin-5-yl)-1H-benzo[d]imidazole (Ex. 14)

To a stirred solution of N-(2-(cyclopropylamino)-4-fluorophenyl)-4-propylpyrimidine-5-carboxamide (200 mg, 0.64 mmol) in EtOH (1 mL) under an inert atmosphere was added 6 N HCl (4 mL) at 0° C. The reaction mixture was heated to reflux temperature and stirred for 1 h. After consumption of starting material (by TLC), the reaction mixture was quenched with saturated sodium carbonate solution (40 mL) and extracted with EtOAc (2×20 mL). The combined organic extracts were washed with water (15 mL), dried over anhydrous $Na_2SO_4$ and concentrated under reduced pressure. The crude material was purified by preparative HPLC to afford 1-cyclopropyl-6-fluoro-2-(4-propylpyrimidin-5-yl)-1H-benzo[d]imidazole Ex. 14 (30 mg, 0.1 mmol, 22%) as dark brown sticky solid.

$^1$H NMR (400 MHz, $CD_3OD$): δ 9.24 (s, 1H), 8.94 (s, 1H), 7.71 (dd, J=8.9, 4.8 Hz, 1H), 7.50 (dd, J=8.7, 2.3 Hz, 1H), 7.18-7.11 (m, 1H), 3.55-3.49 (m, 1H), 2.87-2.81 (m, 2H), 1.78-1.69 (m, 2H), 1.07-1.01 (m, 2H), 0.88 (t, J=7.3 Hz, 3H), 0.74-0.68 (m, 2H).

LC-MS: m/z 297.0 [M+H]$^+$ at 2.23 RT (98.25% purity). HPLC: 99.03%.

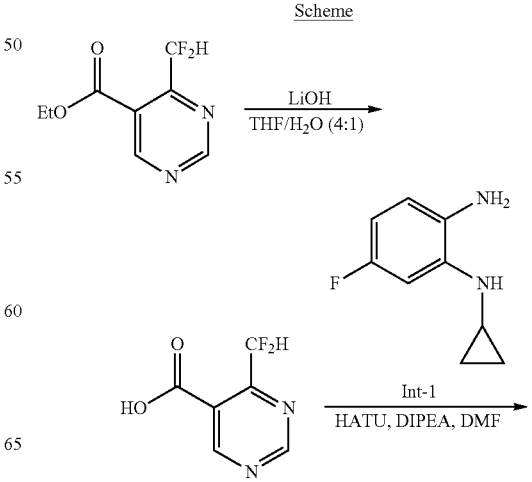

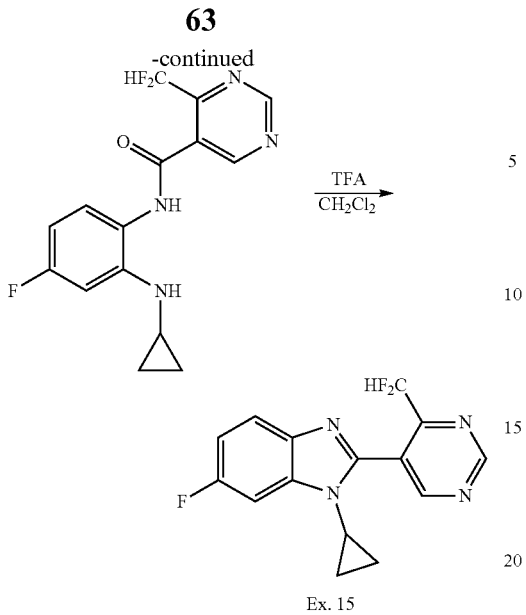

Ex. 15

4-(Difluoromethyl)pyrimidine-5-carboxylic acid

To a stirred solution of ethyl 4-(difluoromethyl)pyrimidine-5-carboxylate (300 mg, 1.48 mmol) in a mixture of THF:water (4:1, 3 mL) was added lithium hydroxide (187 mg, 4.45 mmol) at 0° C. The reaction mixture was warmed to room temperature and stirred for 3 h. The reaction mixture was acidified to pH 4-5 with 6 N HCl. The precipitated solid was filtered, washed with diethylether (2×15 mL) and dried under vacuum to obtain 4-(difluoromethyl)pyrimidine-5-carboxylic acid (210 mg, crude) as an off white solid which was used directly without further purification.

LC-MS: m/z 172.9 [M–H]$^+$ at 2.84 RT (86.81% purity).

N-(2-(Cyclopropylamino)-4-fluorophenyl)-4-(difluoromethyl)pyrimidine-5-carboxamide To a stirred solution of N1-cyclopropyl-5-fluorobenzene-1,2-diamine Int-1 (200 mg, 1.2 mmol) in DMF (2 mL) under an inert atmosphere was added 4-(difluoromethyl)pyrimidine-5-carboxylic acid (210 mg, 1.2 mmol), HATU (549 mg, 1.44 mmol) and ethyldiisopropylamine (0.84 mL, 4.82 mmol) at room temperature. The reaction mixture was stirred at room temperature for 16 h. After consumption of starting material (by TLC), the reaction mixture was quenched with water (30 mL). The obtained solid was filtered and washed with diethylether (2×15 mL) to afford N-(2-(cyclopropylamino)-4-fluorophenyl)-4-(difluoromethyl) pyrimidine-5-carboxamide (200 mg, crude) as black solid which was used directly without further purification.

LC-MS: m/z 322.9 [M+H]$^+$ at 2.72 RT (26.42% purity).

1-Cyclopropyl-2-(4-(difluoromethyl)pyrimidin-5-yl)-6-fluoro-1H-benzo[d]imidazole (Ex. 15)

To a stirred solution of N-(2-(cyclopropylamino)-4-fluorophenyl)-4-(difluoromethyl)pyrimidine-5-carboxamide (200 mg, crude) in CH$_2$Cl$_2$ (2 mL) under an inert atmosphere was added trifluoroacetic acid (0.4 mL) at room temperature. The reaction mixture was stirred at room temperature for 16 h. After consumption of starting material (by TLC), the volatiles were removed under reduced pressure. The residue was quenched with saturated sodium bicarbonate solution (20 mL) and extracted with EtOAc (2×20 mL). The combined organic extracts were dried over anhydrous Na$_2$SO$_4$ and concentrated under reduced pressure. The crude material was purified by preparative HPLC to afford 1-cyclopropyl-2-(4-(difluoromethyl)pyrimidin-5-yl)-6-fluoro-1H-benzo[d]imidazole Ex. 15 (25 mg, 0.08 mmol, 7% for two steps) as an off white solid.

$^1$H NMR (400 MHz, CD$_3$OD): δ 9.48 (s, 1H), 9.33 (s, 1H), 7.72 (dd, J=8.9, 4.8 Hz, 1H), 7.50 (dd, J=8.8, 2.3 Hz, 1H), 7.22-6.91 (m, 2H), 3.62-3.57 (m, 1H), 1.09-1.03 (m, 2H), 0.76-0.71 (m, 2H).

LC-MS: m/z 304.9 [M+H]$^+$ at 2.28 RT (95.93% purity).

HPLC: 97.98%.

Example 16

Scheme

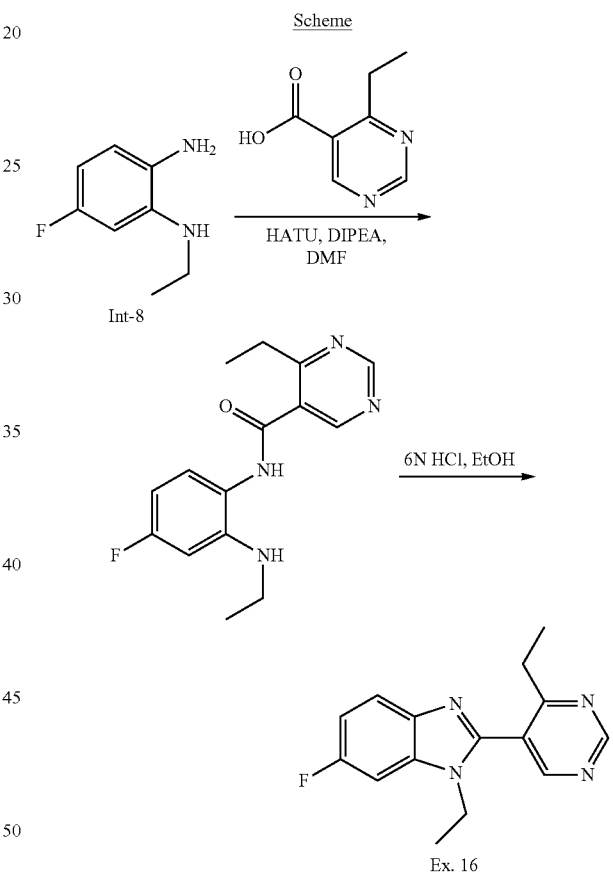

Ex. 16

4-Ethyl-N-(2-(ethylamino)-4-fluorophenyl)pyrimidine-5-carboxamide

To a stirred solution of 4-ethylpyrimidine-5-carboxylic acid (212 mg, 1.4 mmol) in DMF (4 mL) under an inert atmosphere was added N1-ethyl-5-fluorobenzene-1,2-diamine Int-8 (215 mg, 1.4 mmol), HATU (796 mg, 2.09 mmol) and ethyldiisopropylamine (0.97 mL, 5.58 mmol) at 0° C. The reaction mixture was warmed to room temperature and stirred for 16 h. After consumption of starting material (by TLC), the reaction mixture was quenched with water (30 mL). The precipitated solid was filtered, washed with n-pentane (2×10 mL) and dried under vacuum to afford 4-ethyl- N-(2-(ethylamino)-4-fluorophenyl)pyrimidine-5-carboxamide (150 mg, 0.52 mmol, 37%) as an off white solid.

$^1$H NMR (400 MHz, DMSO-$d_6$): δ 9.72 (s, 1H), 9.18 (s, 1H), 9.00 (s, 1H), 7.24 (dd, J=8.5, 6.5 Hz, 1H), 6.46 (dd, J=12.0, 2.8 Hz, 1H), 6.39 (td, J=8.5, 2.8 Hz, 1H), 5.28 (br t, J=4.5 Hz, 1H), 3.15-3.06 (m, 2H), 2.95-2.90 (m, 2H), 1.25 (t, J=7.5 Hz, 3H), 1.17 (t, J=7.1 Hz, 3H).

LC-MS: m/z 289.0 [M+H]$^+$ at 2.11 RT (80.42% purity).

1-Ethyl-2-(4-ethylpyrimidin-5-yl)-6-fluoro-1H-benzo[d]imidazole (Ex. 16)

To a stirred solution of 4-ethyl-N-(2-(ethylamino)-4-fluorophenyl)pyrimidine-5-carboxamide (150 mg, 0.52 mmol) in EtOH (1 mL) under an inert atmosphere was added 6 N HCl (4 mL) at 0° C. The reaction mixture was heated to reflux temperature and stirred for 2 h. After consumption of starting material (by TLC), the reaction mixture was quenched with saturated sodium carbonate solution (40 mL) and extracted with EtOAc (2×20 mL). The combined organic extracts were washed with water (15 mL), dried over anhydrous Na$_2$SO$_4$ and concentrated under reduced pressure. The crude material was purified by preparative HPLC to afford 1-ethyl-2-(4-ethylpyrimidin-5-yl)-6-fluoro-1H-benzo[d]imidazole Ex. 16 (30 mg, 0.11 mmol, 21%) as an off white solid.

$^1$H NMR (400 MHz, CD$_3$OD): δ 9.28 (s, 1H), 8.86 (s, 1H), 7.73 (dd, J=8.9, 4.6 Hz, 1H), 7.48 (dd, J=8.9, 2.4 Hz, 1H), 7.20-7.13 (m, 1H), 4.16 (q, J=7.3 Hz, 2H), 2.74 (q, J=7.5 Hz, 2H), 1.33 (t, J=7.3 Hz, 3H), 1.25 (t, J=7.5 Hz, 3H).

LC-MS: m/z 271.0 [M+H]$^+$ at 1.95 RT (98.04% purity).
HPLC: 97.12%.

Example 17

Scheme:

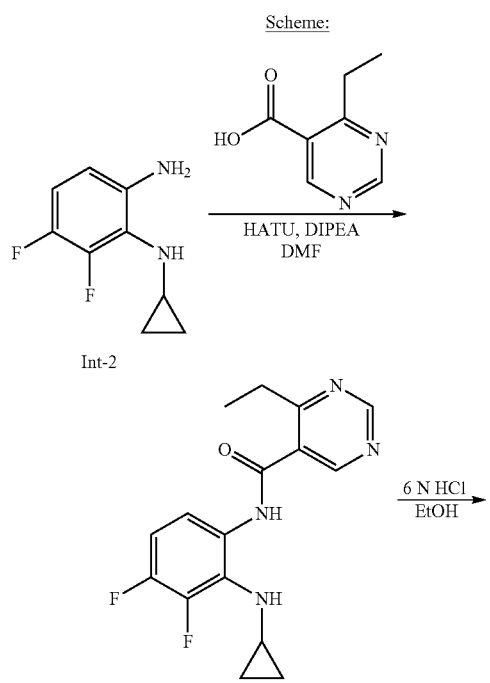

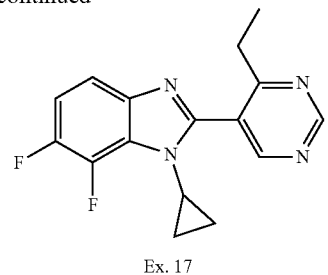

Ex. 17

N-(2-(Cyclopropylamino)-3,4-difluorophenyl)-4-ethylpyrimidine-5-carboxamide

To a stirred solution of N1-cyclopropyl-5,6-difluorobenzene-1,2-diamine Int-2 (200 mg, 1.09 mmol) in DMF (5 mL) under an inert atmosphere was added 4-ethylpyrimidine-5-carboxylic acid (198 mg, 1.3 mmol), HATU (496 mg, 1.3 mmol) and ethyldiisopropylamine (0.76 mL, 4.35 mmol) at room temperature. The reaction mixture was stirred at room temperature for 16 h. After consumption of starting material (by TLC), the reaction mixture was diluted with water (20 mL) and extracted with EtOAc (2×20 mL). The combined organic extracts were dried over anhydrous Na$_2$SO$_4$ and concentrated under reduced pressure to afford N-(2-(cyclopropylamino)-3,4-difluorophenyl)-4-ethylpyrimidine-5-carboxamide (120 mg, crude) as pale yellow solid which was used directly without further purification.

LC-MS: m/z 318.9 [M+H]$^+$ at 2.27 RT (84.81% purity).

1-Cyclopropyl-2-(4-ethylpyrimidin-5-yl)-6,7-difluoro-1H-benzo[d]imidazole (Ex. 17)

To a stirred solution of N-(2-(cyclopropylamino)-3,4-difluorophenyl)-4-ethylpyrimidine-5-carboxamide (100 mg, 0.31 mmol) in ethanol (1 mL) under an inert atmosphere was added 6 N HCl (1 mL) drop wise at room temperature. The reaction mixture was heated to 80° C. and stirred for 1 h. After consumption of starting material (by TLC), the reaction mixture was basified with saturated sodium carbonate solution to pH ~8 and extracted with EtOAc (2×20 mL). The combined organic extracts were dried over anhydrous Na$_2$SO$_4$ and concentrated under reduced pressure. The crude material was purified by silica gel column chromatography (eluent: 30% EtOAc/hexane) to afford 1-cyclopropyl-2-(4-ethylpyrimidin-5-yl)-6,7-difluoro-1H-benzo[d]imidazole Ex. 17 (20 mg, 0.07 mmol, 21%) as pale yellow solid.

$^1$H NMR (400 MHz, CD$_3$OD): δ 9.26 (s, 1H), 8.96 (s, 1H), 7.54-7.47 (m, 1H), 7.32-7.23 (m, 1H), 3.77-3.70 (m, 1H), 2.90 (q, J=7.5 Hz, 2H), 1.28 (t, J=7.5 Hz, 3H), 1.08-1.01 (m, 2H), 0.83-0.77 (m, 2H).

LC-MS: m/z 300.9 [M+H]$^+$ at 2.66 RT (97.28% purity).
HPLC: 97.68%.

Example 18

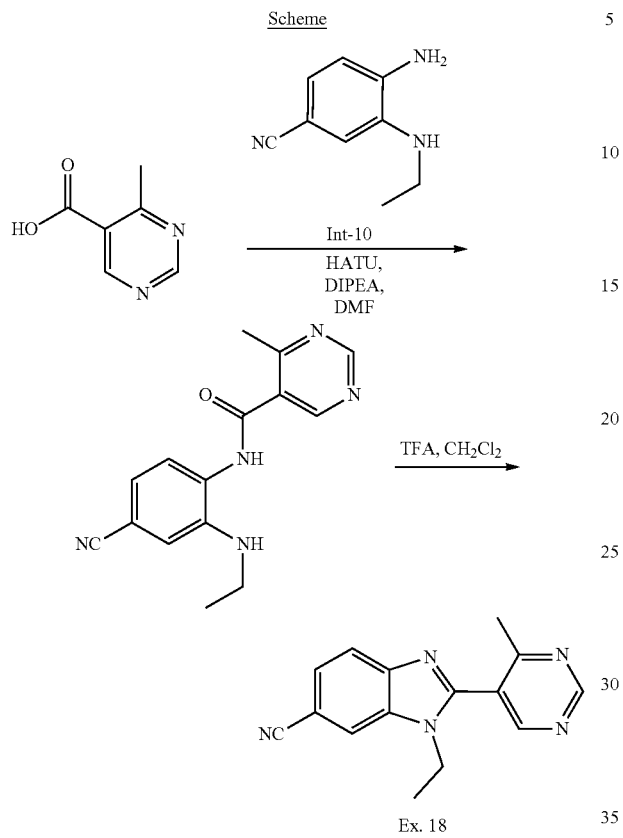

N-(4-Cyano-2-(ethylamino)phenyl)-4-methylpyrimidine-5-carboxamide

To a stirred solution of 4-methylpyrimidine-5-carboxylic acid (86 mg, 0.62 mmol) in DMF (2 mL) under an inert atmosphere was added HATU (354 mg, 0.93 mmol) at room temperature and stirred for 30 min. 4-Amino-3-(ethylamino) benzonitrile Int-10 (100 mg, 0.62 mmol) and ethyldiisopropylamine (0.22 mL, 1.24 mmol) were added to the reaction mixture at room temperature. The reaction mixture was stirred at room temperature for 16 h. After consumption of starting material (by TLC), the reaction mixture was diluted with water (20 mL) and extracted with EtOAc (2×20 mL). The combined organic extracts were dried over anhydrous $Na_2SO_4$ and concentrated under reduced pressure to afford N-(4-cyano-2-(ethylamino)phenyl)-4-methylpyrimidine-5-carboxamide (150 mg, crude) as a brown syrup which was used directly without further purification.

LC-MS: m/z 282.1 [M+H]$^+$ at 2.12 RT (65.87% purity).

1-Ethyl-2-(4-methylpyrimidin-5-yl)-1H-benzo[d]imidazole-6-carbonitrile (Ex. 18)

To a stirred solution of N-(4-cyano-2-(ethylamino)phenyl)-4-methylpyrimidine-5-carboxamide (150 mg, crude) in $CH_2Cl_2$ (5 mL) under an inert atmosphere was added trifluoroacetic acid (0.5 mL) drop wise at room temperature. The reaction mixture was stirred at room temperature for 16 h. After consumption of starting material (by TLC), the volatiles were removed under reduced pressure. The residue was diluted with $CH_2Cl_2$ (30 mL) and washed with saturated sodium bicarbonate solution (20 mL). The organic layer was separated, dried over anhydrous $Na_2SO_4$ and concentrated under reduced pressure. The crude material was purified by preparative HPLC to afford 1-ethyl-2-(4-methylpyrimidin-5-yl)-1H-benzo[d]imidazole-6-carbonitrile Ex. 18 (25 mg, 0.09 mmol, 15% for two steps) as an off white solid.

$^1$H NMR (400 MHz, DMSO-$d_6$): δ 9.28 (s, 1H), 8.96 (s, 1H), 8.45-8.43 (m, 1H), 7.91 (dd, J=8.4, 0.6 Hz, 1H), 7.69 (dd, J=8.3, 1.6 Hz, 1H), 4.21 (q, J=7.3 Hz, 2H), 2.43 (s, 3H), 1.23 (t, J=7.2 Hz, 3H).

LC-MS: m/z 264.0 [M+H]$^+$ at 1.78 RT (99.49% purity).

HPLC: 98.69%.

Example 19

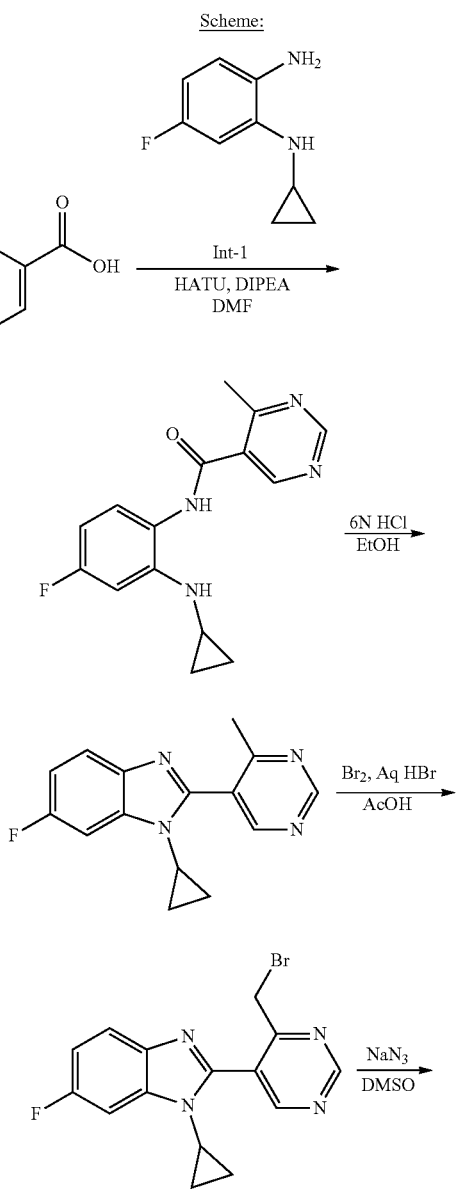

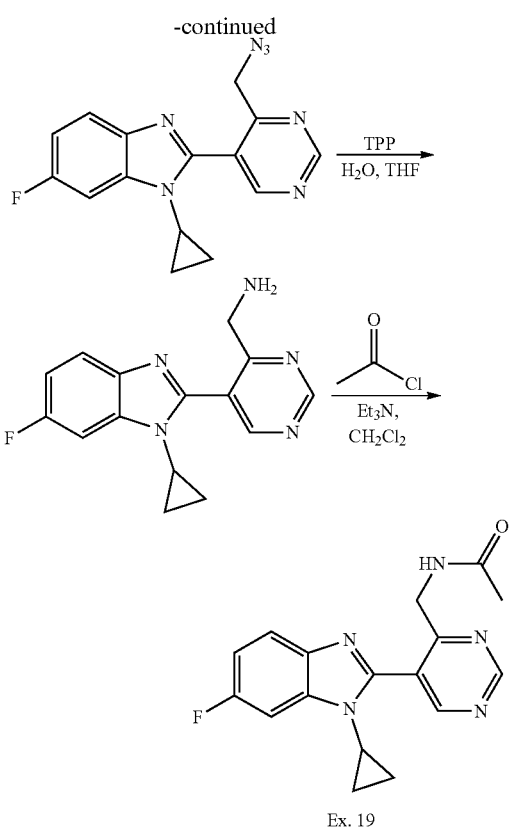

Ex. 19

N-(2-(Cyclopropylamino)-4-fluorophenyl)-4-methylpyrimidine-5-carboxamide

To a stirred solution of 4-methylpyrimidine-5-carboxylic acid (2 g, 12.04 mmol) in DMF (20 mL) under an inert atmosphere was added Int-1 (1.99 g, 14.45 mmol), HATU (5.5 g, 14.15 mmol) and diisopropylethylamine (8.6 mL, 48.19 mmol) at 0° C. The reaction mixture was stirred at room temperature for 16 h. After consumption of starting material (by TLC), the reaction mixture was diluted with water (100 mL) and extracted with EtOAc (2×100 mL). The combined organic extracts were washed with water (100 mL), dried over anhydrous $Na_2SO_4$ and concentrated under reduced pressure. The crude material was purified by silica gel column chromatography (eluent: 20% EtOAc/hexane) to afford N-(2-(cyclopropylamino)-4-fluorophenyl)-4-methylpyrimidine-5-carboxamide (2 g, 6.99 mmol, 58%) as an off-white solid.

$^1$H NMR (400 MHz, $CD_3OD$): δ 9.09 (s, 1H), 8.95 (s, 1H), 7.22 (dd, J=8.7, 6.0 Hz, 1H), 6.86 (dd, J=11.5, 2.9 Hz, 1H), 6.44 (dt, J=8.4, 2.9 Hz, 1H), 2.70 (s, 3H), 2.44-2.41 (m, 1H), 0.82-0.75 (m, 2H), 0.55-0.46 (m, 2H)

1-Cyclopropyl-6-fluoro-2-(4-methylpyrimidin-5-yl)-1H-benzo[d]imidazole

To a stirred solution of N-(2-(cyclopropylamino)-4-fluorophenyl)-4-methylpyrimidine-5-carboxamide (2 g, 6.99 mmol) in EtOH (25 mL) under an inert atmosphere was added 6N HCl (36 mL) at room temperature. The reaction mixture was stirred at 80° C. for 1 h. After consumption of starting material (by TLC), the reaction mixture was diluted with saturated sodium bicarbonate solution (100 mL) and extracted with EtOAc (2×100 mL). The combined organic extracts were dried over anhydrous $Na_2SO_4$ and concentrated under reduced pressure. The crude material was purified by silica gel column chromatography (eluent: 2% MeOH/$CH_2C_2$) to afford 1-cyclopropyl-6-fluoro-2-(4-methylpyrimidin-5-yl)-1H-benzo[d]imidazole (1.5 g, 5.59 mmol, 80%) as an off white solid.

$^1$H NMR (400 MHz, $CDCl_3$): δ 9.46 (s, 1H), 9.34 (s, 1H), 7.81 (dd, J=8.9, 4.8 Hz, 1H), 7.35 (dd, J=8.4, 2.4 Hz, 1H), 7.15 (dt, J=9.2, 2.4 Hz, 1H), 3.75-3.70 (m, 1H), 1.56 (s, 3H), 1.22-1.16 (m, 2H), 0.73-0.67 (m, 2H)

2-(4-(Bromomethyl)pyrimidin-5-yl)-1-cyclopropyl-6-fluoro-1H-benzo[d]imidazole To a stirred solution of 1-cyclopropyl-6-fluoro-2-(4-methylpyrimidin-5-yl)-1H-benzo[d]imidazole (200 mg, 0.74 mmol) in AcOH (2 mL) under an inert atmosphere was added acetic acid (2 mL) and aqueous HBr (catalytic amount) at 0° C. The reaction mixture was stirred at 0° C. for 30 min. After consumption of starting material (by TLC), the reaction mixture was diluted with saturated sodium bicarbonate solution (50 mL) and extracted with $CH_2Cl_2$ (2×50 mL). The combined organic extracts were dried over anhydrous $Na_2SO_4$ and concentrated under reduced pressure. The crude material was purified by silica gel column chromatography (eluent: 2% MeOH/$CH_2Cl_2$) to afford 2-(4-(bromomethyl)pyrimidin-5-yl)-1-cyclopropyl-6-fluoro-1H-benzo[d]imidazole (180 mg, crude) as a yellow solid.

LC-MS: m/z 348.9 [M+H]$^+$ at 2.29 RT (21.13% purity).

2-(4-(Azidomethyl)pyrimidin-5-yl)-1-cyclopropyl-6-fluoro-1H-benzo[d]imidazole To a stirred solution of 2-(4-(bromomethyl)pyrimidin-5-yl)-1-cyclopropyl-6-fluoro-1H-benzo[d]imidazole (180 mg, 0.51 mmol) in dimethylsulfoxide (DMSO) (2 mL) under an inert atmosphere was added sodium azide (101.1 mg, 1.55 mmol) at 0° C. The reaction mixture was stirred at room temperature for 2 h. After consumption of starting material (by TLC), the reaction mixture was diluted with water (30 mL) and extracted with EtOAc (2×30 mL). The combined organic extracts were dried over anhydrous $Na_2SO_4$ and concentrated under reduced pressure. The crude material was purified by silica gel column chromatography (eluent: 2% MeOH/$CH_2C_2$) to afford 2-(4-(azidomethyl)pyrimidin-5-yl)-1-cyclopropyl-6-fluoro-1H-benzo[d]imidazole (35 mg, 0.11 mmol, 21%) as a yellow solid.

$^1$H NMR (400 MHz, $CDCl_3$): δ 9.35 (s, 1H), 9.01 (s, 1H), 7.73 (dd, J=8.8, 4.8 Hz, 1H), 7.32 (dd, J=8.5, 2.4 Hz, 1H), 7.14-7.07 (m, 1H), 4.75 (s, 2H), 3.47-3.42 (m, 1H), 1.14-1.06 (m, 2H), 0.77-0.71 (m, 2H)

(5-(1-Cyclopropyl-6-fluoro-1H-benzo[d]imidazol-2-yl)pyrimidin-4-yl)methanamine To a stirred solution of 2-(4-(azidomethyl)pyrimidin-5-yl)-1-cyclopropyl-6-fluoro-1H-benzo[d]imidazole (40 mg, 0.12 mmol) in THF:water (4:1, 1 mL) under an inert atmosphere was added triphenylphosphine (TPP) (101.7 mg, 0.38 mmol) at 0° C. The reaction mixture was stirred at room temperature for 2 h. After consumption of starting material (by TLC), the volatiles were evaporated under reduced pressure. The residue was dissolved in ethanolic HCl and concentrated under reduced pressure. The crude was washed with ether (3×10 mL) and concentrated under reduced pressure to obtain (5-(1-cyclopropyl-6-fluoro-1H-benzo[d]

imidazol-2-yl)pyrimidin-4-yl)methanamine (50 mg as HCl salt) as a brown solid which was used directly without further purification.

LC-MS: m/z 284 [M+H]⁺ at 1.54 RT (40.51% purity).

N-((5-(1-Cyclopropyl-6-fluoro-1H-benzo[d]imidazol-2-yl)pyrimidin-4-yl)methyl)acetamide (Ex. 19)

To a stirred solution of (5-(1-cyclopropyl-6-fluoro-1H-benzo[d]imidazol-2-yl)pyrimidin-4-yl)methanamine (110 mg, 0.34 mmol) in CH$_2$Cl$_2$ (2 mL) under an inert atmosphere was added triethylamine (0.187 mL, 2.38 mmol) and acetyl chloride (40.5 mg, 0.51 mmol) at 0° C. The reaction mixture was stirred at room temperature for 2 h. After consumption of starting material (by TLC), the reaction mixture was diluted with saturated sodium bicarbonate solution (10 mL) and extracted with CH$_2$Cl$_2$ (2×10 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford N-((5-(1-cyclopropyl-6-fluoro-1H-benzo[d]imidazol-2-yl)pyrimidin-4-yl) methyl) acetamide Ex. 19 (18 mg, 0.05 mmol, 16%) as an off-white solid.

¹H NMR (400 MHz, CD$_3$OD): δ 9.27 (s, 1H), 9.07 (s, 1H), 7.71 (dd, J=8.8, 4.7 Hz, 1H), 7.50 (dd, J=8.8, 2.5 Hz, 1H), 7.18-7.08 (m, 1H), 4.57 (s, 2H), 3.67-3.58 (m, 1H), 1.87 (s, 3H), 1.06-0.99 (m, 2H), 0.83-0.77 (m, 2H)

LC-MS: m/z 325.9 [M+H]⁺ at 1.88 RT (97.75% purity). HPLC: 94.23%.

Example 20

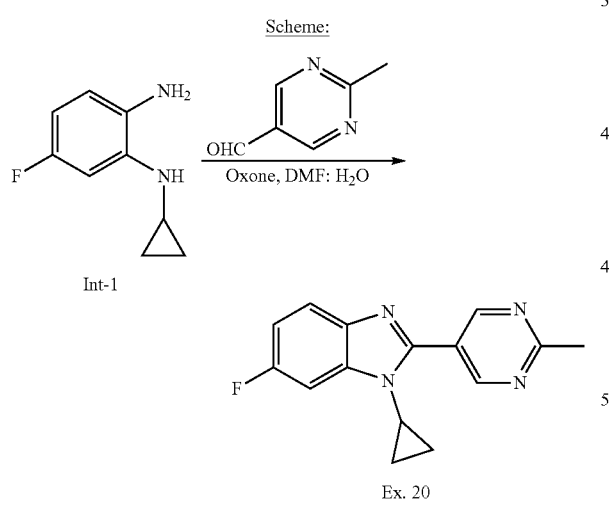

Ex. 20

1-Cyclopropyl-6-fluoro-2-(2-methylpyrimidin-5-yl)-1H-benzo[d]imidazole (Ex. 20)

To a stirred solution of N1-cyclopropyl-5-fluorobenzene-1,2-diamine Int-1 (200 mg, 1.20 mmol) in DMF (2 mL) and water (0.2 mL) under an inert atmosphere was added 2-methylpyrimidine-5-carbaldehyde (176 mg, 1.44 mmol) and oxone (364 mg, 2.40 mmol) at room temperature. The reaction mixture was stirred at room temperature for 2 h. After consumption of starting material (by TLC), the reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford 1-cyclopropyl-6-fluoro-2-(2-methylpyrimidin-5-yl)-1H-benzo[d]imidazole Ex. 20 (70 mg, 0.26 mmol, 22%) as an off white solid.

¹H NMR (400 MHz, CD$_3$OD): δ 9.27 (s, 2H), 7.69 (dd, J=8.8, 4.8 Hz, 1H), 7.48 (dd, J=8.9, 2.4 Hz, 1H), 7.16-7.07 (m, 1H), 3.81-3.75 (m, 1H), 2.81 (s, 3H), 1.27-1.19 (m, 2H), 0.83-0.78 (m, 2H)

LC-MS: m/z 269 [M+H]⁺ at 2.24 RT (99.87% purity). HPLC: 99.35%.

Example 21

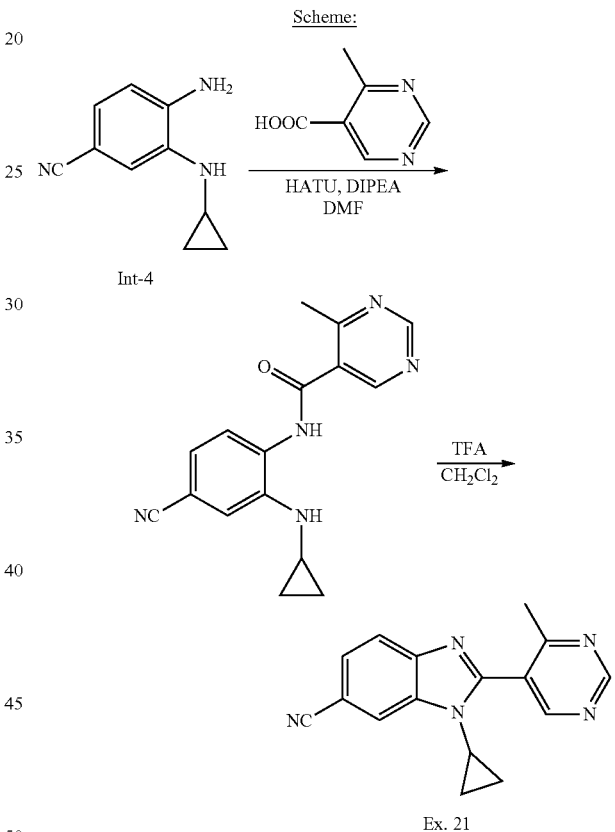

Ex. 21

N-(4-Cyano-2-(cyclopropylamino)phenyl)-4-methylpyrimidine-5-carboxamide

To a stirred solution of 4-amino-3-(cyclopropylamino) benzonitrile Int-4 (300 mg, 1.73 mmol) in DMF (5 mL) under an inert atmosphere was added 4-methylpyrimidine-5-carboxylic acid (239 mg, 1.73 mmol) HATU (988 mg, 2.60 mmol) and ethyldiisopropylamine (1 mL, 5.19 mmol) at room temperature. The reaction mixture was stirred at room temperature for 16 h. After consumption of starting material (by TLC), the reaction mixture was diluted with water (20 mL) and extracted with EtOAc (2×30 mL). The combined organic extracts were dried over anhydrous Na$_2$SO$_4$ and concentrated under reduced pressure. The crude material was purified by silica gel column chromatography (eluent: 40% EtOAc/hexane) to afford N-(4-cyano-2-(cyclopropylamino)phenyl)-4-methylpyrimidine-5-carboxamide (300 mg, 1.02 mmol, 30%) as orange solid.

$^1$H NMR (500 MHz, DMSO-d$_6$): δ 9.83 (s, 1H), 9.14 (s, 1H), 8.99 (s, 1H), 7.65 (d, J=8.1 Hz, 1H), 7.31 (s, 1H), 7.12 (d, J=8.1 Hz, 1H), 6.12 (brs, 1H), 2.59 (s, 3H), 2.45-2.42 (m, 1H), 0.83-0.74 (m, 2H), 0.51-0.40 (m, 2H)

1-Cyclopropyl-2-(4-methylpyrimidin-5-yl)-1H-benzo[d]imidazole-6-carbonitrile (Ex. 21)

To a stirred solution of N-(4-cyano-2-(cyclopropylamino)phenyl)-4-methylpyrimidine-5-carboxamide (300 mg, 1.02 mmol) in CH$_2$Cl$_2$ (10 mL) under an inert atmosphere was added trifluoro acetic acid (2 mL) at 0° C. The reaction mixture was warmed to room temperature and stirred for 16 h. After consumption of starting material (by TLC), the volatiles were evaporated under reduced pressure. The residue was diluted with saturated sodium bicarbonate solution (30 mL) and extracted with CH$_2$Cl$_2$ (2×30 mL). The combined organic extracts were dried over anhydrous Na$_2$SO$_4$ and concentrated under reduced pressure. The crude material purified by preparative HPLC to afford 1-cyclopropyl-2-(4-methylpyrimidin-5-yl)-1H-benzo[d]imidazole-6-carbonitrile Ex. 21 (160 mg, 0.58 mmol, 57%) as an off white solid.

$^1$H NMR (400 MHz, DMSO-d$_6$): δ 9.23 (s, 1H), 9.10 (s, 1H), 8.29 (s, 1H), 7.91 (d, J=8.4 Hz, 1H), 7.70 (dd, J=8.3, 1.6 Hz, 1H), 3.71-3.66 (m, 1H), 2.57 (s, 3H), 1.09-0.95 (m, 2H), 0.75-0.64 (m, 2H)

LC-MS: m/z 276 [M+H]$^+$ at 1.88 RT (99.46% purity).
HPLC: 99.33%.

Example 22

Scheme:

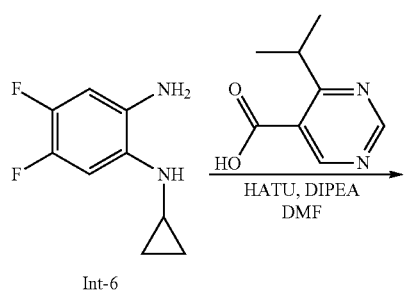

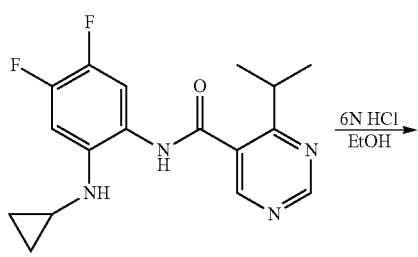

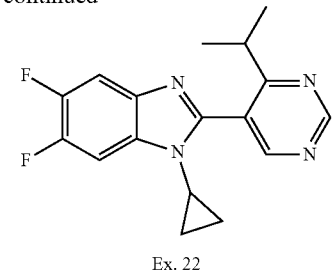

Ex. 22

N-(2-(Cyclopropylamino)-4,5-difluorophenyl)-4-isopropylpyrimidine-5-carboxamide

To a stirred solution of Int-6 (100 mg, 0.54 mmol) in DMF (3 mL) under an inert atmosphere was added 4-isopropylpyrimidine-5-carboxylic acid (108 mg, 0.65 mmol) HATU (250 mg, 0.65 mmol) and ethyldiisopropylamine (0.39 mL, 2.17 mmol) at 0° C. The reaction mixture was warmed to room temperature and stirred for 16 h. After consumption of starting material (by TLC), the reaction mixture was quenched with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 50% EtOAc/hexane) to afford N-(2-(cyclopropylamino)-4,5-difluorophenyl)-4-isopropylpyrimidine-5-carboxamide (100 mg, 0.30 mmol, 55%) as an off-white solid.

$^1$H NMR (500 MHz, DMSO-d$_6$): δ 9.76 (s, 1H), 9.21 (s, 1H), 8.97 (s, 1H), 7.53-7.49 (m, 1H), 6.97-6.93 (m, 1H), 5.76 (s, 1H), 3.43-3.38 (m, 1H), 2.39-2.37 (m, 1H), 1.24 (d, J=6.7 Hz, 6H), 0.79-0.72 (m, 2H), 0.43-0.35 (m, 2H)

1-Cyclopropyl-5,6-difluoro-2-(4-isopropylpyrimidin-5-yl)-1H-benzo[d]imidazole (Ex. 22)

To a stirred solution of N-(2-(cyclopropylamino)-4,5-difluorophenyl)-4-isopropylpyrimidine-5-carboxamide (100 mg, 0.30 mmol) in EtOH (1 mL) under an inert atmosphere was added 6N HCl (3 mL) at 0° C. The reaction mixture was stirred at 80° C. for 45 min. After consumption of starting material (by TLC), the reaction mixture was diluted with saturated sodium bicarbonate solution (10 mL) and extracted with EtOAc (2×10 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford 1-cyclopropyl-5,6-difluoro-2-(4-isopropylpyrimidin-5-yl)-1H-benzo[d]imidazole Ex. 22 (40 mg, 0.12 mmol, 42%) as an off white solid.

$^1$H NMR (500 MHz, DMSO-d$_6$): δ 9.30 (s, 1H), 9.04 (s, 1H), 7.89-7.72 (m, 2H), 3.59-3.57 (m, 1H), 3.33-3.23 (m, 1H), 1.19 (d, J=6.9 Hz, 6H), 1.02-0.94 (m, 2H), 0.66-0.57 (m, 2H)

LC-MS: m/z 314.9 [M+H]$^+$ at 2.88 RT (98.43% purity).
HPLC: 98.84%.

Example 23

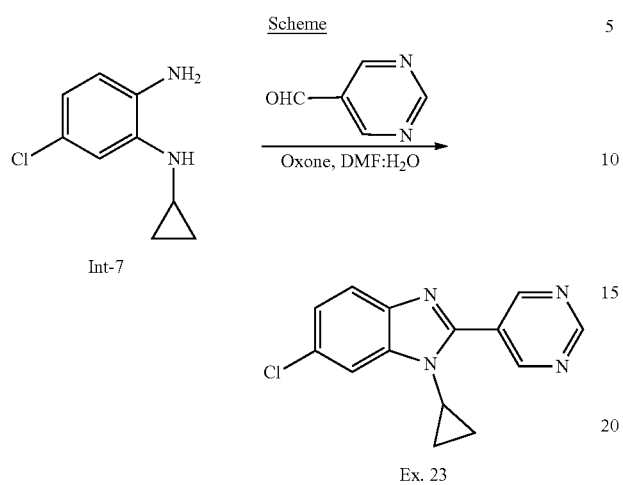

Ex. 23

6-Chloro-1-cyclopropyl-2-(pyrimidin-5-yl)-1H-benzo[d]imidazole (Ex. 23)

To a stirred solution of 5-chloro-N1-cyclopropylbenzene-1,2-diamine Int-7 (100 mg, 0.54 mmol) in DMF (3 mL) and water (0.3 mL) under an inert atmosphere was added pyrimidine-5-carbaldehyde (72 mg, 0.66 mmol) and oxone (167 mg, 1.09 mmol) at room temperature. The reaction mixture was stirred at room temperature for 2 h. After consumption of starting material (by TLC), the reaction mixture was diluted with water (20 mL) which afforded a solid that was filtered and dried under reduced pressure. The crude material was purified by silica gel column chromatography (eluent: 2% MeOH/CH$_2$Cl$_2$) to afford 6-chloro-1-cyclopropyl-2-(pyrimidin-5-yl)-1H-benzo[d]imidazole Ex. 23 (50 mg, 0.18 mmol, 38%) as brown solid.

$^1$H NMR (400 MHz, DMSO-d$_6$): δ 9.41 (s, 2H), 9.35 (s, 1H), 7.78-7.76 (m, 1H), 7.75 (s, 1H), 7.32 (dd, J=8.5, 2.0 Hz, 1H), 3.90-3.85 (m, 1H), 1.20-1.11 (m, 2H), 0.78-0.71 (m, 2H)

LC-MS: m/z 271.2 [M+H]$^+$ at 3.85 RT (99.76% purity).
HPLC: 99.61%

Example 24

Scheme:

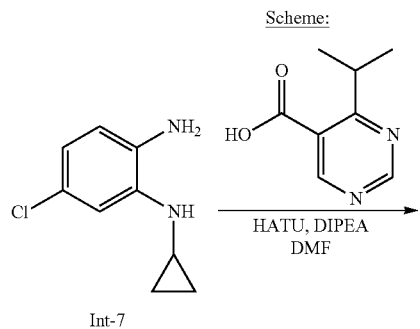

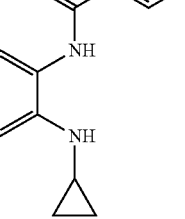

Ex.24

N-(4-Chloro-2-(cyclopropylamino)phenyl)-4-isopropylpyrimidine-5-carboxamide

To a stirred solution of 5-chloro-N1-cyclopropylbenzene-1,2-diamine Int-7 (150 mg, 0.82 mmol) in DMF (3 mL) under an inert atmosphere was added 4-isopropylpyrimidine-5-carboxylic acid (137 mg, 0.82 mmol), HATU (470 mg, 1.23 mmol) and diisopropylethylamine (0.28 mL, 1.65 mmol) at 0° C. The reaction mixture was stirred at room temperature for 16 h. After consumption of starting material (by TLC), the reaction mixture was diluted with water (20 mL) and extracted with EtOAc (2×20 mL). The combined organic extracts were washed with water (20 mL), dried over anhydrous Na$_2$SO$_4$ and concentrated under reduced pressure. The crude material was purified by silica gel column chromatography (eluent: 50% EtOAc/hexane) to afford N-(4-chloro-2-(cyclopropylamino)phenyl)-4-isopropylpyrimidine-5-carboxamide (140 mg, 0.42 mmol, 52%) as an off-white solid.

$^1$H NMR (400 MHz, DMSO-d$_6$): δ 9.72 (s, 1H), 9.21 (s, 1H), 8.98 (s, 1H), 7.36 (d, J=8.4 Hz, 1H), 7.00 (s, 1H), 6.71 (dd, J=8.3, 2.4 Hz, 1H), 3.44-3.37 (m, 2H), 2.43-2.38 (m, 1H), 1.24 (d, J=6.7 Hz, 6H), 0.83-0.64 (m, 2H), 0.49-0.36 (m, 2H)

6-Chloro-1-cyclopropyl-2-(4-isopropylpyrimidin-5-yl)-1H-benzo[d]imidazole (Ex. 24)

To a stirred solution of N-(4-chloro-2-(cyclopropylamino)phenyl)-4-isopropylpyrimidine-5-carboxamide (140 mg, 0.42 mmol) in EtOH (5 mL) under an inert atmosphere was added 6N HCl (3 mL) at room temperature. The reaction mixture was stirred at 80° C. for 2 h. After consumption of starting material (by TLC), the reaction mixture was diluted with saturated sodium bicarbonate solution (20 mL) and extracted with CH$_2$Cl$_2$ (2×20 mL). The combined organic extracts were dried over anhydrous Na$_2$SO$_4$ and concentrated under reduced pressure. The crude material was purified by silica gel column chromatography (eluent: 40% EtOAc/Hexane) to afford 6-chloro-1-cyclopropyl-2-(4-isopropylpyrimidin-5-yl)-1H-benzo[d]imidazole Ex. 24 (30 mg, 0.09 mmol, 23%) as an off white solid.

$^1$H NMR (400 MHz, CD$_3$OD): δ 9.27 (s, 1H), 8.90 (s, 1H), 7.79 (s, 1H), 7.69 (d, J=8.7 Hz, 1H), 7.35 (dd, J=8.6, 1.9 Hz, 1H), 3.53-3.42 (m, 1H), 3.17-3.12 (m, 1H), 1.27 (d, J=6.8 Hz, 6H), 1.09-1.00 (m, 2H), 0.79-0.67 (m, 2H)

LC-MS: m/z 313 [M+H]$^+$ at 2.46 RT (93.63% purity).

HPLC: 94.18%.

Example 25

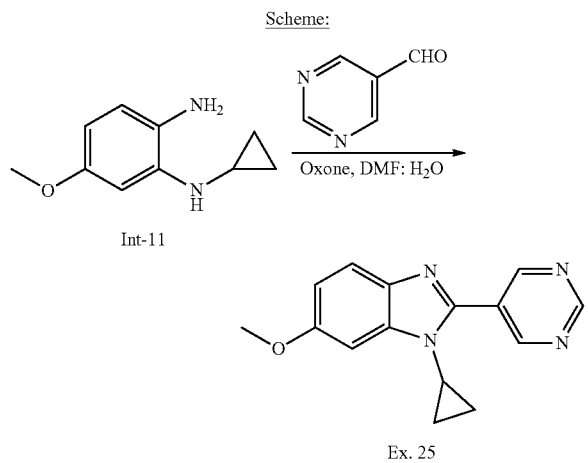

1-Cyclopropyl-6-methoxy-2-(pyrimidin-5-yl)-1H-benzo[d]imidazole (Ex. 25)

To a stirred solution of N-cyclopropyl-5-methoxy-2-methylaniline Int-11 (200 mg, 1.12 mmol) in DMF (4 mL) and water (0.4 mL) under an inert atmosphere was added pyrimidine-5-carbaldehyde (182 mg, 1.68 mmol) and oxone (690 mg, 2.24 mmol) at room temperature. The reaction mixture was stirred at room temperature for 2 h. After consumption of starting material (by TLC), the reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford 1-cyclopropyl-6-methoxy-2-(pyrimidin-5-yl)-1H-benzo[d]imidazole Ex. 25 (95 mg, 0.35 mmol, 32%) as an off white solid.

$^1$H NMR (400 MHz, CD$_3$OD): δ 9.36 (s, 2H), 9.28 (s, 1H), 7.60 (d, J=8.8 Hz, 1H), 7.20 (d, J=2.3 Hz, 1H), 6.98 (dd, J=8.8, 2.4 Hz, 1H), 3.92 (s, 3H), 3.78-3.76 (m, 1H), 1.25-1.22 (m, 2H), 0.84-0.72 (m, 2H)

LC-MS: m/z 267 [M+H]$^+$ at 1.70 RT (98.22% purity).

HPLC: 99.94%.

Example 26

Scheme

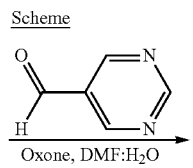

Ex. 26

1-Cyclopropyl-6-(methylsulfonyl)-2-(pyrimidin-5-yl)-1H-benzo[d]imidazole (Ex. 26)

To a stirred solution of N1-cyclopropyl-5-(methylsulfonyl) benzene-1,2-diamine Int-12 (100 mg, 0.44 mmol) in DMF (2 mL) and water (2 mL) under an inert atmosphere was added pyrimidine-5-carbaldehyde (48 mg, 0.44 mmol) and oxone (149 mg, 0.48 mmol) at room temperature. The reaction mixture was stirred at room temperature for 6 h. After consumption of starting material (by TLC), the reaction mixture was diluted with water (20 mL) and extracted with EtOAc (2×20 mL). The combined organic extracts were dried over anhydrous Na$_2$SO$_4$ and concentrated under reduced pressure. The crude material was purified by preparative HPLC to afford 1-cyclopropyl-6-(methylsulfonyl)-2-(pyrimidin-5-yl)-1H-benzo[d]imidazole Ex. 26 (40 mg, 0.12 mmol, 29%) as an off white solid.

$^1$H NMR (400 MHz, DMSO-d$_6$): δ 9.46 (s, 2H), 9.39 (s, 1H), 8.23 (s, 1H), 7.98 (d, J=8.5 Hz, 1H), 7.85 (dd, J=8.5, 1.6 Hz, 1H), 4.00-3.97 (m, 1H), 3.29 (s, 3H), 1.27-1.12 (m, 2H), 0.88-0.78 (m, 2H)

LC-MS: m/z 314.9 [M+H]$^+$ at 1.71 RT (96.70% purity).

HPLC: 97.88%.

Example 27

Scheme

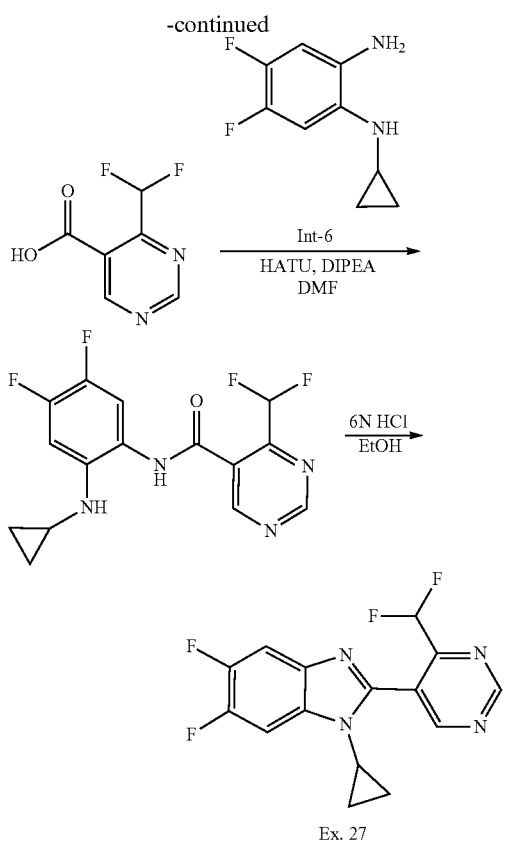

Ex. 27

4-(Difluoromethyl)pyrimidine-5-carboxylic acid

To a stirred solution of ethyl 4-(difluoromethyl)pyrimidine-5-carboxylate (150 mg, 0.74 mmol) in THF:water (4:1, 1 mL) was added lithium hydroxide (94 mg, 2.22 mmol) at 0° C. The reaction mixture was stirred at 0° C. for 2 h. The reaction mixture was warmed to room temperature and stirred for 3 h. After consumption of starting material (by TLC), the volatiles were removed under reduced pressure. The residue was diluted with ether (5 mL) and neutralized with 6 N HCl to pH ~6 which resulted in the formation of a solid. The solid was filtered and dried under reduced pressure to obtain 4-(difluoromethyl)pyrimidine-5-carboxylic acid (120 mg, crude) as an off white solid which was used directly without further purification.

$^1$H NMR (500 MHz, DMSO-$d_6$): δ 9.50 (s, 1H), 9.33 (s, 1H), 7.63 (t, J=50 Hz, 1H).

N-(2-(Cyclopropylamino)-4,5-difluorophenyl)-4-(difluoromethyl)pyrimidine-5-carboxamide To a stirred solution of N1-cyclopropyl-4,5-difluorobenzene-1,2-diamine Int-6 (120 mg, 0.65 mmol) in DMF (3 mL) under an inert atmosphere was added 4-(difluoromethyl)pyrimidine-5-carboxylic acid (113 mg, 0.65 mmol), HATU (297 mg, 0.78 mmol) and ethyldiisopropylamine (0.47 mL, 2.60 mmol) at 0° C. The reaction mixture was warmed to room temperature and stirred for 16 h. After consumption of starting material (by TLC), the reaction mixture was quenched with water (20 mL) and extracted with EtOAc (2×20 mL). The combined organic extracts were dried over anhydrous Na$_2$SO$_4$ and concentrated under reduced pressure to obtain N-(2-(cyclopropylamino)-4,5-difluorophenyl)-4-(difluoromethyl)pyrimidine-5-carboxamide (100 mg, crude) as an off-white solid which was used directly without further purification.

LC-MS: m/z 340.9 [M+H]$^+$ at 2.40 RT (48.29% purity).

1-Cyclopropyl-2-(4-(difluoromethyl)pyrimidin-5-yl)-5,6-difluoro-1H-benzo[d]imidazole (Ex. 27)

To a stirred solution of N-(2-(cyclopropylamino)-4,5-difluorophenyl)-4-(difluoromethyl)pyrimidine-5-carboxamide (100 mg, 0.29 mmol) in EtOH (0.3 mL) under an inert atmosphere was added 6N HCl (2 mL) at room temperature. The reaction mixture was stirred at 80° C. for 45 min. After consumption of starting material (by TLC), the reaction mixture was diluted with saturated sodium bicarbonate solution (10 mL) and extracted with EtOAc (2×10 mL). The combined organic extracts were dried over anhydrous Na$_2$SO$_4$ and concentrated under reduced pressure. The crude material was purified by preparative HPLC to afford 1-cyclopropyl-2-(4-(difluoromethyl)pyrimidin-5-yl)-5,6-difluoro-1H-benzo[d]imidazole Ex. 27 (20 mg, 0.06 mmol, 21%) as an off white solid.

$^1$H NMR (400 MHz, CD$_3$OD): δ 9.49 (s, 1H), 9.33 (s, 1H), 7.72-7.68 (m, 1H), 7.64-7.60 (m, 1H), 7.08 (t, J=56.8 Hz, 1H), 3.69-3.55 (m, 1H), 1.13-1.00 (m, 2H), 0.78-0.67 (m, 2H)

LC-MS: m/z 322.9 [M+H]$^+$ at 2.29 RT (99.87% purity).

HPLC: 98.13%.

Example 28

Scheme:

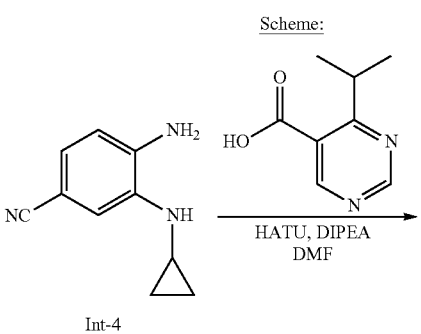

Int-4

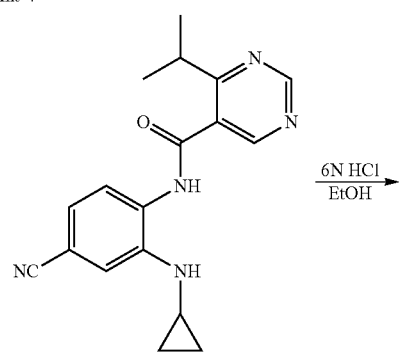

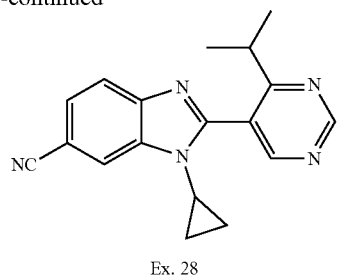

Ex. 28

N-(4-Cyano-2-(cyclopropylamino)phenyl)-4-isopropylpyrimidine-5-carboxamide

To a stirred solution of 4-amino-3-(cyclopropylamino) benzonitrile Int-4 (200 mg, 1.15 mmol) in DMF (10 mL) under an inert atmosphere was added 4-ethylpyrimidine-5-carboxylic acid (192 mg, 1.15 mmol), HATU (658 mg, 1.73 mmol) and diisopropylethylamine (0.4 mL, 2.31 mmol) at 0° C. The reaction mixture was stirred at room temperature for 16 h. After consumption of starting material (by TLC), the reaction mixture was diluted with water (20 mL) and extracted with EtOAc (2×20 mL). The combined organic extracts were washed with water (20 mL), dried over anhydrous $Na_2SO_4$ and concentrated under reduced pressure. The crude material was purified by silica gel column chromatography (eluent: 30-40% EtOAc/hexane) to afford N-(4-cyano-2-(cyclopropylamino)phenyl)-4-isopropylpyrimidine-5-carboxamide (185 mg, 0.57 mmol, 48%) as an off-white solid.

$^1$H NMR (500 MHz, DMSO-$d_6$): δ 9.89 (s, 1H), 9.23 (s, 1H), 8.98 (s, 1H), 7.70 (d, J=8.1 Hz, 1H), 7.32 (s, 1H), 7.13 (d, J=8.1 Hz, 1H), 6.06 (s, 1H), 3.41-3.36 (m, 1H), 2.44 (brs, 1H), 1.24 (d, J=6.4 Hz, 6H), 0.81-0.79 (m, 2H), 0.47-0.37 (m, 2H)

1-Cyclopropyl-2-(4-isopropylpyrimidin-5-yl)-1H-benzo[d]imidazole-6-carbonitrile (Ex. 28)

To a stirred solution of N-(4-cyano-2-(cyclopropylamino) phenyl)-4-isopropylpyrimidine-5-carboxamide (180 mg, 0.56 mmol) in EtOH (2 mL) under an inert atmosphere was added 6N HCl (1 mL) at room temperature. The reaction mixture was stirred at 80° C. for 20 min. After consumption of starting material (by TLC), the reaction mixture was diluted with saturated sodium bicarbonate solution (20 mL) and extracted with $CH_2Cl_2$ (2×20 mL). The combined organic extracts were dried over anhydrous $Na_2SO_4$ and concentrated under reduced pressure. The crude material was purified by silica gel column chromatography (eluent: 30-40% EtOAc/hexane) to afford 1-cyclopropyl-2-(4-isopropylpyrimidin-5-yl)-1H-benzo[d]imidazole-6-carbonitrile Ex. 28 (115 mg, 0.37 mmol, 68%) as an off white solid.

$^1$H NMR (400 MHz, $CD_3OD$): δ 9.28 (s, 1H), 8.92 (s, 1H), 8.21 (s, 1H), 7.86 (dd, J=8.4, 0.6 Hz, 1H), 7.66 (dd, J=8.4, 1.5 Hz, 1H), 3.62-3.51 (m, 1H), 3.17-3.10 (m, 1H), 1.27 (d, J=6.7 Hz, 6H), 1.12-0.97 (m, 2H), 0.80-0.70 (m, 2H)

LC-MS: m/z 303.9 [M+H]$^+$ at 2.56 RT (99.59% purity).
HPLC: 99.47%.

Example 29

Scheme:

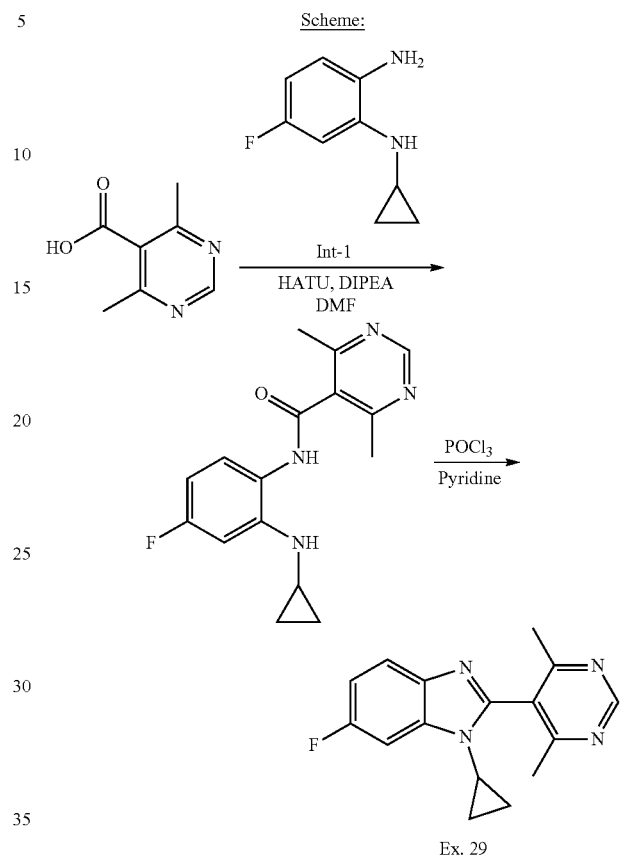

Ex. 29

N-(2-(Cyclopropylamino)-4-fluorophenyl)-4,6-dimethylpyrimidine-5-carboxamide

To a stirred solution of N1-cyclopropyl-5-fluorobenzene-1,2-diamine Int-1 (300 mg, 1.80 mmol) in DMF (6 mL) under an inert atmosphere was added 4,6-dimethylpyrimidine-5-carboxylic acid (274 mg, 1.80 mmol), HATU (829 mg, 2.16 mmol) and diisopropylethylamine (1.3 mL, 7.20 mmol) at 0° C. The reaction mixture was stirred at room temperature for 16 h. After consumption of starting material (by TLC), the reaction mixture was quenched with water (20 mL) to obtain a solid. The solid was filtered and dried under reduced pressure to obtain N-(2-(cyclopropylamino)-4-fluorophenyl)-4,6dimethylpyrimidine-5-carboxamide (200 mg, crude) as an off-white solid which was used directly without further purification.

LC-MS: m/z 301[M+H]$^+$ at 2.39 RT (82.67% purity).

1-Cyclopropyl-2-(4,6-dimethylpyrimidin-5-yl)-6-fluoro-1H-benzo[d]imidazole (Ex. 29)

To a stirred solution of N-(2-(cyclopropylamino)-4-fluorophenyl)-4,6-dimethylpyrimidine-5-carboxamide (100 mg, 0.33 mmol) in pyridine (0.26 mL) under an inert atmosphere was added phosphoryl chloride (0.15 mL, 1.66) at room temperature. The reaction mixture was heated to 100° C. for 4 h. After consumption of starting material (by TLC), the reaction mixture was basified with saturated sodium bicarbonate solution (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 5% MeOH/CH$_2$Cl$_2$) to afford 1-cyclopropyl-2-(4,6dimethylpyrimidin-5-yl)-6-fluoro-1H-benzo[d]imidazole Ex. 29 (30 mg, 0.10 mmol, 32%) as an off-white solid.

$^1$H NMR (400 MHz, DMSO-d$_6$): δ 9.08 (s, 1H), 7.75-7.72 (m, 1H), 7.54-7.51 (m, 1H), 7.23-7.10 (m, 1H), 3.42-3.33 (m, 1H), 2.27 (s, 6H), 0.93-0.83 (m, 2H), 0.69-0.61 (m, 2H)

LC-MS: m/z 282.9 [M+H]$^+$ at 2.03 RT (96.28% purity). HPLC: 93.65%.

Example 30

Scheme:

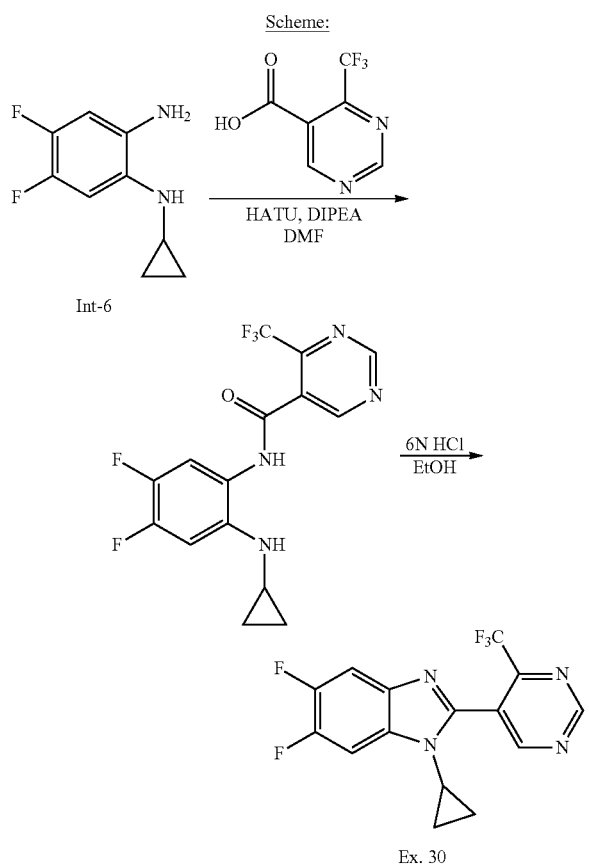

Ex. 30

N-(2-(Cyclopropylamino)-4,5-difluorophenyl)-4-(trifluoromethyl)pyrimidine-5-carboxamide[8]

To a stirred solution of N1-cyclopropyl-4,5-difluorobenzene-1,2-diamine Int-6 (200 mg, 1.10 mmol) in DMF (4 mL) under an inert atmosphere was added 4-(trifluoromethyl)pyrimidine-5-carboxylic acid (208 mg, 1.1 mmol), HATU (486 mg, 1.28 mmol) and ethyldiisopropylamine (0.72 mL, 4.32 mmol) at room temperature. The reaction mixture was stirred at room temperature for 16 h. After consumption of starting material (by TLC), the reaction mixture was diluted with water (30 mL) and extracted with ether (2×40 mL). The combined organic extracts were dried over anhydrous Na$_2$SO$_4$ and concentrated under reduced pressure. The crude material was purified by silica gel column chromatography (eluent: 20% EtOAc/hexane) to afford N-(2-(cyclopropylamino)-4,5-difluorophenyl)-4-(trifluoromethyl)pyrimidine-5-carboxamide (200 mg, 0.55 mmol, 34%) as a dark brown solid.

$^1$H NMR (500 MHz, DMSO-d$_6$): δ 10.00 (s, 1H), 9.57 (s, 1H), 9.51 (s, 1H), 7.42-7.38 (m, 1H), 6.99-6.95 (m, 1H), 5.70 (s, 1H), 2.41-2.37 (m, 1H), 0.79-0.72 (m, 2H), 0.47-0.38 (m, 2H)

1-Cyclopropyl-5,6-difluoro-2-(4-(trifluoromethyl)pyrimidin-5-yl)-1H-benzo[d]imidazole (Ex. 30)

To a stirred solution of N-(2-(cyclopropylamino)-4,5-difluorophenyl)-4-(trifluoromethyl)pyrimidine-5-carboxamide (150 g, 1.50 mmol) in EtOH (3 mL) under an inert atmosphere was added 6N HCl (3 mL) at room temperature. The reaction mixture was stirred at 80° C. for 3 h. After consumption of starting material (by TLC), the reaction mixture was diluted with saturated sodium bicarbonate solution (10 mL) and extracted with EtOAc (2×10 mL). The combined organic extracts were dried over anhydrous Na$_2$SO$_4$ and concentrated under reduced pressure. The crude material was purified by preparative HPLC to afford 1-cyclopropyl-5,6-difluoro-2-(4-(trifluoromethyl)pyrimidin-5-yl)-1H-benzo[d]imidazole Ex. 30 (80 mg, 0.23 mmol, 56%) as an off white solid.

$^1$H NMR (400 MHz, CD$_3$OD): δ 9.59 (s, 1H), 9.33 (s, 1H), 7.74-7.69 (m, 1H), 7.64-7.60 (m, 1H), 3.53-3.39 (m, 1H), 1.09-0.96 (m, 2H), 0.81-0.66 (m, 2H)

LC-MS: m/z 340.9 [M+H]$^+$ at 2.99 RT (99.32% purity). HPLC: 97.45%.

Example 31

Scheme:

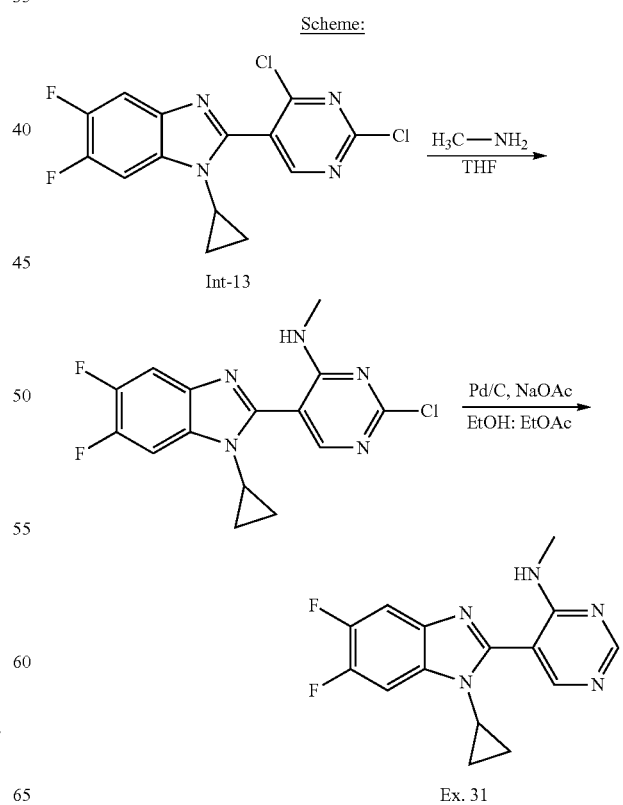

Ex. 31

2-Chloro-5-(1-cyclopropyl-5,6-difluoro-1H-benzo[d]imidazol-2-yl)-N-methylpyrimidin-4-amine To a stirred solution of 1-cyclopropyl-2-(2,4-dichloropyrimidin-5-yl)-5,6-difluoro-1H-benzo[d]imidazole Int-13 (100 mg, 0.29 mmol) in THF (3 mL) under an inert atmosphere was added methylamine (33% in ethanol, 0.03 mL, 0.29 mmol) drop wise at 0° C. The reaction mixture was stirred at 0° C. for 10 min. After consumption of starting material (by TLC), the reaction mixture was diluted with saturated sodium bicarbonate solution (20 mL) and extracted with $CH_2Cl_2$ (2×20 mL). The combined organic extracts were dried over anhydrous $Na_2SO_4$ and concentrated under reduced pressure to obtain 2-chloro-5-(1-cyclopropyl-5,6-difluoro-1H-benzo[d]imidazol-2-yl)-N-methylpyrimidin-4-amine (80 mg, crude) as an off-white solid which was used directly without further purification.

LC-MS: m/z 336 [M+H]$^+$ at 2.63 RT (91.71% purity).

5-(1-Cyclopropyl-5,6-difluoro-1H-benzo[d]imidazol-2-yl)-N-methylpyrimidin-4-amine (Ex. 31)

To a stirred solution of 2-chloro-5-(1-cyclopropyl-5,6-difluoro-1H-benzo[d]imidazol-2-yl)-N-methylpyrimidin-4-amine (100 mg, 0.30 mmol) in EtOH:EtOAc (1:1, 6 mL) under an inert atmosphere was added sodium acetate (73 mg, 0.89 mmol) and 10% Pd/C (50% wet, 50 mg) at room temperature. The reaction mixture was stirred at room temperature under a hydrogen atmosphere (balloon pressure) for 2 h. After consumption of starting material (by TLC), the reaction mixture was filtered through a pad of celite and the celite bed was washed with MeOH (20 mL). The filtrate was concentrated under reduced pressure. The crude material was triturated with n-pentane (2×5 mL) and ether (2×2 mL) to afford 5-(1-cyclopropyl-5,6-difluoro-1H-benzo[d]imidazol-2-yl)-N-methylpyrimidin-4-amine Ex. 31 (60 mg, 0.19 mmol, 67%) as an off white solid.

$^1$H NMR (500 MHz, DMSO-d$_6$): δ 8.74 (s, 1H), 8.59 (s, 1H), 8.23 (brs, 1H), 7.80-7.75 (m, 2H), 3.78-3.65 (m, 1H), 2.97 (d, J=4.6 Hz, 3H), 1.11-1.10 (m, 2H), 0.72-0.75 (m, 2H)

LC-MS: m/z 301.9 [M+H]$^+$ at 1.81 RT (96.39% purity).
HPLC: 96.29%.

Example 32

Scheme:

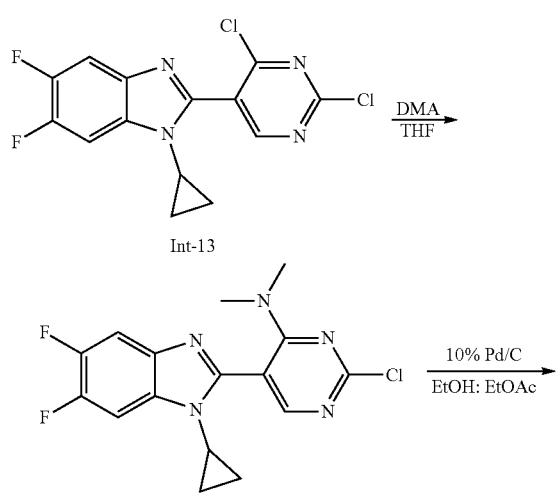

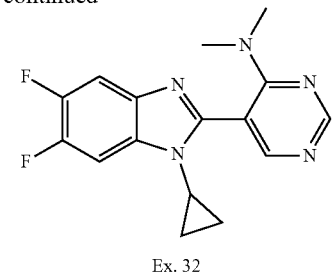

Ex. 32

2-Chloro-5-(1-cyclopropyl-5,6-difluoro-1H-benzo[d]imidazol-2-yl)-N,N-dimethylpyrimidin-4-amine To a stirred solution of 1-cyclopropyl-2-(2 4-dichloropyrimidin-5-yl)-5,6-difluoro-1H-benzo[d]imidazole Int-13 (150 mg, 0.42 mmol) in THF (3 mL) under an inert atmosphere was added dimethylamine (DMA) (2 M in THF, 0.21 mL, 0.42 mmol) drop wise at 0° C. The reaction mixture was warmed to room temperature and stirred for 2 h. After consumption of starting material (by TLC), the volatiles were evaporated under reduced pressure. The crude material was purified by silica gel column chromatography (eluent: 40-50% EtOAc/Hexane) to afford 2-chloro-5-(1-cyclopropyl-5,6-difluoro-1H-benzo[d]imidazol-2-yl)-N,N-dimethylpyrimidin-4-amine (80 mg, 0.22 mmol, 52%) as an off white solid.

$^1$H NMR (400 MHz, CD$_3$OD): δ 8.22 (s, 1H), 7.65 (dd, J=10.1, 7.2 Hz, 1H), 7.56 (dd, J=10.5, 7.2 Hz, 1H), 3.40-3.33 (m, 1H), 2.89 (s, 6H), 1.12-1.03 (m, 2H), 0.83-0.75 (m, 2H)

5-(1-Cyclopropyl-5,6-difluoro-1H-benzo[d]imidazol-2-yl)-N,N-dimethylpyrimidin-4-amine (Ex. 32)

To a stirred solution of 2-chloro-5-(1-cyclopropyl-5,6-difluoro-1H-benzo[d]imidazol-2-yl)-N,N-dimethylpyrimidin-4-amine (100 mg, 0.28 mmol) in EtOH:EtOAc (1:1, 10 mL) under an inert atmosphere was added 10% Pd/C (10% wet, 20 mg) at room temperature. The reaction mixture was stirred at room temperature under a hydrogen atmosphere (balloon pressure) for 2 h. After consumption of starting material (by TLC), the reaction mixture was filtered through a pad of celite and the celite bed was washed with methanol (2×30 mL). The filtrate was concentrated under reduced pressure. The residue was diluted with ice cold water (20 mL) and extracted with EtOAc (2×20 mL). The combined organic extracts were washed with water (20 mL), brine (20 mL), dried over anhydrous Na$_2$SO$_4$ and concentrated under reduced pressure. The crude material was washed with n-pentane (2×10 mL) to afford 5-(1-cyclopropyl-5,6-difluoro-1H-benzo[d]imidazol-2-yl)-N,N-dimethylpyrimidin-4-amine Ex. 32 (58 mg, 0.18 mmol, 64%) as an off white solid.

$^1$H NMR (400 MHz, CD$_3$OD): δ 8.60 (s, 1H), 8.31 (s, 1H), 7.63 (dd, J=10.1, 7.0 Hz, 1H), 7.54 (dd, J=10.5, 7.2 Hz, 1H), 3.37-3.30 (m, 1H), 2.88 (s, 6H), 1.00 (d, J=6.3 Hz, 2H), 0.73-0.70 (m, 2H)

LC-MS: m/z 315.9 [M+H]$^+$ at 2.34 RT (96.99% purity).
HPLC: 97.47%.

Example 33

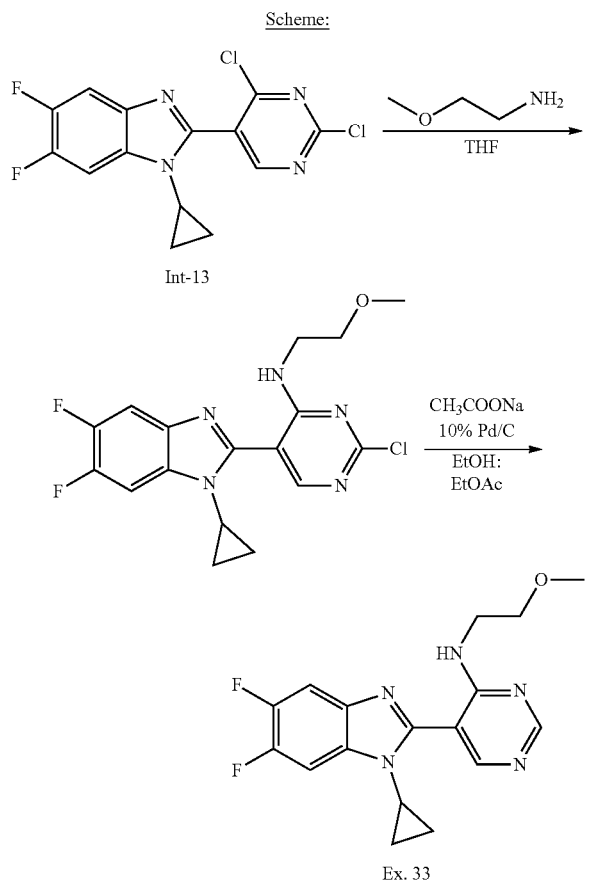

Ex. 33

2-Chloro-5-(1-cyclopropyl-5,6-difluoro-1H-benzo[d]imidazol-2-yl)-N-(2-methoxyethyl)pyrimidin-4-amine To a stirred solution of 1-cyclopropyl-2-(2,4-dichloropyrimidin-5-yl)-5,6-difluoro-1H-benzo[d]imidazole Int-13 (200 mg, 0.58 mmol) in THF (2 mL) under an inert atmosphere was added 2-methoxyethan-1-amine (44 mg, 0.58 mmol) at room temperature. The reaction mixture was stirred at room temperature for 1 h. After consumption of starting material (by TLC), the volatiles were concentrated under reduced pressure. The crude material was purified by silica gel column chromatography (eluent: 40% EtOAc/hexane) to afford 2-chloro-5-(1-cyclopropyl-5,6-difluoro-1H-benzo[d]imidazol-2-yl)-N-(2-methoxyethyl)pyrimidin-4-amine (110 mg, 0.30 mmol, 49%) as an off-white solid.

$^1$H NMR (500 MHz, DMSO-$d_6$): δ 9.01 (t, J=5.2 Hz, 1H), 8.73 (s, 1H), 7.84-7.52 (m, 2H), 3.76-3.71 (m, 1H), 3.64-3.61 (m, 2H), 3.56-3.47 (m, 2H), 3.30 (s, 3H), 1.22-1.08 (m, 2H), 0.79-0.63 (m, 2H)

5-(1-Cyclopropyl-5,6-difluoro-1H-benzo[d]imidazol-2-yl)-N-(2-methoxyethyl)pyrimidin-4-amine (Ex. 33)

To a stirred solution of 2-chloro-5-(1-cyclopropyl-56-difluoro-1H-benzo[d]imidazol-2-yl)-N-(2-methoxyethyl)pyrimidin-4-amine (100 mg, 0.26 mmol) in ethanol:EtOAc (1:1, 2 mL) under an inert atmosphere was added sodium acetate (64.9 mg, 0.79 mmol) and 10% Pd/C (50 mg) at room temperature. The reaction mixture was stirred at room temperature under a hydrogen atmosphere (balloon pressure) for 1 h. After consumption of starting material (by TLC), the reaction mixture was filtered through a pad of celite and the pad was washed with EtOAc (20 mL). The filtrate was concentrated under reduced pressure. The crude material was washed with n-pentane (2×5 mL) to afford 5-(1-cyclopropyl-5,6-difluoro-1H-benzo[d]imidazol-2-yl)-N-(2-methoxyethyl)pyrimidin-4-amine Ex. 33 (50 mg, 0.14 mmol, 55%) as a black solid.

$^1$H NMR (400 MHz, DMSO-$d_6$): δ 8.79 (s, 1H), 8.58 (s, 1H), 8.54 (t, J=5.3 Hz, 1H), 7.79-7.75 (m, 2H), 3.80-3.70 (m, 1H), 3.65-3.63 (m, 2H), 3.55-3.48 (m, 2H), 3.29 (s, 3H), 1.18-1.10 (m, 2H), 0.77-0.67 (m, 2H)

LC-MS: m/z 346 [M+H]$^+$ at 1.90 RT (99.88% purity). HPLC: 97.54%.

Example 34

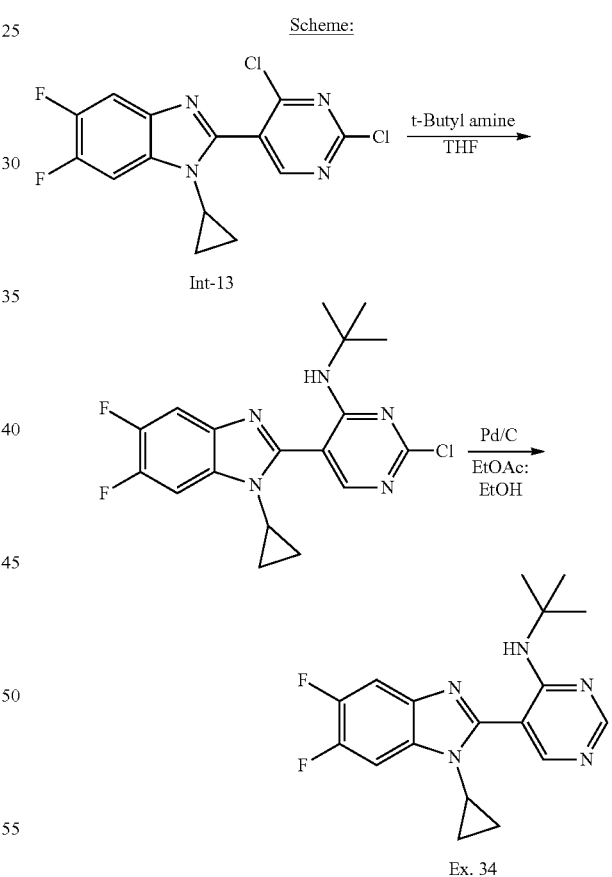

Ex. 34

N-(tert-Butyl)-2-chloro-5-(1-cyclopropyl-5,6-difluoro-1H-benzo[d]imidazol-2-yl)pyrimidin-4-amine To a stirred solution of 1-cyclopropyl-2-(2,4-dichloropyrimidin-5-yl)-5,6-difluoro-1H-benzo[d]imidazole Int-13 (100 mg, 0.29 mmol) in THF (3 mL) under an inert atmosphere was added t-butylamine (0.031 mL, 0.29 mmol) drop wise at 0° C. The reaction mixture was warmed to room temperature and stirred for 2 h. After consumption of starting material (by TLC), the volatiles were evaporated under reduced pressure to obtain N-(tert-butyl)-2-chloro-5-(1-cyclopropyl-5,6-difluoro-1H-benzo[d]imidazol-2-yl)pyrimidin-4-amine (120 mg, crude) as a brown thick syrup which was used directly with out further purification.

$^1$H NMR (500 MHz, DMSO-$d_6$): δ 9.23 (s, 1H), 8.83 (s, 1H), 7.83-7.77 (m, 2H), 3.81-3.77 (m, 1H), 1.48 (s, 9H), 1.27-1.17 (m, 2H), 0.83-0.74 (m, 2H)

N-(tert-Butyl)-5-(1-cyclopropyl-5,6-difluoro-1H-benz[d]imidazol-2-yl)pyrimidin-4-amine (Ex. 34)

To a stirred solution of N-(tert-butyl)-2-chloro-5-(1-cyclopropyl-56-difluoro-1H-benzo [d]imidazol-2-yl)pyrimidin-4-amine (140 mg, 0.37 mmol) in EtOH:EtOAc (1:1, 14 mL) under an inert atmosphere was added 10% Pd/C (10% wet, 70 mg) at room temperature. The reaction mixture was stirred at room temperature under a hydrogen atmosphere (balloon pressure) for 2 h. After consumption of starting material (by TLC), the reaction mixture was filtered through a pad of celite and the celite bed was washed with $CH_2Cl_2$ (2×30 mL). The filtrate was concentrated under reduced pressure. The residue was diluted with ice cold water (20 mL) and extracted with $CH_2Cl_2$ (2×20 mL). The combined organic extracts were washed with water (20 mL), brine (20 mL), dried over anhydrous $Na_2SO_4$ and concentrated under reduced pressure. The crude material was washed with n-pentane (2×10 mL) to afford N-(tert-butyl)-5-(1-cyclopropyl-5,6-difluoro-1H-benzo[d]imidazol-2-yl)pyrimidin-4-amine Ex. 34 (60 mg, 0.17 mmol, 47%) as an off white solid.

$^1$H NMR (400 MHz, $CD_3OD$): δ 8.74 (s, 1H), 8.52 (s, 1H), 7.63 (dd, J=10.2, 7.2 Hz, 1H), 7.55 (dd, J=10.5, 7.3 Hz, 1H), 3.74-3.65 (m, 1H), 1.54 (s, 9H), 1.29-1.21 (m, 2H), 0.81-0.74 (m, 2H)

LC-MS: m/z 344 [M+H]$^+$ at 3.64 RT (95.37% purity).
HPLC: 97.05%.

Example 35

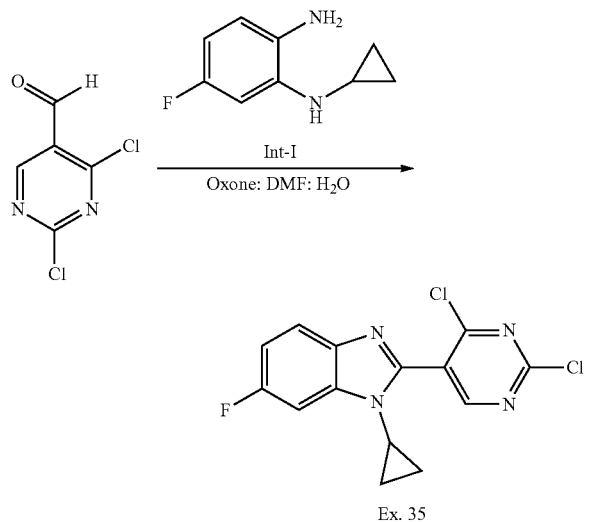

1-Cyclopropyl-2-(2,4-dichloropyrimidin-5-yl)-6-fluoro-1H-benzo[d]imidazole (Ex. 35)

To a stirred solution of 2,4-dichloropyrimidine-5-carbaldehyde (200 mg, 1.20 mmol) in DMF (4 mL) under an inert atmosphere was added N1-cyclopropyl-5-fluorobenzene-1,2-diamine Int-1(320 mg, 1.80 mmol) and oxone (738 mg, 2.40 mmol) followed by water (0.4 mL) at room temperature. The reaction mixture was stirred at room temperature for 3 h. After consumption of starting material (by TLC), the reaction mixture was diluted with water (20 mL) and extracted with EtOAc (2×20 mL). The combined organic extracts were dried over anhydrous $Na_2SO_4$ and concentrated under reduced pressure. The crude material was purified by silica gel column chromatography (eluent: 30% EtOAc/hexane) to afford 1-cyclopropyl-2-(2,4-dichloropyrimidin-5-yl)-6-fluoro-1H-benzo[d]imidazole Ex. 35 (180 mg, 0.55 mmol, 46%) as brown solid.

$^1$H NMR (400 MHz, $CDCl_3$): δ 8.80 (s, 1H), 7.78-7.74 (m, 1H), 7.32 (dd, J=8.5, 2.4 Hz, 1H), 7.14-7.10 (m, 1H), 3.55-3.36 (m, 1H), 1.12-1.07 (m, 2H), 0.79-0.68 (m, 2H)

LC-MS: m/z 324.9 [M+2H]$^+$ at 2.53 RT (97.74% purity).
HPLC: 95.01%.

Example 36

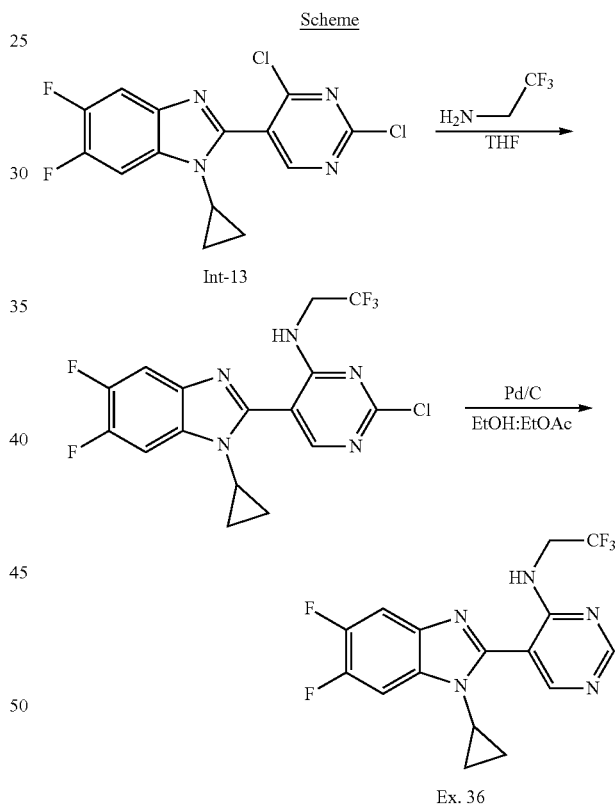

2-Chloro-5-(1-cyclopropyl-5,6-difluoro-1H-benzo[d]imidazol-2-yl)-N-(2,2,2-trifluoroethyl)pyrimidin-4-amine To a stirred solution of 1-cyclopropyl-2-(2,4-dichloropyrimidin-5-yl)-5,6-difluoro-1H-benzo[d]imidazole Int-13 (200 mg, 0.58 mmol) in THF (2 mL) under an inert atmosphere was added 2,2,2-trifluoroethan-1-amine (59 mg, 0.58 mmol) at 0° C. The reaction mixture was stirred at room temperature for 5 h. After consumption of starting material (by TLC), the volatiles were concentrated under reduced pressure. The crude material was purified by silica gel column chromatography (eluent: 30% EtOAc/Hexane) to afford 2-chloro-5-(1-cyclopropyl-5,6-difluoro-1H-benzo[d]imidazol-2-yl)-N-(2,2,2-trifluoroethyl)pyrimidin-4-amine (100 mg, 0.24 mmol, 42%) as an off-white solid.

$^1$H NMR (500 MHz, DMSO-$d_6$): δ 9.09 (t, J=6.4 Hz, 1H), 8.80 (s, 1H), 7.83-7.80 (m, 2H), 4.41-4.31 (m, 2H), 3.73-3.60 (m, 1H), 1.18-1.09 (m, 2H), 0.78-0.72 (m, 2H)

5-(1-Cyclopropyl-5,6-difluoro-1H-benzo[d]imidazol-2-yl)-N-(2,2,2-trifluoroethyl)pyrimidin-4-amine (Ex. 36)

To a stirred solution of 2-chloro-5-(1-cyclopropyl-5,6-difluoro-1H-benzo[d]imidazol-2-yl)-N-(2, 2, 2-trifluoroethyl)pyrimidin-4-amine (100 mg, 0.24 mmol) in EtOH:EtOAc (1:2, 3 mL) under an inert atmosphere was added 10% Pd/C (10% wet, 50 mg) at room temperature. The reaction mixture was stirred at room temperature under a hydrogen atmosphere (balloon pressure) for 1 h. After consumption of starting material (by TLC), the reaction mixture was filtered through a pad of celite and the celite bed was washed with methanol (2×30 mL). The filtrate was concentrated under reduced pressure. The residue was washed with n-pentane (2×10 mL) to afford 5-(1-cyclopropyl-5,6-difluoro-1H-benzo[d]imidazol-2-yl)-N-(2,2,2-trifluoroethyl)pyrimidin-4-amine Ex. 36 (60 mg, 0.16 mmol, 65%) as an off white solid.

$^1$H NMR (400 MHz, CD$_3$OD): δ 8.81 (s, 1H), 8.66 (s, 1H), 7.71-7.52 (m, 2H), 4.42-4.35 (m, 2H), 3.69-3.63 (m, 1H), 1.24-1.16 (m, 2H), 0.84-0.73 (m, 2H)

LC-MS: m/z 369.9 [M+H]$^+$ at 3.18 RT (98.85% purity). HPLC: 98.69%.

Example 37

Scheme

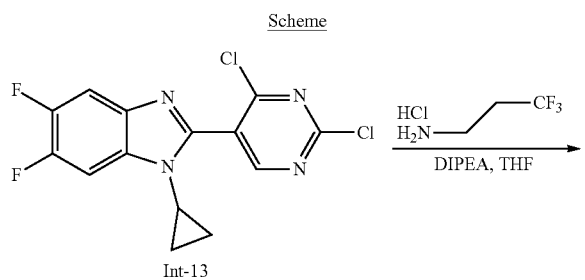

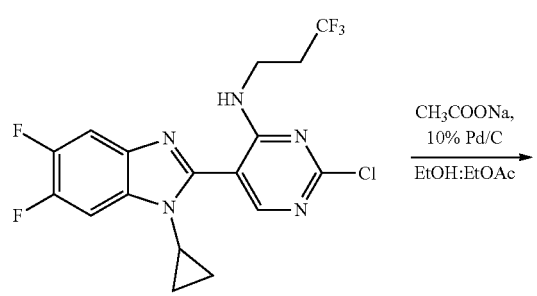

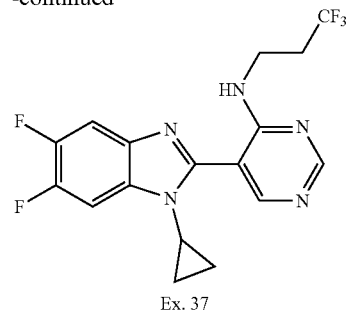

Ex. 37

2-Chloro-5-(1-cyclopropyl-5,6-difluoro-1H-benzo[d]imidazol-2-yl)-N-(3,3,3-trifluoropropylpyrimidin-4-amine To a stirred solution of 1-cyclopropyl-2-(2,4-dichloropyrimidin-5-yl)-5,6-difluoro-1H-benzo[d]imidazole Int-13 (200 mg, 0.58 mmol) in THF (4 mL) under an inert atmosphere was added ethyldiisopropylamine (0.5 mL, 2.94 mmol) and 3,3,3-trifluoropropan-1-amine hydrochloride (87.6 mg, 0.58 mmol) at room temperature. The reaction mixture was stirred at room temperature for 1 h. After consumption of starting material (by TLC), the reaction mixture was diluted with water (20 mL) and extracted with EtOAc (2×20 mL). The combined organic extracts were dried over anhydrous Na$_2$SO$_4$ and concentrated under reduced pressure. The crude material was triturated with n-pentane (2×5 mL) to afford 2-chloro-5-(1-cyclopropyl-5,6-difluoro-1H-benzo[d]imidazol-2-yl)-N-(3,3,3-trifluoropropyl)pyrimidin-4-amine (150 mg, 0.35 mmol, 61%) as a dark brown solid.

$^1$H NMR (400 MHz, DMSO-$d_6$): δ 8.87 (t, J=5.8 Hz, 1H), 8.72 (s, 1H), 7.82-7.74 (m, 2H), 3.77-3.65 (m, 3H), 2.76-2.52 (m, 2H), 1.20-1.08 (m, 2H), 0.78-0.69 (m, 2H)

5-(1-Cyclopropyl-5,6-difluoro-1H-benzo[d]imidazol-2-yl)-N-(3,3,3-trifluoropropyl)pyrimidin-4-amine (Ex. 37)

To a stirred solution of 2-chloro-5-(1-cyclopropyl-5,6-difluoro-1H-benzo[d]imidazol-2-yl)-N-(3,3,3-trifluoropropyl)pyrimidin-4-amine (150 mg, 0.36 mmol) in ethanol:EtOAc (1:1, 3 mL) under an inert atmosphere was added sodium acetate (88.4 mg, 1.07 mmol) and 10% Pd/C (75 mg) at room temperature. The reaction mixture was stirred at room temperature under a hydrogen atmosphere (balloon pressure) for 1 h. After consumption of starting material (by TLC), the reaction mixture was filtered through a pad of celite and washed with EtOAc (20 mL). The filtrate was concentrated under reduced pressure. The crude material was washed with n-pentane (2×5 mL) to afford 5-(1-cyclopropyl-5,6-difluoro-1H-benzo[d]imidazol-2-yl)-N-(3,3,3-trifluoropropyl)pyrimidin-4-amine Ex. 37 (60 mg, 0.15 mmol, 44%) as a black solid.

$^1$H NMR (400 MHz, CD$_3$OD): δ 8.72 (s, 1H), 8.61 (s, 1H), 7.69-7.49 (m, 2H), 3.85-3.81 (m, 2H), 3.66-3.62 (m, 1H), 2.61-2.55 (m, 2H), 1.24-1.16 (m, 2H), 0.82-0.75 (m, 2H)

LC-MS: m/z 384 [M+H]$^+$ at 2.14 RT (98.98% purity). HPLC: 99.66%.

Example 38

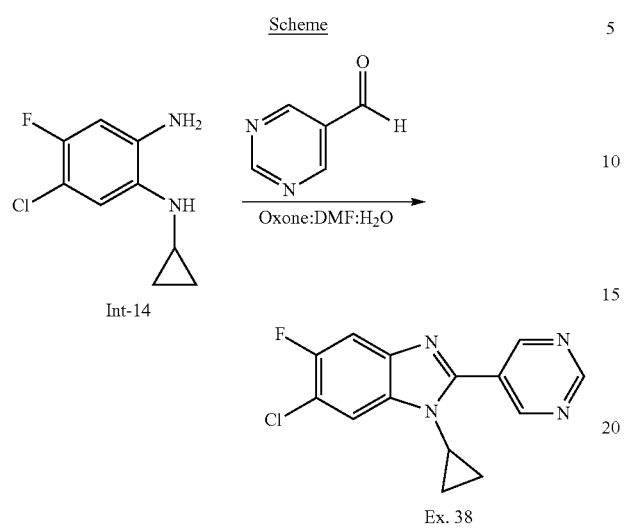

6-Chloro-1-cyclopropyl-5-fluoro-2-(pyrimidin-5-yl)-1H-benzo[d]imidazole (Ex. 38)

To a stirred solution of 5-chloro-N1-cyclopropyl-4-fluorobenzene-1,2-diamine Int-14 (150 mg, 0.75 mmol) in DMF (3 mL) under an inert atmosphere was added pyrimidine-5-carbaldehyde (81 mg, 0.75 mmol) and oxone (253 mg, 0.82 mmol) followed by water (1.04 mL) at room temperature. The reaction mixture was stirred at room temperature for 6 h. After consumption of starting material (by TLC), the reaction mixture was diluted with water (20 mL) and extracted with EtOAc (2×20 mL). The combined organic extracts were dried over anhydrous $Na_2SO_4$ and concentrated under reduced pressure. The crude material was purified by silica gel column chromatography (eluent: 40% EtOAc/hexane) to afford 6-chloro-1-cyclopropyl-5-fluoro-2-(pyrimidin-5-yl)-1H-benzo[d]imidazole Ex. 38 (80 mg, 0.27 mmol, 37%) as a brown solid.

$^1$H NMR (400 MHz, DMSO-$d_6$): δ 9.41 (s, 2H), 9.36 (s, 1H), 7.94 (d, J=6.7 Hz, 1H), 7.82 (d, J=9.8 Hz, 1H), 3.90-3.86 (m, 1H), 1.21-1.11 (m, 2H), 0.80-0.63 (m, 2H)

LC-MS: m/z 288.9 [M+H]$^+$ at 2.49 RT (94.97% purity). HPLC: 98.24%.

Example 39

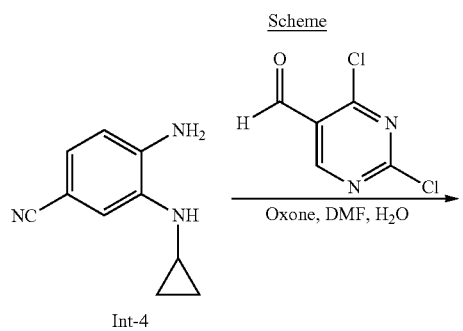

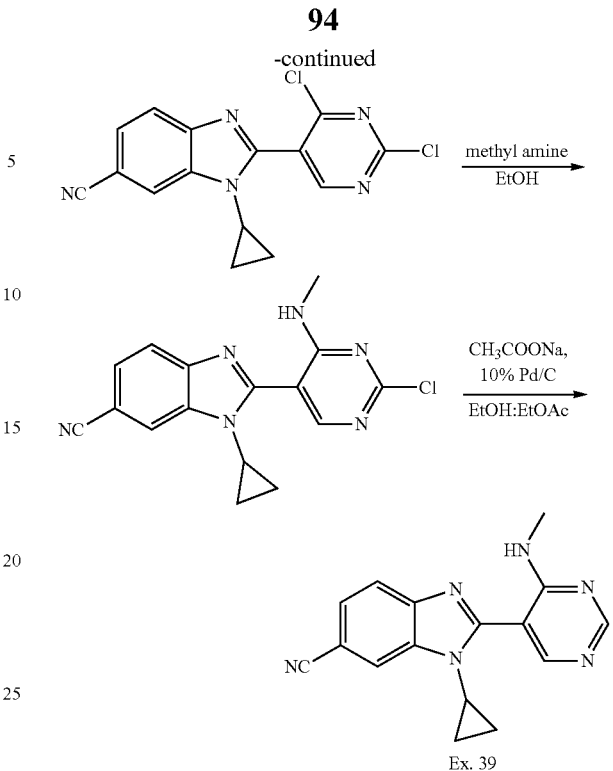

1-Cyclopropyl-2-(2,4-dichloropyrimidin-5-yl)-1H-benzo[d]imidazole-6-carbonitrile To a stirred solution of 4-amino-3-(cyclopropylamino)benzonitrile Int-4 (200 mg, 1.15 mmol) in DMF (5 mL) and water (0.5 mL) under an inert atmosphere was added 2,4-dichloropyrimidine-5-carbaldehyde (245 mg, 1.38 mmol) and oxone (706 mg, 2.30 mmol) at room temperature. The reaction mixture was stirred at room temperature for 2 h. After consumption of starting material (by TLC), the reaction mixture was diluted with water (20 mL), and extracted with EtOAc (2×20 mL). The combined organic extracts were dried over anhydrous $Na_2SO_4$ and concentrated under reduced pressure. The crude material was purified by silica gel column chromatography (eluent: 40% EtOAc/Hexane) to afford 1-cyclopropyl-2-(2,4-dichloropyrimidin-5-yl)-1H-benzo[d]imidazole-6-carbonitrile (120 mg, 0.36 mmol, 31%) as an off white solid.

$^1$H NMR (400 MHz, CD$_3$OD): δ 9.01 (s, 1H), 8.25 (s, 1H), 7.89 (dd, J=8.4, 0.8 Hz, 1H), 7.69 (dd, J=8.4, 1.5 Hz, 1H), 3.69-3.64 (m, 1H), 1.16-1.11 (m, 2H), 0.86-0.74 (m, 2H)

2-(2-Chloro-4-(methylamino)pyrimidin-5-yl)-1-cyclopropyl-1H-benzo[d]imidazole-6-carbonitrile To a stirred solution of 1-cyclopropyl-2-(2,4-dichloropyrimidin-5-yl)-1H-benzo[d]imidazole-6-carbonitrile (100 mg, 0.30 mmol) in EtOH (1 mL) under an inert atmosphere was added methylamine (33% in EtOH, 28.2 mg, 0.30 mmol) at room temperature. The reaction mixture was stirred at room temperature for 1 h. After consumption of starting material (by TLC), the reaction mixture was diluted with water (20 mL) and extracted with EtOAc (2×20 mL). The combined organic extracts were dried over anhydrous $Na_2SO_4$ and concentrated under reduced pressure. The crude material was purified by silica gel column chromatography (eluent: 30% EtOAc/Hexane) to afford 2-(2-chloro-4-(methylamino)pyrimidin-5-yl)-1-cyclopropyl-1H-benzo[d]imidazole-6-carbonitrile (70 mg, 0.21 mmol, 71%) as an off white solid.

$^1$H NMR (400 MHz, CD$_3$OD): δ 8.68 (s, 1H), 8.17 (s, 1H), 7.86 (dd, J=8.3, 0.7 Hz, 1H), 7.64 (dd, J=8.4, 1.5 Hz, 1H), 3.76-3.70 (m, 1H), 3.09 (s, 3H), 1.36-1.24 (m, 2H), 0.94-0.82 (m, 2H)

1-Cyclopropyl-2-(4-(methylamino)pyrimidin-5-yl)-1H-benzo[d]imidazole-6-carbonitrile (Ex. 39)

To a stirred solution of 2-(2-chloro-4-(methylamino)pyrimidin-5-yl)-1-cyclopropyl-1H-benzo[d]imidazole-6-carbonitrile (60 mg, 0.18 mmol) in ethanol:EtOAc (1:1, 1 mL) under an inert atmosphere was added sodium acetate (45 mg, 0.55 mmol) and 10% Pd/C (30 mg) at room temperature. The reaction mixture was stirred at room temperature under a hydrogen atmosphere (balloon pressure) for 1 h. After consumption of starting material (by TLC), the reaction mixture was filtered through a pad of celite and washed with EtOAc (20 mL). The filtrate was concentrated under reduced pressure. The crude material was purified by preparative HPLC to afford 1-cyclopropyl-2-(4-(methylamino)pyrimidin-5-yl)-1H-benzo[d]imidazole-6-carbonitrile Ex. 39 (15 mg, 0.05 mmol, 28%) as an off-white solid.

$^1$H NMR (400 MHz, CD$_3$OD): δ 8.73 (s, 1H), 8.60 (s, 1H), 8.17 (s, 1H), 7.85 (dd, J=8.4, 0.6 Hz, 1H), 7.64 (dd, J=8.4, 1.5 Hz, 1H), 3.79-3.66 (m, 1H), 3.09 (s, 3H), 1.32-1.21 (m, 2H), 0.90-0.79 (m, 2H)

LC-MS: m/z 290.9 [M+H]$^+$ at 1.65 RT (99.47% purity).
HPLC: 99.80%.

Example 40

Scheme

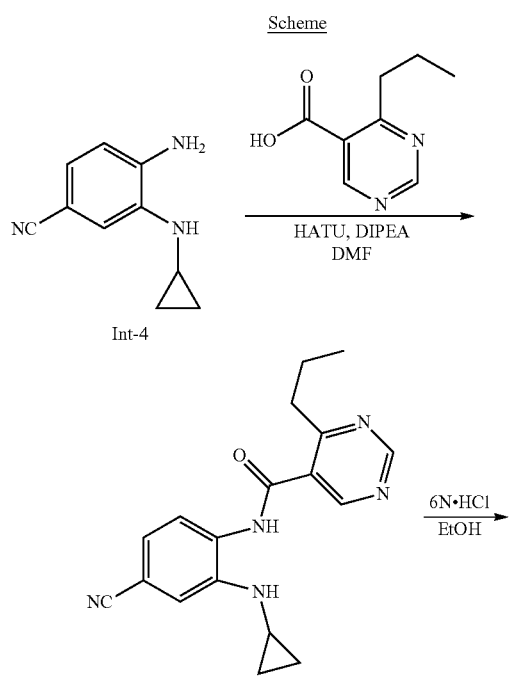

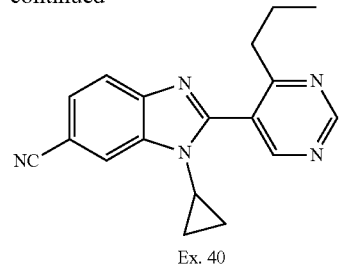

Ex. 40

N-(4-Cyano-2-(cyclopropylamino)phenyl)-4-propylpyrimidine-5-carboxamide

To a stirred solution of 4-amino-3-(cyclopropylamino)benzonitrile Int-4 (100 mg, 0.57 mmol) in DMF (4 mL) under an inert atmosphere was added 4-propylpyrimidine-5-carboxylic acid (95 mg, 0.57 mmol), HATU (330 mg, 0.86 mmol) and diisopropylethylamine (0.2 mL, 1.15 mmol) at 0° C. The reaction mixture was stirred at room temperature for 16 h. After consumption of starting material (by TLC), the reaction mixture was diluted with water (20 mL) and extracted with EtOAc (2×20 mL). The combined organic extracts were washed with water (20 mL), dried over anhydrous Na$_2$SO$_4$ and concentrated under reduced pressure. The crude material was purified by silica gel column chromatography (eluent: 30% EtOAc/hexane) to afford N-(4-cyano-2-(cyclopropylamino)phenyl)-4-propylpyrimidine-5-carboxamide (160 mg, 0.49 mmol, 59%) as a brown syrup.

$^1$H NMR (400 MHz, DMSO-d$_6$): δ 9.88 (s, 1H), 9.19 (s, 1H), 9.00 (s, 1H), 7.65 (d, J=8.1 Hz, 1H), 7.32 (s, 1H), 7.13 (d, J=6.7 Hz, 1H), 6.07 (s, 1H), 2.86 (t, J=7.5 Hz, 2H), 2.50-2.36 (m, 1H), 1.78-1.64 (m, 2H), 0.90 (t, J=7.4 Hz, 3H), 0.81-0.79 (m, 2H), 0.47-0.39 (m, 2H)

1-Cyclopropyl-2-(4-propylpyrimidin-5-yl)-1H-benzo[d]imidazole-6-carbonitrile (Ex. 40)

To a stirred solution of N-(4-cyano-2-(cyclopropylamino)phenyl)-4-propylpyrimidine-5-carboxamide (150 mg, 0.46 mmol) in EtOH (6 mL) under an inert atmosphere was added 6N HCl (3 mL) at room temperature. The reaction mixture was stirred at 80° C. for 1 h. After consumption of starting material (by TLC), the reaction mixture was diluted with saturated sodium bicarbonate solution (20 mL) and extracted with EtOAc (2×20 mL). The combined organic extracts were dried over anhydrous Na$_2$SO$_4$ and concentrated under reduced pressure. The crude material was purified by preparative HPLC to afford 1-cyclopropyl-2-(4-propylpyrimidin-5-yl)-1H-benzo[d]imidazole-6-carbonitrile Ex. 40 (16 mg, 0.05 mmol, 11%) as an off white solid.

$^1$H NMR (400 MHz, CD$_3$OD): δ 9.26 (s, 1H), 8.98 (s, 1H), 8.23 (s, 1H), 7.87 (d, J=8.4 Hz, 1H), 7.67 (dd, J=8.4, 1.5 Hz, 1H), 3.63-3.58 (m, 1H), 2.89-2.81 (m, 2H), 1.79-1.70 (m, 2H), 1.15-1.03 (m, 2H), 0.88 (t, J=7.4 Hz, 3H), 0.79-0.73 (m, 2H)

LC-MS: m/z 303.9 [M+H]$^+$ at 2.50 RT (96.76% purity).
HPLC: 94.52%.

Example 41

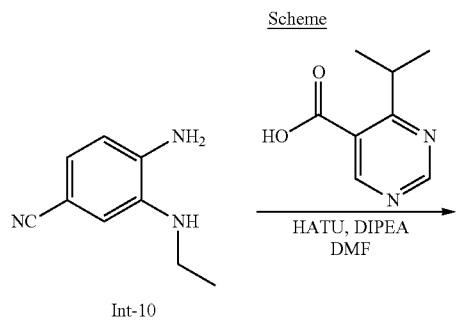

Int-10

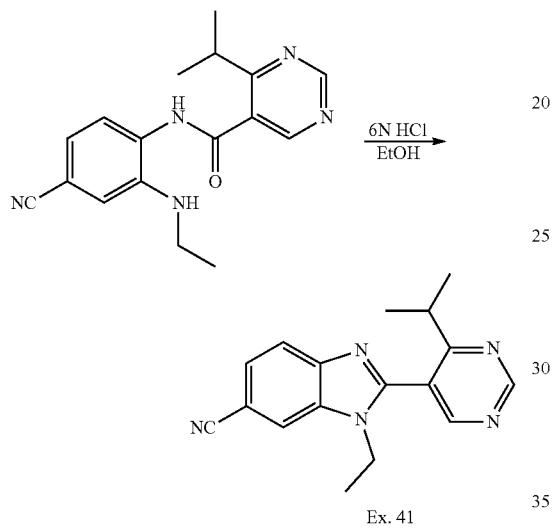

Ex. 41

N-(4-Cyano-2-(ethylamino)phenyl)-4-isopropylpyrimidine-5-carboxamide

To a stirred solution of 4-isopropylpyrimidine-5-carboxylic acid (162 mg, 1 mmol) in DMF (3 mL) under an inert atmosphere was added Int-10 (161 mg, 1 mmol), HATU (570 mg, 1.5 mmol) and diisopropylethylamine (0.64 mL, 4.0 mmol) at room temperature. The reaction mixture was stirred at room temperature for 16 h. After consumption of starting material (by TLC), the reaction mixture was diluted with ammonium chloride solution (20 mL) and extracted with EtOAc (2×20 mL). The combined organic extracts were washed with water (20 mL), dried over anhydrous $Na_2SO_4$ and concentrated under reduced pressure to obtain N-(4-cyano-2-(ethylamino)phenyl)-4-isopropylpyrimidine-5-carboxamide (200 mg, crude) as an off-white solid which was used directly without further purification.

LC-MS: m/z 310.1 [M+H]$^+$ at 2.25 RT (59.87% purity).

1-Ethyl-2-(4-isopropylpyrimidin-5-yl)-1H-benzo[d]imidazole-6-carbonitrile (Ex. 41)

To a stirred solution of N-(4-cyano-2-(ethylamino)phenyl)-4-isopropylpyrimidine-5-carboxamide (180 mg, 0.58 mmol) in EtOH (1 mL) under an inert atmosphere was added 6N HCl (2.5 mL) at room temperature. The reaction mixture was stirred at 60-70° C. for 1 h. After consumption of starting material (by TLC), the reaction mixture was diluted with saturated sodium carbonate solution (20 mL) and extracted with EtOAc (2×20 mL). The combined organic extracts were washed with water (20 mL), dried over anhydrous $Na_2SO_4$ and concentrated under reduced pressure. The crude material was purified by preparative HPLC to afford 1-ethyl-2-(4-isopropylpyrimidin-5-yl)-1H-benzo[d]imidazole-6-carbonitrile Ex. 41 (25 mg, 0.08 mmol, 15%) as an off white solid.

$^1$H NMR (400 MHz, $CD_3OD$): δ 9.33 (s, 1H), 8.87 (s, 1H), 8.24 (s, 1H), 7.90 (dd, J=8.4, 0.6 Hz, 1H), 7.69 (dd, J=8.4, 1.5 Hz, 1H), 4.27-4.22 (m, 2H), 2.95-2.88 (m, 1H), 1.37 (t, J=7.2 Hz, 3H), 1.28 (d, J=6.7 Hz, 6H)

LC-MS: m/z 291.9 [M+H]$^+$ at 2.43 RT (99.58% purity). HPLC: 99.86%.

Example 42

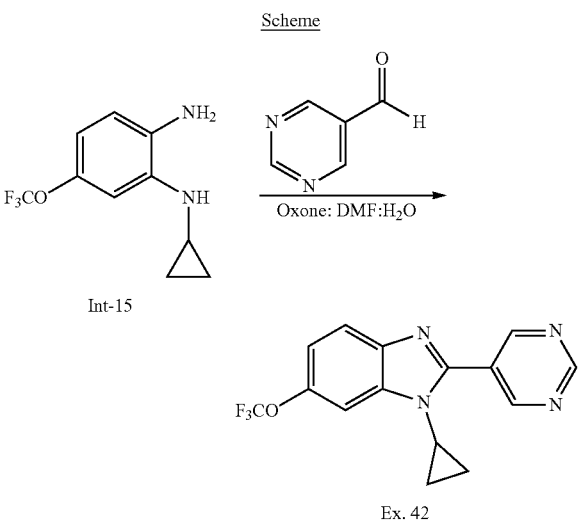

Ex. 42

1-Cyclopropyl-2-(pyrimidin-5-yl)-6-(trifluoromethoxy)-1H-benzo[d]imidazole (Ex. 42)

To a stirred solution of N1-cyclopropyl-5-(trifluoromethoxy)benzene-1,2-diamine Int-15 (100 mg, 0.44 mmol) in DMF (2 mL) under an inert atmosphere was added pyrimidine-5-carbaldehyde (46 mg, 0.44 mmol) and oxone (198 mg, 0.64 mmol) followed by water (1 mmol) at room temperature.

The reaction mixture was stirred at room temperature for 6 h. After consumption of starting material (by TLC), the reaction mixture was diluted with water (20 mL) and extracted with EtOAc (2×20 mL). The combined organic extracts were dried over anhydrous $Na_2SO_4$ and concentrated under reduced pressure. The crude material was purified by silica gel column chromatography (eluent: 40% EtOAc/hexane) to afford 1-cyclopropyl-2-(pyrimidin-5-yl)-6-(trifluoromethoxy)-1H-benzo[d]imidazole Ex. 42 (50 mg, 0.15 mmol, 37%) as an off-white solid.

$^1$H NMR (500 MHz, DMSO-$d_6$): δ 9.40 (s, 2H), 9.35 (s, 1H), 7.84 (d, J=8.7 Hz, 1H), 7.69 (s, 1H), 7.28 (d, J=8.7 Hz, 1H), 3.91-3.88 (m, 1H), 1.20-1.09 (m, 2H), 0.79-0.66 (m, 2H)

LC-MS: m/z 320.9 [M+H]$^+$ at 2.69 RT (97.87% purity). HPLC: 97.48%.

Example 43

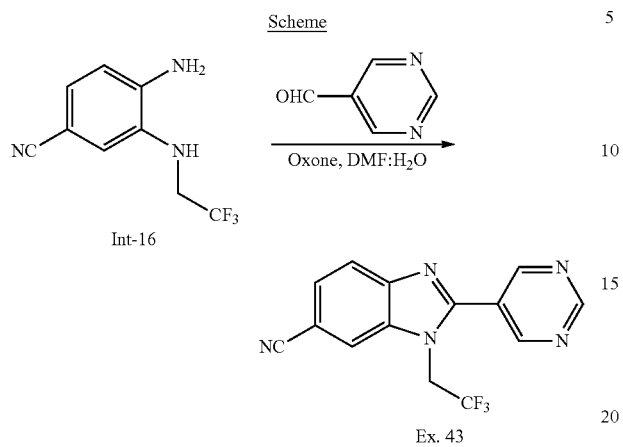

2-(Pyrimidin-5-yl)-1-(2,2,2-trifluoroethyl)-1H-benzo[d]imidazole-6-carbonitrile (Ex. 43)

To a stirred solution of 4-amino-3-((2,2,2-trifluoroethyl)amino)benzonitrile Int-16 (195 mg, 0.90 mmol) in DMF (2 mL) and water (0.2 mL) under an inert atmosphere was added pyrimidine-5-carbaldehyde (117 mg, 1.08 mmol) and oxone (552.6 mg, 1.80 mmol) at room temperature. The reaction mixture was stirred at room temperature for 2 h. After consumption of starting material (by TLC), the reaction mixture was diluted with water (20 mL) and extracted with EtOAc (2×20 mL). The combined organic extracts were dried over anhydrous $Na_2SO_4$ and concentrated under reduced pressure. The crude material was purified by preparative HPLC to afford 2-(pyrimidin-5-yl)-1-(2,2,2-trifluoroethyl)-1H-benzo[d]imidazole-6-carbonitrile Ex. 43 (26 mg, 0.08 mmol, 9.4%) as an off white solid.

$^1$H NMR (400 MHz, $CD_3OD$): δ 9.42 (s, 1H), 9.22 (s, 2H), 8.29 (s, 1H), 7.96 (d, J=8.4 Hz, 1H), 7.75 (dd, J=8.4, 1.4, Hz, 1H), 5.38-5.31 (m, 2H)

LC-MS: m/z 344.9 [M+H]$^+$ at 2.19 RT (99.49% purity).

HPLC: 99.20%.

Example 44

Scheme

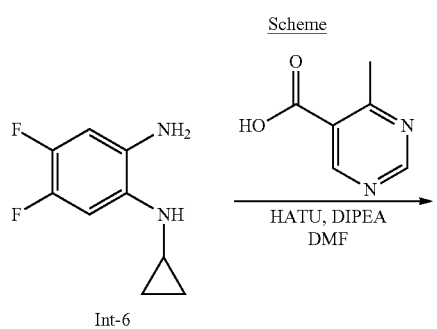

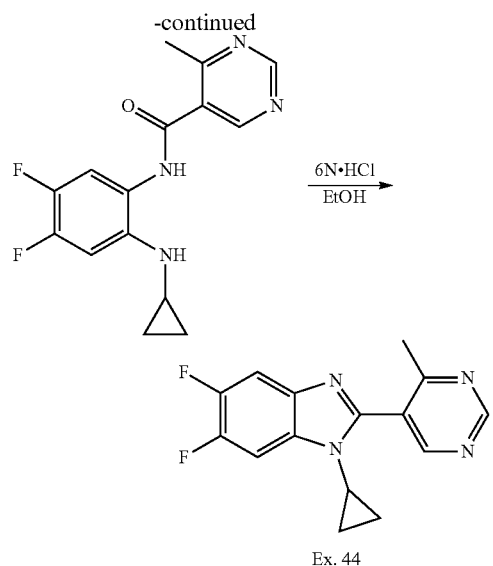

N-(2-(Cyclopropylamino)-4,5-difluorophenyl)-4-methylpyrimidine-5-carboxamide To a stirred solution of N1-cyclopropyl-4,5-difluorobenzene-1,2-diamine Int-6 (300 mg, 1.63 mmol) in DMF (5 mL) under an inert atmosphere was added 4-methylpyrimidine-5-carboxylic acid (309 mg, 1.95 mmol), HATU (745 g, 1.95 mmol) and ethyldiisopropylamine (1.16 mL, 6.52 mmol) at 0° C. The reaction mixture was warmed to room temperature and stirred for 16 h. After consumption of starting material (by TLC), the reaction mixture was diluted with water (20 mL) and extracted with EtOAc (2×20 mL). The combined organic extracts were dried over anhydrous $Na_2SO_4$ and concentrated under reduced pressure. The crude material was purified by silica gel column chromatography (eluent: 2% $MeOH/CH_2Cl_2$) to afford N-(2-(cyclopropylamino)-4,5-difluorophenyl)-4-methylpyrimidine-5-carboxamide (150 mg, 0.50 mmol, 30%) as yellow solid.

$^1$H NMR (400 MHz, DMSO-$d_6$): δ 9.69 (s, 1H), 9.13 (s, 1H), 8.98 (s, 1H), 7.50-7.45 (m, 1H), 6.96-6.91 (m, 1H), 5.84 (s, 1H), 2.60 (s, 3H), 2.37-2.35 (m, 1H), 0.78-0.69 (m, 2H), 0.48-0.36 (m, 2H)

1-Cyclopropyl-5,6-difluoro-2-(4-methylpyrimidin-5-yl)-1H-benzo[d]imidazole (Ex. 44)

To a stirred solution of N-(2-(cyclopropylamino)-4,5-difluorophenyl)-4-methylpyrimidine-5-carboxamide (150 mg, 0.50 mmol) in EtOH (1 mL) under an inert atmosphere was added 6N HCl (3 mL) at room temperature. The reaction mixture was stirred at 80° C. for 45 min. After consumption of starting material (by TLC), the reaction mixture was diluted with saturated sodium carbonate solution (20 mL) and extracted with EtOAc (2×20 mL). The combined organic extracts were dried over anhydrous $Na_2SO_4$ and concentrated under reduced pressure. The crude material was purified by silica gel column chromatography (eluent: 50% EtOAc/Hexane) which was further purified by preparative HPLC to afford 1-cyclopropyl-5,6-difluoro-2-(4-methylpyrimidin-5-yl)-1H-benzo[d]imidazole Ex. 44 (20 mg, 0.07 mmol, 14%) as an off white solid.

$^1$H NMR (400 MHz, $CD_3OD$): δ 9.20 (s, 1H), 8.96 (s, 1H), 7.72-7.68 (m, 1H), 7.62-7.51 (m, 1H), 3.60-3.54 (m, 1H), 2.58 (s, 3H), 1.11-1.01 (m, 2H), 0.77-0.66 (m, 2H)

LC-MS: m/z 287.1 [M+H]$^+$ at 3.16 RT (92.72% purity).

HPLC: 95.34%.

Example 45

1-Cyclopropyl-2-(4-ethylpyrimidin-5-yl)-5,6-difluoro-1H-benzo[d]imidazole (Ex. 45)

Scheme

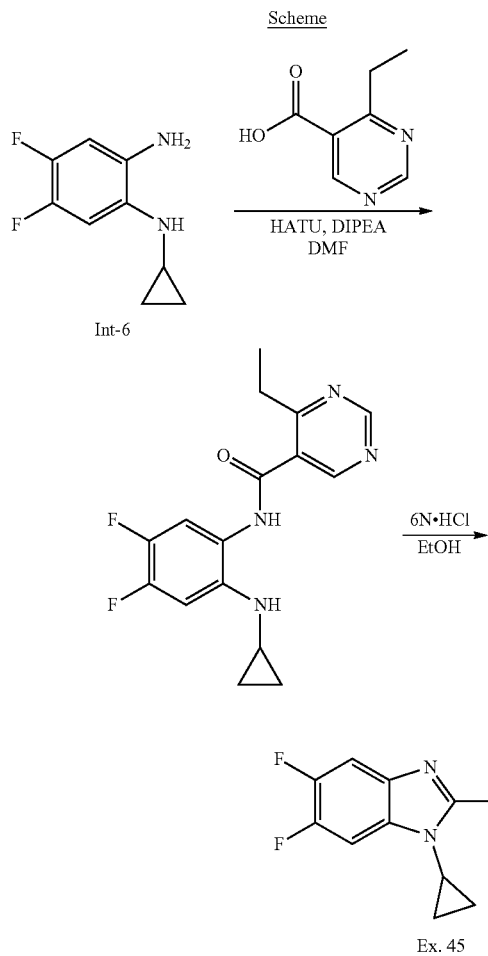

N-(2-(Cyclopropylamino)-4,5-difluorophenyl)-4-ethylpyrimidine-5-carboxamide

To a stirred solution of N1-cyclopropyl-4,5-difluorobenzene-1,2-diamine Int-6 (200 mg, 1.08 mmol) in DMF (6 mL) under an inert atmosphere was added 4-ethylpyrimidine-5-carboxylic acid (160 mg, 1.08 mmol), HATU (610 mg, 1.63 mmol) and diisopropylethylamine (0.37 mL, 2.17 mmol) at 0° C. The reaction mixture was stirred at room temperature for 16 h. After consumption of starting material (by TLC), the reaction mixture was diluted with water (20 mL) and extracted with EtOAc (2×20 mL). The combined organic extracts were washed with water (20 mL), dried over anhydrous $Na_2SO_4$ and concentrated under reduced pressure. The crude material was purified by silica gel column chromatography (eluent: 50% EtOAc/hexane) to afford N-(2-(cyclopropylamino)-4,5-difluorophenyl)-4-ethylpyrimidine-5-carboxamide (170 mg, 0.53 mmol, 50%) as an off-white solid.

$^1$H NMR (400 MHz, DMSO-$d_6$): δ 9.73 (s, 1H), 9.18 (s, 1H), 8.98 (s, 1H), 7.51-7.46 (m, 1H), 6.97-6.91 (m, 1H), 5.81 (s, 1H), 2.94-2.88 (m, 2H), 2.37 (brs, 1H), 1.24 (t, J=7.5 Hz, 3H), 0.78-0.74 (m, 2H), 0.49-0.32 (m, 2H)

To a stirred solution of N-(2-(cyclopropylamino)-4,5-difluorophenyl)-4-ethylpyrimidine-5-carboxamide (170 mg, 0.53 mmol) in EtOH (7 mL) under an inert atmosphere was added 6N HCl (4 mL) at room temperature. The reaction mixture was stirred at 80° C. for 2 h. After consumption of starting material (by TLC), the reaction mixture was diluted with saturated sodium bicarbonate solution (20 mL) and extracted with $CH_2Cl_2$ (2×20 mL). The combined organic extracts were dried over anhydrous $Na_2SO_4$ and concentrated under reduced pressure. The crude material was purified by preparative HPLC to afford 1-cyclopropyl-2-(4-ethylpyrimidin-5-yl)-5,6-difluoro-1H-benzo[d]imidazole Ex. 45 (20 mg, 0.06 mmol, 17%) as an off white solid.

$^1$H NMR (400 MHz, $CD_3OD$): δ 9.24 (s, 1H), 8.93 (s, 1H), 7.72-7.67 (m, 1H), 7.61-7.57 (m, 1H), 3.59-3.52 (m, 1H), 2.89-2.83 (m, 2H), 1.25 (t, J=7.6 Hz, 3H), 1.08-0.97 (m, 2H), 0.74-0.64 (m, 2H)

LC-MS: m/z 300.9 [M+H]$^+$ at 2.22 RT (99.22% purity).

HPLC: 98.11%.

Example 46

Scheme

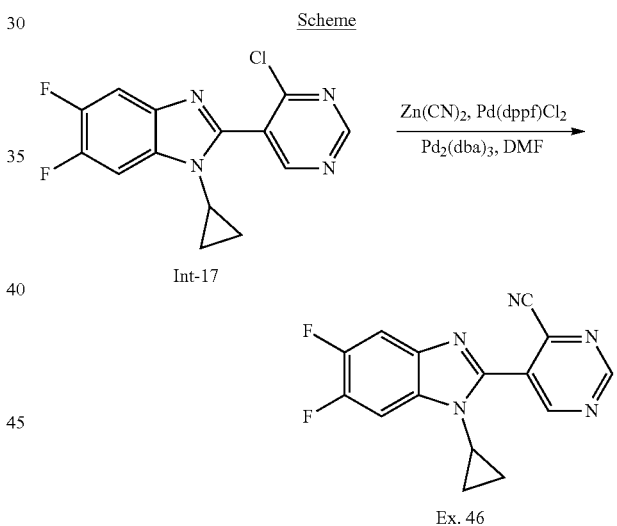

5-(1-Cyclopropyl-5,6-difluoro-1H-benzo[d]imidazol-2-yl) pyrimidine-4-carbonitrile (Ex. 46)

To a stirred solution of 2-(4-chloropyrimidin-5-yl)-1-cyclopropyl-5,6-difluoro-1H-benzo[d]imidazole Int-17 (04180 mg, 0.26 mmol) in DMF (1 mL) was added zinc cyanide (18.2 mg, 0.15 mmol) and the reaction mixture was purged under argon for 10 min. To this was added Pd(dppf)Cl$_2$ (9.5 mg, 0.01 mmol) and Pd$_2$(dba)$_3$ (11.9 mg, 0.01 mmol) and again the mixture was purged under argon for 10 min at room temperature. The reaction mixture was heated to 100° C. for 4 h. After consumption of starting material (by TLC), the reaction mixture was diluted with water (20 mL) and extracted with EtOAc (2×20 mL). The combined organic extracts were dried over anhydrous $Na_2SO_4$ and concentrated under reduced pressure. The crude material was purified by silica gel column chromatography (eluent: 50% EtOAc/hexane) and washed with n-pentane (2×10 mL) to afford 5-(1-cyclopropyl-5,6-difluoro-1H-benzo[d]imidazol-2-yl)pyrimidine-4-carbonitrile Ex. 46 (18 mg, 0.06 mmol, 23%) as brown syrup.

$^1$H NMR (400 MHz, CD$_3$OD): δ 9.51 (s, 1H), 9.50 (s, 1H), 7.77-7.73 (m, 1H), 7.70-7.65 (m, 1H), 3.80-3.74 (m, 1H), 1.22-1.08 (m, 2H), 0.82-0.71 (m, 2H)

LC-MS: m/z 297.9 [M+H]$^+$ at 2.72 RT (94.28% purity). HPLC: 97.51%.

Example 47

Scheme

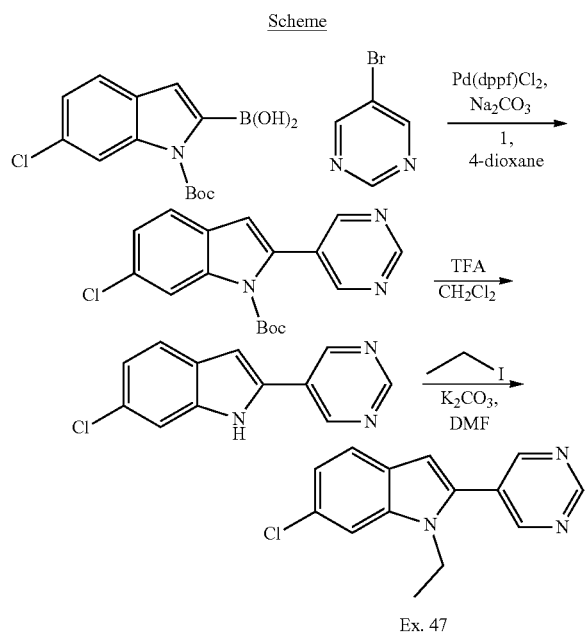

Ex. 47 tert-Butyl 6-chloro-2-(pyrimidin-5-yl)-1H-indole-1-carboxylate

To a stirred solution of {1-[(tert-butoxy)carbonyl]-6-chloro-1H-indol-2-yl}boronic acid (200 mg, 0.68 mmol) in 1,4-dioxane (8 mL) under an inert atmosphere was added 5-bromopyrimidine (107 mg, 0.68 mmol) and sodium carbonate solution (1.0 M solution, 1.3 mL, 2.04 mmol) at room temperature. The reaction mixture was degassed under argon for 10 min. Pd(dppf)Cl$_2$ (55 mg, 0.06 mmol) was added at room temperature and degassed under argon for 10 min. The reaction mixture was heated to 80° C. and stirred for 6 h. After consumption of starting material (by TLC), the reaction mixture was filtered through a pad of celite. The filtrate was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 40% EtOAc/hexane) to afford tert-butyl 6-chloro-2-(pyrimidin-5-yl)-1H-indole-1-carboxylate (150 mg, 0.45 mmol, 67%) as an off-white solid.

$^1$H NMR (500 MHz, DMSO-d$_6$): δ 9.22 (s, 1H), 8.99 (s, 2H), 8.20 (s, 1H), 7.71 (d, J=8.1 Hz, 1H), 7.37 (dd, J=8.7, 1.7 Hz, 1H), 7.00 (s, 1H), 1.33 (s, 9H)

6-Chloro-2-(pyrimidin-5-yl)-1H-indole

To a stirred solution of tert-butyl 6-chloro-2-(pyrimidin-5-yl)-1H-indole-1-carboxylate (50 mg, 0.15 mmol) in CH$_2$Cl$_2$ (3 mL) under an inert atmosphere was added trifluoroacetic acid (0.9 mL) at 0° C. The reaction mixture was warmed to room temperature and stirred for 8 h. After consumption of starting material (by TLC), the volatiles were evaporated under reduced pressure. The residue was washed with n-pentane (2×5 mL) to afford 6-chloro-2-(pyrimidin-5-yl)-1H-indole (30 mg, 0.13 mmol, 86%) as an off white solid.

$^1$H NMR (400 MHz, DMSO-d$_6$): δ 11.99 (br s, 1H), 9.29 (s, 2H), 9.11 (s, 1H), 7.61 (d, J=8.1 Hz, 1H), 7.47 (s, 1H), 7.21 (s, 1H), 7.09 (dd, J=8.7, 1.7 Hz, 1H)

6-Chloro-1-ethyl-2-(pyrimidin-5-yl)-1H-indole (Ex. 47)

To a stirred solution of 6-chloro-2-(pyrimidin-5-yl)-1H-indole (80 mg, 0.34 mmol) in DMF (4 mL) under an inert atmosphere was added potassium carbonate (144 mg, 1.04 mmol) followed by ethyl iodide (144 mg, 1.04 mmol) at room temperature. The reaction mixture was stirred at room temperature for 8 h. After consumption of starting material (by TLC), the reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 30% EtOAc/hexane) to afford 6-chloro-1-ethyl-2-(pyrimidin-5-yl)-1H-indole Ex. 47 (20 mg, 0.07 mmol, 22%) as an off-white solid.

$^1$H NMR (400 MHz, CD$_3$OD): δ 9.22 (s, 1H), 9.01 (s, 2H), 7.59 (d, J=8.5 Hz, 1H), 7.58-7.57 (m, 1H), 7.11 (dd, J=8.39, 1.83 Hz, 1H), 6.75 (s, 1H), 4.29-4.24 (m, 2H), 1.29 (t, J=7.2 Hz, 3H)

LC-MS: m/z 257.9 [M+H]$^+$ at 2.60 RT (94.08% purity). HPLC: 96.05%.

Example 48

Scheme

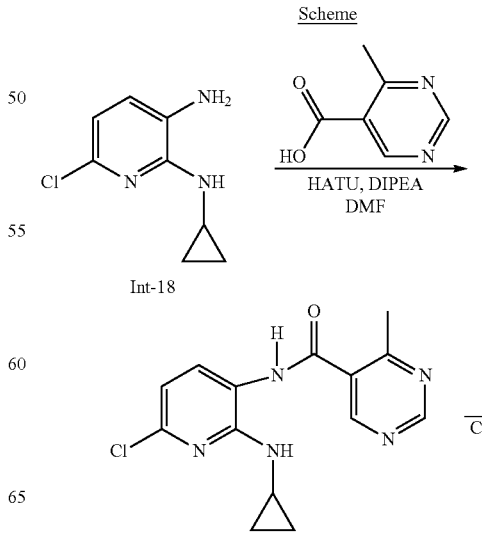

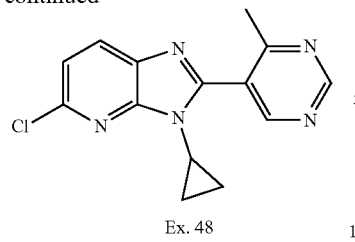

Ex. 48

N-(6-Chloro-2-(cyclopropylamino)pyridin-3-yl)-4-methylpyrimidine-5-carboxamide To a stirred solution of 6-chloro-N2-cyclopropylpyridine-2,3-diamine Int-18 (200 mg, 1.09 mmol) in DMF (2 mL) under an inert atmosphere was added 4-methylpyrimidine-5-carboxylic acid (226 mg, 1.63 mmol), HATU (450 mg, 1.20 mmol) and ethyldiisopropylamine (0.52 mL, 3.27 mmol) at room temperature. The reaction mixture was stirred at room temperature for 16 h. After consumption of starting material (by TLC), the reaction mixture was diluted with ice cold water (20 mL) and extracted with EtOAc (2×20 mL). The combined organic extracts were dried over anhydrous $Na_2SO_4$ and concentrated under reduced pressure to obtain N-(6-chloro-2-(cyclopropylamino)pyridin-3-yl)-4-methylpyrimidine-5-carboxamide (80 mg, crude) as a brown solid which was used directly without further purification.

LC-MS: m/z 303.9 $[M+H]^+$ at 2.11 RT (87.24% purity).

5-Chloro-3-cyclopropyl-2-(4-methylpyrimidin-5-yl)-3H-imidazo[4,5-b]pyridine (Ex. 48)

To a stirred solution of N-(6-chloro-2-(cyclopropylamino) pyridin-3-yl)-4-methylpyrimidine-5-carboxamide (400 mg, 1.32 mmol) in tertiary butanol (5 mL) under an inert atmosphere was added potassium phosphate (533 mg, 2.64 mmol) at room temperature. The reaction mixture was stirred at 90° C. for 16 h. After consumption of starting material (by TLC), the reaction mixture was diluted with water (20 mL) extracted with EtOAc (2×30 mL). The combined organic extracts were dried over anhydrous $Na_2SO_4$ and concentrated under reduced pressure. The crude material was purified by silica gel column chromatography (eluent: 2% $MeOH/CH_2Cl_2$) to afford 5-chloro-3-cyclopropyl-2-(4-methylpyrimidin-5-yl)-3H-imidazo[4,5-b]pyridine Ex. 48 (210 mg, 0.73 mmol, 56%) as an off white solid.

$^1H$ NMR (400 MHz, $CD_3OD$): δ 9.21 (s, 1H), 9.01 (s, 1H), 8.09 (d, J=8.4 Hz, 1H), 7.41 (d, J=8.4 Hz, 1H), 3.55-3.51 (m, 1H), 2.60 (s, 3H), 1.14-1.00 (m, 2H), 0.93-0.76 (m, 2H)

LC-MS: m/z 285.9 $[M+H]^+$ at 2.03 RT (99.59% purity).
HPLC: 99.93%.

Example 49

Scheme

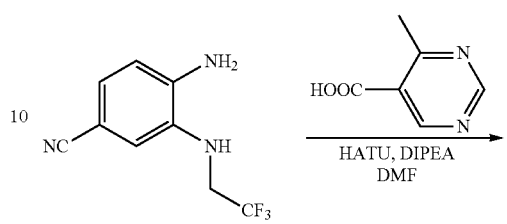

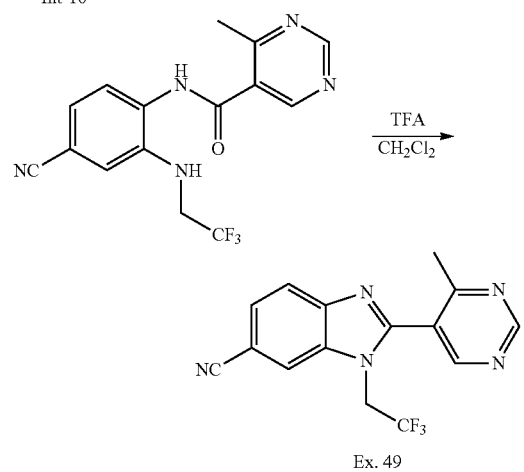

Ex. 49

N-(4-Cyano-2-((2,2,2-trifluoroethyl)amino)phenyl)-4-methylpyrimidine-5-carboxamide To a stirred solution of 4-amino-3-((2,2,2-trifluoroethyl) amino)benzonitrile Int-16 (215 mg, 1.0 mmol) in DMF (3 mL) under an inert atmosphere was added 4-methylpyrimidine-5-carboxylic acid (138 mg, 1.0 mmol), HATU (570 mg, 1.5 mmol) and ethyldiisopropylamine (0.69 mL, 4.0 mmol) at room temperature. The reaction mixture was stirred at room temperature for 16 h. After consumption of starting material (by TLC), the reaction mixture was diluted with aqueous ammonium chloride solution (30 mL) and extracted with EtOAc (2×30 mL). The combined organic extracts were dried over anhydrous $Na_2SO_4$ and concentrated under reduced pressure to obtain N-(4-cyano-2-((2,2,2-trifluoroethyl)amino)phenyl)-4-methylpyrimidine-5-carboxamide (80 mg, crude) as a yellow syrup which was used directly without further purification.

LC-MS: m/z 334.1 $[M-H]^+$ at 3.26 RT (42.53% purity).

2-(4-Methylpyrimidin-5-yl)-1-(2,2,2-trifluoroethyl)-1H-benzo[d]imidazole-6-carbonitrile (Ex. 49)

To a stirred solution of N-(4-cyano-2-((2,2,2-trifluoroethyl)amino)phenyl)-4-methylpyrimidine-5-carboxamide (80 mg, 0.23 mmol) in $CH_2Cl_2$ (0.8 mL) under an inert atmosphere was added trifluoroacetic acid (2.2 mL) at room temperature. The reaction mixture was stirred at room temperature for 52 h. After consumption of starting material (by TLC), the reaction mixture was diluted with saturated sodium carbonate solution (30 mL) and extracted with EtOAc (2×30 mL). The combined organic extracts were washed with water (20 mL), brine (20 mL), dried over anhydrous Na₂SO₄ and concentrated under reduced pressure. The crude material was purified by preparative HPLC to afford 2-(4-methylpyrimidin-5-yl)-1-(2,2,2-trifluoroethyl)-1H-benzo[d]imidazole-6-carbonitrile Ex. 49 (5 mg, 15.77 mmol, 6.6%) as an off-white solid.

¹H NMR (400 MHz, CD₃OD): δ 9.27 (s, 1H), 8.89 (s, 1H), 8.29 (s, 1H), 7.96 (d, J=8.5 Hz, 1H), 7.76 (dd, J=8.4, 1.5 Hz, 1H), 5.21-5.14 (m, 2H), 2.47 (s, 3H)

LC-MS: m/z 316.1 [M−H]⁺ at 2.88 RT (97.15% purity). HPLC: 93.69%.

Example 50

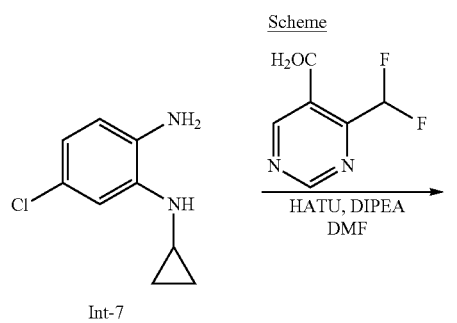

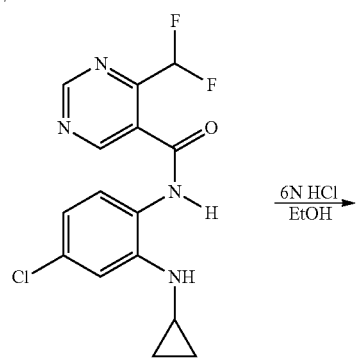

Ex. 50

N-(4-Chloro-2-(cyclopropylamino)phenyl)-4-(difluoromethyl)pyrimidine-5-carboxamide To a stirred solution of 5-chloro-N1-cyclopropylbenzene-1,2-diamine Int-7 (400 mg, 2.18 mmol) in DMF (4 mL) under an inert atmosphere was added 4-(difluoromethyl)pyrimidine-5-carboxylic acid (380 mg, 2.18 mmol), HATU (994 mg, 2.60 mmol) and diisopropylethylamine (1.12 g, 8.7 mmol) at 0° C. The reaction mixture was stirred at room temperature for 16 h. After consumption of starting material (by TLC), the reaction mixture was diluted with water (30 mL) and extracted with ether (2×30 mL). The combined organic extracts were washed with water (30 mL), dried over anhydrous Na₂SO₄ and concentrated under reduced pressure. The crude material was purified by silica gel column chromatography (eluent: 40% EtOAc/hexane) to afford N-(4-chloro-2-(cyclopropylamino)phenyl)-4-(difluoromethyl)pyrimidine-5-carboxamide (300 mg, 0.88 mmol, 38%) as an off-white solid.

¹H NMR (500 MHz, DMSO-d₆): δ 9.95 (s, 1H), 9.47 (s, 1H), 9.41 (s, 1H), 7.31-7.27 (m, 2H), 6.99 (d, J=2.3 Hz, 1H), 6.70 (dd, J=8.1, 2.3 Hz, 1H), 5.99 (s, 1H), 2.42-2.36 (m, 1H), 0.80-0.74 (m, 2H), 0.47-0.42 (m, 2H)

6-Chloro-1-cyclopropyl-2-(4-(difluoromethyl)pyrimidin-5-yl)-1H-benzo[d]imidazole (Ex. 50)

To a stirred solution of N-(4-chloro-2-(cyclopropylamino)phenyl)-4-(difluoromethyl)pyrimidine-5-carboxamide (150 mg, 0.42 mmol) in EtOH (1.5 mL) under an inert atmosphere was added 6N HCl (1.5 mL) at room temperature. The reaction mixture was stirred at 70° C. for 1 h. After consumption of starting material (by TLC), the reaction mixture was diluted with saturated sodium bicarbonate solution (20 mL) and extracted with EtOAc (2×200 mL). The combined organic extracts were dried over anhydrous Na₂SO₄ and concentrated under reduced pressure. The crude material was purified by silica gel column chromatography (eluent: 40% EtOAc/Hexane) to afford 6-chloro-1-cyclopropyl-2-(4-(difluoromethyl)pyrimidin-5-yl)-1H-benzo[d]imidazole Ex. 50 (50 mg, 0.15 mmol, 37%) as an off white solid.

¹H NMR (400 MHz, CD₃OD): δ 9.49 (s, 1H), 9.34 (s, 1H), 7.80 (d, J=1.7 Hz, 1H), 7.71 (d, J=8.7 Hz, 1H), 7.36 (dd, J=8.5, 2.0 Hz, 1H), 7.08 (t, J=53.4 Hz, 1H), 3.63-3.59 (m, 1H), 1.11-1.05 (m, 2H), 0.77-0.69 (m, 2H)

LC-MS: m/z 320.9 [M+H]⁺ at 2.40 RT (98.11% purity). HPLC: 99.08%.

Example 51

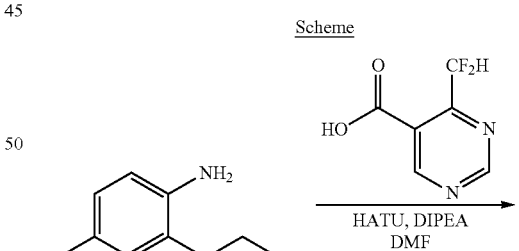

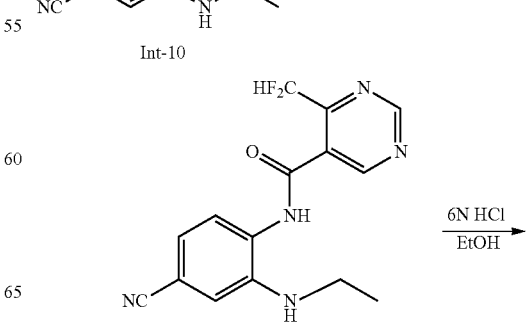

-continued

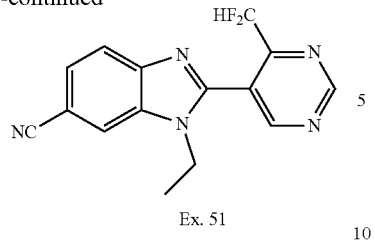

Ex. 51

N-(4-Cyano-2-(ethylamino)phenyl)-4-(difluoromethyl)pyrimidine-5-carboxamide

To a stirred solution of 4-amino-3-(ethylamino)benzonitrile Int-10 (200 mg, 1.24 mmol) in DMF (2 mL) under an inert atmosphere was added 4-(difluoromethyl)pyrimidine-5-carboxylic acid (324 mg, 1.86 mmol), HATU (566 mg, 1.50 mmol) and ethyldiisopropylamine (0.86 mL, 4.96 mmol) at room temperature. The reaction mixture was stirred at room temperature for 16 h. After consumption of starting material (by TLC), the reaction mixture was diluted with water (30 mL) and extracted with EtOAc (2×30 mL). The combined organic extracts were dried over anhydrous Na$_2$SO$_4$ and concentrated under reduced pressure to obtain N-(4-cyano-2-(ethylamino)phenyl)-4-(difluoromethyl)pyrimidine-5-carboxamide (150 mg, crude) as a pale yellow solid which was used directly without further purification.

LC-MS: m/z 316.1 [M−H]$^+$ at 2.05 RT (94.97% purity).

2-(4-(Difluoromethyl)pyrimidin-5-yl)-1-ethyl-1H-benzo[d]imidazole-6-carbonitrile (Ex. 51)

To a stirred solution of N-(4-cyano-2-(ethylamino)phenyl)-4-(difluoromethyl)pyrimidine-5-carboxamide (150 mg, 0.47 mmol) in EtOH (1.5 mL) under an inert atmosphere was added 6N HCl (1.5 mL) at room temperature. The reaction mixture was stirred at 80° C. for 1 h. After consumption of starting material (by TLC), the reaction mixture was diluted with saturated sodium bicarbonate solution (20 mL) and extracted with EtOAc (2×20 mL). The combined organic extracts were dried over anhydrous Na$_2$SO$_4$ and concentrated under reduced pressure. The crude material was purified by preparative HPLC to afford 2-(4-(difluoromethyl)pyrimidin-5-yl)-1-ethyl-1H-benzo[d]imidazole-6-carbonitrile Ex. 51 (15 mg, 0.05 mmol, 11%) as an off-white solid.

$^1$H NMR (400 MHz, CD$_3$OD): δ 9.54 (s, 1H), 9.22 (s, 1H), 8.24 (s, 1H), 7.89 (d, J=8.4 Hz, 1H), 7.68 (dd, J=8.5, 1.4 Hz, 1H), 6.90 (t, J=54.5 Hz, 1H), 4.31-4.26 (m, 2H), 1.36 (t, J=7.2 Hz, 3H)

LC-MS: m/z 299.9 [M+H]$^+$ at 2.27 RT (98.39% purity).
HPLC: 96.87%.

Example 52

Scheme

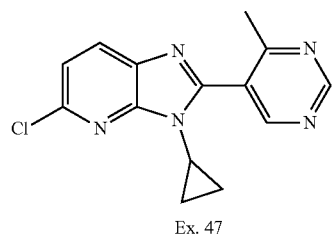

Ex. 47

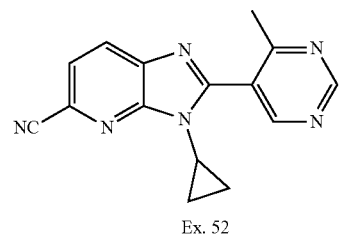

Ex. 52

3-Cyclopropyl-2-(4-methylpyrimidin-5-yl)-3H-imidazo[4,5-b]pyridine-5-carbonitrile (Ex. 52)

To a stirred solution of 5-chloro-3-cyclopropyl-2-(4-methylpyrimidin-5-yl)-3H-imidazo[4,5-b]pyridine Ex. 48 (150 mg, 0.52 mmol) in DMF (0.5 mL) at room temperature was added zinc cyanide (92 mg, 0.78 mmol) and the mixture was degassed under argon for 10 min. Pd(PPh$_3$)$_4$ (60 mg, 0.05 mmol) was added to the reaction mixture. The reaction mixture was heated to 180° C. and stirred for 6 h. After consumption of starting material (by TLC), the reaction mixture was diluted with water (50 mL) and extracted with EtOAc (2×50 mL). The combined organic extracts were dried over anhydrous Na$_2$SO$_4$ and concentrated under reduced pressure. The crude material was purified by preparative HPLC to afford 3-cyclopropyl-2-(4-methylpyrimidin-5-yl)-3H-imidazo [4, 5-b] pyridine-5-carbonitrile Ex. 52 (15 mg, 0.05 mmol, 10%) as a pale yellow solid.

$^1$H NMR (400 MHz, CD$_3$OD): δ 9.22 (s, 1H), 9.03 (s, 1H), 8.25 (d, J=8.1 Hz, 1H), 7.84 (d, J=8.2 Hz, 1H), 3.59-3.55 (m, 1H), 2.62 (s, 3H), 1.13-1.03 (m, 2H), 0.94-0.80 (m, 2H)

LC-MS: m/z 276.9 [M+H]$^+$ at 1.88 RT (95.24% purity).
HPLC: 99.81%.

Example 53

Scheme

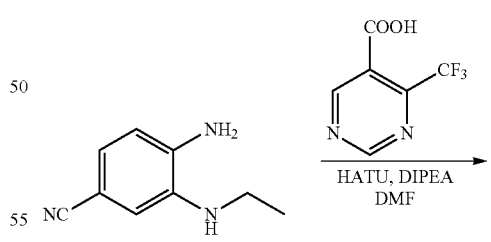

Int-10

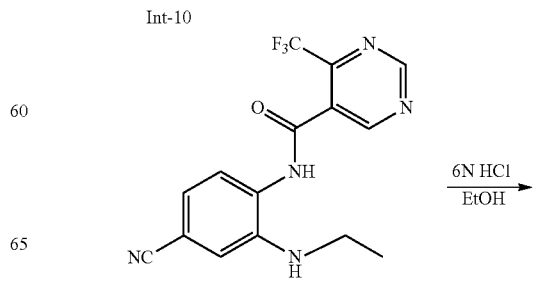

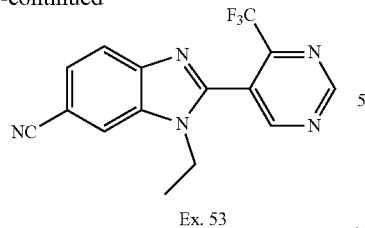

Ex. 53

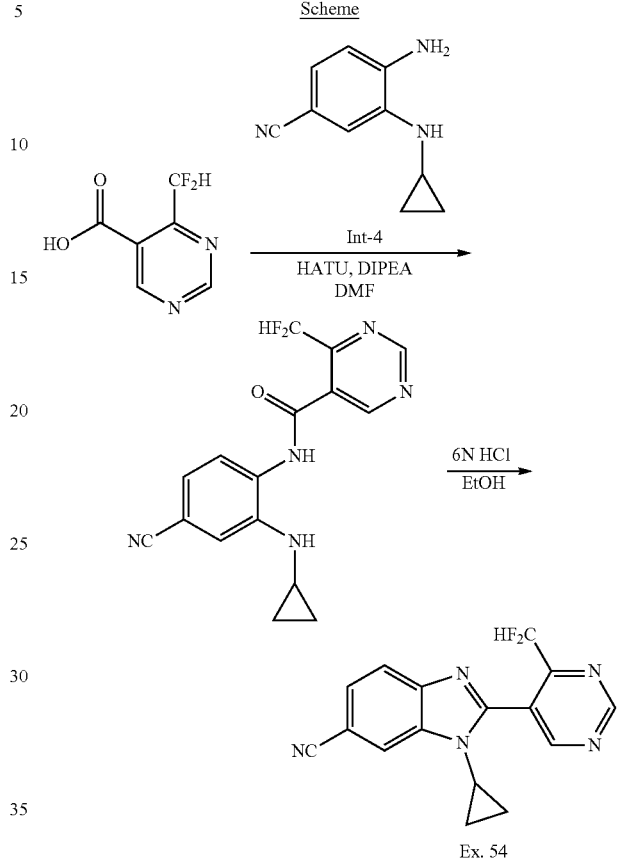

Example 54

Scheme

Ex. 54

N-(4-Cyano-2-(ethylamino)phenyl)-4-(trifluoromethyl)pyrimidine-5-carboxamide To a stirred solution of 4-amino-3-(ethylamino)benzonitrile Int-10 (200 mg, 1.24 mmol) in DMF (2 mL) under an inert atmosphere was added 4-(trifluoromethyl)pyrimidine-5-carboxylic acid (238 mg, 1.24 mmol), HATU (566 mg, 1.50 mmol) and ethyldiisopropylamine (0.9 mL, 4.96 mmol) at room temperature. The reaction mixture was stirred at room temperature for 16 h. After consumption of starting material (by TLC), the reaction mixture was diluted with water (30 mL) and extracted with EtOAc (2×30 mL). The combined organic extracts were dried over anhydrous $Na_2SO_4$ and concentrated under reduced pressure to obtain N-(4-cyano-2-(ethylamino)phenyl)-4-(trifluoromethyl)pyrimidine-5-carboxamide (150 mg, crude) as a pale yellow solid which was used directly without further purification.

LC-MS: m/z 334 [M−H]$^+$ at 2.76 RT (17.40% purity).

2-(4-(Difluoromethyl)pyrimidin-5-yl)-1-ethyl-1H-benzo[d]imidazole-6-carbonitrile (Ex. 53)

To a stirred solution of N-(4-cyano-2-(ethylamino)phenyl)-4-(trifluoromethyl)pyrimidine-5-carboxamide (150 mg, 0.47 mmol) in EtOH (1.5 mL) under an inert atmosphere was added 6N HCl (1.5 mL) at room temperature. The reaction mixture was stirred at 80° C. for 1 h. After consumption of starting material (by TLC), the reaction mixture was diluted with saturated sodium bicarbonate solution (20 mL) and extracted with EtOAc (2×20 mL). The combined organic extracts were dried over anhydrous $Na_2SO_4$ and concentrated under reduced pressure. The crude material was purified by silica gel column chromatography (eluent: 40% EtOAc/hexane) to afford 2-(4-(difluoromethyl)pyrimidin-5-yl)-1-ethyl-1H-benzo[d]imidazole-6-carbonitrile Ex. 53 (15 mg, 0.05 mmol, 11%) as an off-white solid.

$^1$H NMR (400 MHz, CD$_3$OD): δ 9.62 (s, 1H), 9.31 (s, 1H), 8.25 (s, 1H), 7.90 (dd, J=8.5, 0.7 Hz, 1H), 7.70 (dd, J=8.5, 1.4 Hz, 1H), 4.29-4.23 (m, 2H), 1.36 (t, J=7.2 Hz, 3H)

LC-MS: m/z 318.2 [M+H]$^+$ at 3.38 RT (96.78% purity).

HPLC: 99.29%

N-(4-Cyano-2-(cyclopropylamino)phenyl)-4-(difluoromethyl)pyrimidine-5-carboxamide To a stirred solution of 4-(difluoromethyl)pyrimidine-5-carboxylic acid (200 mg, 1.15 mmol) in DMF (2 mL) under an inert atmosphere was added Int-4 (201 mg, 1.15 mmol), HATU (527 mg, 1.38 mmol) and ethyldiisopropylamine (0.8 mL, 4.62 mmol) at room temperature. The reaction mixture was stirred at room temperature for 16 h. After consumption of starting material (by TLC), the reaction mixture was diluted with water (30 mL) and extracted with EtOAc (2×30 mL). The combined organic extracts were dried over anhydrous $Na_2SO_4$ and concentrated under reduced pressure to obtain N-(4-cyano-2-(cyclopropylamino)phenyl)-4-(difluoromethyl)pyrimidine-5-carboxamide (200 mg, crude) as a black liquid which was used directly without further purification.

LC-MS: m/z 328 [M−H]$^+$ at 2.58 RT (21.35% purity).

1-Cyclopropyl-2-(4-(difluoromethyl)pyrimidin-5-yl)-1H-benzo[d]imidazole-6-carbonitrile (Ex. 54)

To a stirred solution of N-(4-cyano-2-(cyclopropylamino)phenyl)-4-(difluoromethyl)pyrimidine-5-carboxamide (100 mg, 0.30 mmol) in EtOH (1 mL) was added 6N HCl (1 mL) at room temperature under an inert atmosphere. The reaction mixture was stirred at 70° C. for 1 h. After consumption of starting material (by TLC), the reaction mixture was diluted with saturated sodium bicarbonate solution (20 mL) and extracted with EtOAc (2×20 mL). The combined organic extracts were dried over anhydrous $Na_2SO_4$ and concentrated under reduced pressure. The crude material was purified by preparative HPLC to afford 1-cyclopropyl-2-(4-(difluoromethyl)pyrimidin-5-yl)-1H-benzo[d]imidazole-6-carbonitrile Ex. 54 (25 mg, 0.08 mmol, 26%) as an off-white solid.

$^1$H NMR (400 MHz, $CD_3OD$): δ 9.52 (s, 1H), 9.36 (s, 1H), 8.24 (s, 1H), 7.89 (dd, J=8.4, 0.6 Hz, 1H), 7.68 (dd, J=8.4, 1.5 Hz, 1H), 7.10 (t, 51.70 Hz, 1H), 3.68-3.64 (m, 1H), 1.14-1.09 (m, 2H), 0.84-0.72 (m, 2H)

LC-MS: m/z 352.9 [M+ACN]$^+$ at 2.44 RT (98.91% purity).

HPLC: 99.26%.

Example 55

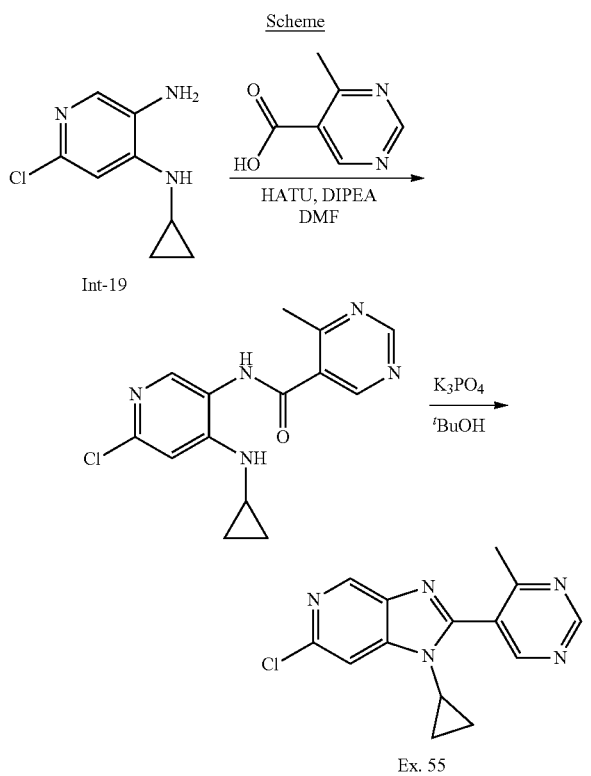

N-(6-Chloro-4-(cyclopropylamino)pyridin-3-yl)-4-methylpyrimidine-5-carboxamide

To a stirred solution of 6-chloro-N4-cyclopropylpyridine-3,4-diamine Int-19 (500 mg, 2.73 mmol) in DMF (10 mL) under an inert atmosphere was added 4-methylpyrimidine-5-carboxylic acid (414 mg, 3.00 mmol), HATU (1 g, 3.00 mmol) and ethyldiisopropylamine (1.3 mL, 8.19 mmol) at room temperature. The reaction mixture was stirred at room temperature for 16 h. After consumption of starting material (by TLC), the reaction mixture was diluted with water (30 mL) and extracted with EtOAc (2×30 mL). The combined organic extracts were dried over anhydrous $Na_2SO_4$ and concentrated under reduced pressure. The crude material was purified by silica gel column chromatography (eluent: 3% MeOH/$CH_2Cl_2$) to afford N-(6-chloro-4-(cyclopropylamino)pyridin-3-yl)-4-methylpyrimidine-5-carboxamide (411 mg, 1.35 mmol, 50%) as a brown solid.

$^1$H NMR (500 MHz, DMSO-d$_6$): δ 9.74 (s, 1H), 9.13 (s, 1H), 9.04 (s, 1H), 8.02 (s, 1H), 6.90 (s, 1H), 6.84 (brs, 1H), 2.61 (s, 3H), 2.49-2.46 (m, 1H), 0.87-0.74 (m, 2H), 0.56-0.41 (m, 2H)

6-Chloro-1-cyclopropyl-2-(4-methylpyrimidin-5-yl)-1H-imidazo[4,5-c]pyridine (Ex. 55)

To a stirred solution of N-(6-chloro-4-(cyclopropylamino) pyridin-3-yl)-4-methylpyrimidine-5-carboxamide (100 mg, 0.33 mmol) in tertiary butanol (tBuOH)(1 mL) under an inert atmosphere was added potassium phosphate (133 mg, 0.66 mmol) at room temperature. The reaction mixture was stirred at 90° C. for 16 h. After consumption of starting material (by TLC), the reaction mixture was diluted with water (30 mL) and extracted with EtOAc (2×30 mL). The combined organic extracts were dried over anhydrous $Na_2SO_4$ and concentrated under reduced pressure. The crude material was purified by silica gel column chromatography (eluent: 2% MeOH/$CH_2Cl_2$) to afford 6-chloro-1-cyclopropyl-2-(4-methylpyrimidin-5-yl)-1H-imidazo[4,5-c]pyridine Ex. 55 (35 mg, 0.12 mmol, 36%) as a pale yellow solid.

$^1$H NMR (400 MHz, $CD_3OD$): δ 9.22 (s, 1H), 9.02 (s, 1H), 8.77 (s, 1H), 7.85 (s, 1H), 3.63-3.58 (m, 1H), 2.62 (s, 3H), 1.12-1.04 (m, 2H), 0.79-0.74 (m, 2H)

LC-MS: m/z 285.9 [M+H]$^+$ at 1.82 RT (97.42% purity).
HPLC: 96.62%.

Example 56

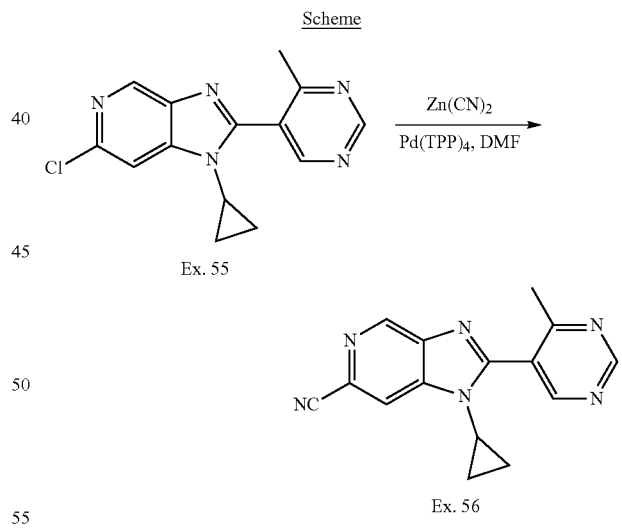

1-Cyclopropyl-2-(4-methylpyrimidin-5-yl)-1H-imidazo[4,5-c]pyridine-6-carbonitrile (Ex. 56)

To a stirred solution of 6-chloro-1-cyclopropyl-2-(4-methylpyrimidin-5-yl)-1H-imidazo [4, 5-c]pyridine Ex. 55 (130 mg, 0.45 mmol) in DMF (1 mL) was added zinc cyanide (106 mg, 0.91 mmol) and the mixture was degassed under argon for 10 min. Then Pd(PPh$_3$)$_4$ (52 mg) was added to the reaction mixture at room temperature. The reaction mixture was heated to 180° C. and stirred for 6 h. After consumption of starting material (by TLC), the reaction mixture was diluted with water (50 mL) and extracted with EtOAc (2×50 mL). The combined organic extracts were dried over anhydrous Na₂SO₄ and concentrated under reduced pressure. The crude material was purified by silica gel column chromatography (eluent: 2% MeOH/CH₂Cl₂) to afford 1-cyclopropyl-2-(4-methylpyrimidin-5-yl)-1H-imidazo[4,5-c]pyridine-6-carbonitrile Ex. 56 (20 mg, 0.07 mmol, 16%) as a pale brown solid.

¹H NMR (400 MHz, DMSO-d₆): δ 9.26 (s, 1H), 9.17 (s, 1H), 9.13 (s, 1H), 8.55 (s, 1H), 3.73-3.70 (m, 1H), 2.58 (s, 3H), 1.06-0.96 (m, 2H), 0.76-0.69 (m, 2H)

LC-MS: m/z 277.2 [M+H]⁺ at 2.18 RT (98.80% purity). HPLC: 99.39%.

Example 57

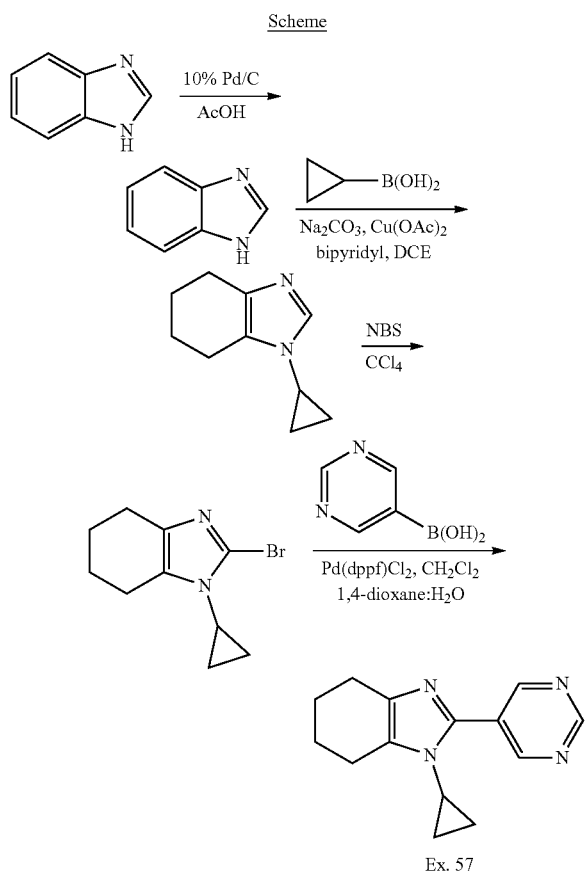

Ex. 57

4, 5, 6, 7-Tetrahydro-1H-benzo[d]imidazole

To a stirred solution of 1H-benzo[d]imidazole (2 g, 16.94 mmol) in acetic acid (25 mL) under an inert atmosphere was added 10% Pd/C (50% wet, 600 mg) at room temperature. The reaction mixture was stirred at 90-95° C. under a hydrogen atmosphere (75 PSI) for 24 h. After consumption of starting material (by TLC), the reaction mixture was filtered through a pad of celite and the pad was washed with EtOAc (100 mL). The filtrate was basified with saturated sodium bicarbonate solution (100 mL) and extracted with EtOAc (2×100 mL). The combined organic extracts were dried over anhydrous Na₂SO₄ and concentrated under reduced pressure to obtain 4,5,6,7-tetrahydro-1H-benzo[d]imidazole (800 mg, 6.55 mmol, 40%) as an off white solid.

¹H NMR (400 MHz, DMSO-d₆): δ 11.52 (brs, 1H), 7.35 (s, 1H), 2.45 (brs, 4H), 1.74-1.67 (m, 4H)

1-Cyclopropyl-4,5,6,7-tetrahydro-1H-benzo[d]imidazole

To a stirred solution of 4,5,6,7-tetrahydro-1H-benzo[d]imidazole (500 mg, 4.09 mmol) in 1,2-dichloroethane (DCE) (5 mL) under an inert atmosphere was added cyclopropylboronic acid (700 mg, 8.19 mmol), copper(II) acetate (810 mg, 4.09 mmol), sodium carbonate (1.25 g, 12.29 mmol) and 2,2'-bipyridine (640 mg, 4.09 mmol) in a sealed tube at room temperature. The reaction mixture was heated to 100° C. and stirred for 16 h. After consumption of starting material (by TLC), the reaction mixture was poured into ice cold water (30 mL) and extracted with EtOAc (2×30 mL). The combined organic extracts were dried over anhydrous Na₂SO₄ and concentrated under reduced pressure. The crude material was purified by silica gel column chromatography (eluent: EtOAc) to afford 1-cyclopropyl-4,5,6,7-tetrahydro-1H-benzo[d]imidazole (140 mg, 0.65 mmol, 22%) as pale yellow solid.

¹H NMR (500 MHz, DMSO-d₆): δ 7.43 (brs, 1H), 3.20-3.07 (m, 1H), 2.58-2.54 (m, 2H), 2.41-2.39 (m, 2H), 1.80-1.62 (m, 4H), 0.93-0.79 (m, 4H)

2-Bromo-1-cyclopropyl-4,5,6,7-tetrahydro-1H-benzo[d]imidazole

A stirred solution of 1-cyclopropyl-4,5,6 7-tetrahydro-1H-benzo[d]imidazole (400 mg, 2.46 mmol) in CCl₄ (5 mL) under an inert atmosphere was added N-bromosuccinimide (650 mg, 3.70 mmol) at room temperature. The reaction mixture was stirred at reflux for 3 h. After consumption of starting material (by TLC), the reaction mixture was diluted with water (20 mL) and extracted with CH₂Cl₂ (2×20 mL). The combined organic extracts were dried over anhydrous Na₂SO₄ and concentrated under reduced pressure. The crude material was purified by silica gel column chromatography (eluent: 70% EtOAc/Hexane) to afford 2-bromo-1-cyclopropyl-4,56, 7-tetrahydro-1H-benzo[d]imidazole (230 mg, 0.95 mmol, 38%) as pale yellow solid.

¹H NMR (500 MHz, DMSO-d₆): δ 3.09-3.02 (m, 1H), 2.58-2.56 (m, 2H), 2.40-2.38 (m, 2H), 1.72-1.67 (m, 4H), 1.09-1.03 (m, 2H), 0.98-0.83 (m, 2H)

1-Cyclopropyl-2-(pyrimidin-5-yl)-4,5,67-tetrahydro-1H-benzo[d]imidazole (Ex. 57)

To a stirred solution of 2-bromo-1-cyclopropyl-4,5,6,7-tetrahydro-1H-benzo[d]imidazole (150 mg, 0.62 mmol) in 1,4-dioxane (3 mL) and water (1 mL) under an inert atmosphere was added pyrimidin-5-ylboronic acid (5, 95 mg, 0.75 mmol) and cesium carbonate (610 mg, 1.87 mmol) at room temperature. The reaction mixture was degassed under argon for 10 min. To this was added Pd(dppf)C12 and CH₂Cl₂ (76.5 mg, 93.75 mmol) at room temperature and the mixture was degassed under argon for 10 min. The reaction mixture was heated to 150° C. and stirred for 5 h. After consumption of starting material (by TLC), the reaction mixture was filtered through a pad of celite. The filtrate was diluted with water (20 mL) and extracted with EtOAc (2×20 mL). The combined organic extracts were dried over anhydrous Na₂SO₄ and concentrated under reduced pressure. The crude material was purified by preparative HPLC to afford 1-cyclopropyl-2-(pyrimidin-5-yl)-4,5,6,7-tetrahydro-1H-benzo[d]imidazole Ex. 57 (14 mg, 0.06 mmol, 10%) as an off-white solid.

$^1$H NMR (400 MHz, CD$_3$OD): δ 9.15 (s, 1H), 9.15 (s, 2H), 3.56-3.44 (m, 1H), 2.77-2.74 (m, 2H), 2.61-2.58 (m, 2H), 1.99-1.71 (m, 4H), 1.12-1.04 (m, 2H), 0.70-0.61 (m, 2H)

LC-MS: m/z 241 [M+H]$^+$ at 2.02 RT (98.17% purity).
HPLC: 92.62%.

Example 58

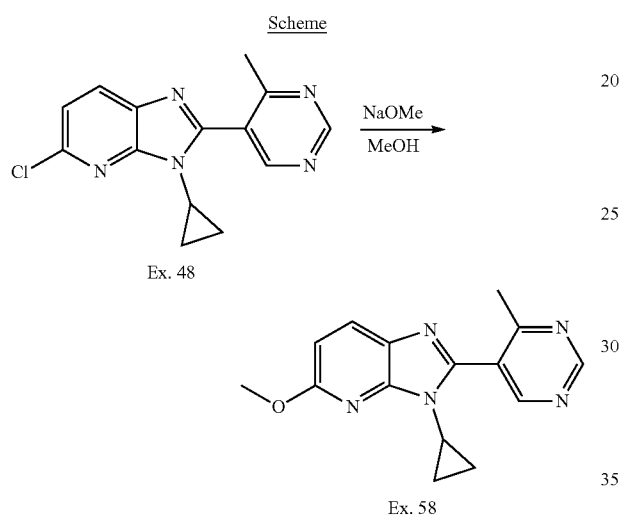

3-Cyclopropyl-5-methoxy-2-(4-methylpyrimidin-5-yl)-3H-imidazo[4,5-b]pyridine (Ex. 58)

To a stirred solution of 5-chloro-3-cyclopropyl-2-(4-methylpyrimidin-5-yl)-3H-imidazo[4,5-b]pyridine Ex. 48 (65 mg, 0.22 mmol) in MeOH (1 mL) under an inert atmosphere was added sodium methoxide (36.94 mg, 0.68 mmol) at room temperature. The reaction mixture was stirred at 80° C. for 12 h. After consumption of starting material (by TLC), the reaction mixture was diluted with water (20 mL) and extracted with CH$_2$Cl$_2$ (2×20 mL). The combined organic extracts were dried over anhydrous Na$_2$SO$_4$ and concentrated under reduced pressure. The crude material was purified by silica gel column chromatography (eluent: 5% MeOH/CH$_2$C2) to afford 3-cyclopropyl-5-methoxy-2-(4-methylpyrimidin-5-yl)-3H-imidazo[4,5-b]pyridine Ex. 58 (13 mg, 0.04 mmol, 20%) as an off white solid.

$^1$H NMR (400 MHz, CDCl$_3$): δ 9.21 (s, 1H), 8.83 (s, 1H), 7.95 (d, J=8.7 Hz, 1H), 6.76 (d, J=8.7 Hz, 1H), 4.04 (s, 3H), 3.39-3.20 (m, 1H), 2.63 (s, 3H), 1.06-0.99 (m, 2H), 0.98-0.90 (m, 2H)

LC-MS: m/z 282 [M+H]$^+$ at 1.93 RT (99.89% purity).
HPLC: 94.35%.

Example 59

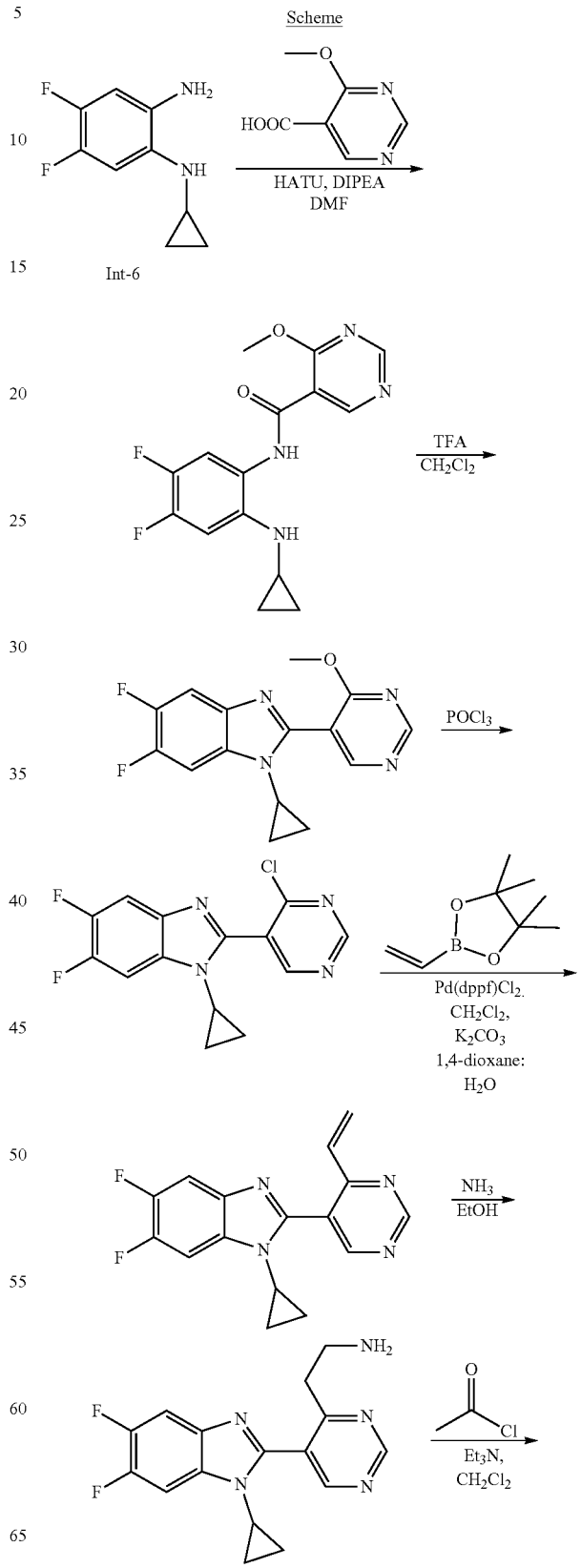

-continued

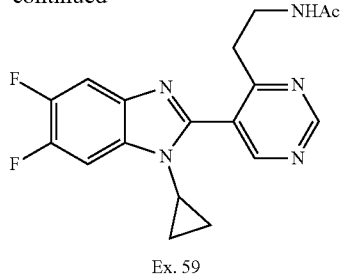

Ex. 59

N-(2-(Cyclopropylamino)-4,5-difluorophenyl)-4-methoxypyrimidine-5-carboxamide To a stirred solution of N-1-cyclopropyl-4,5-difluorobenzene-1,2-diamine Int-6 (300 mg, 1.63 mmol) in DMF (3 mL) under an inert atmosphere were added 4-methoxypyrimidine-5-carboxylic acid (251 mg, 1.63 mmol), HATU (743 mg, 1.95 mmol) and ethyldiisopropylamine (1.1 mL, 6.52 mmol) at room temperature. The reaction mixture was stirred at room temperature for 16 h. After consumption of starting material (by TLC), the reaction mixture was diluted with water (20 mL) and extracted with EtOAc (2×20 mL). The combined organic extracts were dried over anhydrous $Na_2SO_4$ and concentrated under reduced pressure. The crude material was purified by silica gel column chromatography (eluent: 50% EtOAc/hexane) to afford N-(2-(cyclopropylamino)-4,5-difluorophenyl)-4-methoxypyrimidine-5-carboxamide (300 mg, 0.93 mmol, 57%) as an off-white solid.

$^1$H NMR (400 MHz, $CD_3OD$): δ 9.05 (s, 1H), 8.89 (s, 1H), 7.48-7.43 (m, 1H), 7.03-6.98 (m, 1H), 4.21 (s, 3H), 2.46-2.41 (m 1H), 0.80-0.78 (m, 2H), 0.54-0.40 (m, 2H)

1-Cyclopropyl-5,6-difluoro-2-(4-methoxypyrimidin-5-yl)-1H-benzo[d]imidazole

To a stirred solution of N-(2-(cyclopropylamino)-4,5-difluorophenyl)-4-methoxypyrimidine-5-carboxamide (300 mg, 0.93 mmol) in $CH_2Cl_2$ (5 mL) under an inert atmosphere was added trifluoroacetic acid (0.5 mL) at room temperature. The reaction mixture was stirred at room temperature for 16 h. After consumption of starting material (by TLC), the reaction mixture quenched with saturated sodium bicarbonate solution (20 mL) and extracted with EtOAc (2×20 mL). The combined organic extracts were dried over anhydrous $Na_2SO_4$ and concentrated under reduced pressure. The crude material was purified by silica gel column chromatography (eluent: 80% EtOAc/Hexane) to afford 1-cyclopropyl-5,6-difluoro-2-(4-methoxypyrimidin-5-yl)-1H-benzo[d]imidazole (100 mg, 0.33 mmol, 35%) as an off white solid.

$^1$H NMR (400 MHz, $CD_3OD$): δ 8.95 (s, 1H), 8.74 (s, 1H), 7.68-7.63 (m, 1H), 7.58-7.54 (m, 1H), 4.13 (s, 3H), 3.58-3.52 (m, 1H), 1.08-0.95 (m, 2H), 0.78-0.53 (m, 2H)

2-(4-Chloropyrimidin-5-yl)-1-cyclopropyl-5,6-difluoro-1H-benzo[d]imidazole

A stirred solution of 1-cyclopropyl-5,6-difluoro-2-(4-methoxypyrimidin-5-yl)-1H-benzo[d]imidazole (400 mg, 1.32 mmol) in phosphoryl chloride (2.4 mL) under an inert atmosphere was heated at 80° C. for 2 h. After consumption of starting material (by TLC), the reaction mixture was cooled to room temperature and volatiles were evaporated under reduced pressure. The residue was basified with saturated sodium bicarbonate solution (50 mL) and extracted with EtOAc (2×50 mL). The combined organic extracts were dried over anhydrous $Na_2SO_4$ and concentrated under reduced pressure. The crude material was washed with n-pentane (2×10 mL) to obtain 2-(4-chloropyrimidin-5-yl)-1-cyclopropyl-5,6-difluoro-1H-benzo[d]imidazole (350 mg, 1.14 mmol, 86%) as an off white solid.

$^1$H NMR (500 MHz, $CD_3OD$): δ 9.20 (s, 1H), 9.03 (s, 1H), 7.73-7.70 (m, 1H), 7.63-7.60 (m, 1H), 3.63-3.52 (m, 1H), 1.10-0.99 (m, 2H), 0.79-0.66 (m, 2H)

LC-MS: m/z 306.9 $[M+H]^+$ at 2.62 RT (94.11% purity).

1-Cyclopropyl-5,6-difluoro-2-(4-vinylpyrimidin-5-yl)-1H-benzo[d]imidazole

To a stirred solution of 2-(4-chloropyrimidin-5-yl)-1-cyclopropyl-5,6-difluoro-1H-benzo[d]imidazole (400 mg, 1.30 mmol) in 1,4-dioxane (6 mL) and water (1 mL) under an inert atmosphere was added 4,4,5,5-tetramethyl-2-vinyl-1 3,2-dioxaborolane (242 mg, 1.56 mmol) and potassium carbonate (541 mg, 3.92 mmol) at room temperature. The reaction mixture was degassed under argon for 10 min. Pd(dppf)C12 and $CH_2Cl_2$ (11 mg, 0.01 mmol) were added at room temperature and the mixture was degassed under argon for 10 min. The reaction mixture was heated to 80° C. and stirred for 4 h. After consumption of starting material (by TLC), the reaction mixture was filtered through a pad of celite and the pad was washed with methanol (30 mL). The filtrate was concentrated under reduced pressure. The crude material was purified by silica gel column chromatography (eluent: 20% EtOAc/Hexane) to afford 1-cyclopropyl-5,6-difluoro-2-(4-vinylpyrimidin-5-yl)-1H-benzo[d]imidazole (55 mg, 0.18 mmol, 14%) as an off-white solid.

$^1$H NMR (400 MHz, $CDCl_3$): δ 9.29 (s, 1H), 8.90 (s, 1H), 7.62-7.58 (m, 1H), 7.43-7.39 (m, 1H), 6.82 (s, 1H), 6.81-6.79 (m, 1H), 5.77-5.69 (m, 1H), 3.35-3.29 (m, 1H), 1.05-1.00 (m, 2H), 0.69-0.65 (m, 2H).

2-(5-(1-Cyclopropyl-5,6-difluoro-1H-benzo[d]imidazol-2-yl)pyrimidin-4-yl)ethan-1-amine To a stirred solution of 1-cyclopropyl-5,6-difluoro-2-(4-vinylpyrimidin-5-yl)-1H-benzo[d]imidazole (55 mg, 0.20 mmol) in EtOH (4 mL) under an inert atmosphere was added an aqueous ammonia solution (0.4 mL) at room temperature. The reaction mixture was stirred at 70° C. for 5 h. After consumption of starting material (by TLC), the volatiles were concentrated under reduced pressure. The crude material was washed with n-pentane (2×5 mL) to obtain 2-(5-(1-cyclopropyl-5,6-difluoro-1H-benzo[d]imidazol-2-yl)pyrimidin-4-yl)ethan-1-amine (50 mg, crude) as brown solid.

LC-MS: m/z 316.1 $[M+H]^+$ at 1.74 RT (56.04% purity).

N-(2-(5-(1-Cyclopropyl-5,6-difluoro-1H-benzo[d]imidazol-2-yl)pyrimidin-4-yl)ethyl)acetamide (Ex. 59)

To a stirred solution of 2-(5-(1-cyclopropyl-5,6-difluoro-1H-benzo[d]imidazol-2-yl)pyrimidin-4-yl)ethan-1-amine (50 mg, 0.15 mmol) in $CH_2Cl_2$ (2 mL) under an inert atmosphere was added triethylamine (48 mg, 0.47 mmol) and acetyl chloride (18.6 mg, 0.23 mmol) at 0° C. The reaction mixture was stirred at 0° C. for 1 h. After consumption of starting material (by TLC), the reaction mixture was diluted with saturated sodium bicarbonate solution (20 mL) and extracted with $CH_2Cl_2$ (2×20 mL). The combined organic extracts were dried over anhydrous $Na_2SO_4$ and concentrated under reduced pressure. The crude material was purified by silica gel column chromatography (eluent: 2% MeOH/CH$_2$Cl$_2$) to afford N-(2-(5-(1-cyclopropyl-5,6-difluoro-1H-benzo[d]imidazol-2-yl)pyrimidin-4-yl)ethyl)acetamide Ex. 59 (16 mg, 0.04 mmol, 28%) as an off-white solid.

$^1$H NMR (400 MHz, CDCl$_3$): δ 9.29 (s, 1H), 8.90 (s, 1H), 7.72 (brs, 1H), 7.57-7.52 (m, 1H), 7.47-7.43 (m, 1H), 3.83-3.66 (m, 2H), 3.48-3.42 (m, 1H), 3.15-2.98 (m, 2H), 1.96 (s, 3H), 1.15-1.02 (m, 2H), 0.81-0.65 (m, 2H)

LC-MS: m/z 358.1 [M+H]$^+$ at 1.87 RT (98.21% purity). HPLC: 98.09%.

Example 60

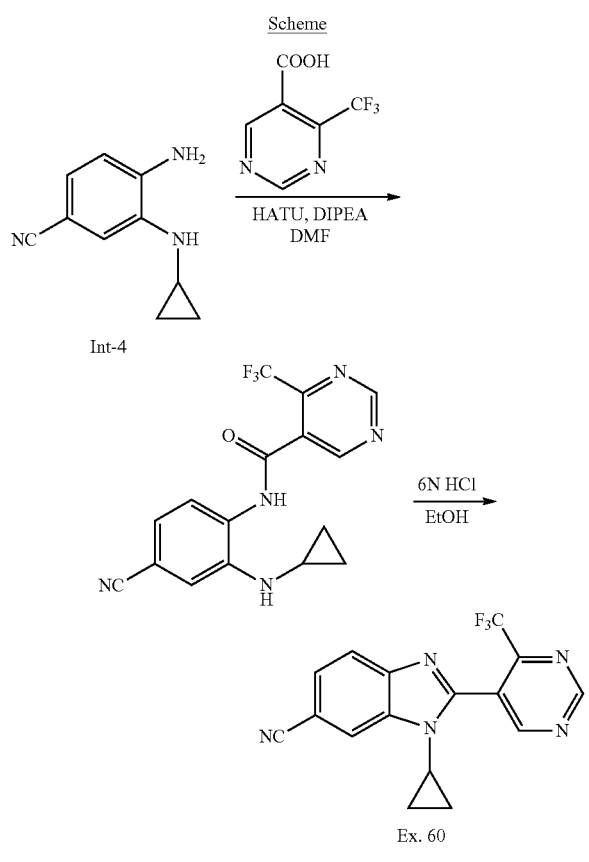

Ex. 60

N-(4-Cyano-2-(cyclopropylamino)phenyl)-4-(trifluoromethyl)pyrimidine-5-carboxamide To a stirred solution of 4-amino-3-(cyclopropylamino)benzonitrile Int-4 (346 mg, 2.00 mmol) in DMF (6 mL) under an inert atmosphere was added 4-(trifluoromethyl)pyrimidine-5-carboxylic acid 2 (384 mg, 2.00 mmol), HATU (1.14 g, 3.00 mmol) and ethyldiisopropylamine (1.39 mL, 8.00 mmol) at room temperature. The reaction mixture was stirred at room temperature for 16 h. After consumption of starting material (by TLC), the reaction mixture was quenched with saturated ammonium chloride solution (30 mL) and extracted with EtOAc (2×30 mL). The combined organic extracts were dried over anhydrous Na$_2$SO$_4$ and concentrated under reduced pressure to obtain N-(4-cyano-2-(cyclopropylamino)phenyl)-4-(trifluoromethyl)pyrimidine-5-carboxamide (120 mg, crude) as a brown syrup.

LC-MS: m/z 348.1 [M+H]$^+$ at 2.38 RT (17.87% purity).

1-Cyclopropyl-2-(4-(trifluoromethyl)pyrimidin-5-yl)-1H-benzo[d]imidazole-6-carbonitrile (Ex. 60)

To a stirred solution of N-(4-cyano-2-(cyclopropylamino)phenyl)-4-(trifluoromethyl)pyrimidine-5-carboxamide (120 mg, 0.34 mmol) in EtOH (1 mL) under an inert atmosphere was added 6N HCl (2 mL) at room temperature. The reaction mixture was stirred at 65° C. for 45 min. After consumption of starting material (by TLC), the reaction mixture was diluted with saturated sodium bicarbonate solution (20 mL) and extracted with EtOAc (2×20 mL). The combined organic extracts were dried over anhydrous Na$_2$SO$_4$ and concentrated under reduced pressure. The crude material was purified by preparative HPLC to afford 1-cyclopropyl-2-(4-(trifluoromethyl)pyrimidin-5-yl)-1H-benzo[d]imidazole-6-carbonitrile Ex. 60 (6.5 mg, 0.18 mmol, 6%) as an off white solid.

$^1$H NMR (400 MHz, CD$_3$OD): δ 9.62 (s, 1H), 9.37 (s, 1H), 8.25 (s, 1H), 7.90 (d, J=8.5 Hz, 1H), 7.70 (dd, J=8.4, 1.5 Hz, 1H), 3.59-3.50 (m, 1H), 1.12-1.02 (m, 2H), 0.84-0.75 (m, 2H)

LC-MS: m/z 329.9 [M+H]$^+$ at 2.71 RT (99.21% purity). HPLC: 99.66%.

Example 61

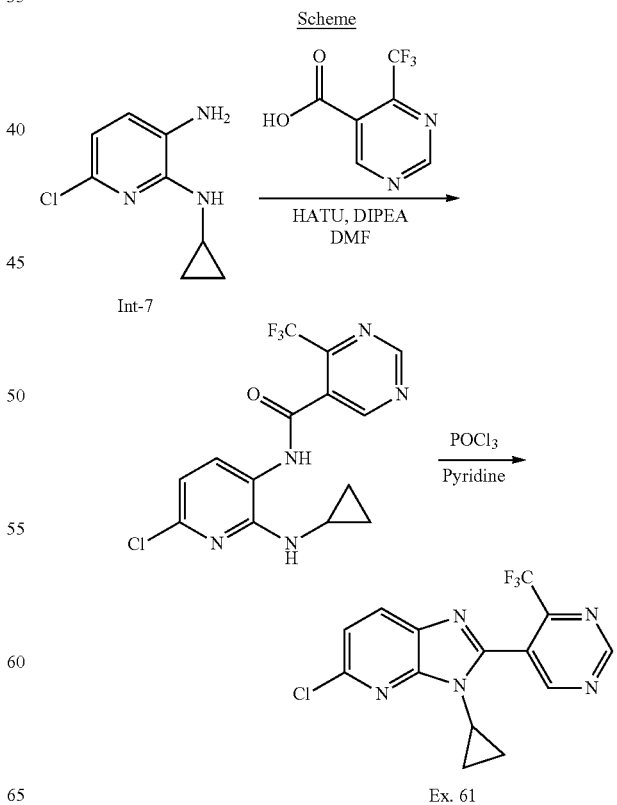

Ex. 61

N-(6-Chloro-2-(cyclopropylamino)pyridin-3-yl)-4-(trifluoromethyl)pyrimidine-5-carboxamide To a stirred solution of 6-chloro-N2-cyclopropylpyridine-2,3-diamine Int-7 (500 mg, 2.73 mmol) in DMF (6 mL) under an inert atmosphere was added 4-(trifluoromethyl)pyrimidine-5-carboxylic acid (630 mg, 3.27 mmol), HATU (1.25 g, 3.27 mmol) and ethyldiisopropylamine (1.96 mL, 10.92 mmol) at room temperature. The reaction mixture was stirred at room temperature for 16 h. After consumption of starting material (by TLC), the reaction mixture was diluted with water (30 mL) and extracted with EtOAc (2×30 mL). The combined organic extracts were dried over anhydrous $Na_2SO_4$ and concentrated under reduced pressure to obtain N-(6-chloro-2-(cyclopropylamino)pyridin-3-yl)-4-(trifluoromethyl)pyrimidine-5-carboxamide (400 mg, 1.12 mmol, 41%) as a brown solid.

$^1$H NMR (400 MHz, DMSO-$d_6$): δ 10.00 (s, 1H), 9.58 (s, 1H), 9.52 (s, 1H), 7.64 (d, J=7.9 Hz, 1H), 6.72 (d, J=7.9 Hz, 1H), 6.57 (s, 1H), 2.75-2.71 (m, 1H), 0.78-0.70 (m, 2H), 0.49-0.42 (m, 2H)

5-Chloro-3-cyclopropyl-2-(4-(trifluoromethyl)pyrimidin-5-yl)-3H-imidazo[4,5-b]pyridine (Ex. 61)

To a stirred solution of N-(6-chloro-2-(cyclopropylamino)pyridin-3-yl)-4-(trifluoromethyl)pyrimidine-5-carboxamide (200 mg, 0.56 mmol) in pyridine (0.4 mL) under an inert atmosphere was added phosphoryl chloride (0.3 mL, 2.80 mmol) at room temperature. The reaction mixture was heated to 120° C. and stirred for 16 h. After consumption of starting material (by TLC), the reaction mixture was basified with saturated sodium carbonate solution (30 mL) and extracted with EtOAc (2×30 mL). The combined organic extracts were dried over anhydrous $Na_2SO_4$ and concentrated under reduced pressure. The crude material was purified by silica gel column chromatography (eluent: 25% EtOAc/hexane) to afford 5-chloro-3-cyclopropyl-2-(4-(trifluoromethyl)pyrimidin-5-yl)-3H-imidazo[4,5-b]pyridine Ex. 61(20 mg, 0.06 mmol, 10%) as a white solid.

$^1$H NMR (400 MHz, CD$_3$OD): δ 9.61 (s, 1H), 9.38 (s, 1H), 8.12 (d, J=8.4 Hz, 1H), 7.44 (d, J=8.4 Hz, 1H), 3.44-3.39 (m, 1H), 1.08-1.00 (m, 2H), 0.95-0.90 (m, 2H)

LC-MS: m/z 340 [M+H]$^+$ at 2.82 RT (99.33% purity).

HPLC: 99.27%.

Example 62

Scheme

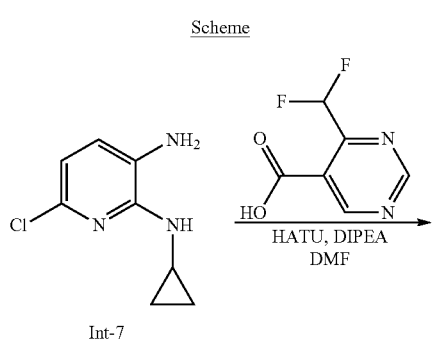

Int-7

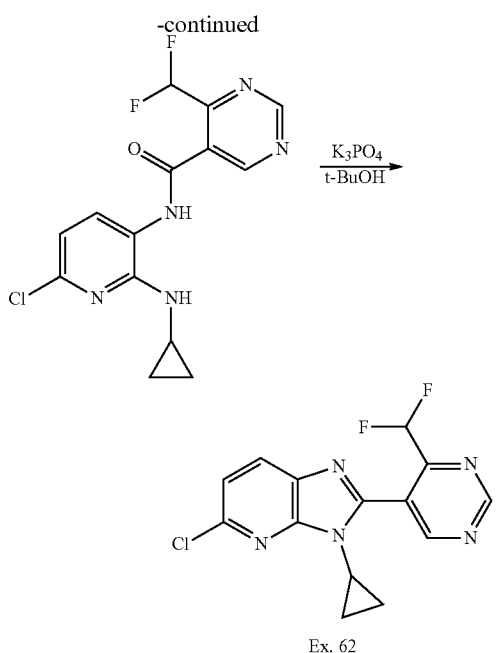

Ex. 62

N-(6-Chloro-2-(cyclopropylamino)pyridin-3-yl)-4-(difluoromethyl)pyrimidine-5-carboxamide To a stirred solution of 6-chloro-N2-cyclopropylpyridine-2,3-diamine Int-7 (200 mg, 1.09 mmol) in DMF (2 mL) under an inert atmosphere was added 4-(difluoromethyl)pyrimidine-5-carboxylic acid (228 mg, 1.31 mmol), HATU (456 mg, 1.20 mmol) and ethyldiisopropylamine (422 mg, 3.27 mmol) at room temperature. The reaction mixture was stirred at room temperature for 16 h. After consumption of starting material (by TLC), the reaction mixture was diluted with water (30 mL) and extracted with EtOAc (2×30 mL). The combined organic extracts were dried over anhydrous $Na_2SO_4$ and concentrated under reduced pressure. The crude material was purified by silica gel column chromatography (eluent: 40% EtOAc/hexane) to afford N-(6-chloro-2-(cyclopropylamino)pyridin-3-yl)-4-(difluoromethyl)pyrimidine-5-carboxamide (189 mg, 0.55 mmol, 51%) as a brown solid.

$^1$H NMR (400 MHz, CD$_3$OD): δ 9.40 (s, 1H), 9.29 (s, 1H), 7.57 (d, J=7.6 Hz, 1H), 7.14 (t, J=53.6 Hz, 1H), 6.67 (d, J=8.0 Hz, 1H), 2.80-2.75 (m, 1H), 0.80-0.75 (m, 2H), 0.52-0.59 (m, 2H).

5-Chloro-3-cyclopropyl-2-(4-(difluoromethyl)pyrimidin-5-yl)-3H-imidazo[4,5-b]pyridine (Ex. 62)

To a stirred solution of N-(6-chloro-2-(cyclopropylamino)pyridin-3-yl)-4-(difluoromethyl)pyrimidine-5-carboxamide (120 mg, 0.35 mmol) in tertiary butanol (4 mL) under an inert atmosphere was added potassium phosphate (145 mg, 0.70 mmol) at room temperature. The reaction mixture was stirred at 100° C. for 16 h. After consumption of starting material (by TLC), the reaction mixture was diluted with water (30 mL) and extracted with EtOAc (2×30 mL). The combined organic extracts were dried over anhydrous $Na_2SO_4$ and concentrated under reduced pressure. The crude material was purified by preparative HPLC to afford 5-chloro-3-cyclopropyl-2-(4-(difluoromethyl)pyrimidin-5-yl)-3H-imidazo[4,5-b]pyridine Ex. 62 (20 mg, 0.06 mmol, 17%) as an off-white solid.

$^1$H NMR (400 MHz, CD$_3$OD): δ 9.50 (s, 1H), 9.37 (s, 1H), 8.11 (d, J=8.0 Hz, 1H), 7.42 (d, J=8.4 Hz, 1H), 7.10 (t, J=53.6 Hz, 1H), 3.58-3.53 (m, 1H), 1.09-1.04 (m, 2H), 0.89-0.85 (m, 2H)

LC-MS: m/z 321.9 [M+H]$^+$ at 2.51 RT (96.59% purity). HPLC: 99.88%.

Example 63

Scheme

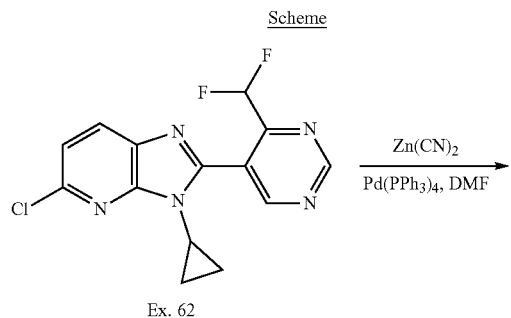

Ex. 62

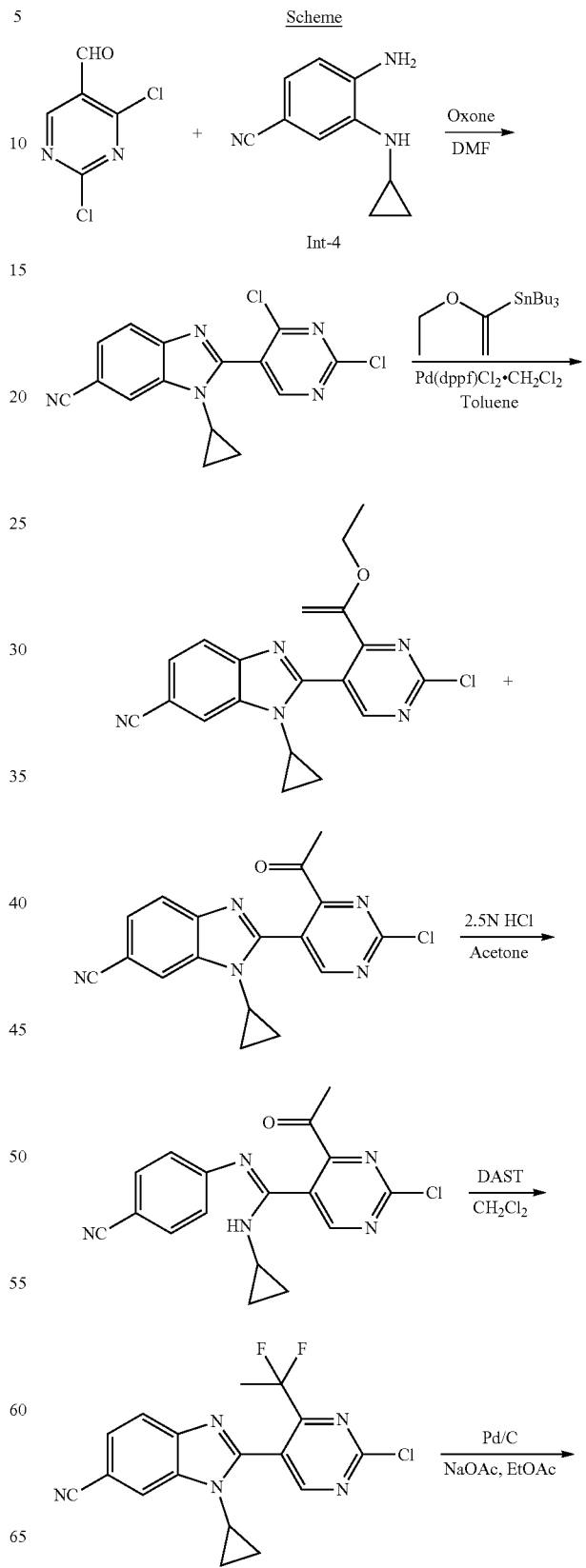

Ex. 63

3-Cyclopropyl-2-(4-(difluoromethyl)pyrimidin-5-yl)-3H-imidazo[4,5-b]pyridine-5-carbonitrile (Ex. 63)

To a stirred solution of 5-chloro-3-cyclopropyl-2-(4-(difluoromethyl) pyrimidin-5-yl)-3H-imidazo[4, 5-b]pyridine Ex. 62 (120 mg, 0.37 mmol) in DMF (3 mL) at room temperature was added zinc cyanide (87 mg, 0.74 mmol) and Pd(PPh$_3$)$_4$ (43 mg, 0.74 mmol). The solution was purged under argon for 10 min and then heated to 180° C. for 4 h in sealed tube. The reaction mixture was cooled, diluted with ice cold water (20 mL), and extracted with EtOAc (2×20 mL). The combined organic extracts were dried over anhydrous Na$_2$SO$_4$ and concentrated under reduced pressure. The crude material was purified by preparative HPLC to afford 3-cyclopropyl-2-(4-(difluoromethyl) pyrimidin-5-yl)-3H-imidazo [4, 5-b] pyridine-5-carbonitrile Ex. 63 (80 mg, 0.25 mmol, 68%) as an off-white solid.

$^1$H NMR (400 MHz, CD$_3$OD): δ 9.54 (s, 1H), 9.41 (s, 1H), 8.29 (d, J=8.2 Hz, 1H), 7.86 (d, J=8.2 Hz, 1H), 7.12 (t, J=51.3 Hz, 1H), 3.64-3.59 (m, 1H), 1.17-1.05 (m, 2H), 0.98-0.86 (m, 2H)

LC-MS: m/z 312.9 [M+H]$^+$ at 2.34 RT (99.36% purity) HPLC: 99.54%

Example 64

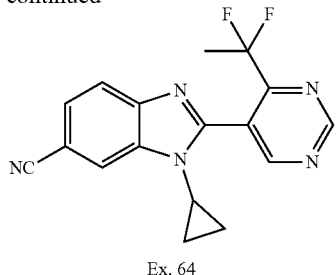

Ex. 64

1-Cyclopropyl-2-(2,4-dichloropyrimidin-5-yl)-1H-benzo[d]imidazole-6-carbonitrile To a stirred solution of 4-amino-3-(cyclopropylamino)benzonitrile Int-4 (500 mg, 2.89 mmol) in DMF (10 mL) and water (2 mL) was added 2,4-dichloropyrimidine-5-carbaldehyde (613 mg, 3.46 mmol) and Oxone (1.77 g, 5.78 mmol) at room temperature and the mixture was stirred for 5 h. After consumption of starting material (by TLC), the reaction mixture was diluted with water (50 mL) and extracted with EtOAc (2×60 mL). The combined organic extracts were dried over anhydrous $Na_2SO_4$ and concentrated under reduced pressure. The crude material was purified by silica gel column chromatography (eluent: 15% EtOAc/Hexane) to afford 1-cyclopropyl-2-(2,4-dichloropyrimidin-5-yl)-1H-benzo[d] imidazole-6-carbonitrile (300 mg, 0.91 mmol, 31%) as an off white solid.

$^1$H NMR (400 MHz, DMSO-$d_6$): δ 9.19 (s, 1H), 8.33 (dd, J=1.5, 0.6 Hz, 1H), 7.94 (dd, J=8.4, 0.6 Hz, 1H), 7.73 (dd, J=8.5, 1.6 Hz, 1H), 3.634-3.59 (m, 1H), 1.09-1.03 (m, 2H), 0.78-0.73 (m, 2H)

2-(2-Chloro-4-(1-ethoxyvinyl)pyrimidin-5-yl)-1-cyclopropyl-1H-benzo[d]imidazole-6-carbonitrile & 2-(4-acetyl-2-chloropyrimidin-5-yl)-1-cyclopropyl-1H-benzo[d]imidazole-6-carbonitrile To stirred solution of 1-cyclopropyl-2-(2,4-dichloropyrimidin-5-yl)-1H-benzo [d] imidazole-6-carbonitrile (300 mg, 0.91 mmol) in toluene (10 mL) was added tributyl (1-ethoxyvinyl) stannane (395 mg, 1.09 mmol) at room temperature and the solution was purged under argon for 30 min. Pd(dppf)$Cl_2$.$CH_2Cl_2$ was added to the reaction mixture at room temperature and the mixture was heated to 80° C. for 2 h. After consumption of starting material (by TLC), the reaction mixture was filtered through a pad of celite and the pad was washed with EtOAc (30 mL). The filtrate was concentrated under reduced pressure. The crude material was purified by silica gel column chromatography (eluent: 20% EtOAc/Hexane) to afford a mixture of 2-(2-chloro-4-(1-ethoxyvinyl)pyrimidin-5-yl)-1-cyclopropyl-1H-benzo[d]imidazole-6-carbonitrile & 2-(4-acetyl-2-chloropyrimidin-5-yl)-1-cyclopropyl-1H-benzo[d]imidazole-6-carbonitrile (150 mg, mixture) as a colorless liquid.

LC-MS: m/z 366.4 [M+H]$^+$ at 3.84 RT (44.64% purity) & m/z 338.3 [M+H]$^+$ at 3.56 RT (46.97% purity)

2-(4-Acetyl-2-chloropyrimidin-5-yl)-1-cyclopropyl-1H-benzo[d]imidazole-6-carbonitrile To a stirred solution of 2-(2-chloro-4-(1-ethoxyvinyl)pyrimidin-5-yl)-1-cyclopropyl-1H-benzo[d]imidazole-6-carbonitrile & 2-(4-acetyl-2-chloropyrimidin-5-yl)-1-cyclopropyl-1H-benzo[d]imidazole-6-carbonitrile (130 g, 0.35 mmol) in acetone (5 mL) was added 2.5 N HCl (1 mL) at room temperature and the reaction was stirred for 5 h. After consumption of starting material (by LCMS), the volatiles were evaporated under reduced pressure. The residue was diluted with $CH_2Cl_2$(30 mL) and washed with saturated sodium bicarbonate solution (20 mL). The organic layer was dried over anhydrous $Na_2SO_4$ and concentrated under reduced pressure to afford 2-(4-acetyl-2-chloropyrimidin-5-yl)-1-cyclopropyl-1H-benzo[d]imidazole-6-carbonitrile (80 mg, 0.23 mmol, 67%) as a pale yellow solid.

LC-MS: m/z 337.9 [M+H]$^+$ at 2.82 RT (88.29% purity)

2-(2-Chloro-4-(1,1-difluoroethylpyrimidin-5-yl)-1-cyclopropyl-1H-benzo[d]imidazole-6-carbonitrile To a stirred solution of 2-(4-acetyl-2-chloropyrimidin-5-yl)-1-cyclopropyl-1H-benzo[d]imidazole-6-carbonitrile (150 mg, 0.44 mmol) in $CH_2Cl_2$ (3 mL) under inert atmosphere was added DAST (0.2 mL) at 0° C. The reaction mixture was warmed to room temperature and stirred for 12 h. After consumption of starting material (by TLC), the reaction mixture was poured into ice cold water (30 mL) and extracted with $CH_2Cl_2$ (2×40 mL). The combined organic extracts were dried over anhydrous $Na_2SO_4$ and concentrated under reduced pressure. The crude material was purified by silica gel column chromatography (eluent: 20% EtOAc/Hexane) to afford 2-(2-chloro-4-(1,1-difluoroethyl pyrimidin-5-yl)-1-cyclopropyl-1H-benzo [d] imidazole-6-carbonitrile (40 mg, 0.11 mmol, 25%) as a pale yellow solid.

LC-MS: m/z 360.4 [M+H]$^+$ at 3.90 RT (63.96% purity)

1-Cyclopropyl-2-(4-(1,1-difluoroethyl)pyrimidin-5-yl)-1H-benzo[d]imidazole-6-carbonitrile (Ex. 64)

To a stirred solution of 2-(2-chloro-4-(1,1-difluoroethyl pyrimidin-5-yl)-1-cyclopropyl-1H-benzo[d]imidazole-6-carbonitrile (50 mg, 0.14 mmol) in ethyl acetate (5 mL) under inert atmosphere was added sodium acetate (10 mg) and 10% Pd/C (50% wet, 50 mg) at room temperature. The reaction mixture was stirred at room temperature under hydrogen atmosphere (balloon pressure) for 12 h. After consumption of starting material (by TLC), the reaction mixture was filtered through a pad of celite and the pad was washed with EtOAc (10 mL). The filtrate was concentrated under reduced pressure. The crude material was purified by normal phase HPLC to afford 1-cyclopropyl-2-(4-(1,1-difluoroethylpyrimidin-5-yl)-1H-benzo[d]imidazole-6-carbonitrile Ex. 64 (7 mg, 0.02 mmol, 15%) as an off white solid.

$^1$H NMR (400 MHz, $CD_3OD$): δ 9.50 (s, 1H), 9.17 (s, 1H), 8.22-8.21 (m, 1H), 7.86 (dd, J=8.4, 0.6 Hz, 1H), 7.67 (dd, J=8.3, 1.6 Hz, 1H), 3.49-3.44 (m, 1H), 2.07 (t, J=19.3 Hz, 3H), 1.06-1.03 (m, 2H), 0.85-0.81 (m, 2H)

LC-MS: m/z 326.0 [M+H]$^+$ at 2.59 RT (97.42% purity)

HPLC: 94.40%

Example 65

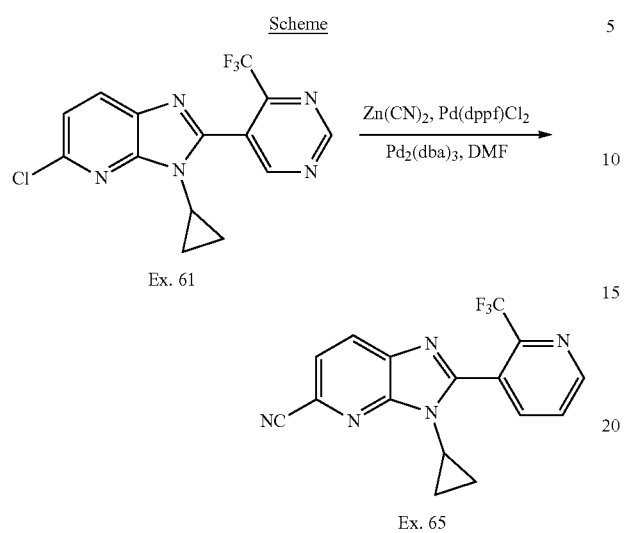

Ex. 65

3-Cyclopropyl-2-(4-(trifluoromethyl)pyrimidin-5-yl)-3H-imidazo[4,5-b]pyridine-5-carbonitrile (Ex. 65)

To a stirred solution of 5-chloro-3-cyclopropyl-2-(4-(trifluoromethyl)pyrimidin-5-yl)-3H-imidazo[4,5-b]pyridine Ex. 61(70 mg, 0.21 mmol) in DMF (1 mL) at room temperature was added zinc cyanide (48.3 mg, 0.41 mmol) and the mixture was purged under argon for 10 min. Pd(dppf)Cl$_2$ (7.53 mg, 0.01 mmol) and Pd$_2$(dba)$_3$ (9.42 mg, 0.01 mmol) were added and the mixture was purged under argon for an additional 10 min. The reaction mixture was heated to 130-140° C. for 16 h in sealed tube and then cooled, diluted with ice cold water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 20% EtOAc/hexane) to afford 3-cyclopropyl-2-(4-(trifluoromethyl)pyrimidin-5-yl)-3H-imidazo[4,5-b]pyridine-5-carbonitrile Ex. 65 (26 mg, 0.08 mmol, 38%) as a pale yellow solid.

$^1$H NMR (400 MHz, CDCl$_3$): δ 9.60 (s, 1H), 9.13 (s, 1H), 8.21 (d, J=8.3 Hz, 1H), 7.74 (d, J=8.3 Hz, 1H), 3.39-3.31 (m, 1H), 1.14-1.08 (m, 2H), 0.96-0.91 (m, 2H)

LC-MS: m/z 331 [M+H]$^+$ at 2.33 RT (98.34% purity)
HPLC: 99.53%

Example 66

Scheme

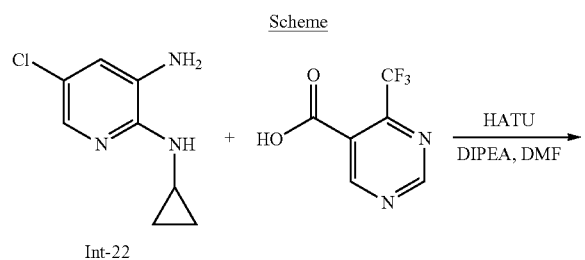

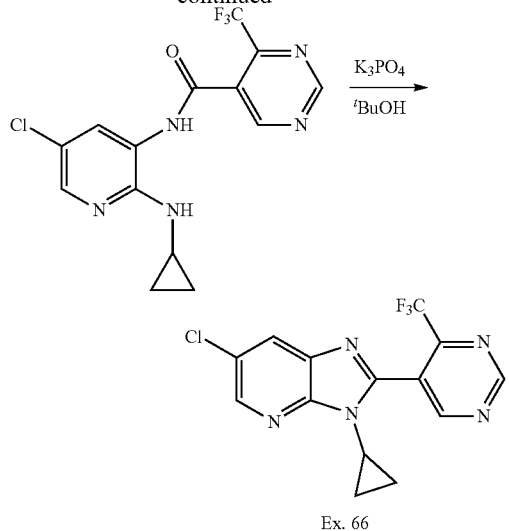

Ex. 66

N-(5-Chloro-2-(cyclopropylamino)pyridin-3-yl)-4-(trifluoromethyl)pyrimidine-5-carboxamide To a stirred solution of 4-(trifluoromethyl) pyrimidine-5-carboxylic acid (50 mg, 0.27 mmol) in DMF (2 mL) under inert atmosphere was added HATU (148 mg, 0.39 mmol) at room temperature and the mixture was stirred for 20 min. 5-Chloro-N$^2$-cyclopropylpyridine-2,3-diamine Int-22 (52 mg, 0.28 mmol) and ethyldiisopropylamine (0.13 mL, 0.78 mmol) were added and the mixture was stirred at room temperature for 16 h. After consumption of starting material (by TLC), the reaction mixture was diluted with water (20 mL) and extracted with EtOAc (2×30 mL). The combined organic extracts were dried over anhydrous Na$_2$SO$_4$ and concentrated under reduced pressure. The crude material was purified by silica gel column chromatography (eluent: 15% EtOAc/hexane) to afford N-(5-chloro-2-(cyclopropylamino)pyridin-3-yl)-4-(trifluoromethyl)pyrimidine-5-carboxamide (30 mg) as a brown solid. The crude material was used in the next step without further purification.

LC-MS: m/z 356.2 [M−H]$^+$ at 3.49 RT (42.49% purity)

6-Chloro-3-cyclopropyl-2-(4-(trifluoromethyl)pyrimidin-5-yl)-3H-imidazo[4,5-b]pyridine (Ex. 66)

To a stirred solution of N-(5-chloro-2-(cyclopropylamino) pyridin-3-yl)-4-(trifluoromethyl) pyrimidine-5-carboxamide (150 mg crude) in $^t$BuOH (6 mL) under inert atmosphere was added tripotassium phosphate (222 mg, 1.05 mmol) at room temperature. The reaction mixture was stirred at 150° C. for 2 h under microwave and cooled. The reaction mixture was diluted with water (30 mL) and extracted with EtOAc (2×40 mL). The combined organic extracts were dried over anhydrous Na$_2$SO$_4$ and concentrated under reduced pressure. The crude material was purified by preparative HPLC to afford 6-chloro-3-cyclopropyl-2-(4-(trifluoromethyl)pyrimidin-5-yl)-3H-imidazo[4, 5-b]pyridine Ex. 66 (20 mg, 0.05 mmol, 14%) as an off white solid.

$^1$H NMR (400 MHz, CD$_3$OD): δ 9.61 (s, 1H), 9.39 (s, 1H), 8.50 (d, J=2.3 Hz, 1H), 8.19 (d, J=2.3 Hz, 1H), 3.46-3.40 (m, 1H), 1.08-1.00 (m, 2H), 0.97-0.89 (m, 2H)

LC-MS: m/z 340.0 [M+H]$^+$ at 2.80 RT (98.88% purity)
HPLC: 98.66%

Example 67

Scheme

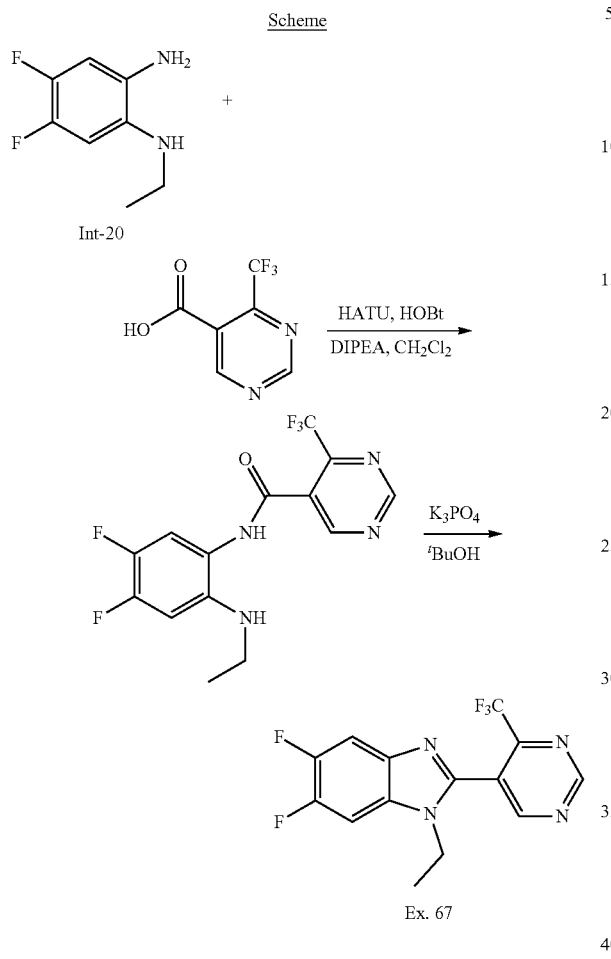

Ex. 67

N-(2-(Ethylamino)-4,5-difluorophenyl)-4-(trifluoromethyl)pyrimidine-5-carboxamide To a stirred solution of 4-(trifluoromethyl) pyrimidine-5-carboxylic acid (334 mg, 1.74 mmol) in $CH_2Cl_2$ (10 mL) was added HOBt (366 mg, 1.91 mmol) and HATU (729 mg, 1.91 mmol) at room temperature and the reaction was stirred for 20 min. $N^1$-Ethyl-4,5-difluorobenzene-1,2-diamine Int-20 (300 mg, 1.74 mmol) and diisopropylethylamine (0.9 mL, 5.23 mmol) were added to the reaction mixture. The reaction mixture was stirred at RT for 12 h and then diluted with water (30 mL) and extracted with $CH_2Cl_2$ (2×30 mL). The combined organic extracts were dried over anhydrous $Na_2SO_4$ and concentrated under reduced pressure. The crude material was purified by silica gel column chromatography (eluent: 10% EtOAc/hexane) to afford N-(2-(ethylamino)-4,5-difluorophenyl)-4-(trifluoromethyl)pyrimidine-5-carboxamide (150 mg, 0.43 mmol, 25%) as a white solid.

$^1$H NMR (500 MHz, DMSO-$d_6$): δ10.08 (s, 1H), 9.58 (s, 1H), 9.51 (s, 1H), 7.38 (dd, J=11.6, 8.7 Hz, 1H), 6.71 (dd, J=13.6, 7.8 Hz, 1H), 5.01 (brs, 1H), 3.13-3.06 (m, 2H), 1.17 (t, J=7.2 Hz, 3H)

LC-MS: m/z 345 [M−H]$^+$ at 3.76 RT (98.55% purity)

1-Ethyl-5,6-difluoro-2-(4-(trifluoromethyl)pyrimidin-5-yl)-1H-benzo[d]imidazole (Ex. 67)

To a stirred solution of N-(2-(ethylamino)-4,5-difluorophenyl)-4-(trifluoromethyl) pyrimidine-5-carboxamide (150 mg, 0.43 mmol) in $^t$BuOH (12 mL) was added tripotassium phosphate (229 mg, 1.08 mmol) at RT under inert atmosphere. The reaction mixture was stirred at 150° C. for 2 h under microwave and cooled. The reaction mixture was diluted with water (30 mL) and extracted with EtOAc (2×40 mL). The combined organic extracts were dried over anhydrous $Na_2SO_4$ and concentrated under reduced pressure. The crude material was purified by silica gel column chromatography (eluent: 15% EtOAc/Hexane) to afford 1-ethyl-5,6-difluoro-2-(4-(trifluoromethyl)pyrimidin-5-yl)-1H-benzo[d]imidazole Ex. 67 (30 mg, 0.09 mmol, 21%) as an off white solid.

$^1$H NMR (400 MHz, DMSO-$d_6$): δ 9.69 (s, 1H), 9.46 (s, 1H), 8.00 (dd, J=10.5, 7.3 Hz, 1H), 7.85 (dd, J=11.0, 7.5 Hz, 1H), 4.17 (q, J=7.1 Hz, 2H), 1.21 (t, J=7.2 Hz, 3H)

LC-MS: m/z 328.9 [M+H]$^+$ at 2.84 RT (99.96% purity)
HPLC: 99.20%

Example 68

Scheme

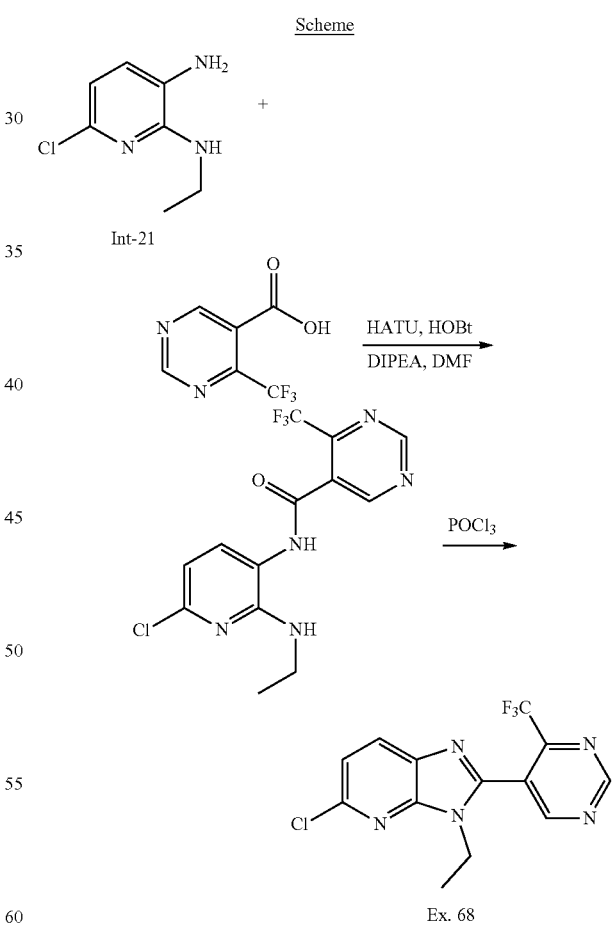

Ex. 68

N-(6-Chloro-2-(ethylamino)pyridin-3-yl)-4-(trifluoromethyl)pyrimidine-5-carboxamide To a stirred solution of 6-chloro-N2-ethylpyridine-2,3-diamine Int-21 (450 mg, 2.63 mmol) in DMF (10 mL) was added 4-(trifluoromethyl)pyrimidine-5-carboxylic acid (505 mg, 2.63 mmol), HATU (1.5 g, 3.94 mmol) and diisopropylethylamine (1.88 mL, 10.52 mmol) at 0° C. under inert atmosphere. The reaction mixture was stirred at room temperature for 16 h. After consumption of starting material (by TLC), the reaction mixture was diluted with water (30 mL) and extracted with ether (2×30 mL). The combined organic extracts were washed with water (30 mL), dried over anhydrous $Na_2SO_4$ and concentrated under reduced pressure. The crude material was purified by Combi-flash chromatography to afford N-[6-chloro-2-(ethylamino)pyridin-3-yl]-4-(trifluoromethyl)pyrimidine-5-carboxamide (110 mg, 0.31 mmol, 12%) as an off-white solid.

LC-MS: m/z 345.9 $[M+H]^+$ at 2.89 RT (67.62% purity)

5-Chloro-3-ethyl-2-(4-(trifluoromethyl)pyrimidin-5-yl)-3H-imidazo[4, 5-b]pyridine Ex. 68)

A solution of N-(6-chloro-2-(ethylamino)pyridin-3-yl)-4-(trifluoromethyl)pyrimidine-5-carboxamide (65 mg, 0.18 mmol) in phosphoryl chloride (0.5 mL) in a microwave vessel under inert atmosphere was irradiated to 150° C. and stirred for 4 h and cooled. The volatiles were evaporated under reduced pressure and the residue was treated with saturated sodium carbonate solution (10 mL) and extracted with EtOAc (2×10 mL). The combined organic extracts were dried over anhydrous $Na_2SO_4$ and concentrated under reduced pressure. The crude material was purified by preparative HPLC to afford 5-chloro-3-ethyl-2-(4-(trifluoromethylpyrimidin-5-yl)-3H-imidazo [4, 5-b] pyridine Ex. 68 (15 mg, 0.04 mmol, 24%) as a white solid.

$^1$H NMR (400 MHz, $CD_3OD$): δ 9.62 (s, 1H), 9.32 (s, 1H), 8.13 (d, J=8.4 Hz, 1H), 7.44 (d, J=8.4 Hz, 1H), 4.26-4.20 (m, 2H), 1.36 (t, J=7.2 Hz, 3H)

LC-MS: m/z 328 $[M+H]^+$ at 2.81 RT (93.96% purity)
HPLC: 95.03%

Example 69

Scheme

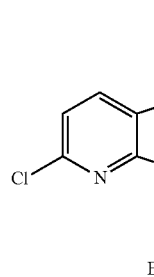

Ex. 68

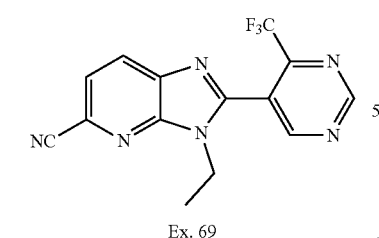

Ex. 69

5-Chloro-3-ethyl-2-(4-(trifluoromethyl)pyrimidin-5-yl)-3H-imidazo[4,5-b]pyridine (Ex. 69)

To a stirred solution of 5-chloro-3-ethyl-2-(4-(trifluoromethyl)pyrimidin-5-yl)-3H-imidazo[4,5-b]pyridine Ex. 68

(90 mg, 0.27 mmol) in DMF (1.5 mL) at room temperature was added zinc cyanide (64.4 mg, 0.55 mmol) and $Pd(PPh_3)_4$ (31.7 mg, 0.02 mmol) and the mixture was purged under argon for 10 min. The reaction mixture was heated to 180° C. for 2 h in sealed tube and cooled. The reaction mixture was diluted with ice cold water (20 mL) and extracted with EtOAc (2×20 mL). The combined organic extracts were dried over anhydrous $Na_2SO_4$ and concentrated under reduced pressure. The crude material was purified by Combi-flash chromatography to afford a solid which was washed with n-pentane (2×10 mL) to afford 5-chloro-3-ethyl-2-(4-(trifluoromethyl) pyrimidin-5-yl)-3H-imidazo [4,5-b] pyridine Ex. 69 (30 mg, 0.09 mmol, 34%) as an off-white solid.

$^1$H NMR (400 MHz, $CDCl_3$): δ 9.61 (s, 1H), 9.08 (s, 1H), 8.23 (d, J=8.2 Hz, 1H), 7.75 (d, J=8.2 Hz, 1H), 4.27-4.21 (m, 2H), 1.40 (t, J=7.3 Hz, 3H)

LC-MS: m/z 319 $[M+H]^+$ at 2.64 RT (99.45% purity)
HPLC: 99.78%

Example 70

Scheme

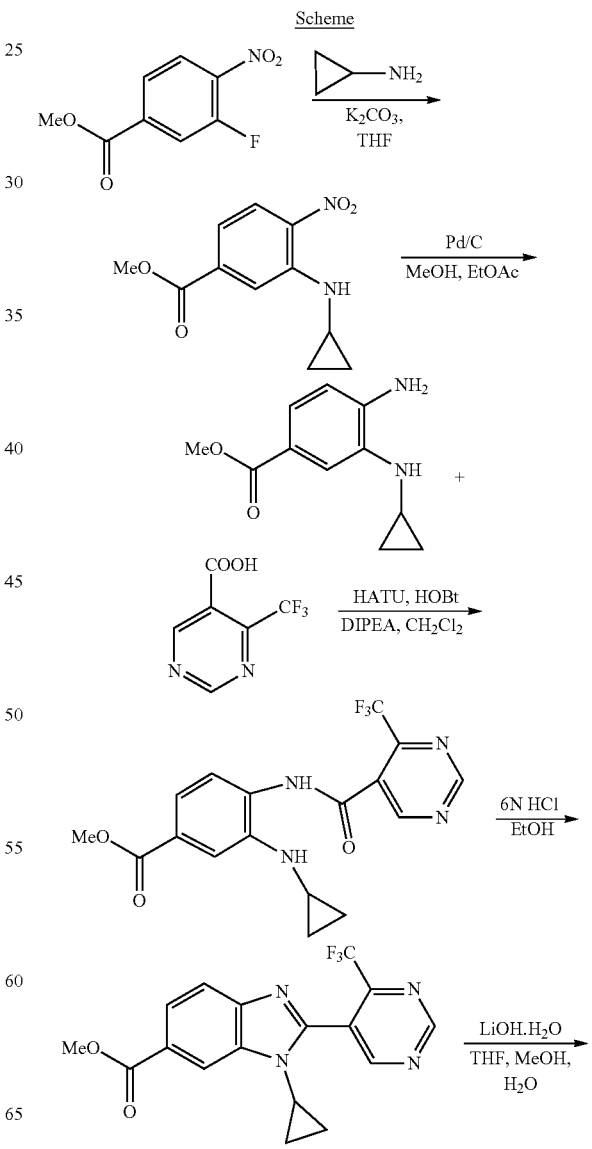

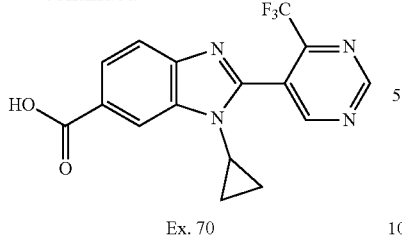

Ex. 70

Methyl 3-(cyclopropylamino)-4-nitrobenzoate

To a stirred solution of methyl 3-fluoro-4-nitrobenzoate (1 g, 5.02 mmol) in THF (30 mL) under an inert atmosphere was added potassium carbonate (2.07 g, 15.06 mmol) followed by cyclopropanamine (429 mg, 7.53 mmol) drop wise at 0° C. The reaction mixture was stirred at room temperature for 16 h. After consumption of starting material (by TLC), the volatiles were evaporated under reduced pressure. The reaction mixture was diluted with water (60 mL) and extracted with EtOAc (80 mL). The organic layer was dried over anhydrous $Na_2SO_4$ and concentrated under reduced pressure to afford methyl 3-(cyclopropylamino)-4-nitrobenzoate (900 mg, 3.81 mmol, 76%) as an orange solid.

$^1$H NMR (400 MHz, DMSO-$d_6$): δ 8.17 (d, J=8.8 Hz, 1H), 8.03 (s, 1H), 7.94 (d, J=1.8 Hz, 1H), 7.24 (dd, J=8.8, 1.8 Hz, 1H), 3.90 (s, 3H), 2.73-2.65 (m, 1H), 0.93-0.86 (m, 2H), 0.69-0.63 (m, 2H)

LC-MS: m/z 237.0 [M+H]$^+$ at 3.23 RT (99.78% purity)

Methyl 4-amino-3-(cyclopropylamino)benzoate

To a stirred solution of methyl 3-(cyclopropylamino)-4-nitrobenzoate (900 mg, 3.81 mmol) in ethyl acetate (30 mL) and methanol (30 mL) under an inert atmosphere was added 10% Pd/C (50% wet, 90 mg) at room temperature. The reaction mixture was stirred at room temperature under a hydrogen atmosphere (balloon pressure) for 3 h. After consumption of starting material (by TLC), the reaction mixture was filtered through a pad of celite and the pad was washed with methanol (50 mL) and EtOAc (50 mL). The filtrate was concentrated under reduced pressure to obtain methyl 4-amino-3-(cyclopropylamino) benzoate (700 mg) as colorless viscous syrup. The crude material was used in the next step without further purification.

LC-MS: m/z 207.1 [M+H]$^+$ at 2.85 RT (52.59% purity)

Methyl 3-(cyclopropylamino)-4-(4-(trifluoromethyl)pyrimidine-5-carboxamido)benzoate To a stirred solution of methyl 4-amino-3-(cyclopropylamino)benzoate (300 mg, crude) in $CH_2Cl_2$ (10 mL) was added 4-(trifluoromethyl)pyrimidine-5-carboxylic acid (279 mg, 1.45 mmol), diisopropylethylamine (1.02 mL, 5.82 mmol), HATU (608 mg, 1.60 mmol) and HOBt (217 mg, 1.60 mmol) at room temperature and the mixture was stirred for 16 h. After consumption of starting material (by TLC), the reaction mixture was diluted with water (40 mL) and extracted with $CH_2Cl_2$ (50 mL). The organic layer washed with water (40 mL), dried over anhydrous $Na_2SO_4$ and concentrated under reduced pressure. The crude material was purified by silica gel column chromatography (eluent: 20% EtOAc/hexane) to afford methyl 3-(cyclopropylamino)-4-(4-(trifluoromethyl)pyrimidine-5-carboxamido)benzoate (160 mg, 0.43 mmol, 25%) as a pale orange thick solid.

LC-MS: m/z 381.1 [M+H]$^+$ at 2.89 RT (47.61% purity)

Methyl 1-cyclopropyl-2-(4-(trifluoromethyl)pyrimidin-5-yl)-1H-benzo[d]imidazole-6-carboxylate To a stirred solution of methyl 3-(cyclopropylamino)-4-(4-(trifluoromethyl)pyrimidine-5-carboxamido)benzoate (140 mg, 0.36 mmol) in EtOH (1 mL) under an inert atmosphere was added 6N HCl (1.5 mL) at room temperature. The reaction mixture was heated to 70° C. and stirred for 1 h. After consumption of starting material (by TLC), the reaction mixture was diluted with water (15 mL) and washed with diethyl ether (20 mL). The aqueous layer was neutralized with saturated Sodium bicarbonate solution (10 mL) and extracted with $CH_2Cl_2$ (2×30 mL). The combined organic extracts were dried over anhydrous $Na_2SO_4$ and concentrated under reduced pressure to afford methyl 1-cyclopropyl-2-(4-(trifluoromethyl)pyrimidin-5-yl)-1H-benzo[d]imidazole-6-carboxylate (80 mg) as a thick syrup. The crude material was used in the next step further purification.

1-Cyclopropyl-2-(4-(trifluoromethyl)pyrimidin-5-yl)-1H-benzo[d]imidazole-6-carboxylic acid (Ex. 70)

To a stirred solution of methyl 1-cyclopropyl-2-(4-(trifluoromethyl)pyrimidin-5-yl)-1H-benzo[d]imidazole-6-carboxylate 6 (80 mg, crude) in a mixture of THF:MeOH:water (2:1:1, 4 mL) was added lithium hydroxide (13.26 g, 0.31 mmol) at 0° C. The reaction mixture was gradually warmed to room temperature and stirred for 2 h. After consumption of starting material (by TLC), the volatiles were concentrated under reduced pressure. The residue was diluted with water (10 mL) and washed with diethyl ether (20 mL). Then the aqueous layer was acidified to pH 2 with saturated potassium bisulfate solution and extracted with $CH_2Cl_2$ (2×40 mL). The combined organic extracts were dried over anhydrous $Na_2SO_4$ and concentrated under reduced pressure. The crude material was purified by preparative HPLC to afford 1-cyclopropyl-2-(4-(trifluoromethyl)pyrimidin-5-yl)-1H-benzo[d]imidazole-6-carboxylic acid Ex. 70 (13 mg, 0.03 mmol, 18%) as an off white solid.

$^1$H NMR (400 MHz, DMSO-$d_6$): δ 13.03 (br s, 1H), 9.71 (s, 1H), 9.59 (s, 1H), 8.31 (s, 1H), 7.93 (dd, J=8.5, 1.6 Hz, 1H), 7.83 (d, J=8.8 Hz, 1H), 3.63-3.56 (m, 1H), 1.06-0.99 (m, 2H), 0.73-0.66 (m, 2H)

LC-MS: m/z 349.0 [M+H]$^+$ at 1.99 RT (99.57% purity)
HPLC: 95.46%

Example 71

Scheme

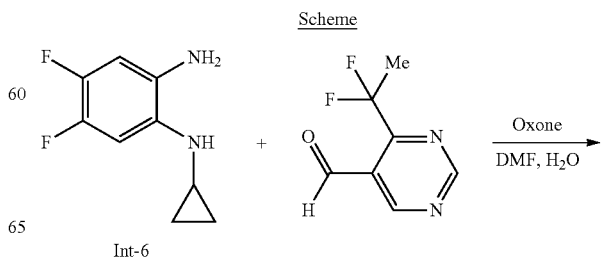

Int-6

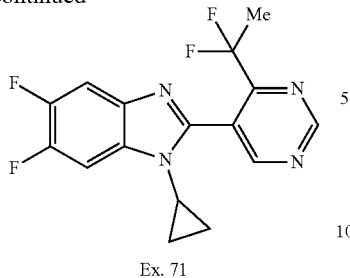

Ex. 71

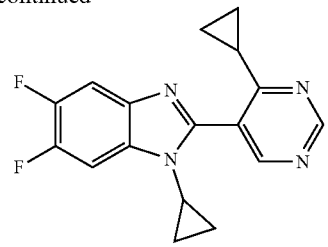

Ex. 72

1-Cyclopropyl-2-(4-(1,1-difluoroethyl)pyrimidin-5-yl)-5,6-difluoro-1H-benzo[d]imidazole (Ex. 71)

To a stirred solution of N-cyclopropyl-4, 5-difluorobenzene-1,2-diamine Int-6 (100 mg, 0.54 mmol) in a mixture of DMF:water (8:2, 1 mL) was added 4-(1,1-difluoroethyl)pyrimidine-5-carbaldehyde (112 mg, 0.65 mmol) and Oxone (165 mg, 1.08 mmol) at room temperature. The reaction mixture was stirred at room temperature for 2 h. After consumption of starting material (by TLC), the reaction mixture was diluted with water (20 mL) and extracted with EtOAc (2×25 mL). The combined organic extracts were dried over anhydrous $Na_2SO_4$ and concentrated under reduced pressure. The crude material was purified by silica gel column chromatography (eluent: 80% EtOAc/hexane) to afford 1-cyclopropyl-2-(4-(1,1-difluoroethyl)pyrimidin-5-yl)-5,6-difluoro-1H-benzo[d]imidazole Ex. 71 (50 mg, 0.14 mmol, 27%) as an off white solid.

$^1$H NMR (400 MHz, $CDCl_3$): δ 9.44 (s, 1H), 8.93 (s, 1H), 7.56 (dd, J=10.2, 7.2 Hz, 1H), 7.41 (dd, J=9.7, 7.0 Hz, 1H), 3.35-3.28 (m, 1H), 2.07 (t, J=19.1 Hz, 3H), 1.01-0.95 (m, 2H), 0.78-0.72 (m, 2H)

LC-MS: m/z 337.0 $[M+H]^+$ at 2.87 RT (98.17% purity)
HPLC: 97.61%

Example 72

Scheme

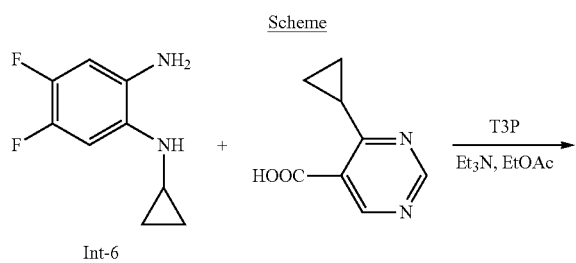

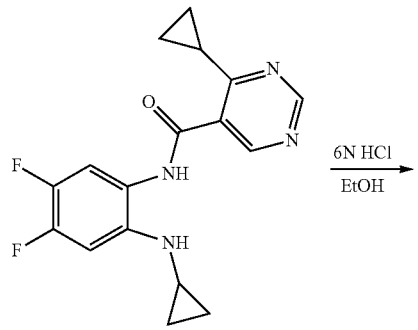

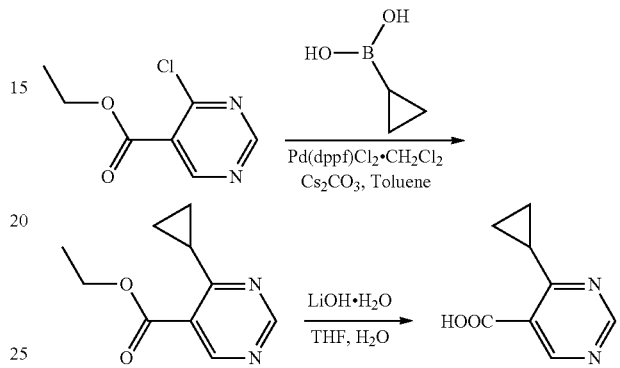

Ethyl 4-cyclopropylpyrimidine-5-carboxylate

To a stirred solution of ethyl 4-chloropyrimidine-5-carboxylate (1 g, 5.35 mmol) in toluene (50 mL) under an inert atmosphere was added cyclopropylboronic acid (829 mg, 9.64 mmol) and cesium carbonate (2.62 mg, 8.03 mmol) at room temperature in a sealed tube. The reaction mixture was degassed under argon for 15 min. Pd(dppf)C12 (218 mg, 0.26 mmol) was added at room temperature and the solution was degassed under argon for another 10 min. The reaction mixture was heated to 100° C. and stirred for 5 h. After consumption of starting material (by TLC), the reaction mixture was filtered through a pad of celite, and the pad was washed with EtOAc (100 mL). The filtrate was concentrated under reduced pressure. The crude material was purified by silica gel column chromatography (eluent: 20% EtOAc/Hexane) to afford ethyl 4-cyclopropylpyrimidine-5-carboxylate (150 mg, 0.78 mmol, 15%) as a pale yellow syrup.

$^1$H NMR (400 MHz, DMSO-$d_6$): δ 9.08 (s, 1H), 8.98 (s, 1H), 4.37 (q, J=7.1 Hz, 2H), 3.01-2.93 (m, 1H), 1.35 (t, J=7.1 Hz, 3H), 1.18-1.15 (m, 4H)

LC-MS: m/z 192.9 $[M+H]^+$ at 2.40 RT (95.93% purity)

4-Cyclopropylpyrimidine-5-carboxylic acid

To a stirred solution of ethyl 4-cyclopropylpyrimidine-5-carboxylate (100 mg, 0.52 mmol) in a mixture of THF:water (4:1, 2 mL) was added lithium hydroxide monohydrate (65 mg, 1.56 mmol) at 0° C. The reaction mixture was warmed to room temperature and stirred for 3 h. After consumption of starting material (by TLC), the volatiles were concentrated under reduced pressure. The residue was acidified to pH 3 using 2N HCl solution and the resulting solid was filtered and dried to afford 4-cyclopropylpyrimidine-5-carboxylic acid (100 mg) as a brown solid. The crude material was used in the next step without further purification.

LC-MS: m/z 165.3 $[M+H]^+$ at 2.06 RT (91.84% purity)

4-Cyclopropyl-N-(2-(cyclopropylamino)-4,5-difluorophenyl)pyrimidine-5-carboxamide To a stirred solution of $N^1$-cyclopropyl-4,5-difluorobenzene-1,2-diamine Int-6 (110 mg, 0.60 mmol) in EtOAc (6 mL) under an inert atmosphere was added 4-cyclopropylpyrimidine-5-carboxylic acid (100 mg, 0.60 mmol), triethylamine (0.17 mL, 1.2 mmol) and propylphosphonic anhydride (50% in EtOAc, 0.96 mL, 1.5 mmol) at 0° C. The reaction mixture was warmed to room temperature and stirred for 2 h. After consumption of starting material (by TLC), the reaction mixture was quenched with saturated sodium bicarbonate solution (20 mL) and extracted with EtOAc (2×30 mL). The combined organic extracts were dried over anhydrous $Na_2SO_4$ and concentrated under reduced pressure. The crude material was purified by silica gel column chromatography (eluent: 30% EtOAc/hexane) to afford 4-cyclopropyl-N-(2-(cyclopropylamino)-4,5-difluorophenyl)pyrimidine-5-carboxamide (110 mg, 0.33 mmol, 55%) as a brown solid.

$^1$H NMR (400 MHz, DMSO-$d_6$): δ 9.78 (s, 1H), 9.04 (s, 1H), 8.91 (s, 1H), 7.54 (dd, J=12.0, 8.7 Hz, 1H), 6.94 (dd, J=13.6, 8.0 Hz, 1H), 5.83 (s, 1H), 3.29-3.28 (m, 1H), 2.40-2.34 (m, 1H), 1.16-1.09 (m, 4H), 0.78-0.72 (m, 2H), 0.46-0.40 (m, 2H)

LC-MS: m/z 329.1 [M–H]$^-$ at 2.89 RT (94.64% purity)

1-Cyclopropyl-2-(4-cyclopropylpyrimidin-5-yl)-5,6-difluoro-1H-benzo[d]imidazole (Ex. 72)

To a stirred solution of 4-cyclopropyl-N-(2-(cyclopropylamino)-4,5-difluorophenyl) pyrimidine-5-carboxamide (90 mg, 0.27 mmol) in EtOH (3 mL) was added 6 N HCl (0.9 mL) at room temperature. The reaction mixture was heated to 60° C. and stirred for 2 h. After consumption of starting material (by TLC), the reaction mixture was quenched with saturated sodium bicarbonate solution (15 mL) and extracted with EtOAc (2×20 mL). The combined organic extracts were dried over anhydrous $Na_2SO_4$ and concentrated under reduced pressure. The crude material was purified by silica gel column chromatography (eluent: 20-30% EtOAc/Hexane) which was further purified by preparative HPLC to afford 1-cyclopropyl-2-(4-cyclopropylpyrimidin-5-yl)-5,6-difluoro-1H-benzo[d]imidazole Ex. 72 (7 mg, 0.02 mmol, 8%) as an off white solid.

$^1$H NMR (400 MHz, $CD_3OD$): δ 9.09 (s, 1H), 8.77 (s, 1H), 7.69 (dd, J=10.1, 7.1 Hz, 1H), 7.59 (dd, J=10.4, 7.3 Hz, 1H), 3.61-3.54 (m, 1H), 2.03-1.95 (m, 1H), 1.37-1.28 (m, 2H), 1.19-1.12 (m, 2H), 1.08-1.00 (m, 2H), 0.78-0.71 (m, 2H)

LC-MS: m/z 312.9 [M+H]$^+$ at 2.74 RT (97.77% purity)
HPLC: 98.46%

Example 73

Scheme

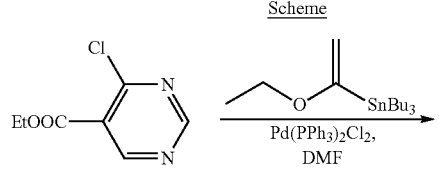

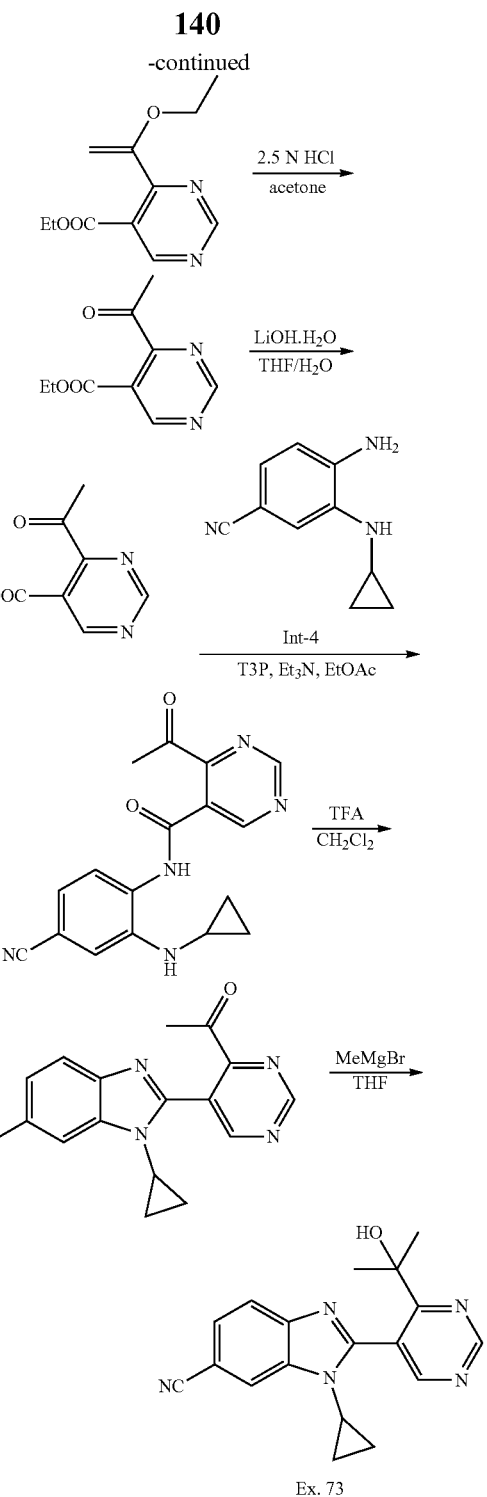

Ethyl 4-(1-ethoxyvinyl)pyrimidine-5-carboxylate

To a stirred solution of ethyl 4-chloropyrimidine-5-carboxylate (1 g, 6.47 mmol) in DMF (10 mL) was added tributyl(1-ethoxyvinyl)stannane (2.81 g, 7.77 mmol) at room temperature under an inert atmosphere and the mixture was purged under argon for 15 min. Pd(PPh$_3$)$_2$Cl$_2$ (454 mg, 0.65 mmol) was added and the mixture was purged under argon for another 5 min at room temperature. The reaction mixture was heated to 100° C. for 16 h and cooled. The reaction mixture was diluted with water (40 mL) and extracted with EtOAc (2×40 mL). The combined organic extracts were dried over anhydrous $Na_2SO_4$ and concentrated under reduced pressure. The crude material was purified by silica gel column chromatography (eluent: 30% EtOAc/hexane) to afford ethyl 4-(1-ethoxyvinyl)pyrimidine-5-carboxylate (800 mg, 3.6 mmol, 56%) as a colorless viscous liquid.

$^1$H NMR (500 MHz, DMSO-$d_6$): δ 9.24 (s, 1H), 8.93 (s, 1H), 5.29 (d, J=2.3 Hz, 1H), 4.68 (d, J=2.3 Hz, 1H), 4.28 (q, J=7.3 Hz, 2H), 3.88 (q, J=7.0 Hz, 2H), 1.32-1.21 (m, 6H)

LC-MS: m/z 222.9 [M+H]$^+$ at 2.43 RT (89.93% purity)

Ethyl 4-acetylpyrimidine-5-carboxylate

To a stirred solution of ethyl 4-(1-ethoxyvinyl)pyrimidine-5-carboxylate (800 mg, 3.6 mmol) in acetone (24 mL) was added HCl (2.5 N, 12 mL) at 0° C. under an inert atmosphere and the reaction was stirred at room temperature for 3 h. The volatiles were removed under reduced pressure. The residue was neutralized using saturated $NaHCO_3$ solution (pH ~7) and extracted with $CH_2Cl_2$ (2×30 mL). The combined organic extracts were dried over anhydrous $Na_2SO_4$ and concentrated under reduced pressure to afford ethyl 4-acetylpyrimidine-5-carboxylate (600 mg) as pale brown viscous syrup. The crude material was taken to the next step without further purification.

$^1$H NMR (500 MHz, DMSO-$d_6$): δ 9.47 (s, 1H), 9.27 (s, 1H), 4.33 (q, J=7.3 Hz, 2H), 2.60 (s, 3H), 1.30 (t, J=7.2 Hz, 3H)

4-Acetylpyrimidine-5-carboxylic acid

To a stirred solution of ethyl 4-acetylpyrimidine-5-carboxylate (400 mg, crude) in a mixture of THF (10 mL) and water (4 mL) was added lithium hydroxide monohydrate (260 mg, 6.18 mmol) at 0° C. The reaction mixture was gradually warmed to room temperature and stirred for 3 h. The reaction mixture was diluted with water (10 mL) and washed with ether (10 mL). The organic layer was separated and the aqueous layer was acidified using saturated $KHSO_4$ solution (pH ~4) and extracted with EtOAc (2×20 mL). The combined organic extracts were dried over anhydrous $Na_2SO_4$ and concentrated under reduced pressure to afford 4-acetylpyrimidine-5-carboxylic acid (250 mg) as a pale brown viscous syrup. The crude material was taken to the next step without further purification.

LC-MS: m/z 167.6 [M+H]$^+$ at 1.96 RT (21.40% purity)

4-Acetyl-N-(4-cyano-2-(cyclopropylamino)phenyl)pyrimidine-5-carboxamide

To a stirred solution of 4-amino-3-(cyclopropylamino)benzonitrile Int-4 (250 mg, 1.44 mmol) and 4-acetylpyrimidine-5-carboxylic acid (240 mg, crude) in ethylacetate (5 mL) was added triethylamine (0.4 mL, 2.89 mmol) followed by propylphosphonic anhydride (50% in EtOAc, 2.3 mL, 3.61 mmol) drop wise at 0° C. under an inert atmosphere. The reaction mixture was stirred for 4 h, saturated $NaHCO_3$ solution (pH ~8) was added, and the mixture was extracted with EtOAc (2×25 mL). The combined organic extracts were dried over anhydrous $Na_2SO_4$ and concentrated under reduced pressure. The crude material was purified by silica gel column chromatography (eluent: 30% EtOAc/hexane) to afford 4-acetyl-N-(4-cyano-2-(cyclopropylamino)phenyl)pyrimidine-5-carboxamide (150 mg, 0.47 mmol, 32%) as a pale yellow solid.

LC-MS: m/z 320.1 [M−H]$^+$ at 2.14 RT (54.95% purity)

2-(4-Acetylpyrimidin-5-yl)-1-cyclopropyl-1H-benzo[d]imidazole-6-carbonitrile

To a stirred solution of 4-acetyl-N-(4-cyano-2-(cyclopropylamino)phenyl)pyrimidine-5-carboxamide (20 mg, 0.06 mmol) in $CH_2Cl_2$ (2 mL) was added trifluoroacetic acid (0.01 mL, 0.19 mmol) at 0° C. under an inert atmosphere. The reaction mixture was gradually warmed to room temperature and stirred for 2 h. The volatiles were removed under reduced pressure and the residue was diluted with water (5 mL), neutralized with saturated $NaHCO_3$ solution (pH ~7) and extracted with $CH_2Cl_2$ (2×10 mL). The combined organic extracts were dried over anhydrous $Na_2SO_4$ and concentrated under reduced pressure to afford 2-(4-acetylpyrimidin-5-yl)-1-cyclopropyl-1H-benzo[d]imidazole-6-carbonitrile (10 mg) as a brown solid. The crude material was taken to the next step without further purification.

LC-MS: m/z 303.9 [M+H]$^+$ at 2.33 RT (53.47% purity)

1-Cyclopropyl-2-(4-(2-hydroxypropan-2-yl)pyrimidin-5-yl)-1H-benzo[d]imidazole-6-carbonitrile (Ex. 73)

To a stirred solution of 2-(4-acetylpyrimidin-5-yl)-1-cyclopropyl-1H-benzo[d]imidazole-6-carbonitrile (110 mg, crude) in THF (5 mL) was added methylmagnesium bromide (3 M in THF, 0.12 mL, 0.36 mmol) at 0° C. under an inert atmosphere. The reaction mixture was gradually warmed to room temperature and stirred for 4 h. The reaction mixture was quenched with saturated $NH_4Cl$ solution and extracted with EtOAc (2×20 mL). The combined organic extracts were dried over anhydrous $Na_2SO_4$ and concentrated under reduced pressure. The crude material was purified by preparative HPLC to afford 1-cyclopropyl-2-(4-(2-hydroxypropan-2-yl)pyrimidin-5-yl)-1H-benzo[d]imidazole-6-carbonitrile Ex. 73 (18 mg, 0.06 mmol, 16%) as an off white solid.

$^1$H NMR (400 MHz, DMSO-$d_6$): δ 9.31 (s, 1H), 8.90 (s, 1H), 8.19 (dd, J=1.5, 0.6 Hz, 1H), 7.82 (dd, J=8.3, 0.6 Hz, 1H), 7.64 (dd, J=8.3, 1.6 Hz, 1H), 5.14 (s, 1H), 3.45-3.40 (m, 1H), 1.52 (s, 6H), 0.92-0.89 (m, 2H), 0.83-0.80 (m, 2H)

LC-MS: m/z 319.9 [M+H]$^+$ at 1.86 RT (97.56% purity)
HPLC: 95.26%

Example 74: Metalloenzyme Activity

A. V79-4 cells expressing recombinant andrenodoxin and andrenodoxin reductase with either recombinant human CYP11B2 or CYP11B1 was prepared according to methods previously described (LaSala et al 2009 Anal Bioch 394:56-61). An enzyme enriched microsomal fraction was prepared from cellular lysates and subsequently used as the enzyme source for determining inhibitor $IC_{50}$s. The substrate Km values were experimentally determined for 11-deoxycorticosterone (CYP11B2 substrate) and 11-deoxycortisol (CYP11B1 substrate). Enzyme assays for inhibitor screening employed CYP11B2 and CYP11B1 enzyme enriched microsomes and were run at the Km of the respective substrates. Products of the enzyme reactions, aldosterone for CYP11B2 or cortisol for CYP11B1, were measured by LC-MS. Assays were run under conditions of less than 20% substrate turnover. Inhibitor $IC_{50}$s were generated by determining the product formation in the absence or presence of inhibitor at various concentrations. In the absence of the test compound, the product formed (Pr) in each data set was defined as 100% activity. In the absence of enzyme, the product formed ($P_b$) in each data set was defined as 0% activity. The percent activity in the presence of each inhibitor was calculated according to the following equation: % activity=$(P-P_b)/(P_t-P_b)$, where P=the product formed in the presence of the inhibitor. The $IC_{50}$ value was defined as the inhibitor concentration causing a 50% decrease in activity relative to the no inhibitor control reaction.

TABLE 2

Results: CYP11B2 Activity

| | hCYP11B2 IC$_{50}$[g] | hCYP11B1 IC$_{50}$[g] | HPLC Retention Time[f] | LCMS (M + 1)[f] | Structure |
|---|---|---|---|---|---|
| 1 | ++++ | ++ | 7.83[a] | 2.55 [M + H][a] | 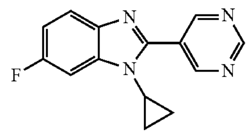 [SMILES: Fc1ccc2nc(-c3cncnc3)n(C3CC3)c2c1] |
| 2 | +++ | ++ | 8.00[b] | 272.9 [M + H][a] | 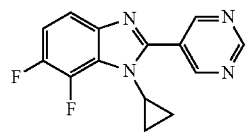 [SMILES: Fc1ccc2nc(-c3cncnc3)n(C3CC3)c2c1F] |
| 3 | ++++ | ++ | 8.08[c] | 262 [M + H][a] | 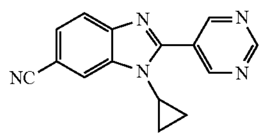 [SMILES: N#Cc1ccc2nc(-c3cncnc3)n(C3CC3)c2c1] |
| 4 | ++++ | ++ | 6.24[b] | 269 [M + H][a] | 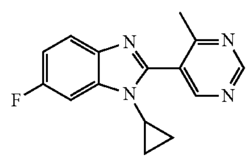 [SMILES: Cc1ncncc1-c1nc2ccc(F)cc2n1C1CC1] |
| 5 | ++++ | ++ | 7.25[b] | 282.9 [M + H][a] | 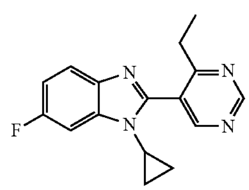 [SMILES: CCc1ncncc1-c1nc2ccc(F)cc2n1C1CC1] |
| 6 | +++ | + | 9.39[c] | 284.9 [M + H][a] | 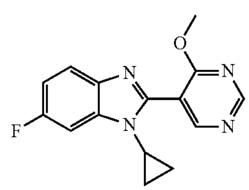 [SMILES: COc1ncncc1-c1nc2ccc(F)cc2n1C1CC1] |
| 7 | ++++ | ++ | 7.31[b] | 273.3 [M + H][d] | 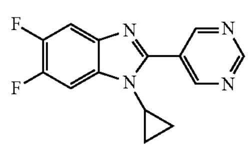 [SMILES: Fc1cc2nc(-c3cncnc3)n(C3CC3)c2cc1F] |
| 8 | ++++ | ++ | 9.20[d] | 289.9 [M + H][b] | 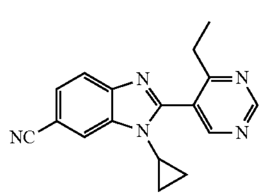 [SMILES: CCc1ncncc1-c1nc2ccc(C#N)cc2n1C1CC1] |
| 9 | ++++ | ++ | 8.53[b] | 288.9 [M + H][b] | 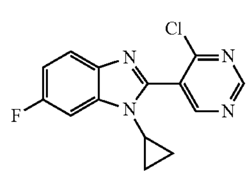 [SMILES: Fc1ccc2nc(-c3cncnc3Cl)n(C3CC3)c2c1] |

TABLE 2-continued
Results: CYP11B2 Activity
| | hCYP11B2 IC$_{50}$[g] | hCYP11B1 IC$_{50}$[g] | HPLC Retention Time[f] | LCMS (M + 1)[f] | Structure |
|---|---|---|---|---|---|
| 10 | ++++ | ++ | 10.07[e] | 279.9 [M + H][b] | 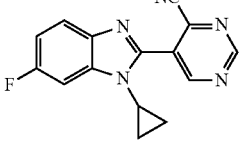 |
| 11 | ++++ | ++ | 8.80[b] | 298.9 [M + H][b] | 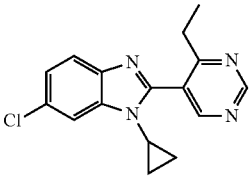 [SMILES: CCc1ncncc1-c1nc2ccc(Cl)cc2n1C1CC1] |
| 12 | ++++ | +++ | 9.59[c] | 283.9 [M + H][b] | 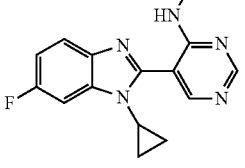 |
| 13 | ++++ | ++ | 8.69[b] | 297 [M + H][C] | 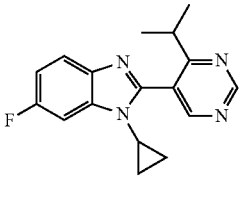 |
| 14 | ++++ | ++ | 8.02[b] | 297 [M + H][C] | 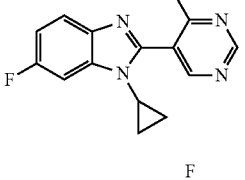 |
| 15 | ++++ | ++ | 8.82[b] | 304.9 [M + H][C] | 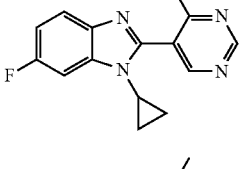 |
| 16 | +++ | ++ | 6.70[b] | 271 [M + H][C] | 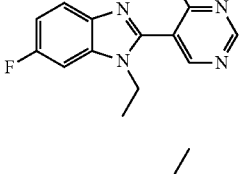 |
| 17 | ++++ | ++ | 10.04[e] | 300.9 [M + H][b] | 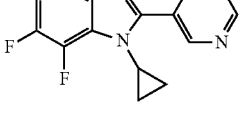 |

TABLE 2-continued

Results: CYP11B2 Activity

| | hCYP11B2 IC$_{50}$$^g$ | hCYP11B1 IC$_{50}$$^g$ | HPLC Retention Time$^f$ | LCMS (M + 1)$^f$ | Structure |
|---|---|---|---|---|---|
| 18 | ++++ | ++ | 6.47$^b$ | 264 [M + H]$^c$ | 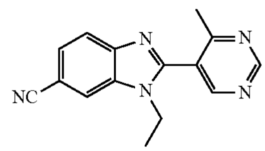 [SMILES: CCn1c(-c2cncnc2C)nc2ccc(C#N)cc21] |
| 19 | ++ | + | 5.81$^b$ | 325.9 [M + H]$^b$ | 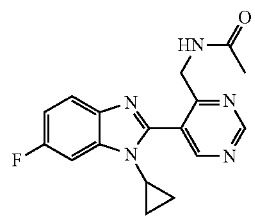 [SMILES: CC(=O)NCc1ncncc1-c1nc2ccc(F)cc2n1C1CC1] |
| 20 | ++ | + | 6.60$^b$ | 269 [M + H]$^b$ | 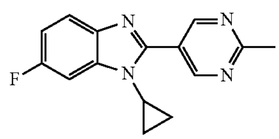 [SMILES: Cc1ncc(-c2nc3ccc(F)cc3n2C2CC2)cn1] |
| 21 | ++++ | ++ | 6.89$^b$ | 276 [M + H]$^c$ | 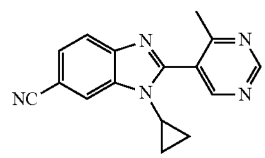 [SMILES: Cc1ncncc1-c1nc2ccc(C#N)cc2n1C1CC1] |
| 22 | ++++ | +++ | 9.66$^b$ | 314.9 [M + H]$^b$ | 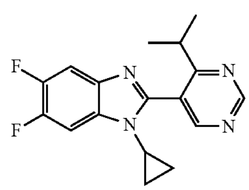 [SMILES: CC(C)c1ncncc1-c1nc2cc(F)c(F)cc2n1C1CC1] |
| 23 | ++++ | ++ | 786$^b$ | 271.2 [M + H]$^d$ | 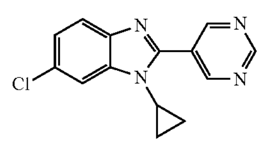 [SMILES: Clc1ccc2nc(-c3cncnc3)n(C3CC3)c2c1] |
| 24 | ++++ | ++ | 9.76$^b$ | 313 [M + H]$^c$ | 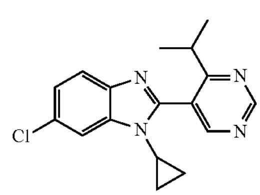 [SMILES: CC(C)c1ncncc1-c1nc2ccc(Cl)cc2n1C1CC1] |
| 25 | +++ | + | 553$^b$ | 267 [M + H]$^c$ | 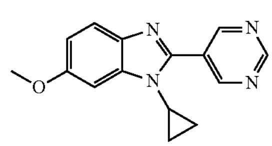 [SMILES: COc1ccc2nc(-c3cncnc3)n(C3CC3)c2c1] |
| 26 | ++ | + | 5.37$^b$ | 314.9 [M + H]$^b$ | 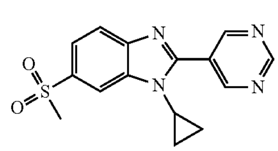 [SMILES: CS(=O)(=O)c1ccc2nc(-c3cncnc3)n(C3CC3)c2c1] |

TABLE 2-continued

| | | | | | |
|---|---|---|---|---|---|
| | | Results: CYP11B2 Activity | | | |
| | hCYP11B2 IC$_{50}$$^g$ | hCYP11B1 IC$_{50}$$^g$ | HPLC Retention Time$^f$ | LCMS (M + 1)$^f$ | Structure |
| 27 | ++++ | ++ | 9.25$^b$ | 322.9 [M + H]$^c$ | 5,6-difluoro-1-cyclopropyl-2-[4-(difluoromethyl)pyrimidin-5-yl]benzimidazole |
| 28 | ++++ | ++ | 8.74$^b$ | 303.9 [M + H]$^b$ | 6-cyano-1-cyclopropyl-2-(4-isopropylpyrimidin-5-yl)benzimidazole |
| 29 | + | + | 7.50$^b$ | 282.9 [M + H]$^c$ | 6-fluoro-1-cyclopropyl-2-(4,6-dimethylpyrimidin-5-yl)benzimidazole |
| 30 | ++++ | ++ | 10.09$^b$ | 340.9 [M + H]$^b$ | 5,6-difluoro-1-cyclopropyl-2-[4-(trifluoromethyl)pyrimidin-5-yl]benzimidazole |
| 31 | ++++ | +++ | 6.16$^b$ | 301.9 [M + H]$^c$ | 5,6-difluoro-1-cyclopropyl-2-[4-(methylamino)pyrimidin-5-yl]benzimidazole |
| 32 | ++++ | ++ | 5.58$^b$ | 315.9 [M + H]$^b$ | 5,6-difluoro-1-cyclopropyl-2-[4-(dimethylamino)pyrimidin-5-yl]benzimidazole |
| 33 | ++++ | ++ | 6.58$^b$ | 346 [M + H]$^c$ | 5,6-difluoro-1-cyclopropyl-2-{4-[(2-methoxyethyl)amino]pyrimidin-5-yl}benzimidazole |

TABLE 2-continued

Results: CYP11B2 Activity

| | hCYP11B2 IC$_{50}$$^g$ | hCYP11B1 IC$_{50}$$^g$ | HPLC Retention Time$^f$ | LCMS (M + 1)$^f$ | Structure |
|---|---|---|---|---|---|
| 34 | ++++ | +++ | 7.92$^b$ | 344 [M + H]$^b$ | 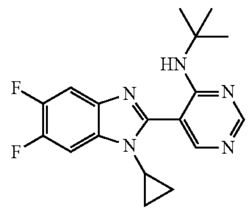 [SMILES: CC(C)(C)Nc1ncncc1-c1nc2cc(F)c(F)cc2n1C1CC1] |
| 35 | ++ | + | 10.70$^C$ | 322.9 [M + H]$^C$ | 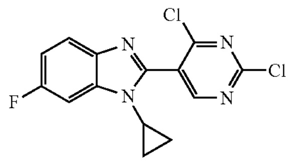 [SMILES: Fc1ccc2nc(-c3cnc(Cl)nc3Cl)n(C3CC3)c2c1] |
| 36 | ++++ | +++ | 8.70$^b$ | 369.9 [M + H]$^b$ | 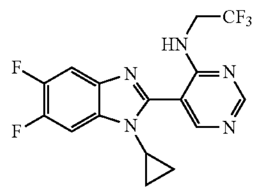 [SMILES: Fc1cc2nc(-c3cncnc3NCC(F)(F)F)n(C3CC3)c2cc1F] |
| 37 | ++++ | +++ | 6.87$^b$ | 384 [M + H]$^C$ | 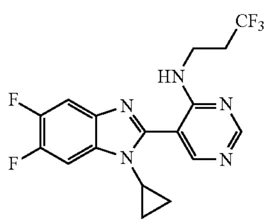 [SMILES: Fc1cc2nc(-c3cncnc3NCCC(F)(F)F)n(C3CC3)c2cc1F] |
| 38 | ++++ | ++ | 8.53$^b$ | 288.9 [M + H]$^b$ | 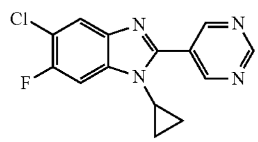 [SMILES: Fc1cc2c(cc1Cl)nc(-c1cncnc1)n2C1CC1] |
| 39 | ++++ | +++ | 8.37$^b$ | 290.9 [M + H]$^C$ | 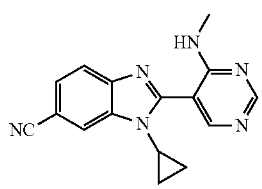 [SMILES: CNc1ncncc1-c1nc2ccc(C#N)cc2n1C1CC1] |
| 40 | ++++ | +++ | 9.45$^d$ | 303.9 [M + H]$^b$ | 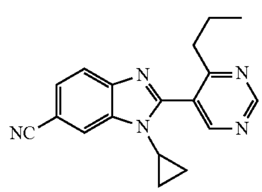 |
| 41 | ++++ | ++ | 8.39$^b$ | 291.9 [M + H]$^b$ | 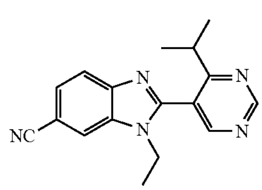 [SMILES: CCn1c(-c2cncnc2C(C)C)nc2ccc(C#N)cc21] |

TABLE 2-continued

Results: CYP11B2 Activity

| | hCYP11B2 IC$_{50}$$^g$ | hCYP11B1 IC$_{50}$$^g$ | HPLC Retention Time$^f$ | LCMS (M + 1)$^f$ | Structure |
|---|---|---|---|---|---|
| 42 | +++ | ++ | 8.88$^b$ | 320.9 [M + H]$^b$ | F$_3$CO-benzimidazole-N-cyclopropyl, 2-pyrimidinyl |
| 43 | ++ | + | 8.82$^c$ | 303.9 [M + H]$^b$ | NC-benzimidazole-N-CH$_2$CF$_3$, 2-pyrimidinyl |
| 44 | ++++ | ++ | 7.35$^b$ | 287.1 [M + H]$^e$ | F,F-benzimidazole-N-cyclopropyl, 4-methylpyrimidinyl |
| 45 | ++++ | ++ | 8.63$^b$ | 300.9 [M + H]$^c$ | F,F-benzimidazole-N-cyclopropyl, 4-ethylpyrimidinyl |
| 46 | ++++ | ++ | 9.20$^b$ | 297.9 [M + H]$^b$ | F,F-benzimidazole-N-cyclopropyl, 4-cyanopyrimidinyl |
| 47 | ++++ | +++ | 10.26$^b$ | 257.9 [M + H]$^c$ | Cl-benzimidazole-N-ethyl, 2-pyrimidinyl |
| 48 | ++++ | ++ | 7.14$^b$ | 285.9 [M + H]$^b$ | Cl-benzimidazole-N-cyclopropyl, 4-methylpyrimidinyl |
| 49 | +++ | + | 7.61$^b$ | 316.1 [M − H]$^e$ | NC-benzimidazole-N-CH$_2$CF$_3$, 4-methylpyrimidinyl |
| 50 | ++++ | ++ | 9.66$^b$ | 320.9 [M + H]$^c$ | Cl-benzimidazole-N-cyclopropyl, 4-(CHF$_2$)pyrimidinyl |

TABLE 2-continued

| | | | | Results: CYP11B2 Activity | |
|---|---|---|---|---|---|
| | hCYP11B2 IC$_{50}$[g] | hCYP11B1 IC$_{50}$[g] | HPLC Retention Time[f] | LCMS (M + 1)[f] | Structure |
| 51 | ++++ | + | 7.53[b] | 299.9 [M + H][b] | |
| 52 | ++++ | ++ | 7.53[b] | 276.9 [M + H][b] | |
| 53 | ++++ | ++ | 9.81[c] | 318.2 [M + H][e] | |
| 54 | ++++ | ++ | 9.45[c] | 311.9 [M + H][b] | |
| 55 | +++ | + | 6.00[b] | 285.9 [M + H][b] | |
| 56 | +++ | + | 5.74[b] | 277.2 [M + H][e] | |
| 57 | ++ | + | 8.15[d] | 241 [M + H][b] | |
| 58 | +++ | + | 6.74[b] | 282 [M + H][C] | |

TABLE 2-continued

Results: CYP11B2 Activity

| | hCYP11B2 IC50[g] | hCYP11B1 IC50[g] | HPLC Retention Time[f] | LCMS (M + 1)[f] | Structure |
|---|---|---|---|---|---|
| 59 | ++ | + | 6.62[b] | 358.1 [M + H][c] | 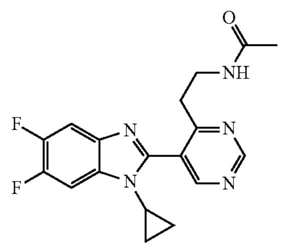 [SMILES: CC(=O)NCCc1ncncc1-c1nc2cc(F)c(F)cc2n1C1CC1] |
| 60 | ++++ | ++ | 8.92[b] | 329.9 [M + H][b] | 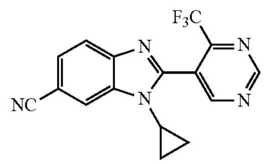 [SMILES: N#Cc1ccc2nc(-c3cncnc3C(F)(F)F)n(C3CC3)c2c1] |
| 61 | ++++ | ++ | 9.43[b] | 340 [M + H][b] | 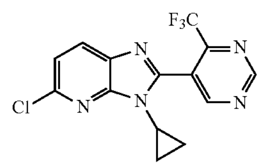 [SMILES: FC(F)(F)c1ncncc1-c1nc2ccc(Cl)nc2n1C1CC1] |
| 62 | +++ | ++ | 4.15[b] | 321.9 [M + H][b] | 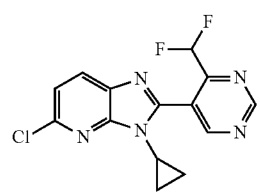 [SMILES: FC(F)c1ncncc1-c1nc2ccc(Cl)nc2n1C1CC1] |
| 63 | ++++ | ++ | 7.99 (min)[b] | 312.9 [M + H][+b] | 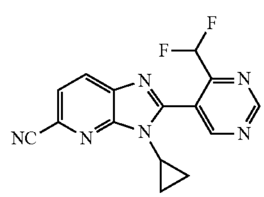 [SMILES: N#Cc1ccc2nc(-c3cncnc3C(F)F)n(C3CC3)c2n1] |
| 64 | ++++ | ++ | 9.95 (min)[b] | 326.0 [M + H][+b] | 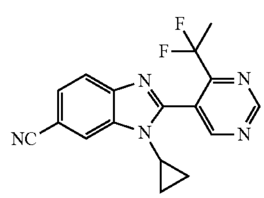 [SMILES: CC(F)(F)c1ncncc1-c1nc2ccc(C#N)cc2n1C1CC1] |
| 65 | ++++ | ++ | 8.66 (min)[b] | 331 [M + H][+c] | 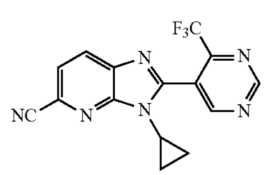 [SMILES: N#Cc1ccc2nc(-c3cncnc3C(F)(F)F)n(C3CC3)c2n1] |
| 66 | ++ | + | 9.44 (min)[b] | 340.0 [M + H][+b] | 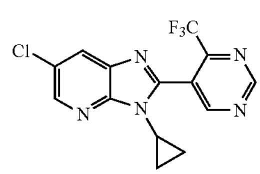 [SMILES: FC(F)(F)c1ncncc1-c1nc2cc(Cl)cnc2n1C1CC1] |

TABLE 2-continued

| | hCYP11B2 IC$_{50}$[g] | hCYP11B1 IC$_{50}$[g] | HPLC Retention Time[f] | LCMS (M + 1)[f] | Structure |
|---|---|---|---|---|---|
| 67 | +++ | + | 9.00 (min)[b] | 328.9 [M + H]$^{+b}$ | 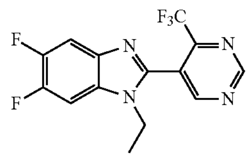 [SMILES: CCn1c(-c2cncnc2C(F)(F)F)nc2cc(F)c(F)cc21] |
| 68 | +++ | + | 9.11 (min)[b] | 328 [M + H]$^{+b}$ | 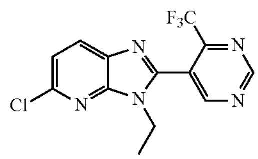 [SMILES: CCn1c(-c2cncnc2C(F)(F)F)nc2ccc(Cl)nc21] |
| 69 | +++ | + | 8.67 (min)[b] | 319 [M + H]$^{+b}$ | 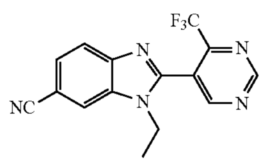 [SMILES: CCn1c(-c2cncnc2C(F)(F)F)nc2ccc(C#N)cc21] |
| 70 | + | + | 7.67 (min)[b] | 349.0 [M + H]$^{+c}$ | 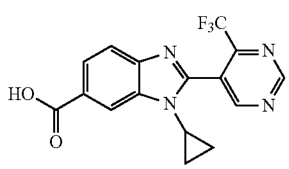 [SMILES: O=C(O)c1ccc2nc(-c3cncnc3C(F)(F)F)n(C3CC3)c2c1] |
| 71 | ++++ | ++ | 9.43 (min)[b] | 337.0 [M + H]$^{+b}$ | 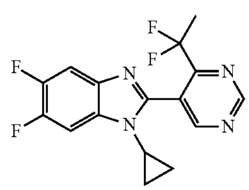 [SMILES: CC(F)(F)c1ncncc1-c1nc2cc(F)c(F)cc2n1C1CC1] |
| 72 | +++ | + | 8.81 (min)[b] | 312.9 [M + H]$^{+b}$ | 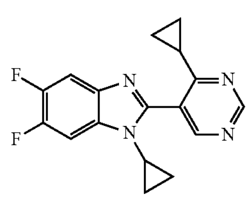 [SMILES: Fc1cc2nc(-c3cncnc3C3CC3)n(C3CC3)c2cc1F] |
| 73 | +++ | + | 6.67 (min)[b] | 319.9 [M + H]$^{+c}$ | 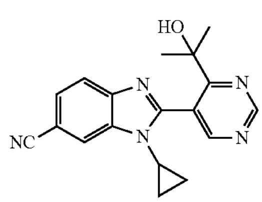 [SMILES: CC(C)(O)c1ncncc1-c1nc2ccc(C#N)cc2n1C1CC1] |

[f]See table 1 for HPLC and LCMS methods

[g]IC$_{50}$ ranges: + >10 μM; ++ 1-10 μM; +++ 0.1-1 μM; ++++ 0.001-0.1 μM

The results in Table 2 demonstrate that compounds of Formula I have potent activity against CYP11B2, and many compounds of Formula I have significant selectivity for inhibiting CYP11B2 over CYP11B1.

Comparison Examples were also prepared. Table 3 shows that replacing the pyrimidine of compounds of Formula I with a pyridine results in compounds (e.g., Examples 74, 75, and 76) that show increased inhibition of CYP11B1 and/or a significant loss of selectivity for CYP11B2 over CYP11B1. Both of these features are undesirable in a CYP11B2 inhibitor because, as described above, CYP11B1 activity is integral to cortisol production. Examples 27 and 30 also showed much greater metabolic stability when exposed to cynomolgus monkey and rat liver microsomes than their pyridine counterpart, Example 76. The metabolic stability of Examples 27 and 30 results in long in vivo half-lives in cynomolgus monkeys. Taken together, these results demonstrate that the pyrimidine compounds of Formula I are potentially of greater therapeutic utility in humans than known compounds, due in part to their decreased inhibition of CYP11B1, increased selectivity for inhibition of CYP11B2 over other related metalloenzymes, and their metabolic stability.

TABLE 3

Comparison Results

[Structure: benzimidazole core with $R^6$ substituent, F substituent, N-cyclopropyl, and Ar group at 2-position]

| Ex. No. | 1 | 74 | 44 | 75 | 27 | 30 | 76 |
|---|---|---|---|---|---|---|---|
| Ar | pyrimidin-5-yl | pyridin-3-yl | 4-methylpyrimidin-5-yl | 4-methylpyridin-3-yl | 4-(CHF$_2$)pyrimidin-5-yl | 4-(CF$_3$)pyrimidin-5-yl | 4-(CF$_3$)pyridin-3-yl |
| $R^6$ | H | H | F | F | F | F | F |
| pKa[a] | 0.24 | 3.69 | 1.31 | 5.29 | −0.21 | −0.27 | 3.48 |
| cLogP[a] | 2.09 | 2.91 | 2.40 | 3.52 | 2.69 | 3.51 | 3.93 |
| tPSA[a] (Å$^2$) | 43.60 | 30.71 | 43.60 | 30.71 | 43.60 | 43.60 | 30.71 |
| CYP11B2 IC$_{50}$(µM) | 0.040 | 0.005 | 0.017 | 0.011 | 0.017 | 0.032 | 0.036 |
| CYP11B1 IC$_{50}$(µM) | 5.380 | 0.858 | 4.157 | 1.074 | 4.719 | 6.370 | 4.121 |
| Selectivity[b] | 134 | 192 | 244 | 99 | 278 | 199 | 115 |
| Cyno LM Stability[c] | 70 | 1 | 72 | 25 | 106 | 99 | 58 |
| Rat LM Stability[c] | 0 | 12 | 96 | 22 | 108 | 108 | 52 |
| Cyno T½ (h)[d] | | | | | | 16.9 | 37.5 |

[a] pKa, LogP (Chemaxon method), and total polar surface area (tPSA) calculated with MarvinSketch 15.5.4.0
[b] Selectivity = CYP11B1 IC$_{50}$/CYP11B2 IC$_{50}$
[c] % Compound remaining at 65 min in rat or cyno liver microsomes.
[d] Half life (T½) from a 1 mg/kg PO dose.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:

1. A method of reducing one or more symptoms of an aldosterone related disease or disorder in a subject suffering from said disease or disorder, comprising administering to said subject in need thereof, an effective amount of a compound of the formula

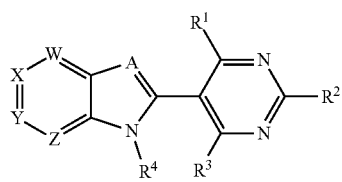

or a pharmaceutically acceptable salt thereof; wherein
A is N;
W is CR6;
X is CR6;
Y is CR6;
Z is CR6;
R1 is hydrogen, halogen, cyano, acyl, alkyl, alkenyl, alkynyl, haloalkyl, alkoxy, haloalkoxy, cycloalkyl, cycloalkoxy, aryl, arylalkyl, heteroaryl, heteroarylalkyl, heterocycloalkyl, heterocycloalkylalkyl, NRaRb, NHSO2Rc, (CH2)nNRaRb, (CH2)nNHSO2Rd, (CH2)nNHCO2Rd, CO2Re, CORf, (CH2)nORf, or CReRfOH;

R2 is hydrogen, cyano, acyl, alkyl, alkenyl, alkynyl, haloalkyl, alkoxy, haloalkoxy, cycloalkyl, cycloalkoxy, aryl, arylalkyl, heteroaryl, heteroarylalkyl, heterocycloalkyl, heterocycloalkylalkyl, NHSO2Rc, CH2NRaRb, CH2NHSO2Rd, CO2Re, CORf, CH2ORf, or CReRfOH;

R3 is hydrogen, halogen, cyano, acyl, alkyl, alkenyl, alkynyl, haloalkyl, alkoxy, haloalkoxy, cycloalkyl, cycloalkoxy, aryl, arylalkyl, heteroaryl, heteroarylalkyl, heterocycloalkyl, heterocycloalkylalkyl, NRaRb, NHSO2Rc, (CH2)nNRaRb, (CH2)nNHSO2Rd, CO2Re, CORf, (CH2)nORf, or CReRfOH;

each n is independently 1, 2, 3, 4, 5, 6, 7, 8, 9, or 10;

R4 is alkyl, cycloalkyl, haloalkyl, or heteroalkyl;

each occurrence of R6 is, independently, hydrogen, halogen, cyano, haloalkyl, alkyl, cycloalkyl, haloalkyl, alkoxy, haloalkoxy, alkylsulfonyl, or carboxyl; and each occurrence of Ra, Rb, Rc, Rd, Re, and Rf are, independently, hydrogen, acyl, alkyl, alkenyl, alkynyl, heteroalkyl, haloalkyl, cycloalkyl, heterocycloalkyl, aryl, heteroaryl, alkoxyalkyl, C(O)OC1-6 alkyl, C(O)C1-6 alkyl, a nitrogen protecting group when attached to a nitrogen atom, or an oxygen protecting group when attached to an oxygen atom; or Ra and Rb together with the atoms to which they are attached form a heterocycloalkyl ring; or Re and Rf together with the atoms to which they are attached form a cycloalkyl ring.

2. The method of claim 1, wherein the aldosterone related disorder or disease is mediated by aldosterone synthase (CYP11B2) or 11-beta-hydroxylase (CYP11B1).

3. The method of claim 1, wherein the aldosterone related disorder or disease is cardiovascular disease, endocrinologic disease, inflammatory disease, gynecologic disease, urologic disease, or gastrointestinal disease.

4. The method of claim 1, wherein the aldosterone related disorder or disease is hypertension, resistant hypertension, morbidities associated with primary or secondary hyperaldosteronism and adrenal hyperplasia, pulmonary arterial hypertension, heart failure, diastolic dysfunction, left ventricular diastolic dysfunction, diastolic heart failure, systolic dysfunction, systolic heart failure, hypokalemia, renal failure, chronic renal failure, restenosis, nephropathy, post-myocardial infarction, coronary heart disease, fibrosis, diseases characterized by increased collagen formation, fibrosis and matrix remodeling following hypertension, fibrosis and matrix remodeling following endothelial cell dysfunction, cardiovascular diseases, atrial fibrillation, renal dysfunction, liver diseases, non-alcoholic steatohepatitis, vascular diseases, retinopathy, neuropathy, insulinopathy, endothelial dysfunction, myocardial fibrosis, vascular fibrosis, myocardial necrotic lesions, vascular damage, myocardial infarction, left ventricular hypertrophy, vascular wall hypertrophy, endothelial thickening, fibrinoid necrosis of the arteries, kidney diseases, diabetic nephropathy, glomerulosclerosis, glomerulonephritis, nephritic syndrome, polycystic kidney disease, diabetes mellitus, metabolic syndrome, insulin resistance, sleep apnea, obstructive sleep apnea, muscular dystrophy, liver cirrhosis, non-alcoholic fatty liver disease, renal disorders, diabetic renal disorders, or stroke.

\* \* \* \* \*